US011964960B2

(12) United States Patent
Hla et al.

(10) Patent No.: US 11,964,960 B2
(45) Date of Patent: Apr. 23, 2024

(54) PYRIDINONE- AND PYRIDAZINONE-BASED COMPOUNDS AND USES THEREOF

(71) Applicants: Cornell University, Ithaca, NY (US); Tri-Institutional Therapeutics Discovery Institute, New York, NY (US)

(72) Inventors: Timothy Hla, Wellesley, MA (US); Irina Jilishitz, New York, NY (US); Peter Meinke, Scotch Plains, NJ (US); Andrew Stamford, Chatham, NJ (US); Michael Foley, New York, NY (US); Ayumu Sato, Zushi (JP); Yasufimi Wada, Fujisawa (JP); Yoshiyuki Fukase, Edgewater, NJ (US); Asato Kina, Fujisawa (JP); Hiroki Takahagi, Fujisawa (JP); Hideyuki Igawa, Edgewater, NJ (US); William J. Polvino, Trinton Falls, NJ (US)

(73) Assignees: Cornell University, Ithaca, NY (US); Tri-Institutional Therapeutics Discovery Institute, New York, NY (US)

( * ) Notice: Subject to any disclaimer, the term of this patent is extended or adjusted under 35 U.S.C. 154(b) by 0 days.

(21) Appl. No.: 16/979,506

(22) PCT Filed: Mar. 8, 2019

(86) PCT No.: PCT/US2019/021482
§ 371 (c)(1),
(2) Date: Sep. 9, 2020

(87) PCT Pub. No.: WO2019/173790
PCT Pub. Date: Sep. 12, 2019

(65) Prior Publication Data
US 2020/0407339 A1 Dec. 31, 2020

Related U.S. Application Data

(60) Provisional application No. 62/641,077, filed on Mar. 9, 2018, provisional application No. 62/701,155, filed on Jul. 20, 2018, provisional application No. 62/756,914, filed on Nov. 7, 2018.

(51) Int. Cl.
| | |
|---|---|
| C07D 401/06 | (2006.01) |
| A61P 1/16 | (2006.01) |
| C07D 403/06 | (2006.01) |
| C07D 413/06 | (2006.01) |
| C07D 417/06 | (2006.01) |
| C07D 471/04 | (2006.01) |

(52) U.S. Cl.
CPC .............. *C07D 401/06* (2013.01); *A61P 1/16* (2018.01); *C07D 403/06* (2013.01); *C07D 413/06* (2013.01); *C07D 417/06* (2013.01); *C07D 471/04* (2013.01)

(58) Field of Classification Search
CPC .. C07D 403/06; C07D 413/06; C07D 417/06; C07D 471/04; C07D 401/06
See application file for complete search history.

(56) References Cited

U.S. PATENT DOCUMENTS 9,663,511 B2  5/2017 Swenson

FOREIGN PATENT DOCUMENTS

| EP | 3263133 A1 | 1/2018 |
|---|---|---|
| WO | WO-2019173790 A1 | 9/2019 |

OTHER PUBLICATIONS

Tajiri et al., 2017, Cell Reports 19, 969-980 (May 2, 2017).*
Registry No. 1276519-39-1, File Registry on STN, Apr. 7, 2011.*
Registry No. 1241307-28-7, File Registry on STN, Sep. 15, 2010.*
Registry No. 1036097-93-4, File Registry on STN, entered Jul. 25, 2008.*
Registry No. 930083-42-4, File Registry on STN, entered Apr. 13, 2007.*
Registry No. 1011456-45-3, File Registry on STN, entered Apr. 1, 2008.*
Registry No. 849013-47-4, File Registry on STN, entered Apr. 22, 2005.*
"International Application Serial No. PCT/US2019/021482, International Search Report dated Jul. 15, 2019", 10 pgs.
"International Application Serial No. PCT/US2019/021482, Invitation to Pay Additional Fees and Partial Search Regort dated May 24, 2019", 8 pgs.
"International Application Serial No. PCT/US2019/021482, Written Opinion dated Jul. 15, 2019", 10 pgs.
Maity, P K, et al., "Silica-Supported Oligomeric Benzyl Phosphate (Si-OBP) and Triazole Phosphate (Si-OTP) Alkylating Reagents", Journal of Organic Chemistry, vol. 80, No. 20, (Oct. 16, 2015), 9 pgs.
Saskala, R, et al., "Lanthanum loaded CuO nanoparticles: synthesis and characterization of a recyclable catalyst for the synthesis of 1,4-disubstituted 1,2,3-triazoles and propargyl amines", RSC Advances, vol. 5, No. 70, (Jun. 9, 2015), 12 pgs.
Satsu, H, et al., "A sphingosine 1-phosphate receptor 2 selective allosteric agonist", Bioorganic & Medicinal Chemistry, vol. 21, No. 17, ISSN: 0968-0896, DOI: 10.1016/J.BMC.2013.06.012 cited in the application the whole document, (Jun. 15, 2013), 19 pgs.

(Continued)

*Primary Examiner* — Rebecca L Anderson
(74) *Attorney, Agent, or Firm* — Schwegman Lundberg & Woessner, P.A.

(57) ABSTRACT

The various examples presented herein are directed to compounds of the formula A-$L^1$-$Het^1$-$L^2$-$Cy^1$ or a pharmaceutical acceptable salt, polymorph, prodrug, solvate or clathrate thereof, wherein: A is cycloalkyl, aryl, arylalkyl or heterocyclyl; $Het^1$ is heterocyclyl containing at least two heteroatoms; $Cy^1$ is a heterocyclyl; $L^1$ is a bond, alkyl, alkenyl or alkynyl linker; $L^2$ is an acyl or alkyl linker; and A and $Cy^1$ are different. The compounds are useful in the treatment of fibrotic diseases, abnormal vascular leak and pathological angiogenesis.

5 Claims, 5 Drawing Sheets

(56) References Cited

OTHER PUBLICATIONS

Slivarichova, M, et al., "Silver and Palladium Complexes Containing Ditopic N-Heterocyclic Carbene-Thione Ligands", Organometallics, vol. 31, No. 18, (Sep. 24, 2012), 13 pgs.

"2(1H)-Pyridinone, 1-[2-[4-[1-(2-chlorophenyl)ethyl]-1-pipera zinyl]-2-oxoethyl]-4-hydroxy-6-methyl-", Abstract, Database Accession No. 2175522-30-0, Chemical Abstracts Service, Columbus, Ohio, (Feb. 18, 2018), 1 pg.

"2(1H)-Pyridinone, 1-[2-[4-[1-(4-chlorophenyl)ethyl]-1-pipera zinyl]-2-oxoethyl]-4-hydroxy-6-methyl-", Abstract, Database Accession No. 2176215-19-1, Chemical Abstracts Service, Columbus, OH, (Feb. 19, 2018), 1 pg.

"2(1H)-Pyridinone, 1-[2-[4-[1-(3-fluorophenyl)ethyl]-1-pipera zinyl]-2-oxoethyl]-4-hydroxy-6-methyl-", Abstract, Database Accession No. 2178356-46-0, Chemical Abstracts Service, Columbus, OH, (Feb. 22, 2018), 1 pg.

"2(1H)-Pyridinone, 4-hydroxy-6-methyl-1-[2-[4-[(3-methyl phenyl)methyl]-1-piperazinyl]-2-oxoethyl]-", Abstract, Database Accession No. 2178264-14-5, Chemical Abstracts Service, Columbus, OH, (Feb. 22, 2018), 1 pg.

"2(1H)-Pyrimidinone, 1-[2-[2-(hydroxymethyl)-2-[(2-methyl phenyl)methyl]-4-morpholinyi]-2-oxoethyl]-", Abstract, Database Accession No. 2127051-84-5, Chemical Abstracts Service, Columbus, OH, (Sep. 13, 2017), 1 pg.

"2(1H)-Pyrimidinone, 1- [2-[2-(hydroxymethyl)-2-(phenylmethyl)-4-morpholl nyl]-2-oxoethyl]-", Abstract, Database Accession No. 2127206-01-1, Chemical Abstracts Service, Columbus, OH, (Sep. 14, 2017), 1 pg.

"2(1H)-Pyrimidinone, 4,6-dimethyl-1-[2-[4-methyl-3-(phenylmethyl)-1-piperazinyl]-2-oxoethyl]-", Abstract, Database Accession No. 2186433-67-8, Chemical Abstracts Service, Columbus, OH, (Mar. 7, 2018), 1 pg.

"2(1H)-Pyrimidinone, 1-[2-[2-(hydroxymethyl)-2-[(4-methylphenyl)methyl]-4-morpholinyl]-2-oxoethyl]-", Abstract, Database Accession No. 2125596-37-2, Chemical Abstracts Service, Columbus, OH, (Sep. 6, 2017), 1 pg.

"4-Pyridazinecarbonitrile, 2,3-dihydro-5,6-dimethyl-2-[2-[4-[(2-methylphenyl)methyl]-1-piperazinyl]-2-oxoethyl]", Abstract, Database Accession No. 2186584-22-3, Chemical Abstracts Service, Columbus, OH, (Mar. 7, 2018), 1 pg.

"European Application Serial No. 19714268.0, Response filed Apr. 29, 2021 to Communication pursuant to Rules 161(1) and 162 EPC dated Oct. 29, 2020", 26 pgs.

"International Application Serial No. PCT/US2019/021482, International Preliminary Report on Patentability dated Sep. 24, 2020", 12 pgs.

Ikeda, Hitoshi, "Sphingosine 1-phosphate regulates regeneration and fibrosis after liver injury via sphingosine 1-phosphate receptor 2", J Lipid Res., 50(3), (2009), 556-564.

Imasawa, Toshiyuki, et al., "Blockade of sphingosine 1-phosphate receptor 2 signaling attenuates streptozotocin-induced apoptosis of pancreatic β-cells", Biochem Biophys Res Commun., 392(2), (2010), 207-211.

Kim, Gab S., et al., "Critical role of sphingosine-1-phosphate receptor-2 in the disruption of cerebrovascular integrity in experimental stroke", Nat Commun., 6:7893, (2015), 1-15.

Ko, Jaesang, et al., "Sphingosine-1-Phosphate Mediates Fibrosis in Orbital Fibroblasts in Graves' Orbitopathy", Invest Ophthalmol Vis Sci., 58(5), (2017), 2544-2553.

Lee, Jen-Fu F., et al., "Balance of $S1P_1$ and $S1P_2$ signaling regulates peripheral microvascular permeability in rat cremaster muscle vasculature", Am J Physiol Heart Circ Physiol.,296(1), (2009), H33-H42.

Li, Mei-Hong, et al., "Antitumor Activity of a Novel Sphingosine-1-Phosphate 2 Antagonist, AB1, in Neuroblastoma", J Pharmacol Exp Ther.,354(3), (2015), 261-268.

Li, Mei-Hong, et al., "Induction of Antiproliferative Connective Tissue Growth Factor Expression in Wilms' Tumor Cells by Sphingosine-1-Phosphate Receptor 2", Mol Cancer Res., 6(10), (2008), 1649-1656.

Osada, Makoto, et al., "Enhancement of sphingosine 1-phosphate-induced migration of vascular endothelial cells and smooth muscle cells by an EDG-5 antagonist", Biochem Biophys Res Commun,, 299(3), (2002), 483-487.

Oskeritzian, Carole A., et al., "Essential roles of sphingosine-1-phosphate receptor 2 in human mast cell activation, anaphylaxis, and pulmonary edema", J Exp Med., 207(3), (2010), 465-474.

Sanchez, Teresa, et al., "Induction of vascular permeability by the sphingosine-1-phosphate receptor-2 (S1P2R) and its downstream effectors ROCK and PTEN", Arterioscler Thromb Vasc Biol., 27(6), (2007), 1312-1318.

Sato, Masaya, et al., "Sphingosine kinase-1, S1P transporter spinster homolog 2 and S1P2 mRNA expressions are increased in liver with advanced fibrosis in human", Sci Rep., 6:32119, (2016), 1-8.

Shea, Barry S., et al., "Sphingolipid regulation of tissue fibrosis", Open Rheumatol J., 6, (2012), 123-129.

Skoura, Athanasia, et al., "Essential role of sphingosine 1-phosphate receptor 2 in pathological angiogenesis of the mouse retina", J Clin Invest., 117(9), (2007), 2506-1256.

Skoura, Athanasia, et al., "Regulation of vascular physiology and pathology by the $S1P_2$ receptor subtype", Cardiovasc Res., 82(2), (2009), 221-228.

Szczepaniak, William S., et al., "$S1P_2$ receptor-dependent Rho-kinase activation mediates vasoconstriction in the murine pulmonary circulation induced by sphingosine 1-phosphate", Am J Physiol Lung Cell Mol Physiol, 299, (2010), L137-L145.

Takuwa, Yoh, et al., "Sphingosine-1-phosphate as a mediator involved in development of fibrotic diseases", Biochim Biophys Acta., 1831(1), 185-192, (2013), 45 pgs.

Terashita, Tomomi, et al., "Administration of JTE013 abrogates experimental asthma by regulating proinflammatory cytokine production from bronchial epithelial cells", Respir Res., 7(1): 146, (2016), 8 pgs.

Zhang, Guoqi, et al., "Critical role of sphingosine-1-phosphate receptor 2 (S1PR2) in acute vascular inflammation", Blood, 122(3), (2013), :443-455.

"European Application Serial No. 19714268.0, Communication Pursuant to Article 94(3) EPC dated Feb. 2, 2022", 6 pgs.

"European Application Serial No. 19714268.0, Communication Pursuant to Article 94(3) EPC dated Sep. 22, 2022", 5 pgs.

"European Application Serial No. 19714268.0, Response Filed Jun. 9, 2022 to Communication Pursuant to Article 94(3) EPC dated Feb. 2, 2022", 32 pgs.

"European Application Serial No. 19714268.0, Response Filed Jan. 20, 2023 to Communication Pursuant to Article 94(3) EPC dated Sep. 22, 2022", 32 pgs.

"European Application Serial No. 19714268.0, Communication Pursuant to Article 94(3) EPC mailed Jan. 30, 2024", 3 pgs.

\* cited by examiner

PYRIDINONE- AND PYRIDAZINONE-BASED COMPOUNDS AND USES THEREOF

RELATED APPLICATIONS

This application is a U.S. national stage filing under 35 U.S.C. § 371 from International Application No. PCT/US2019/021482, filed on Mar. 8, 2019, and published as WO2019/173790 A1 on Sep. 12, 2019, which claims benefit of priority to the filing date of U.S. Provisional Application Ser. No. 62/641,077, filed Mar. 9, 2018; U.S. Provisional Application Ser. No. 62/701,155, filed Jul. 20, 2018; and U.S. Provisional Application Ser. No. 62/756,914, filed Nov. 7, 2018.

BACKGROUND OF THE INVENTION

The sphingosine 1-phosphate receptor-2 ($S1P_2$) is coupled preferentially to the heterotrimeric G13 and small GTPase Rho pathway. It is induced during pathological conditions in fibrogenic, immune and vascular cells. Activation of this pathway in fibroblasts induces the Rho/Rho kinase (ROCK)-dependent fibrogenic factors, for example, connective tissue growth factor (CTGF) and the Hippo/YAP signaling pathway are key downstream mediators that induce pathologic fibrosis. In vascular endothelial cells, the $S1P_2$ receptor induces inflammatory responses, promotes vascular permeability and is induced during pathologic responses. Thus, it is thought to be one of the key drivers of tissue injury, fibrosis, and pathologic angiogenesis.

The S1P signaling system is unique in that the ligand SIP is present abundantly in circulation during homeostatic conditions. Thus, receptor expression on the cell surface is critical for biological events such as cell migration and junction assembly. The first FDA-approved S1P receptor inhibitor, Fingolimod/Gilenya induces irreversible receptor internalization, followed by ubiquitinylation, and protesomal degradation. Fingolimod belongs to a crass of S1P receptor inhibitors called functional antagonists and it appears that this class of compounds work better than competitive inhibitors against the receptor. However, Fingolimod and related molecules that were designed to block lymphocyte trafficking by targeting the $S1P_1$ receptor do not interact with $S1P_2$ receptor. Thus, there is a need to develop effective inhibitors of the $S1P_2$ receptor.

SUMMARY

Select embodiments of the present disclosure include, but are not limited to, the following:

Embodiment 1 relates to a compound of the Formula (I):

$$A\text{-}L^1\text{-}Het^1\text{-}L^2\text{-}Cy^1 \quad (I)$$

or a pharmaceutically acceptable salt, polymorph, prodrug, solvate or clathrate thereof, wherein:
A is cycloalkyl, aryl, arylalkyl or heterocyclyl;
$Het^1$ is heterocyclyl containing at least two heteroatoms;
$Cy^1$ is a heterocyclyl;
$L^1$ is a bond, alkyl, alkenyl or alkynyl linker;
$L^2$ is an acyl or alkyl linker; and
A and $Cy^1$ are different.

Embodiment 2 relates to a compound of the Formula (II):

$$A\text{-}L^1\text{-}Het^2\text{-}L^2\text{-}Cy^2 \quad (II)$$

or a pharmaceutically acceptable salt, polymorph, prodrug, solvate or clathrate thereof, wherein:
A is cycloalkyl, aryl, arylalkyl or heterocyclyl containing at least one N or O;
$Het^2$ is an aromatic heterocyclyl group;
$Cy^2$ is a heterocyclyl containing one keto group and at least one nitrogen in the heterocyclyl ring, wherein the heterocyclyl is mono-substituted with fluoro, chloro, bromo, iodo, cyano, methyl, $(C_2\text{-}C_8)$alkyl, methoxy, $(C_2\text{-}C_8)$alkoxy, acetamido, $(C_3\text{-}C_8)$alkylamido, $(C_2\text{-}C_8)$alkenyl, $(C_2\text{-}C_8)$alkynyl, methoxycarbonyl, $(C_2\text{-}C_8)$alkoxy-carbonyl or carboxy or di-substituted with fluoro, chloro, bromo, iodo, cyano, methyl, $(C_2\text{-}C_8)$alkyl, $(C_2\text{-}C_8)$alkenyl, $(C_2\text{-}C_8)$alkynyl, methoxy or $(C_2\text{-}C_8)$alkoxy provided that the two substituents are not the same;
$L^1$ is a bond, alkyl, alkenyl or alkynyl linker;
$L^2$ is an aryl or alkyl linker;
wherein A and $Cy^2$ are different;
wherein when $Cy^2$ is mono-substituted with cyano, bromo or methyl and A is aryl, then A is substituted aryl, $L^1$ comprises at least two carbons, $L^2$ comprises at least three carbons, or $Cy^2$ contains two nitrogens in the heterocyclyl ring; and
when $Cy^2$ is mono-substituted with t-butyl or benzodioxepinyl and A is aryl, then A is substituted aryl, $L^1$ comprises at least two carbons, $L^2$ comprises at least three carbons or $Cy^2$ contains no more than one nitrogen in the heterocyclyl ring.

Embodiment 3 relates to a compound of the Formula (II):

$$A\text{-}L^1\text{-}Het^2\text{-}L^2\text{-}Cy^2 \quad (II)$$

or a pharmaceutically acceptable salt, polymorph, prodrug, solvate or clathrate thereof, wherein:
A is cycloalkyl, aryl, arylalkyl or heterocyclyl containing at least one N or O;
$Het^2$ is an aromatic heterocyclyl group;
$Cy^2$ is a heterocyclyl containing one keto group and at least one nitrogen in the heterocyclyl ring, wherein the heterocyclyl is mono-substituted with fluoro, chloro, iodo, methoxy, $(C_2\text{-}C_8)$alkoxy, acetamido, $(C_3\text{-}C_8)$alkylamido, $(C_2\text{-}C_8)$alkenyl, $(C_2\text{-}C_8)$alkynyl, methoxycarbonyl, $(C_2\text{-}C_8)$alkoxy-carbonyl or carboxy or di-substituted with fluoro, chloro, bromo, iodo, cyano, methyl, $(C_2\text{-}C_8)$alkyl, $(C_2\text{-}C_8)$alkenyl, $(C_2\text{-}C_8)$alkynyl, methoxy or $(C_2\text{-}C_8)$alkoxy provided that the two substituents are not the same;
$L^1$ is a bond, alkyl, alkenyl or alkynyl linker;
$L^2$ is an acyl or alkyl linker; and
wherein A and $Cy^2$ are different.

Embodiment 4 relates to a compound of the Formula (A):

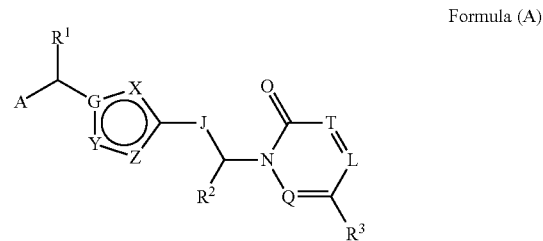

Formula (A)

or a pharmaceutically acceptable salt, polymorph, prodrug, solvate or clathrate thereof, wherein:
A is cycloalkyl, aryl, arylalkyl or heterocyclyl containing at least one N or O;
$R^1$ is H or $(C_1\text{-}C_8)$alkyl;
$R^2$ is H or $(C_1\text{-}C_8)$alkyl;

$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; and
at least two of G, X, Y and Z is independently N, O or S.

Embodiment 5 relates to a compound of the Formula (A):

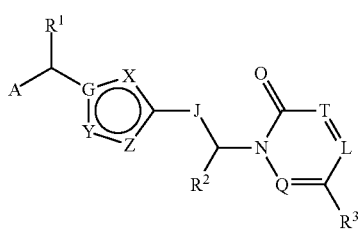

Formula (A)

or a pharmaceutically acceptable salt, polymorph, prodrug, solvate or clathrate thereof, wherein:

A is cycloalkyl, aryl, arylalkyl or heterocyclyl containing at least one N or O;
$R^1$ is H or $(C_1-C_8)$alkyl;
$R^2$ is H or $(C_1-C_8)$alkyl;
$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
at least one of G, X, Y and Z is N; and
when $R^3$ is cyano or bromo and A is aryl, then A is substituted aryl, $R^1$ is $(C_1-C_8)$alkyl, $R^2$ is $(C_1-C_8)$alkyl, L is $CR^6$, T is $CR^7$, G is C, or Q is N; and when $R^3$ is t-butyl or benzodioxepinyl and A is aryl, then A is substituted aryl, $R^1$ is $(C_1-C_8)$alkyl, $R^2$ is $(C_1-C_8)$alkyl, L is $CR^6$, T is $CR^7$, G is C, or Q is CH.

Embodiment 6 relates to a compound of the Formula (A):

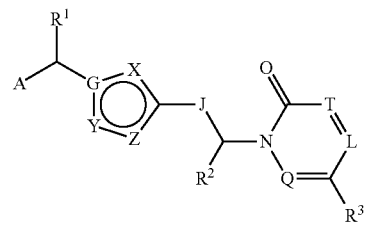

Formula (A)

or a pharmaceutically acceptable salt, polymorph, prodrug, solvate or clathrate thereof, wherein:

A is cycloalkyl, aryl, arylalkyl or heterocyclyl containing at least one N or O;
$R^1$ is H or $(C_1-C_8)$alkyl;
$R^2$ is H or $(C_1-C_8)$alkyl;
$R^3$ is H, fluoro, chloro, iodo, methyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, bromo, iodo, $(C_2-C_8)$alkyl, methoxy, $(C_1-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
at least one of G, X, Y and Z is N; and
when $R^3$ is H, then L is $CR^6$ or T is $CR^7$, or both.

Embodiment 7 relates to a compound having the Formula (B):

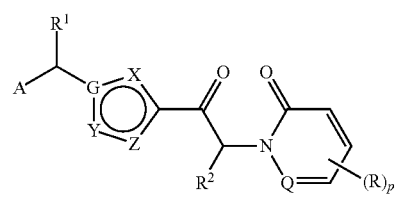

Formula (B)

or a pharmaceutically acceptable salt, polymorph, prodrug, solvate or clathrate thereof, wherein:

A is cycloalkyl, aryl, arylalkyl or heterocyclyl containing at least one N or O;
$R^1$ is H or $(C_1-C_8)$alkyl;
$R^2$ is H or $(C_1-C_8)$alkyl;
p is 1 or 2;
when p is 1 then R is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy when p is 2 then each instance of R is independently fluoro, chloro, bromo, iodo, cyano, methyl, (C$_2$-C$_8$)alkyl, (C$_2$-C$_8$)alkenyl, (C$_2$-C$_8$)alkynyl, methoxy or (C$_2$-C$_8$)alkoxy provided that each instance of R is not the same;

G is C or N;

X is N, O, S, CH or CR$^4$, wherein R$^4$ is (C$_1$-C$_8$)alkyl:

Y is N, O, S, CH or CR$^5$, wherein R$^5$ is (C$_1$-C$_8$)alkyl;

Z is N, O, S, CH or CCH$_3$; and

Q is N, CH or CCH$_3$.

Embodiment 8 relates to a compound of the Formula (C):

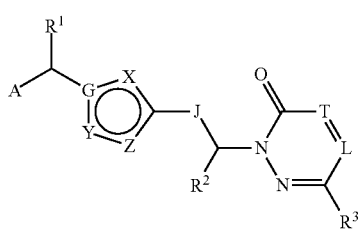

Formula (C)

or a pharmaceutically acceptable salt, polymorph, prodrug, solvate or clathrate thereof, wherein:

A is cycloalkyl, aryl, arylalkyl or heterocyclyl;

R$^1$ is H or (C$_1$-C$_8$)alkyl;

R$^2$ is H or (C$_1$-C$_8$)alkyl;

R$^3$ is H, fluoro, chloro, bromo, iodo, cyano, methyl, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_2$-C$_8$)alkoxy-carbonyl or carboxy;

G is C or N;

X is N, O, S, CH or CR$^4$, wherein R$^4$ is (C$_1$-C$_8$)alkyl;

Y is N, O, S, CH or CR$^5$, wherein R$^5$ is (C$_1$-C$_8$)alkyl;

Z is N, O, S, CH or CCH$_3$;

J is CO, (C$_1$)alkyl or a bond;

L is N, CH or CR$^6$, wherein R$^6$ is fluoro, chloro, bromo, iodo, cyano, (C$_2$-C$_8$)alkyl, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_2$-C$_8$)alkoxy-carbonyl or carboxy;

T is N, CH or CR$^7$, wherein R$^7$ is fluoro, bromo, iodo, (C$_2$-C$_8$)alkyl, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_2$-C$_8$)alkoxy-carbonyl or carboxy, at least one of G, X, Y and Z is N, and when R$^3$ is H, then L is CR$^6$ or T is CR$^7$, or both.

Embodiment 9 relates to a compound of the Formula (D):

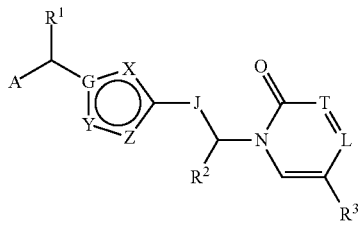

Formula (D)

or a pharmaceutically acceptable salt, polymorph, prodrug, solvate or clathrate thereof, wherein:

A is cycloalkyl, aryl, arylalkyl or heterocyclyl containing at least one N or O;

R$^1$ is H or (C$_1$-C$_8$)alkyl;

R$^2$ is H or (C$_1$-C$_8$)alkyl;

R$^3$ is H, fluoro, chloro, iodo, methyl, (C$_2$-C$_8$)alkyl, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_2$-C$_8$)alkoxy-carbonyl or carboxy;

G is C or N;

X is N, O, S, CH or CR$^4$, wherein R$^4$ is (C$_1$-C$_8$)alkyl;

Y is N, O, S, CH or CR$^5$, wherein R$^5$ is (C$_1$-C$_8$)alkyl;

Z is N, O, S, CH or CCH$_3$;

J is CO, (C$_1$)alkyl or a bond;

L is N, CH or CR$^6$, wherein R$^6$ is fluoro, chloro, bromo, iodo, cyano, (C$_2$-C$_8$)alkyl, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_1$-C$_8$)alkoxy-carbonyl or carboxy;

T is N, CH or CR$^7$, wherein R$^7$ is fluoro, bromo, iodo, (C$_2$-C$_8$)alkyl, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_2$-C$_8$)alkoxy-carbonyl or carboxy;

at least one of G, X, Y and Z is N, and when R$^3$ is H, then L is CR$^6$ or T is CR$^7$, or both.

Embodiment 10 relates to a compound of Formula (E1), Formula (E2), Formula (E3), Formula (E4), Formula (E5), Formula (E6) or Formula (E7):

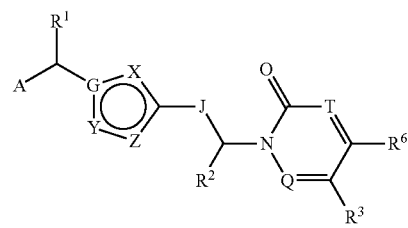

Formula (E1)

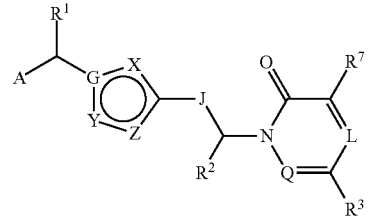

Formula (E2)

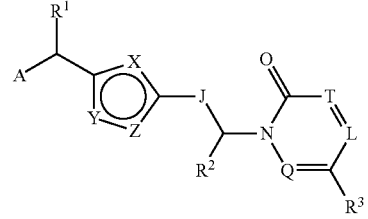

Formula (E3)

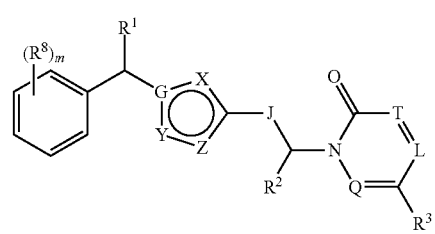

Formula (E4)

-continued

Formula (E5)

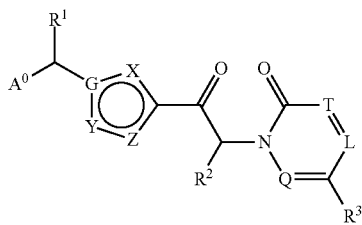

Formula (E6)

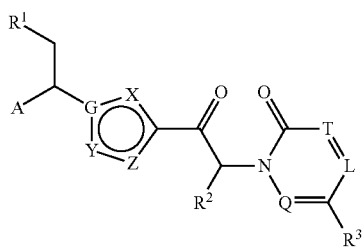

Formula (E7)

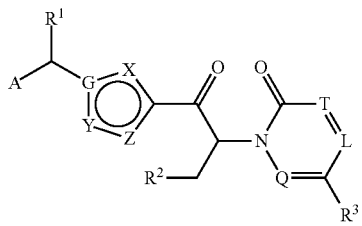

or a pharmaceutically acceptable salt, polymorph, prodrug, solvate or clathrate thereof, wherein:

A, if present, is cycloalkyl, aryl, arylalkyl or heterocyclyl;

$A^0$, if present, is cycloalkyl, arylalkyl or heterocyclyl containing at least one N or O;

$R^1$ is H or $(C_1-C_8)$alkyl;

$R^2$ is H or $(C_1-C_8)$alkyl;

$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

G is C or N;

X is N, O, S, CH or $CR^4$, wherein $R^4$ is $(C_1-C_8)$alkyl;

Y is N, O, S, CH or $CR^5$, wherein $R^5$ is $(C_1-C_8)$alkyl;

Z is N, O, S, CH or $CCH_3$;

J is CO, $(C_1)$alkyl or a bond;

Q is N, CH, CF or $CCH_3$;

L, if present, is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

T, if present, is N, CH or $CR^7$, wherein $R^7$ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy, $R^8$, if present, is alkylsulfonyl, alkyl, alkoxy, cyano, halo, difluoromethyl or carboxy or two adjacent instances of $R^8$ can form a fused dioxolane ring;

n, if present, is 0-5;

m, if present, is 1-5; and at least one of X, Y, Z and G, if present, is N.

Embodiment 11 relates to the compound of Embodiments 1-10 having the Formula (B):

Formula (B)

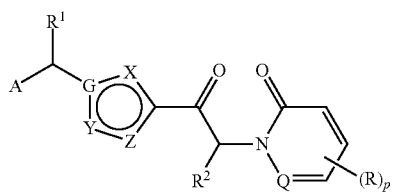

or a pharmaceutically acceptable salt, polymorph, prodrug, solvate or clathrate thereof, wherein:

A is cycloalkyl, aryl, arylalkyl or heterocyclyl containing at least one N or O;

$R^1$ is H or $(C_1-C_8)$alkyl;

$R^2$ is H or $(C_1-C_8)$alkyl;

p is 1 or 2;

when p is 1 then R is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy when p is 2 then each instance of R is independently fluoro, chloro, bromo, iodo, cyano, methyl, $(C_2-C_8)$alkyl, $(C_2-C_8)$alkenyl, $(C_2-C_8)$alkynyl, methoxy or $(C_2-C_8)$alkoxy provided that each instance of R is not the same;

G is C or N;

X is N, O, S, CH or $CR^4$, wherein $R^4$ is $(C_1-C_8)$alkyl;

Y is N, O, S, CH or $CR^5$, wherein $R^5$ is $(C_1-C_8)$alkyl;

Z is N, O, S, CH or $CCH_3$; and

Q is N, CH or $CCH_3$.

Embodiment 12 relates to the compound of Embodiments 1-11, wherein A is substituted cycloalkyl, unsubstituted cycloalkyl, substituted aryl, unsubstituted aryl, substituted arylalkyl, unsubstituted arylalkyl, substituted nonaromatic heterocyclyl, unsubstituted nonaromatic heterocyclyl, substituted aromatic heterocyclyl or unsubstituted aromatic heterocyclyl.

Embodiment 13 relates to the compound of Embodiments 1-12, wherein A is cycloalkyl, aryl, arylalkyl or heterocyclyl and is substituted by alkylsulfonyl, alkyl, alkoxy, cyano, halo, difluoromethyl or carboxy.

Embodiment 14 relates to the compound of Embodiments 1-13, wherein A or $A^0$ is substituted cycloalkyl, unsubstituted cycloalkyl, substituted arylalkyl, unsubstituted arylalkyl, substituted nonaromatic heterocyclyl, unsubstituted nonaromatic heterocyclyl, substituted aromatic heterocyclyl or unsubstituted aromatic heterocyclyl.

Embodiment 15 relates to the compound of Embodiments 1-14, wherein A or $A^0$ is cycloalkyl, arylalkyl or heterocyclyl and is substituted by alkylsulfonyl, alkyl, alkoxy, cyano, halo, difluoromethyl or carboxy.

Embodiment 16 relates to the compound of Embodiments 1-15, wherein A or $A^0$ is tetrahydrofuranyl, tetrahydropyranyl, pyrrolidinyl, piperidinyl, piperazinyl, pyrrolyl, furanyl, oxazolyl, thiazolyl, isoxazole, isothiazole, pyrazolyl, imidazolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, benzo[d][1,3]dioxole, pyridinyl or pyrimidinyl.

Embodiment 17 relates to the compound of Embodiments 1-16, wherein A or $A^0$ is cyclopropyl, cyclobutyl, or bicyclo[1.1.1]pentane.

Embodiment 18 relates to the compound of Embodiments 1-17, wherein A is phenyl.

Embodiment 19 relates to the compound of Embodiments 1-18, wherein A is substituted phenyl.

Embodiment 20 relates to the compound of Embodiments 1-19, wherein A is phenyl substituted with alkylsulfonyl, alkyl, alkoxy, cyano, halo, difluoromethyl or carboxy.

Embodiment 21 relates to the compound of Embodiments 1-20, wherein A or $A^0$ is:

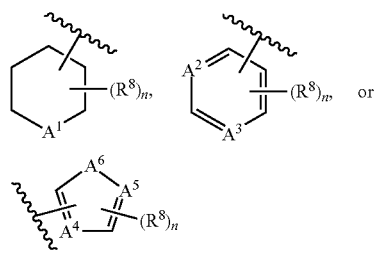

wherein:

n is 0-3;

$A^1$ is O or NH, N-Alkyl;

each of $A^2$ and $A^3$ is independently, CH, $CR^8$ or N;

each of $A^4$, $A^5$, and $A^6$ is independently CH, C-alkyl, N, $NR^9$ or O, provided that at least one of $A^4$, $A^5$, and $A^6$ is N or $NR^9$; and $R^8$ is independently alkylsulfonyl, alkyl, alkoxy, cyano, halo, difluoromethyl or carboxy; and $R^9$ is H or alkyl.

Embodiment 22 The compound of Embodiments 1-21, wherein A or $A^0$ is:

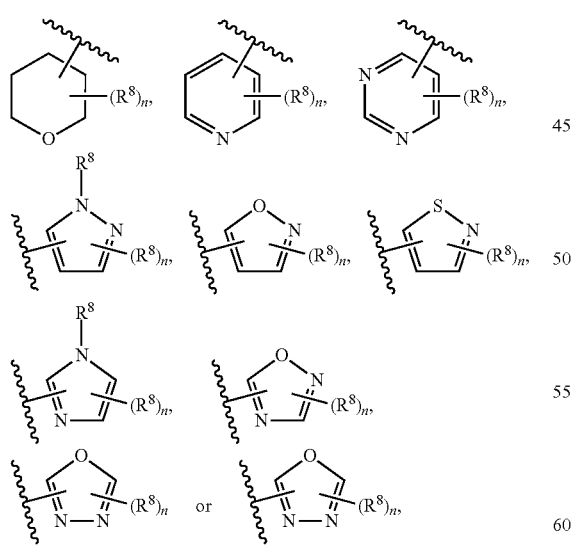

wherein:

n is 0-3;

$R^8$ is independently alkylsulfonyl, alkyl, alkoxy, cyano, halo, difluoromethyl or carboxy.

Embodiment 23 relates to the compound of Embodiments 1-22, wherein A or $A^0$ is:

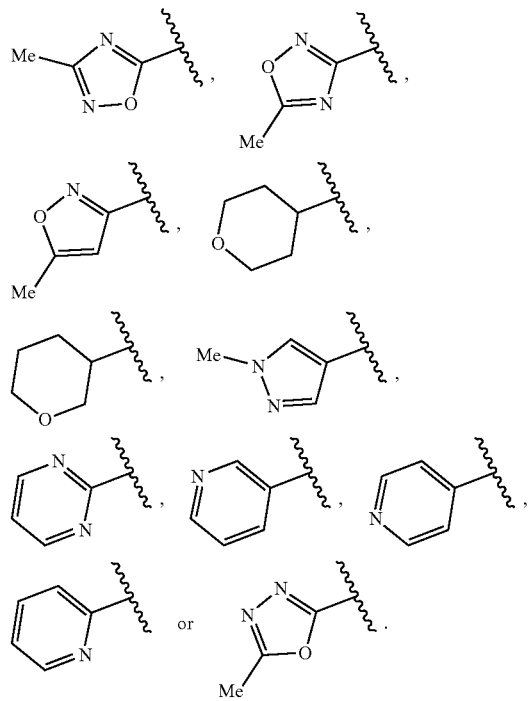

Embodiment 24 relates to the compound of Embodiments 1-23, wherein A is:

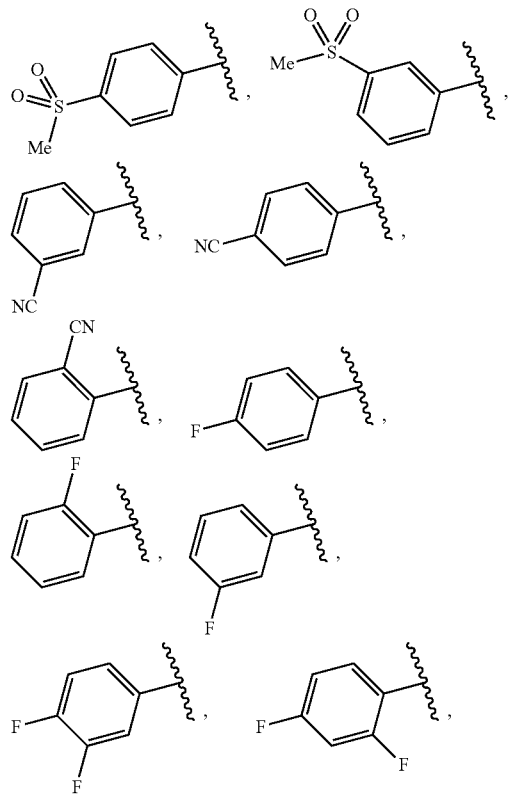

-continued

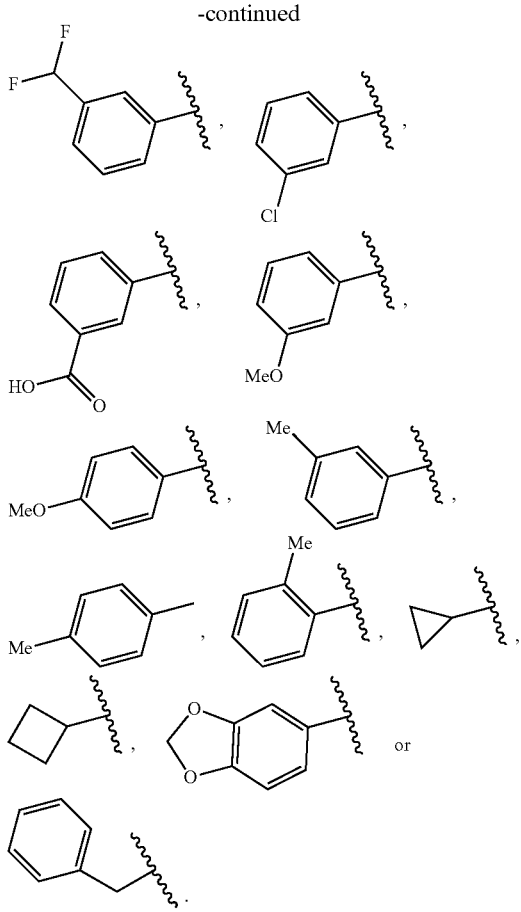

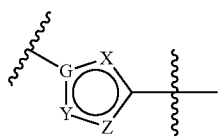

Embodiment 25 relates to the compound of Embodiments 1-24, wherein A is cycloalkyl, aryl, arylalkyl or heterocyclyl and is unsubstituted.

Embodiment 26 relates to the compound of Embodiments 1-25, wherein A or $A^0$ is cycloalkyl, arylalkyl or heterocyclyl and is unsubstituted.

Embodiment 27 relates to the compound of Embodiments 1-26, wherein $Het^1$ or $Het^2$ is a 5-membered heterocyclyl group containing at least two heteroatoms.

Embodiment 28 relates to the compound of Embodiments 1-27, wherein $Het^1$ or $Het^2$ is a furanyl, oxazolyl, pyrazolyl, imidazolyl, thiazole, isothiazole, 1,2,3-oxadiazolyl, 1,2,4-oxadiazolyl, 1,2,5-oxadiazolyl, 1,3,4-oxadiazolyl, 1,2,3-triazolyl or 1,2,4-triazolyl.

Embodiment 29 relates to the compound of Embodiments 1-28, wherein $Het^1$ or $Het^2$ is:

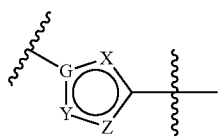

wherein
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl; and
Z is N, O, S, CH or $CCH_3$.

Embodiment 30 relates to the compound of Embodiments 4-11 and 29, wherein at least two of G, X, Y and Z is N.

Embodiment 31 relates to the compound of Embodiments 4-11 and 29, wherein at least one of G, X, Y and Z is N, S or O.

Embodiment 32 relates to the compound of Embodiments 4-11 and 29, wherein at least one of G, X, Y and Z is N and one of G, X, Y and Z is S or O.

Embodiment 33 relates to the compound of Embodiments 4-11 and 29, wherein G is C.

Embodiment 34 relates to the compound of Embodiments 4-11 and 29, wherein G is N.

Embodiment 35 relates to the compound of Embodiments 4-11 and 29, wherein at least two of G, X, Y and Z is N and one of G, X, Y and Z is S or O.

Embodiment 36 relates to the compound of Embodiments 4-11 and 29, wherein at least three of G, X, V and Z is N.

Embodiment 37 relates to the compound of Embodiments 4-11 and 29, wherein X is $CR^4$ or Y is $CR^5$ or both.

Embodiment 38 relates to the compound of Embodiments 4-11 and 29, wherein at least two of G, X, Y and Z are other than N, O and S.

Embodiment 39 relates to the Embodiments 1-38, wherein $Het^1$ or $Het^2$ is:

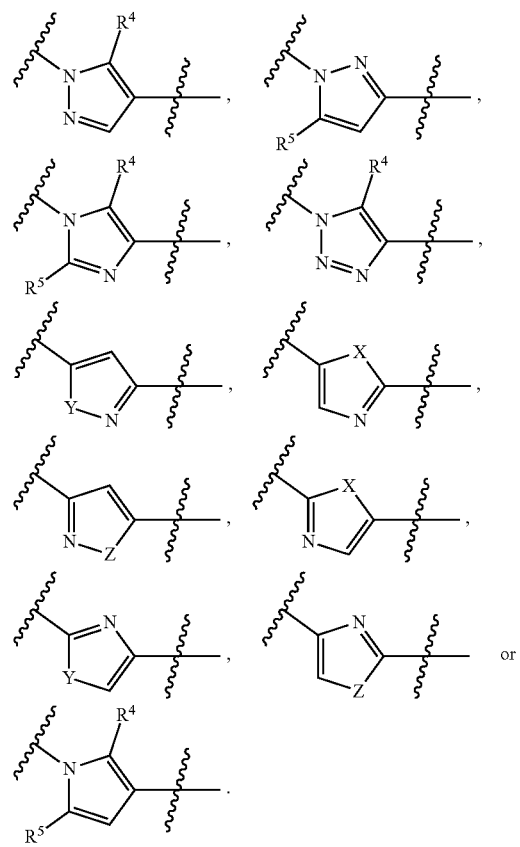

Embodiment 40 relates to the compound of Embodiments 1-39, wherein $Het^1$ or $Het^2$ is:

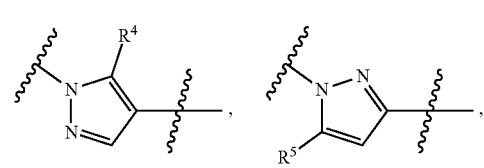

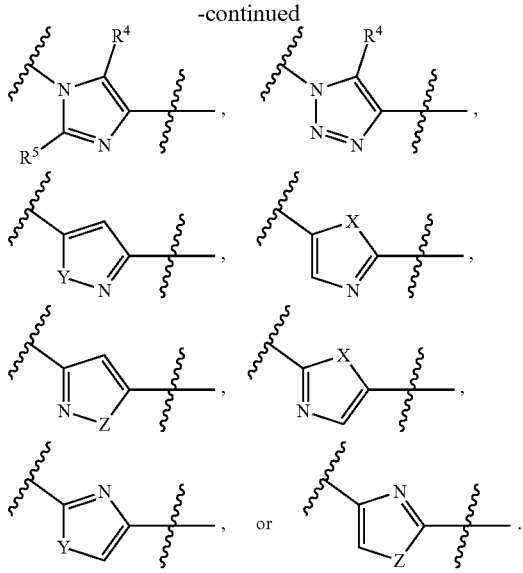

Embodiment 41 relates to the compound of Embodiments 1-40, wherein Het² is a pyrrole.

Embodiment 42 relates to the compound of Embodiments 1-41, wherein Het² is a non-pyrrole aromatic heterocyclyl group.

Embodiment 43 relates to the compound of Embodiments 1-42, wherein Het² is a pyrrolyl, furanyl, oxazolyl, pyrazolyl, imidazolyl, thiazole, isothiazole, 1,2,3-oxadiazolyl, 1,2,4-oxadiazolyl, 1,2,5-oxadiazolyl, 1,3,4-oxadiazolyl, 1,2,3-triazolyl or 1,2,4-triazolyl.

Embodiment 44 relates to the compound of Embodiments 1-43, wherein Cy¹ or Cy² is pyridin-2-one, pyridazin-3-one, pyrazin-2-one, pyrimidin-2-one or pyrimidin-4-one.

Embodiment 45 relates to the compound of Embodiments 1-44, wherein Cy¹ or Cy² is:

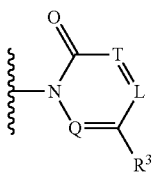

wherein:
R³ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
Q is N, CH, CF or CCH₃;
L is N, CH or CR⁶, wherein R⁶ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy;
T is N, CH or CR⁷, wherein R⁷ is fluoro, chloro, bromo, iodo, cyano methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

Embodiment 46 relates to the compound of Embodiments 1-45, wherein no more than one of Q, L and T is N.

Embodiment 47 relates to the compound of Embodiments 1-46, wherein Q is N.

Embodiment 48 relates to the compound of Embodiments 1-47, wherein R³, R⁶ and R⁷ are different.

Embodiment 49 relates to the compound of Embodiments 1-48, wherein L is CR⁶ or T is CR⁷, and R³ is other than H.

Embodiments 50 relates to the compound of Embodiments 1-49, wherein L is CR⁶, T is CR⁷, and R³ is H.

Embodiment 51 relates to the compound of Embodiments 1-50, wherein L is CH or T is CH, and R³ is other than H.

Embodiment 52 relates to the compound of Embodiments 1-51, wherein L is CR⁶ or T is CR⁷, and R³ is H.

Embodiment 53 relates to the compound of Embodiments 1-52, wherein Cy¹ or Cy² is:

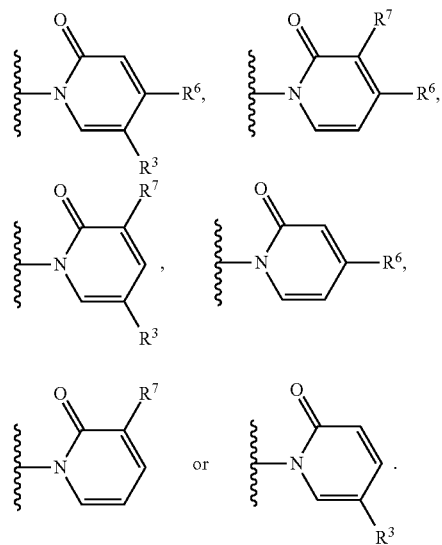

Embodiment 54 relates to the compound of Embodiments 1-53, wherein Cy¹ or Cy² is:

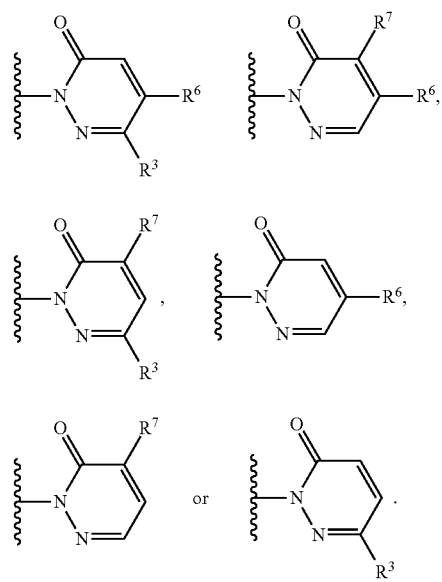

Embodiment 55 relates to the compound of Embodiments 1-54, wherein $Cy^1$ or $Cy^2$ is:

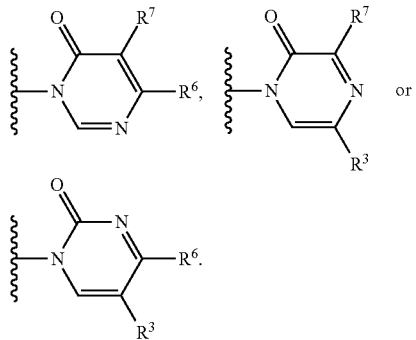

Embodiment 56 relates to the compound of Embodiments 1-55, wherein $Cy^1$ or $Cy^2$ is:

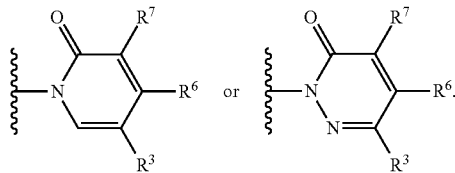

Embodiment 57 relates the compound of Embodiments 1-56, wherein $Cy^1$ or $Cy^2$ is:

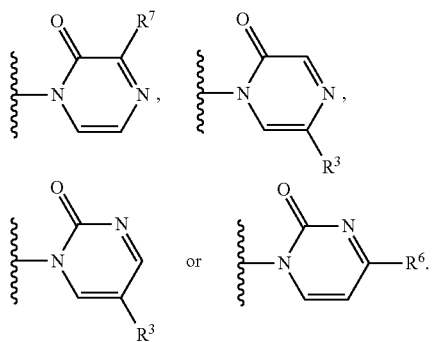

Embodiment 58 relates to the compound of Embodiments 1-57, wherein $L^1$ is a bond or unsubstituted alkyl.

Embodiment 59 relates to the compound of Embodiments 1-58, wherein $L^1$ is

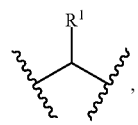

wherein $R^1$ is H, methyl or $(C_2-C_8)$alkyl.

Embodiment 60 relates the compound of Embodiments 1-59, wherein $R^1$ is H.

Embodiment 61 relates to the compound of Embodiments 1-60, wherein $R^1$ is methyl or $(C_2-C_8)$alkyl.

Embodiment 62 relates to the compound of Embodiments 1-61, wherein $L^1$ is a —$CH_2$—.

Embodiment 63 relates to the compound of Embodiments 1-62, wherein $L^2$ is

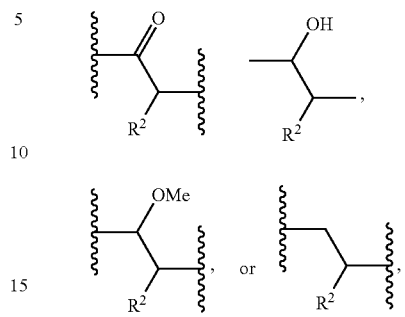

wherein $R^2$ is H or $(C_1-C_8)$alkyl.

Embodiment 64 relates to the compound of Embodiments 1-63, wherein $L^2$ is of the formula

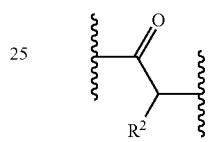

wherein $R^2$ is H or $(C_1-C_8)$alkyl.

Embodiment 65 relates to the compound of Embodiments 1-64, wherein $R^2$ is H.

Embodiment 66 relates to the compound of Embodiments 1-65, wherein $R^2$ is methyl, $(C_2-C_8)$alkyl, benzyl, or biphenylmethyl.

Embodiment 67 relates to the compound of Embodiments 1-66, wherein $L^2$ is of the formula -$alk^1$-C(O)—, wherein $alk^1$ is a linear or branched, substituted or unsubstituted divalent alkyl group.

Embodiment 68 relates to the compound of Embodiments 1-67, wherein $L^2$ is

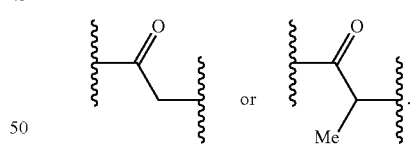

Embodiment 69 relates to the compound of Embodiments 1-68, wherein J is

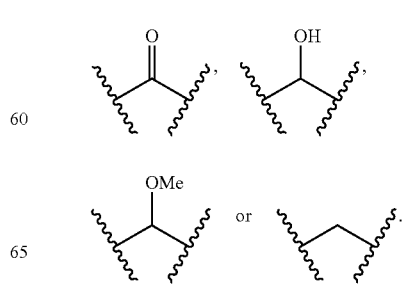

Embodiment 70 relates to the compound of Embodiments 1-69, wherein J is

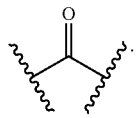 [SMILES: *C(*)=O]

Embodiment 71 relates to the compound of Embodiments 1-70, $R^4$ is methyl.

Embodiment 72 relates to the compound of Embodiments 1-71, $R^5$ is methyl.

Embodiment 73 relates to the compound of Embodiments 1-72, $R^4$ and $R^5$ are the same.

Embodiment 74 relates the compound of Embodiments 1-73, $R^4$ is ethyl, $(C_3-C_8)$alkyl, difluoromethyl or trifluoromethyl.

Embodiment 75 relates to the compound of Embodiments 1-74, $R^5$ is ethyl, $(C_3-C_8)$alkyl, difluoromethyl or trifluoromethyl.

Embodiment 76 relates to the compound of Embodiments 1-75, $L^2$-$Cy^1$ or $L^2$-$Cy^2$ has the formula:

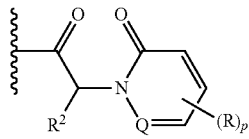

wherein
$R^2$ is H or $(C_1-C_8)$alkyl;
Q is N, CH or $CCH_3$.
p is 1 or 2;
when p is 1 then R is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy
when p is 2 then each instance of R is independently fluoro, chloro, bromo, iodo, cyano, methyl, $(C_2-C_8)$alkyl, $(C_2-C_8)$alkenyl, $(C_2-C_8)$alkynyl, methoxy or $(C_2-C_8)$alkoxy provided that each instance of R is not the same.

Embodiment 77 relates to the compound of Embodiments 1-76, wherein $L^2$-$Cy^1$ or $L^2$-$Cy^2$ has the formula:

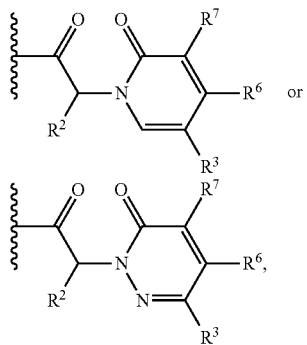

wherein
$R^2$ is H or $(C_1-C_8)$alkyl;
$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

$R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; and $R^7$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

Embodiment 78 relates to the compound of Embodiments 4-6, having the formula:

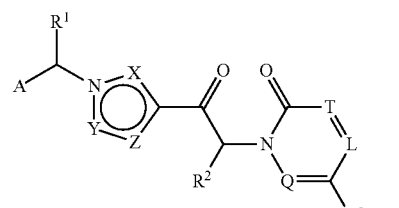

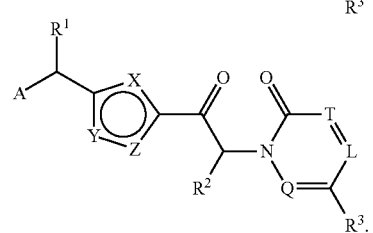

Embodiment 79 relates to the compound of Embodiments 4-6, wherein the compound is a compound of the formula:

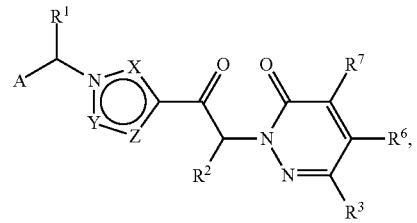

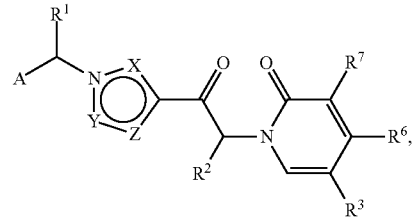

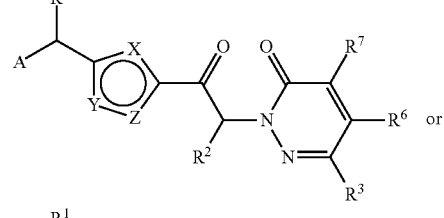

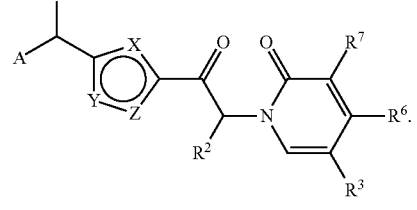

Embodiment 80 relates to the compound of Embodiments 4-6, wherein the compound is a compound of the formula:
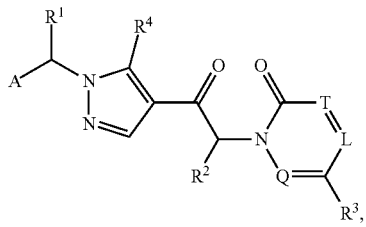
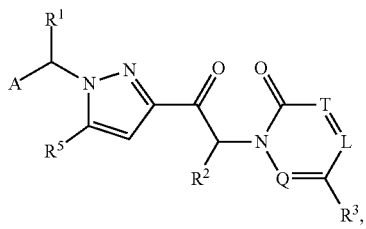
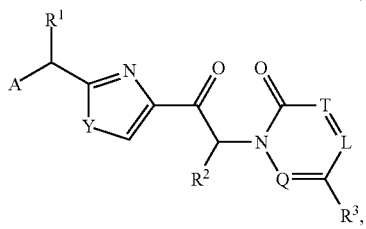
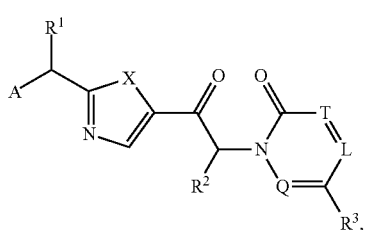
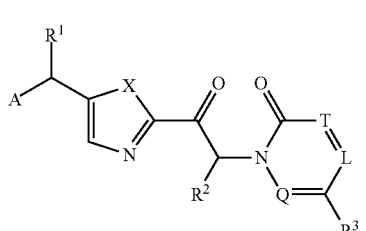
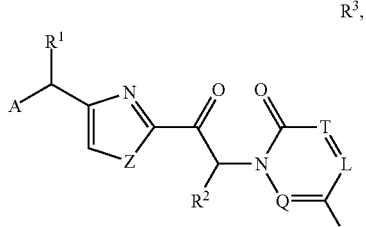
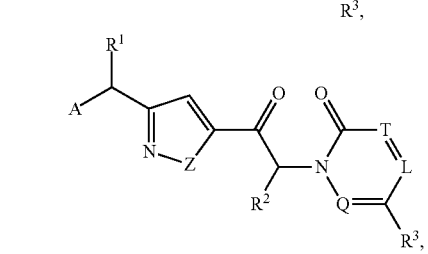
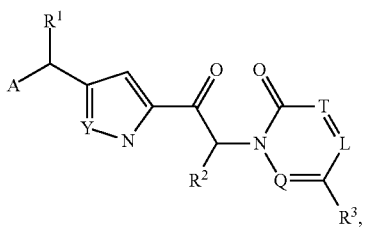
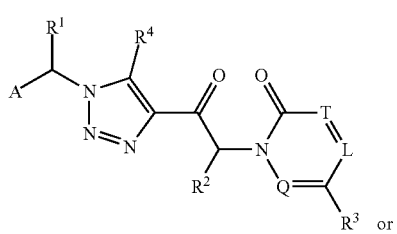
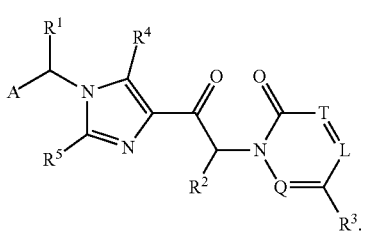 or
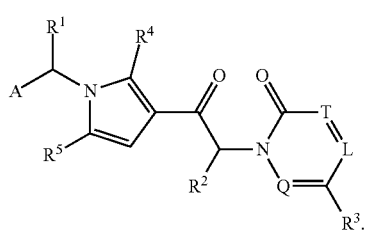
Embodiment 81 relates to the compound of Embodiment 5 or 6, wherein the compound has the formula:
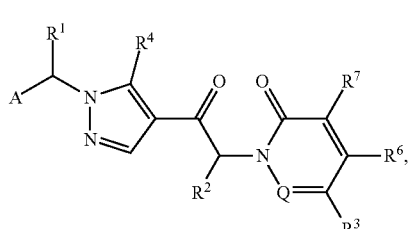
Embodiment 82 relates to the compound of Embodiments 4-6, wherein the compound has the formula:
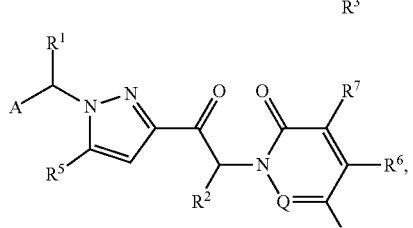

-continued

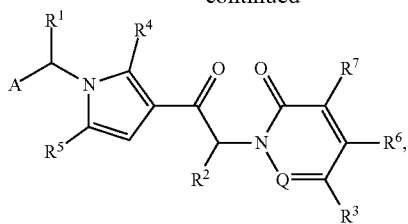

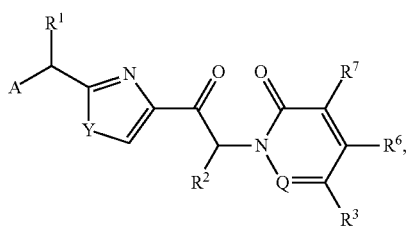

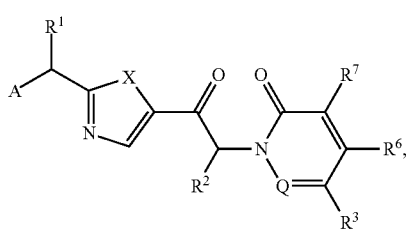

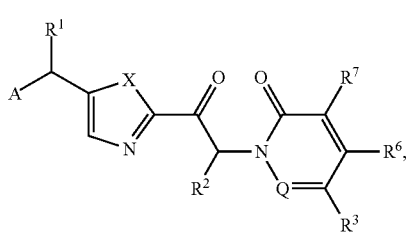

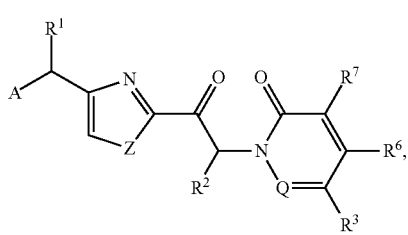

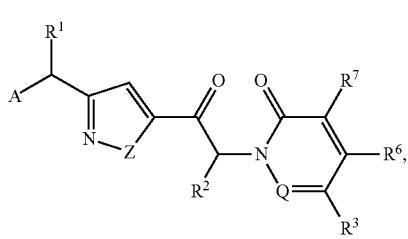

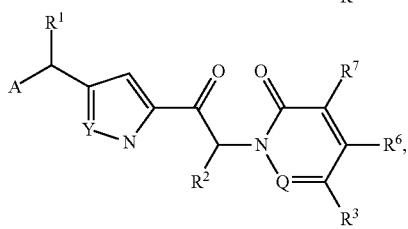

-continued

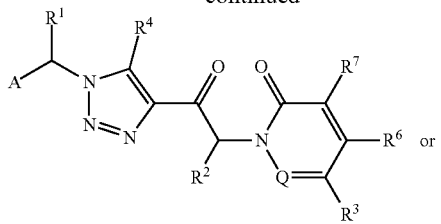 or

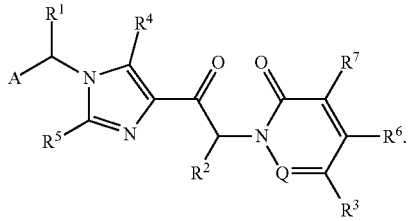

Embodiment 83 relates to a compound having the structure of Formula (F):

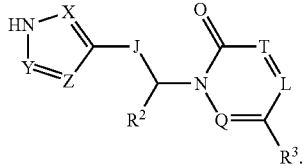

Formula (F)

or a pharmaceutically acceptable salt, polymorph, prodrug, solvate or clathrate thereof, wherein:

$R^2$ is H or $(C_1\text{-}C_8)$alkyl;

$R^3$ is H, fluoro, chloro, bromo, iodo, cyano, methyl, $(C_2\text{-}C_8)$alkyl, methoxy, $(C_2\text{-}C_8)$alkoxy, acetamido, $(C_3\text{-}C_8)$alkylamido, $(C_2\text{-}C_8)$alkenyl, $(C_2\text{-}C_8)$alkynyl, methoxycarbonyl, $(C_2\text{-}C_8)$alkoxy-carbonyl or carboxy;

X is N, O, S, CH or $CR^4$, wherein $R^4$ is $(C_1\text{-}C_8)$alkyl;

Y is N, O, S, CH or $CR^5$, wherein $R^5$ is $(C_1\text{-}C_8)$alkyl;

Z is N, O, S, CH or $CCH_3$;

J is CO, $(C_1)$alkyl or a bond;

Q is N, CH, CF or $CCH_3$;

L is N, CH or $CR^6$, wherein RB is fluoro, chloro, bromo, iodo, cyano, methyl, $(C_2\text{-}C_8)$alkyl, methoxy, $(C_2\text{-}C_8)$alkoxy, acetamido, $(C_3\text{-}C_8)$alkylamido, $(C_2\text{-}C_8)$alkenyl, $(C_2\text{-}C_8)$alkynyl, methoxycarbonyl, $(C_2\text{-}C_8)$alkoxy-carbonyl or carboxy;

T is N, CH or $CR^7$, wherein $R^7$ is fluoro, chloro, bromo, iodo, cyano, methyl, $(C_2\text{-}C_8)$alkyl, methoxy, $(C_2\text{-}C_8)$alkoxy, acetamido, $(C_3\text{-}C_8)$alkylamido, $(C_2\text{-}C_8)$alkenyl, $(C_2\text{-}C_8)$alkynyl, methoxycarbonyl, $(C_2\text{-}C_8)$alkoxy-carbonyl or carboxy.

Embodiment 84 relates to the compound of Embodiments 1-83 having the structure:

Embodiment 85 relates to the compound of Embodiments 1-84 having the structure:

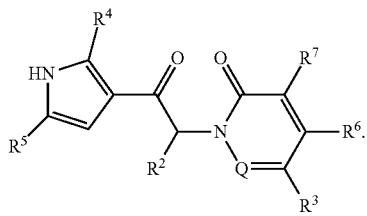

Embodiment 86 relates to the compound of Embodiments 1-85 having the structure:

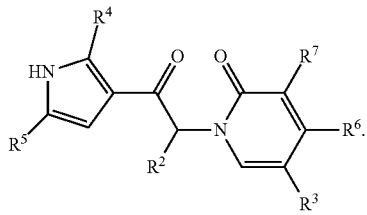

Embodiment 87 relates to the compound of Embodiments 1-86 having the structure:

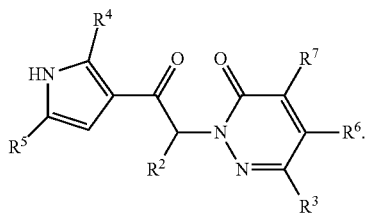

Embodiment 88 relates to a compound of the Formula (G):

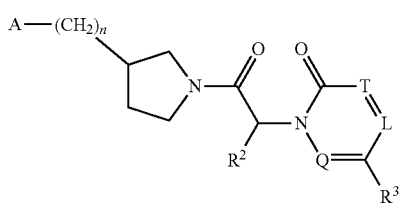

Formula (G)

or a pharmaceutically acceptable salt, polymorph, prodrug, solvate or clathrate thereof, wherein:
A is cycloalkyl, aryl, arylalkyl or heterocyclyl;
n is 0-6;
$R^2$ is H or $(C_1-C_8)$alkyl;
$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
Q is N, CH, CF or CCH$_3$;
L is N, CH or CR$^6$, wherein R$^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; and
T is N, CH or CR$^7$, wherein R$^7$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_7)$alkoxy-carbonyl or carboxy.

Embodiment 89 relates to the compound of Embodiments 1-88 having the structure:

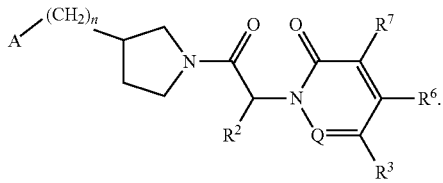

Embodiment 90 relates to the compound of Embodiments 1-89 having the structure:

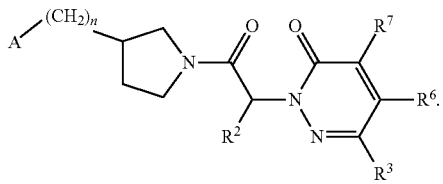

Embodiment 91 relates to the compound of Embodiments 1-90 having the structure:

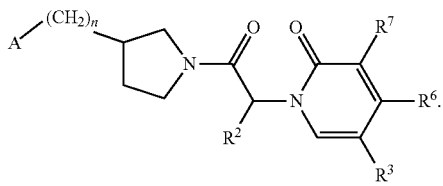

Embodiment 92 relates to the compound of Embodiments 1-91 having the structure:

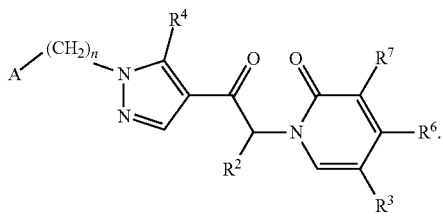

Embodiment 93 relates to the compound of Embodiment 1-92, wherein the compound is not

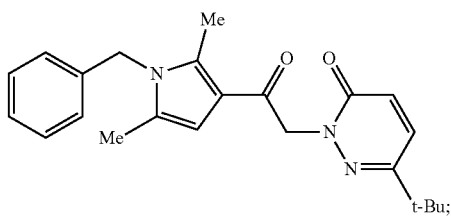

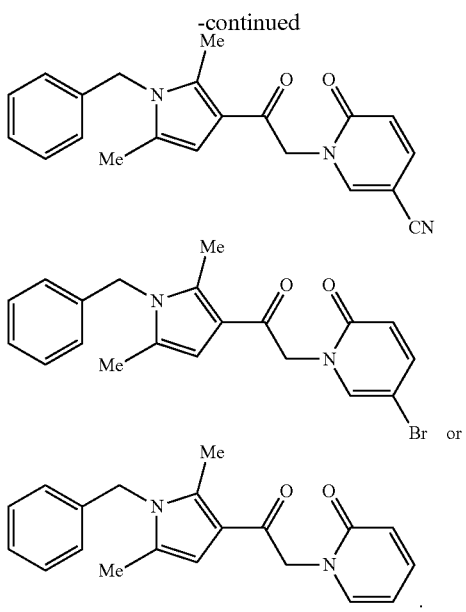

Embodiment 94 relates to a pharmaceutical composition comprising one or more compounds of Embodiments 1-93 and a pharmaceutically acceptable carrier.

Embodiment 95 relates to a method for treating a fibrotic disease, abnormal vascular leak and pathological angiogenesis, and tumor-associated angiogenesis comprising administering a therapeutically effective amount of a compound of Embodiments 1-92 or a pharmaceutical composition comprising a compound of Embodiments 1-92 to a subject in need thereof.

Embodiment 96 the method of Embodiment 95, wherein the abnormal vascular leak and pathological angiogenesis is associated with the wet form of age-related macular degeneration and diabetic retinopathy.

Embodiment 97 the method of Embodiment 96, wherein the fibrotic disease is fibrosis of the lung, liver, kidney, retina, skin or heart.

Embodiment 98 relates to a method for treating highly vascular tumors comprising administering a therapeutically effective amount of a compound of Embodiments 1-92 or a pharmaceutical composition comprising a compound of Embodiments 1-92 to a subject in need thereof.

Embodiment 99 relates to the method of claim 98, wherein the highly vascular tumors are renal carcinoma, glioblastoma, sarcomas, and neuroblastoma.

Embodiment 100 relates to the method of Embodiment 98, wherein the tumors are highly fibrotic such as pancreatic cancer.

Embodiment 101 relates to a method for treating a fibrotic disease, abnormal vascular leak and pathological angiogenesis, and tumor-associated angiogenesis comprising administering a therapeutically effective amount of a compound of Embodiments 1-92 or a pharmaceutical composition comprising a compound of Embodiments 1-92 to a subject in need thereof.

Embodiment 102 relates to a method for chimeric antigen receptor T-cell therapy comprising administering a therapeutically effective amount of a compound of Embodiments 1-92 or a pharmaceutical composition comprising a compound of Embodiments 1-92 to a subject in need thereof.

Embodiment 103 relates to a compound of the Formula (I):

A-L$^1$-Het$^1$-L$^2$-Cy$^1$     (I)

or a pharmaceutically acceptable salt thereof, wherein:
A is cycloalkyl, aryl, arylalkyl or heterocyclyl;
Het$^1$ is heterocyclyl containing at least two heteroatoms;
Cy$^1$ is a heterocyclyl;
L$^1$ is a bond, alkyl, alkenyl or alkynyl linker;
L$^2$ is an acyl, alkyl or an alkoxy linker; and
A and Cy$^1$ are different.

Embodiment 104 relates to the compound of Embodiment 103, wherein:
Het$^1$ is:

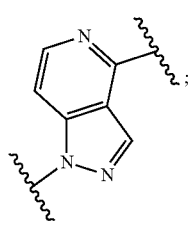 [SMILES: *c1nccc2c1cnn2*]

L$^1$ and L$^2$ are each —CH$_2$—;
A is:

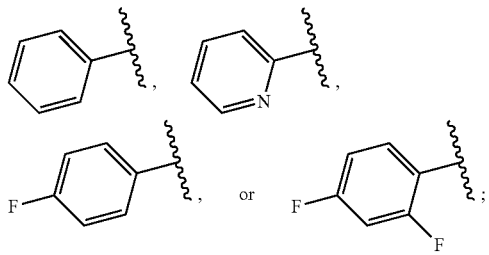

Cy$^1$ is:

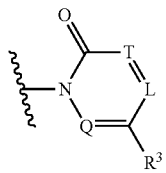

wherein:
Q is N or CH;
L is N or CH;
T is N, CH or C—CN; and
R$^3$ is H, bromo, —CHCH$_2$, —C≡CH, —CFCH$_2$, —C(CF$_3$)CH$_2$, —C(CH$_3$)CH$_2$ or —C≡C(CH$_3$).

Embodiment 105 relates to the compound of Embodiment 103, wherein the compound of the formula (I) is a compound of the formula:

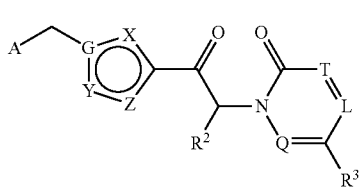

A is

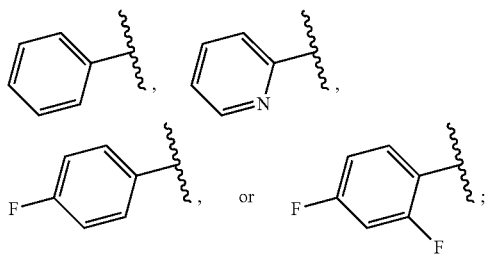

G is N;
Y is N or C(CH$_3$);
X is CH or C(CH$_3$);
Z is CH, C(CH$_3$) or N;
R$^2$ H or CH$_3$;
Q is N or CH;
L is N or CH;
T is N, CH or C—CN; and
R$^3$ is H, bromo, —CHCH$_2$, —C≡CH, —CFCH$_2$, —C(CF$_3$)CH$_2$, —C(CH$_3$)CH$_2$ or —C≡C(CH$_3$).

Embodiment 106 relates to the compound of Embodiment 105, wherein the group:

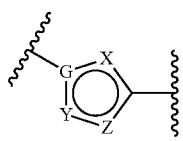

is a group of the formula:

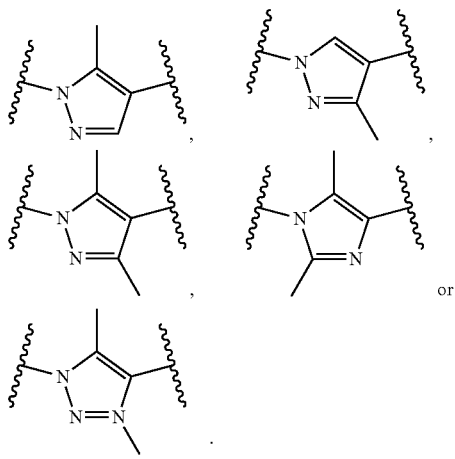

Embodiment 107 relates to the compound of Embodiments 104-106, wherein Cy$^1$ is:

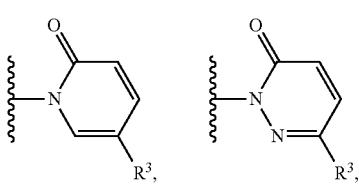

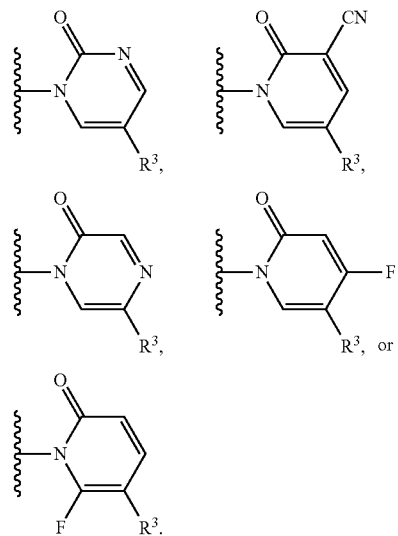

Embodiment 108 relates to the compound of Embodiments 104-107, wherein R$^3$ is —CHCH$_2$, —C≡CH or —C(CF$_3$)CH$_2$.

Embodiment 109 relates to the compound of Embodiment 103, wherein the compound is:

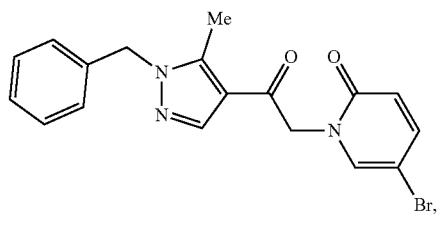

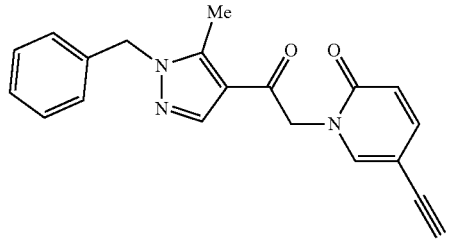

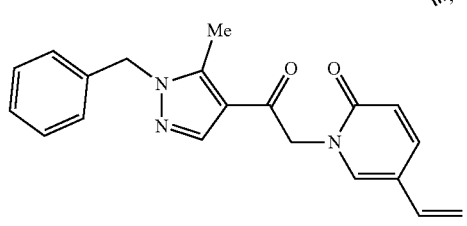

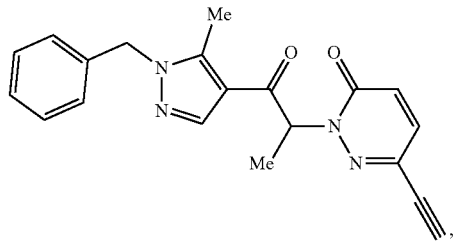

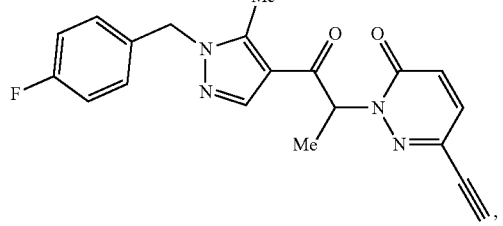
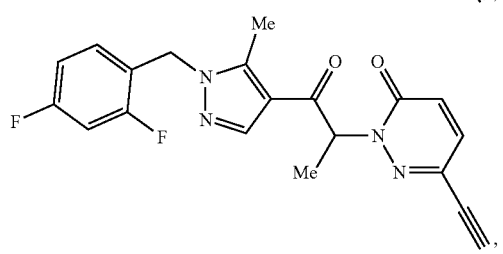
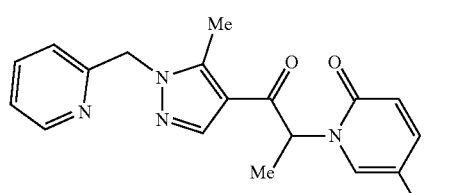
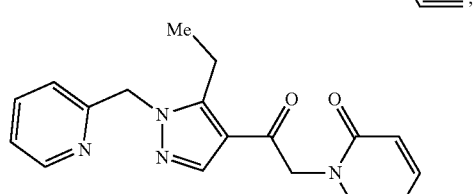
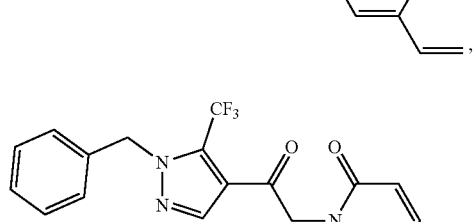
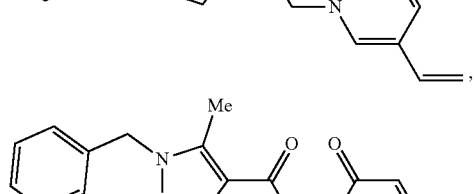
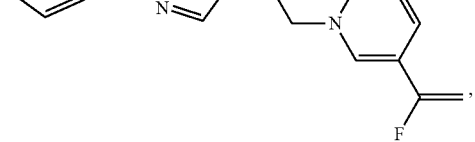
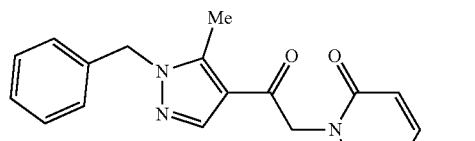
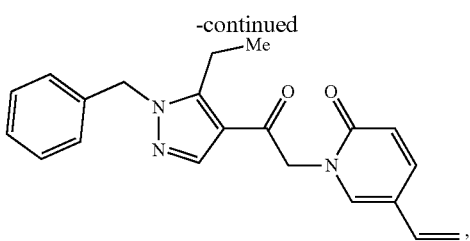
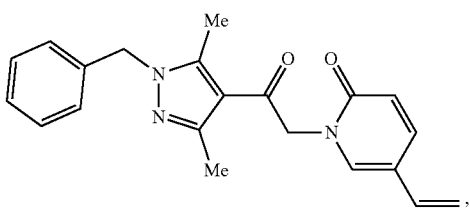
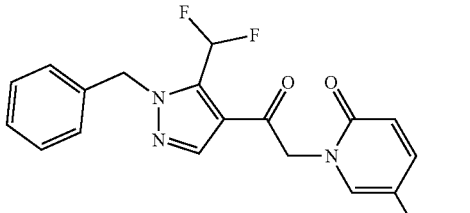
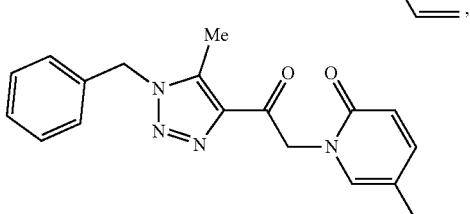
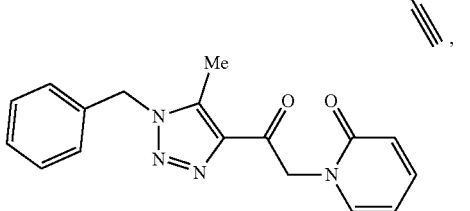
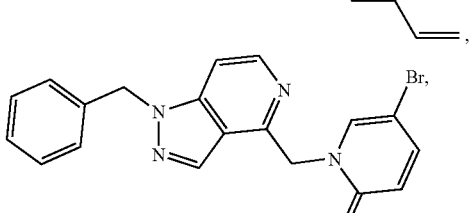
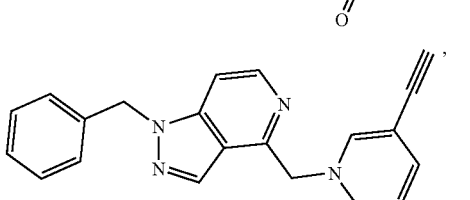
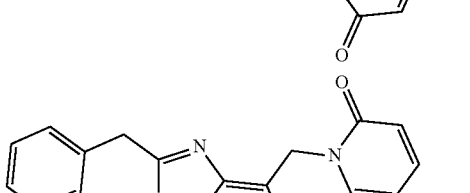
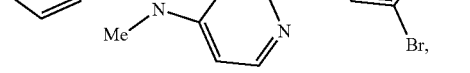

31
-continued
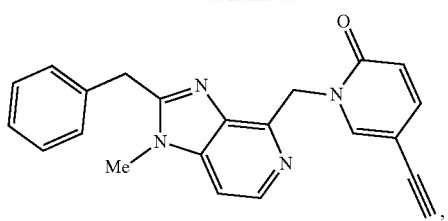
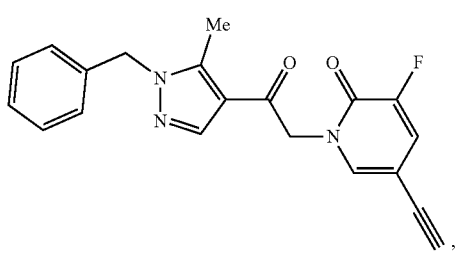
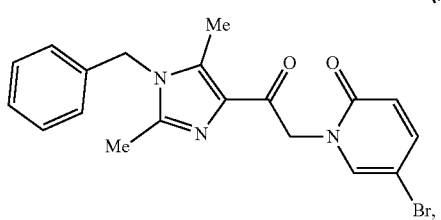
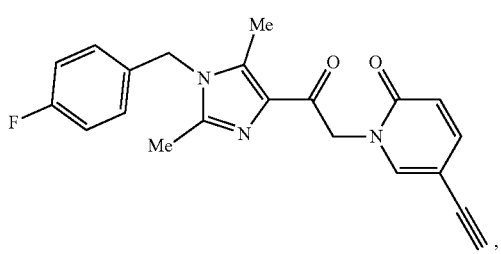
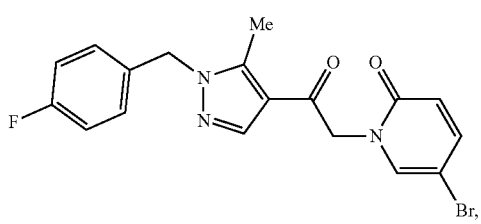
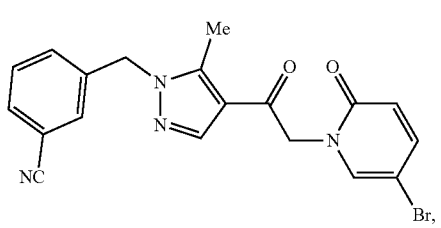
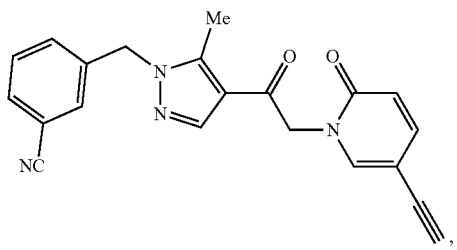
32
-continued
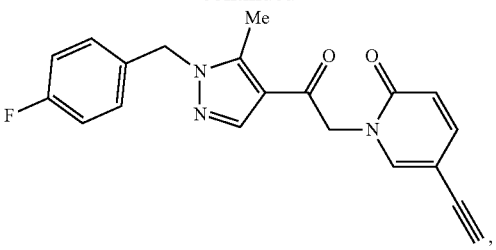
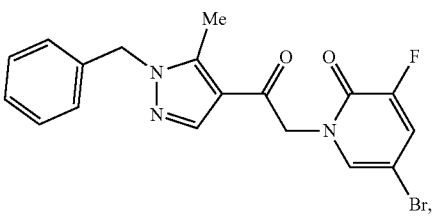
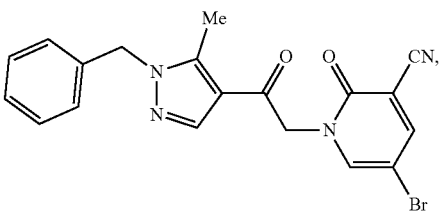
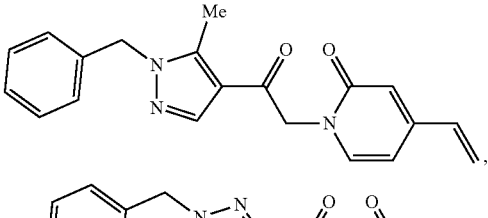
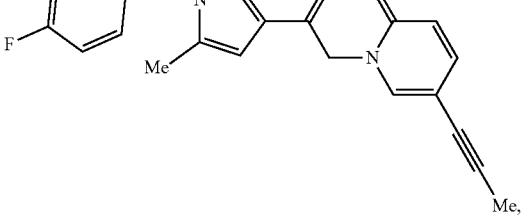
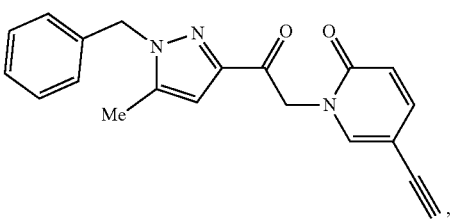
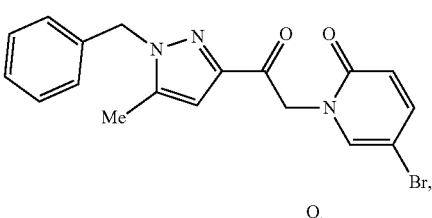
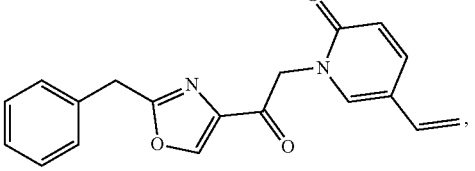

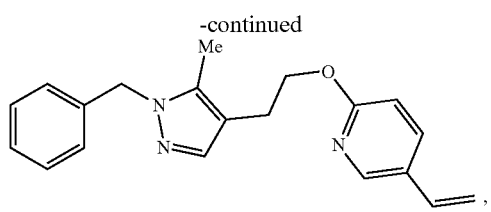
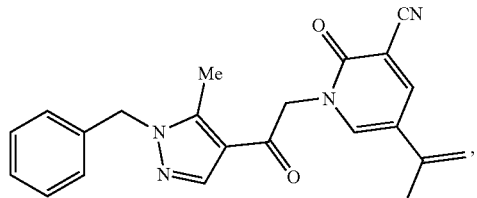
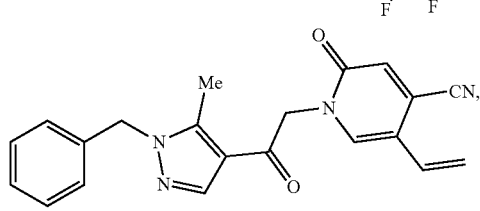
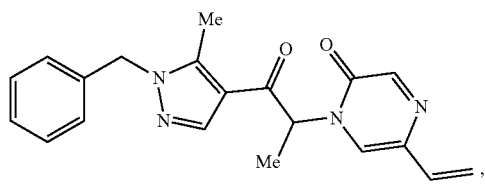
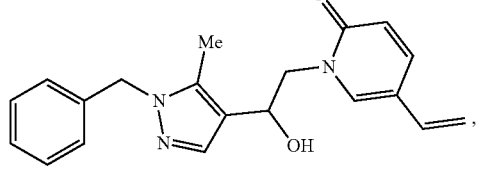
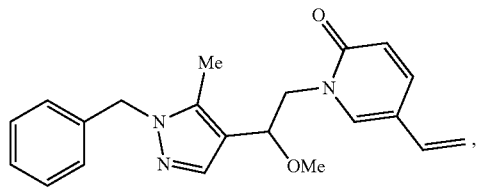
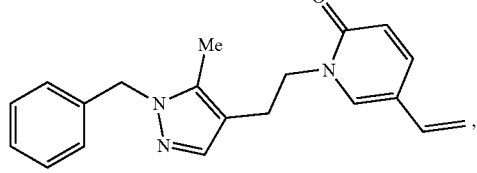
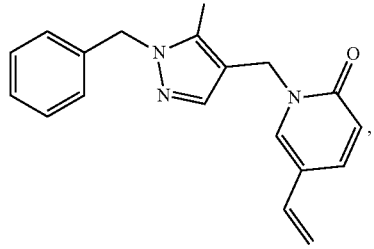
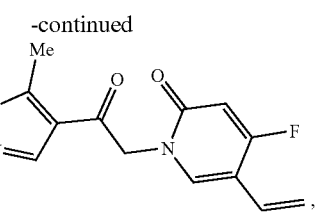
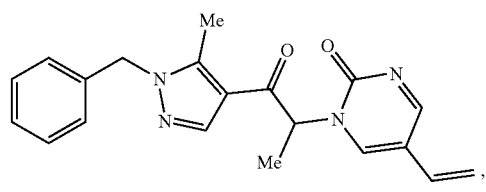
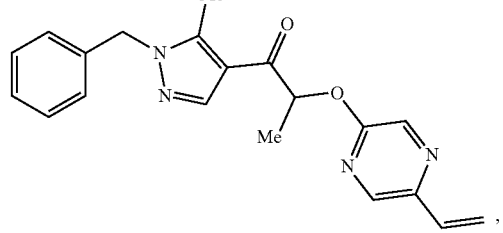
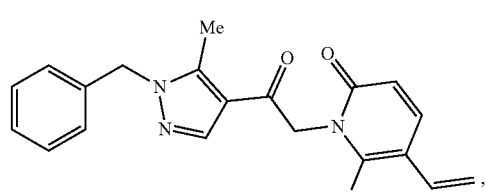
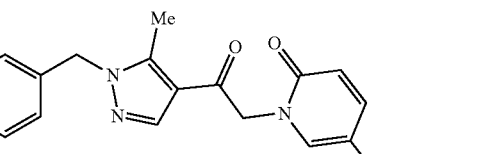
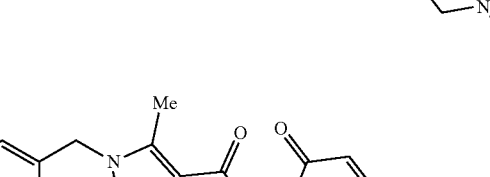
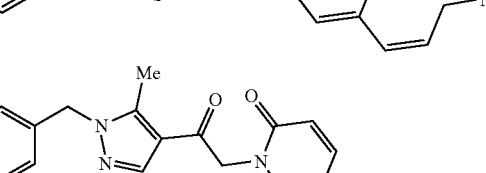
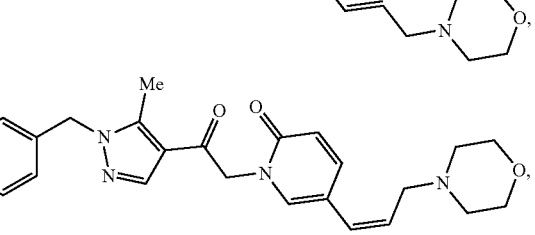

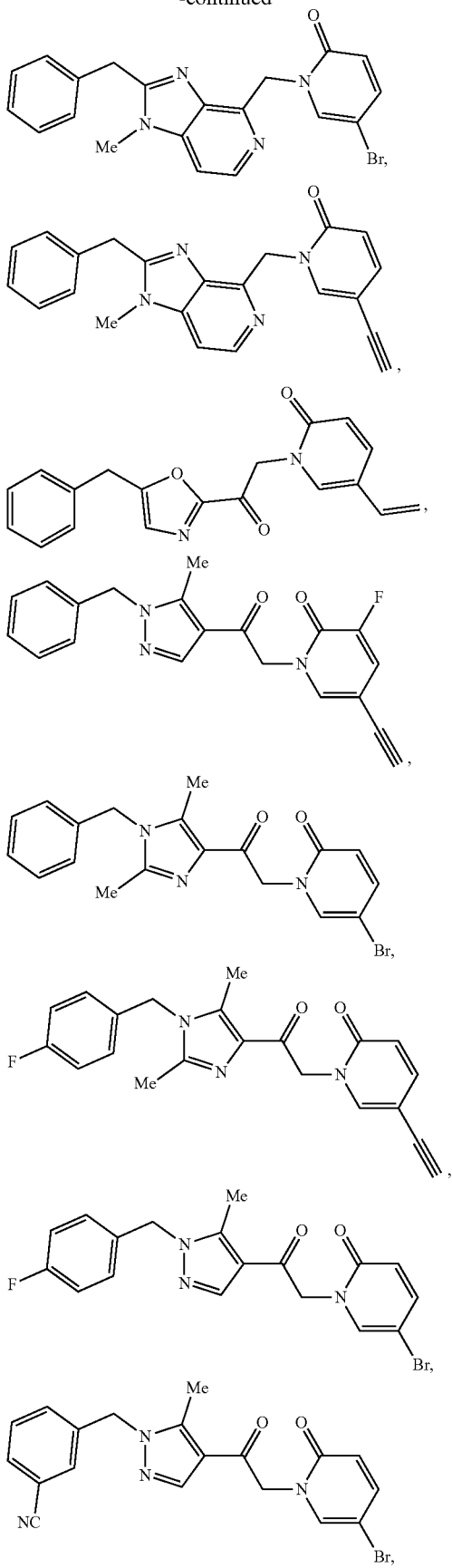

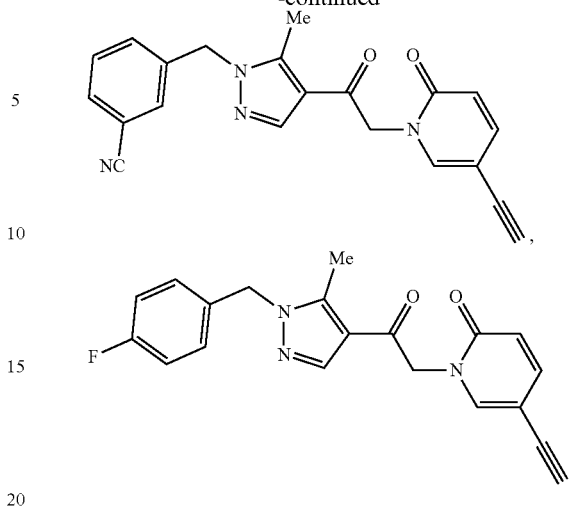

or a pharmaceutically acceptable salt thereof.

Embodiment 110 relates to a compound of the Formula (II):

$$A-L^1-Het^2-L^2-Cy^2 \quad (II)$$

or a pharmaceutically acceptable salt thereof, wherein:
A is cycloalkyl, aryl, arylalkyl or heterocyclyl containing at least one N or O;
$Het^2$ is an aromatic heterocyclyl group comprising at least two heteroatoms;
$Cy^2$ is a heterocyclyl containing one keto group and at least one nitrogen in the heterocyclyl ring, wherein the heterocyclyl is mono-substituted with fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy or di-substituted with fluoro, chloro, bromo, iodo, cyano, methyl, $(C_2-C_8)$alkyl, $(C_2-C_8)$alkenyl, $(C_2-C_8)$alkynyl, methoxy or $(C_2-C_8)$alkoxy provided that the two substituents are not the same;
$L^1$ is a bond, alkyl, alkenyl or alkynyl linker;
$L^2$ is an acyl or alkyl linker;
wherein A and $Cy^2$ are different;
wherein when $Cy^2$ is mono-substituted with cyano, bromo or methyl and A is aryl, then A is substituted aryl, $L^1$ comprises at least two carbons, $L^2$ comprises at least three carbons, or $Cy^2$ contains two nitrogens in the heterocyclyl ring; and
when $Cy^2$ is mono-substituted with t-butyl or benzodioxepinyl and A is aryl, then A is substituted aryl, $L^1$ comprises at least two carbons, $L^2$ comprises at least three carbons or $Cy^2$ contains no more than one nitrogen in the heterocyclyl ring.

Embodiment 111 relates to a compound of the Formula (II):

$$A-L^1-Het^2-L^2-Cy^2 \quad (II)$$

or a pharmaceutically acceptable salt thereof, wherein:
A is cycloalkyl, aryl, arylalkyl or heterocyclyl containing at least one N or O;
$Het^2$ is an aromatic heterocyclyl group comprising at least two heteroatoms;
$Cy^2$ is a heterocyclyl containing one keto group and at least one nitrogen in the heterocyclyl ring, wherein the heterocyclyl is mono-substituted with fluoro, chloro, iodo, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy or di-substituted with fluoro, chloro, bromo, iodo, cyano, methyl, $(C_2-C_8)$alkyl, $(C_2-C_8)$alkenyl, $(C_2-C_8)$alkynyl, methoxy or $(C_2-C_8)$alkoxy provided that the two substituents are not the same;

$L^1$ is a bond, alkyl, alkenyl or alkynyl linker;
$L^2$ is an acyl or alkyl linker; and
wherein A and $Cy^2$ are different.

Embodiment 112 relates to a compound of the Formula (A):

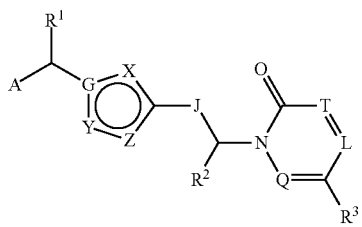

Formula (A)

or a pharmaceutically acceptable salt thereof, wherein:
A is cycloalkyl, aryl, arylalkyl or heterocyclyl containing at least one N or O;
$R^1$ is H or $(C_1-C_8)$alkyl;
$R^2$ is H or $(C_1-C_8)$alkyl;
$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; and
at least two of G, X, Y and Z is independently N, O or S.

Embodiment 113 relates to a compound of the Formula (A):

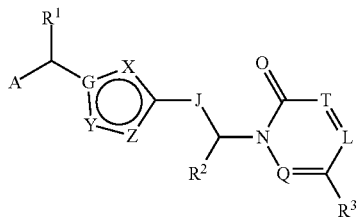

Formula (A)

or a pharmaceutically acceptable salt thereof, wherein:
A is cycloalkyl, aryl, arylalkyl or heterocyclyl containing at least one N or O;
$R^1$ is H or $(C_1-C_8)$alkyl;
$R^2$ is H or $(C_1-C_8)$alkyl;
$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
at least one of G, X, Y and Z is N and the five-membered heterocyclic ring containing G, X, Y, and Z comprises at least a second heteroatom selected from N, O, and S;
when $R^3$ is H, then L is $CR^6$ or T is $CR^7$, or both; and
when $R^3$ is cyano or bromo and A is aryl, then A is substituted aryl, $R^1$ is $(C_1-C_8)$alkyl, $R^2$ is $(C_1-C_8)$alkyl, L is $CR^6$, T is $CR^7$, G is C, or Q is N; and
when $R^3$ is t-butyl or benzodioxepinyl and A is aryl, then A is substituted aryl, $R^1$ is $(C_1-C_8)$alkyl, $R^2$ is $(C_1-C_8)$alkyl, L is $CR^6$, T is $CR^7$, G is C, or Q is CH.

Embodiment 114 relates to a compound of the Formula (A):

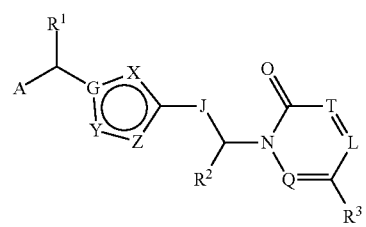

Formula (A)

or a pharmaceutically acceptable salt thereof, wherein:
A is cycloalkyl, aryl, arylalkyl or heterocyclyl containing at least one N or O;
$R^1$ is H or $(C_1-C_8)$alkyl;
$R^2$ is H or $(C_1-C_8)$alkyl;
$R^3$ is H, fluoro, chloro, iodo, methyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

T is N, CH or CR⁷, wherein R⁷ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

at least one of G, X, Y and Z is N and the five-membered heterocyclic ring containing G, X, Y, and Z comprises at least a second heteroatom selected from N, O, and S; and when R³ is H, then L is CR⁶ or T is CR⁷, or both.

Embodiment 115 relates to a compound having the Formula (B):

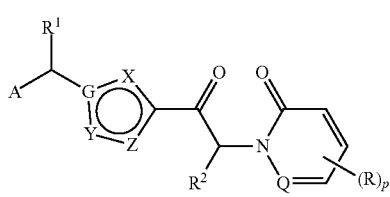

Formula (B)

or a pharmaceutically acceptable salt thereof, wherein:

A is cycloalkyl, aryl, arylalkyl or heterocyclyl containing at least one N or O;

R¹ is H or $(C_1-C_8)$alkyl;

R² is H or $(C_1-C_8)$alkyl;

p is 1 or 2;

when p is 1 then R is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy when p is 2 then each instance of R is independently fluoro, chloro, bromo, iodo, cyano, methyl, $(C_2-C_8)$alkyl, $(C_2-C_8)$alkenyl, $(C_2-C_8)$alkynyl, methoxy or $(C_2-C_8)$alkoxy provided the each instance of R is not the same;

G is C or N;

X is N, O, S, CH or CR⁴, wherein R⁴ is $(C_1-C_8)$alkyl;

Y is N, O, S, CH or CR⁵, wherein R⁵ is $(C_1-C_8)$alkyl;

Z is N, O, S, CH or CCH₃;

wherein the five-membered heterocyclic ring containing G, X, Y, and Z comprises at least two heteroatoms selected from N, O, and S; and Q is N, CH or CCH₃.

Embodiment 116 relates to a compound of the Formula (C):

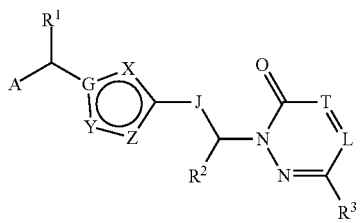

Formula (C)

or a pharmaceutically acceptable salt thereof, wherein:

A is cycloalkyl, aryl, arylalkyl or heterocyclyl;

R¹ is H or $(C_1-C_8)$alkyl;

R² is H or $(C_1-C_8)$alkyl;

R³ is H, fluoro, chloro, bromo, iodo, cyano, methyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

G is C or N;

X is N, O, S, CH or CR⁴, wherein R⁴ is $(C_1-C_8)$alkyl;

Y is N, O, S, CH or CR⁵, wherein R⁵ is $(C_1-C_8)$alkyl;

Z is N, O, S, CH or CCH₃;

J is CO, $(C_1)$alkyl or a bond;

L is N, CH or CR⁶, wherein R⁶ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

T is N, CH or CR⁷, wherein R⁷ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy, at least one of G, X, Y and Z is N and the five-membered heterocyclic containing G, X, Y, and Z comprises at least a second heteroatom selected from N, O, and S, and when R³ is H, then L is CR⁶ or T is CR⁷, or both.

Embodiment 117 relates to a compound of the Formula (D):

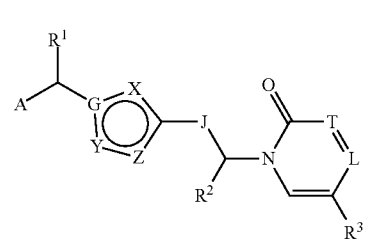

Formula (D)

or a pharmaceutically acceptable salt thereof, wherein:

A is cycloalkyl, aryl, arylalkyl or heterocyclyl containing at least one N or O;

R¹ is H or $(C_1-C_8)$alkyl;

R² is H or $(C_1-C_8)$alkyl;

R³ is H, fluoro, chloro, iodo, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

G is C or N;

X is N, O, S, CH or CR⁴, wherein R⁴ is $(C_1-C_8)$alkyl;

Y is N, O, S, CH or CR⁵, wherein R⁵ is $(C_1-C_8)$alkyl;

Z is N, O, S, CH or CCH₃;

J is CO, $(C_1)$alkyl or a bond;

L is N, CH or CR⁶, wherein R⁶ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_1-C_8)$alkynyl, methoxycarbonyl, $(C_1-C_8)$alkoxy-carbonyl or carboxy;

T is N, CH or CR⁷, wherein R⁷ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_1-C_8)$alkoxy-carbonyl or carboxy;

at least one of G, X, Y and Z is N and the five-membered heterocyclic ring containing G, X, Y, and Z comprises at least a second heteroatom selected from N, O, and S, and when R³ is H, then L is CR⁶ or T is CR⁷, or both.

Embodiment 118 relates to a compound of Formula (E1), Formula (E2), Formula (E3), Formula (E4), Formula (E5), Formula (E6) or Formula (E7):

Formula (E1)
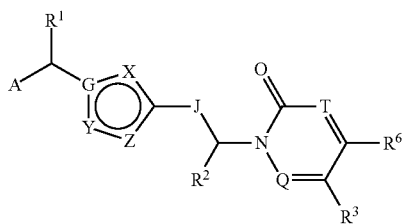

Formula (E2)
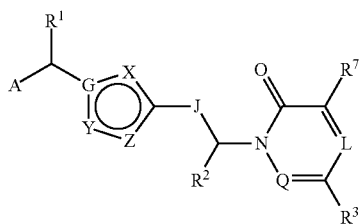

Formula (E3)
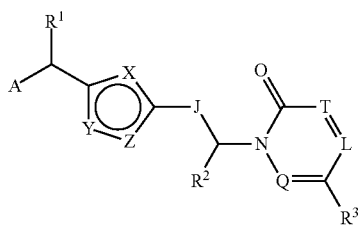

Formula (E4)
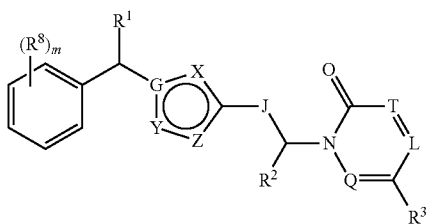

Formula (E5)
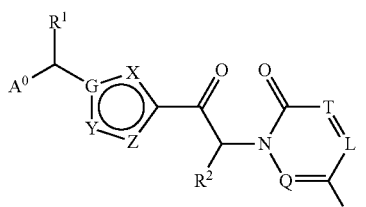

Formula (E6)
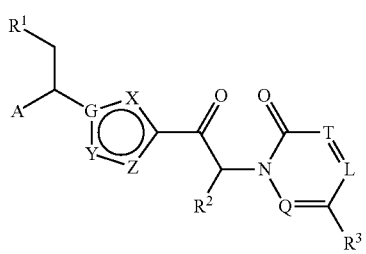

Formula (E7)
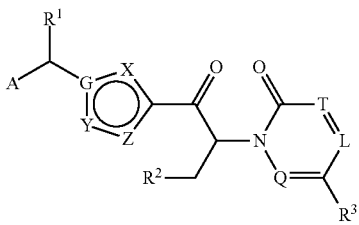

or a pharmaceutically acceptable salt thereof, wherein:

A, if present, is cycloalkyl, aryl, arylalkyl or heterocyclyl;
$A^0$, if present, is cycloalkyl, arylalkyl or heterocyclyl containing at least one N or O;
$R^1$ is H or $(C_1$-$C_8)$alkyl;
$R^2$ is H or $(C_1$-$C_8)$alkyl;
$R^3$ is H, fluoro, chloro, bromo, iodo, cyano, methyl, $(C_2$-$C_8)$alkyl, methoxy, $(C_2$-$C_8)$alkoxy, acetamido, $(C_3$-$C_8)$alkylamido, $(C_2$-$C_8)$alkenyl, $(C_2$-$C_8)$alkynyl, methoxycarbonyl, $(C_2$-$C_8)$alkoxy-carbonyl or carboxy;
G is C or N;
X is N, O, S, CH or $CR^4$, wherein $R^4$ is $(C_1$-$C_8)$alkyl;
Y is N, O, S, CH or $CR^5$, wherein $R^5$ is $(C_1$-$C_8)$alkyl;
Z is N, O, S, CH or $CCH_3$;
J is CO, $(C_1)$alkyl or a bond;
Q is N, CH, CF or $CCH_3$;
L, if present, is N, CH or $CR^6$, wherein $R^6$ is fluoro, chloro, bromo, iodo, cyano, $(C_2$-$C_8)$alkyl, methoxy, $(C_2$-$C_8)$alkoxy, acetamido, $(C_3$-$C_8)$alkylamido, $(C_2$-$C_8)$alkenyl, $(C_2$-$C_8)$alkynyl, methoxycarbonyl, $(C_2$-$C_8)$ alkoxy-carbonyl or carboxy;
T, if present, is N, CH or $CR^7$, wherein $R^7$ is fluoro, bromo, iodo, $(C_2$-$C_8)$alkyl, methoxy, $(C_2$-$C_8)$alkoxy, acetamido, $(C_3$-$C_8)$alkylamido, $(C_2$-$C_8)$alkenyl, $(C_2$-$C_8)$alkynyl, methoxycarbonyl, $(C_2$-$C_8)$alkoxy-carbonyl or carboxy,
$R^8$, if present, is alkylsulfonyl, alkyl, alkoxy, cyano, halo, difluoromethyl or carboxy or two adjacent instances of $R^8$ can form a fused dioxolane ring;
n, if present, is 0-5;
m, if present, is 1-5; and at least one of X, Y, Z and G, if present, is N and the five-membered heterocyclic ring containing X, Y, Z and G, if present, comprises at least a second heteroatom selected from N, O, and S.

Embodiment 119 relates to a compound having the structure of Formula (F):

Formula (F)
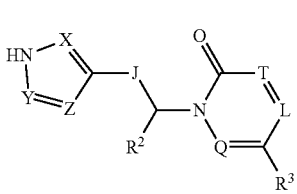

or a pharmaceutically acceptable salt thereof, wherein:
$R^2$ is H or $(C_1$-$C_8)$alkyl;
$R^3$ is H, fluoro, chloro, bromo, iodo, cyano, methyl, $(C_2$-$C_8)$alkyl, methoxy, $(C_1$-$C_8)$alkoxy, acetamido, $(C_3$-$C_8)$alkylamido, $(C_2$-$C_8)$alkenyl, $(C_2$-$C_8)$alkynyl, methoxycarbonyl, $(C_2$-$C_8)$alkoxy-carbonyl or carboxy;
X is N, O, S, CH or $CR^4$, wherein $R^4$ is $(C_1$-$C_8)$alkyl;
Y is N, O, S, CH or $CR^5$, wherein $R^5$ is $(C_1$-$C_8)$alkyl;
Z is N, O, S, CH or $CCH_3$;

J is CO, (C₁)alkyl or a bond;
Q is N, CH, CF or CCH₃;
L is N, CH or CR⁶, wherein R⁶ is fluoro, chloro, bromo, iodo, cyano, methyl, (C₂-C₈)alkyl, methoxy, (C₂-C₈) alkoxy, acetamido, (C₃-C₈)alkylamido, (C₂-C₈)alkenyl, (C₂-C₈)alkynyl, methoxycarbonyl, (C₂-C₈) alkoxy-carbonyl or carboxy;
T is N, CH or CR⁷, wherein R⁷ is fluoro, chloro, bromo, iodo, cyano, methyl, (C₂-C₈)alkyl, methoxy, (C₂-C₈) alkoxy, acetamido, (C₃-C₈)alkylamido, (C₂-C₈)alkenyl, (C₂-C₈)alkynyl, methoxycarbonyl, (C₂-C₈) alkoxy-carbonyl or carboxy.

BRIEF DESCRIPTION OF THE DRAWINGS

The drawings illustrate generally, by way of example, but not by way of limitation, various embodiments discussed in the present document.

Figure 1A:
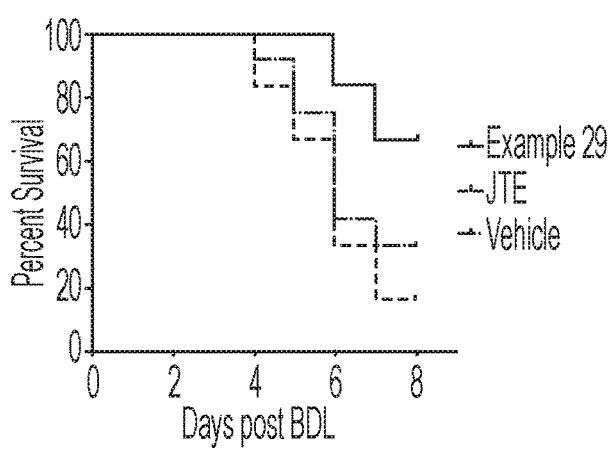
FIG. 1A is a plot of percent survival as a function of days post bile duct ligation (BDL) showing the survival of mice treated with compound 29 (30 mg/kg), JTE-013 (30 mg/kg) or vehicle in bile duct ligated mice.

It should be understood that numerous other modifications and examples can be devised by those skilled in the art, which fall within the scope and spirit of the principles of the disclosure.

DETAILED DESCRIPTION OF THE INVENTION

Past medicinal chemistry efforts have been used to target the S1P₂ receptor and associated pathological conditions. For example, CYM-5520 was previously disclosed as a weak allosteric agonist of the S1PR₂ receptor (*Bioorg. Med. Chem.* 21: 5373-5382 (2013).

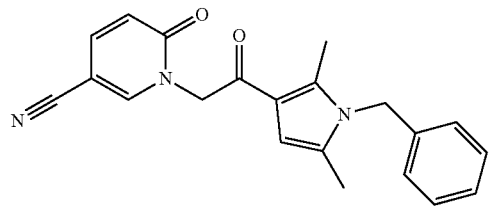 [SMILES: Cc1cc(C(=O)Cn2cc(C#N)ccc2=O)c(C)n1Cc1ccccc1]

But for development of a therapeutic agent, CYM-5520's liabilities are significant. Its low potency and its high lipophilicity impart unfavorable drug characteristics including high metabolic susceptibility leading to poor pharmacokinetic properties and poor aqueous solubility. In particular, CYM-5520 possesses a lipophilic, electron rich central pyrrole ring which is a metabolic liability. Thus, one aspect of the disclosure is the recognition that the central pyrrole ring of CYM-5520 may be replaced with five-membered heterocyclic rings comprising two or more heteroatoms to, among other things, reduce lipophilicity. In combination with modifications elsewhere in the molecule, the incorporation of five-membered heterocyclic rings comprising two or more heteroatoms in compounds disclosed herein leads to compounds with potent S1PR₂ antagonist activity, lower lipophilicity, and improved pharmacokinetic properties, thus addressing at least some of CYM-5520's liabilities as a therapeutic agent. Compounds described herein exhibit potent functional antagonist properties in that they elicit S1PR₂ receptor degradation. Non-limiting examples of such compounds include, for example, compounds 29 and 34, which have the following formulae, respectively:

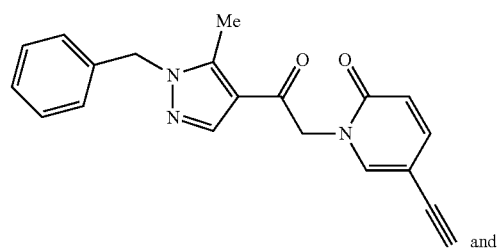
and
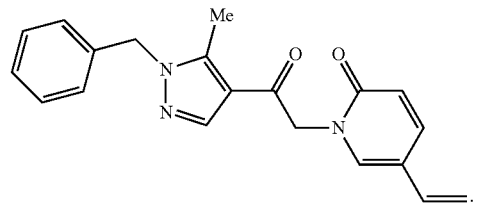

The present disclosure provides a compound of the Formula (I):

A-L¹-Het¹-L²-Cy¹          Formula (I)

or a pharmaceutically acceptable salt, polymorph, prodrug, solvate or clathrate thereof, wherein:

A is cycloalkyl, aryl, arylalkyl or heterocyclyl; Het¹ is heterocyclyl containing at least two heteroatoms; Cy¹ is a heterocyclyl; L¹ is a bond, alkyl, alkenyl or alkynyl linker; L² is an acyl or alkyl linker; and A and Cy¹ are different.

In various embodiments of Formula (I), A is substituted cycloalkyl, unsubstituted cycloalkyl, substituted aryl, unsubstituted aryl, substituted arylalkyl, unsubstituted arylalkyl, substituted nonaromatic heterocyclyl, unsubstituted nonaromatic heterocyclyl, substituted aromatic heterocyclyl or unsubstituted aromatic heterocyclyl. In further embodiments, A can be cycloalkyl, aryl, arylalkyl or heterocyclyl which is substituted by alkylsulfonyl, alkyl, alkoxy, cyano, halo, difluoromethyl or carboxy. In some embodiments, A can be other than phenyl, for example A can be cycloalkyl, arylalkyl or heterocyclyl, which is substituted by alkylsulfonyl, alkyl, alkoxy, cyano, halo, difluoromethyl or carboxy. A can also be an aryl other than phenyl. In yet further various embodiments, A can be cycloalkyl, aryl, arylalkyl or heterocyclyl which is substituted by, for example, one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. In some embodiments, A can be monosubstituted, disubstituted, trisubstituted or fully substituted.

In various embodiments of Formula (I), A is a heterocyclyl. For example, A can be thiolane, thiane, thiophene, thiazole, thiazole, isothiazole, tetrahydrofuranyl, tetrahydropyranyl, indole, quinoline, isoquinoline, pyrrolidinyl, piperidinyl, piperazinyl, pyrrolyl, furanyl, oxazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, benzo[d][1,3]dioxole, pyridinyl or pyrimidinyl. In some embodiments, A can be a heterocyclyl other than thiolane, thiane or thiophene. In some embodiments, A is an aromatic heterocyclyl. In some embodiments, A is an aromatic heterocyclyl containing at least one O or N. In some embodiments, A is an aromatic heterocyclyl other than furan. In some embodiments, A is an aromatic heterocyclyl other than thiophene. In some embodiments, the heterocyclyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. As a further example, A can be heterocyclyl substituted with alkylsulfonyl, alkyl, alkoxy, cyano, halo, difluoromethyl or carboxy.

In various embodiments of Formula (I), A is cycloalkyl. For example, A can be cyclopropyl, cyclobutyl, cyclopentane, cyclohexane or bicyclo[1.1.1]pentane. In some embodiments, the cycloalkyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. As a further example, A can be cycloalkyl substituted with alkylsulfonyl, alkyl, alkoxy, cyano, halo, difluoromethyl or carboxy.

In various embodiments of Formula (I), A is aryl. For example, A can be unsubstituted phenyl or substituted phenyl. As another example, A can be unsubstituted naphthalene or substituted naphthalene. As a further example, A can be phenyl substituted with alkylsulfonyl, alkyl, alkoxy, cyano, halo, difluoromethyl or carboxy. As a further example, A can be a phenyl substituted with fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido.

In various embodiments of Formula (I), A is

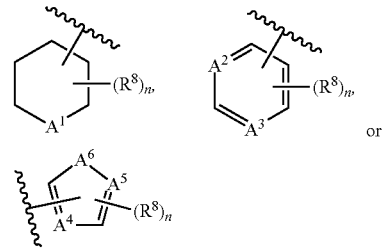

wherein:

n is 0-3; $A^1$ is O, NH or N-Alkyl; each of $A^2$ and $A^3$ is independently, CH, $CR^8$ or N; each of $A^4$, $A^5$, and $A^6$ is independently CH, C-alkyl, N, $NR^9$ or O, provided that at least one of $A^4$, $A^5$, and $A^6$ is N or $NR^9$; and $R^8$ independently is fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido; and $R^9$ is independently H or alkyl. In some embodiments, $R^8$ is independently alkylsulfonyl, alkyl, alkoxy, cyano, halo, difluoromethyl or carboxy.

In various embodiments of Formula (I), A is

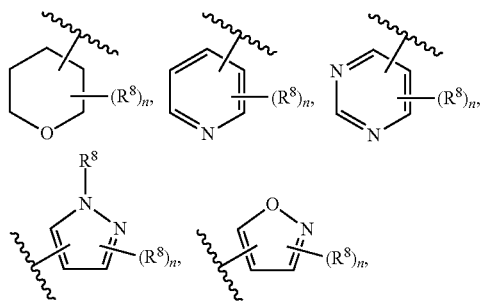

-continued

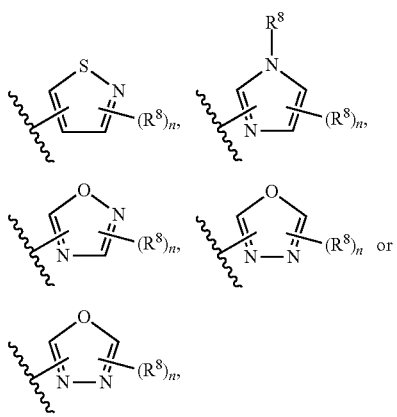

wherein: n is 0-3; $R^8$ is independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, $R^9$ independently is alkylsulfonyl, alkyl, alkoxy, cyano, halo, difluoromethyl or carboxy.

In various embodiments of Formula (I), A is

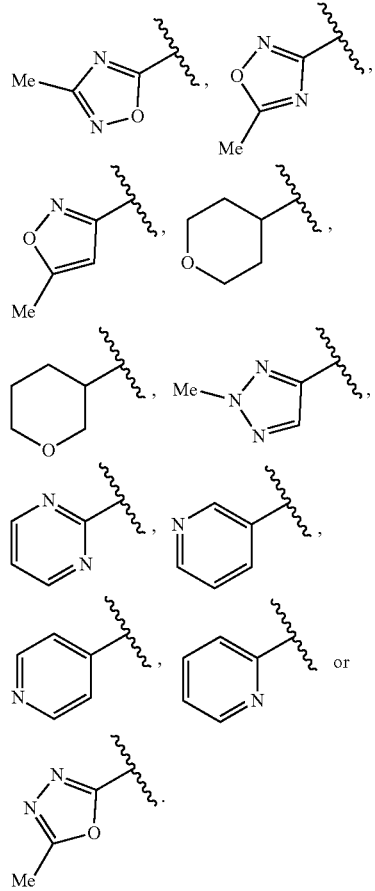

In various embodiments of Formula (I), A is

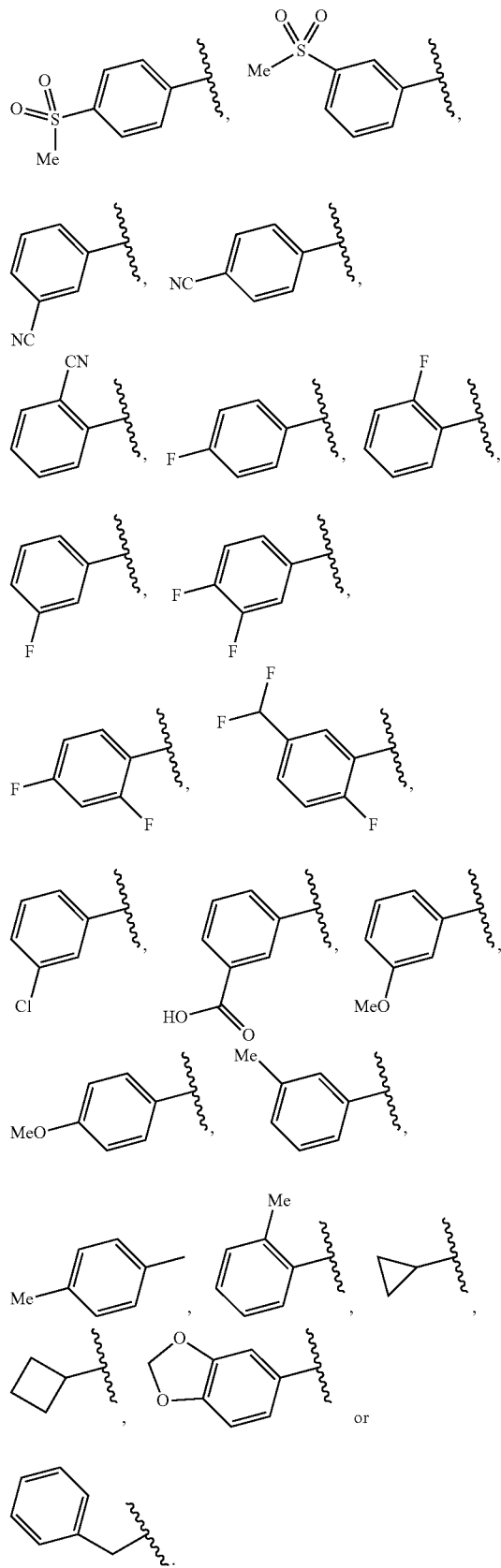

In some embodiments of Formula (I), A is a

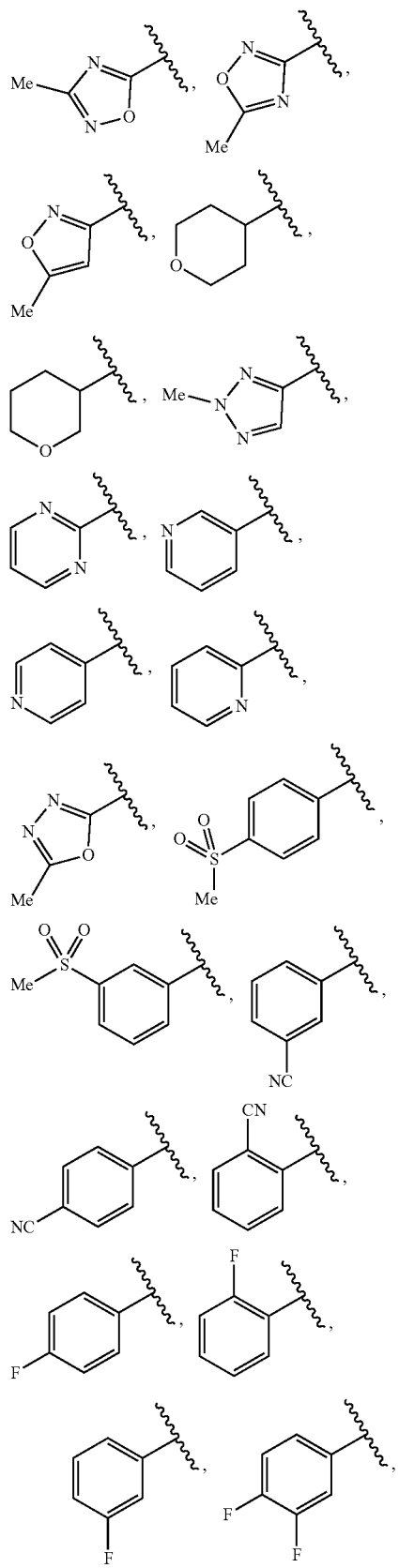

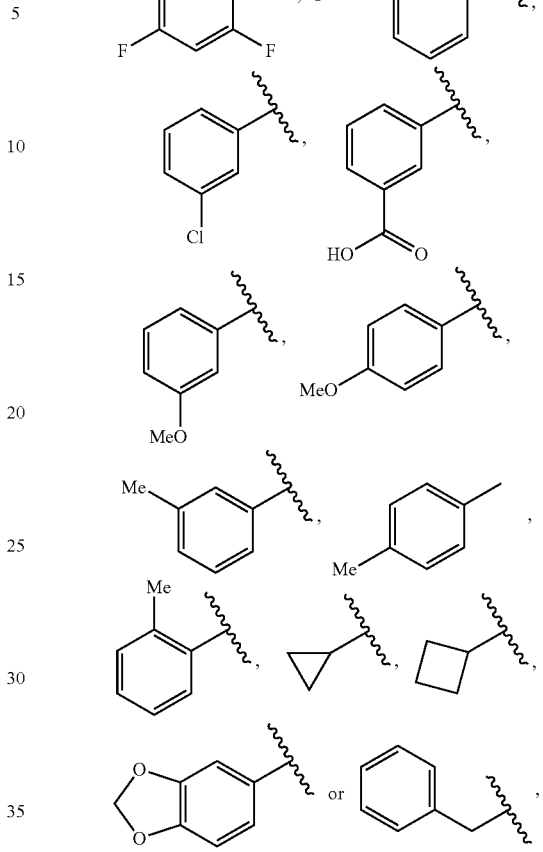

or which is further substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof.

In various embodiments of Formula (I), A is cycloalkyl, aryl, arylalkyl or heterocyclyl and is unsubstituted. In certain embodiments, A can be selected from substituted aryl and substituted or unsubstituted cycloalkyl, arylalkyl and heterocyclyl.

In various embodiments of Formula (I), Het$^1$ is a 5-membered heterocyclyl group containing at least two heteroatoms. For example, Het$^1$ can be a oxazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl and tetrazole.

In various embodiments of Formula (I), Het$^1$ contains at least one nitrogen. In some embodiments, Het$^1$ contains two nitrogen atoms in its ring. In further various embodiments, Het$^1$ contains at least one S or O. In yet further various embodiments, Het$^1$ contains at least one nitrogen atoms and one sulfur atom or one oxygen atom. Het$^1$ can contain two nitrogen atoms and one sulfur atom or one oxygen atom. Het$^1$ can contain three nitrogen atoms.

In various embodiments of Formula (I), Het$^1$ has the structure:

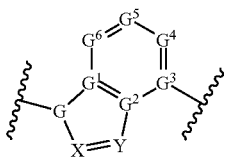

wherein G is CH or N; $G^1$ is C or N, but when $G^1$ is N, there is not a double bond between $G^1$ and $G^2$; $G^2$ is C or N, but when $G^2$ is N, there is not a double bond between $G^1$ and $G^2$; $G^3$ is C or N; $G^4$ is CH or N; $G^5$ is CH or N; $G^6$ is CH or N; X is N, O, S, CH or $CR^4$, but when X is O or S, there is not a double bond between X and Y, wherein $R^4$ is $(C_1-C_8)$alkyl; and Y is N, O, S, CH or $CR^5$, but when Y is O or S, there is not a double bond between X and Y wherein $R^5$ is $(C_1-C_8)$alkyl. In various embodiments one of $G^1$, $G^2$, $G^3$, $G^4$, $G^5$ and $G^6$ is N and the remainder are each C. In various embodiments two of $G^1$, $G^2$, $G^3$, $G^4$, $G^5$ and $G^6$ is N and the remainder are each C. In various embodiments each of $G^1$, $G^2$, $G^3$, $G^4$, $G^5$ and $G^6$ is C. In various embodiments, at least two of G, X and Y is N; at least one of G, X, and Y and is N, S or O; at least one of G, X, and Y is N and one of G, X, and Y is S or O; and/or at least two of G, X, and Y is N and one of G, X, and Y is S or O. In various embodiments, G can be C. In other various embodiments G can be N. In some embodiments, at least two of G, X, and Y are other than N, O and S. In further embodiments, X is $CR^4$ or Y is $CR^5$ or both. In various embodiments $R^4$ is methyl, or $R^5$ is methyl, or both. In some embodiments $R^4$ and $R^5$ are the same and in other embodiments $R^4$ and $R^5$ are different. In further embodiments, $R^4$ is ethyl, $(C_3-C_8)$alkyl, difluoromethyl or trifluoromethyl. In yet further embodiments, $R^5$ is ethyl, $(C_3-C_8)$alkyl, difluoromethyl or trifluoromethyl. In various embodiments of Formula (I), $Het^1$ has the structure

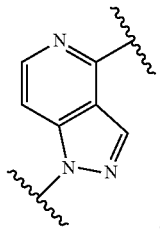

In various embodiments of Formula (I), $Het^1$ has the structure:

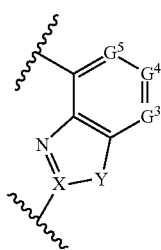

wherein $G^3$, $G^4$, and $G^5$ are CH or N; X is C or N; and Y is $CR^4$ or $NR^4$. In various embodiments one of $G^3$, $G^4$, and $G^5$ is N and the remainder are each CH. In various embodiments two of $G^3$, $G^4$, and $G^5$ is N and the remainder are each CH. In various embodiments, Y is $NR^4$ and $G^5$ is N. In various embodiments $R^4$ is methyl. In various embodiments of Formula (I), $Het^1$ has the structure

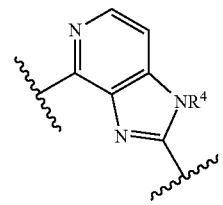

and more specifically the structure

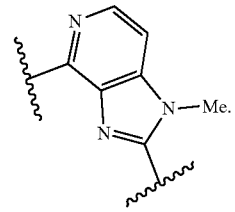 [SMILES: *c1nccc2c1nc(*)n2C]

$Het^1$ in Formula (I) and $Het^2$ in Formula (II) can be:

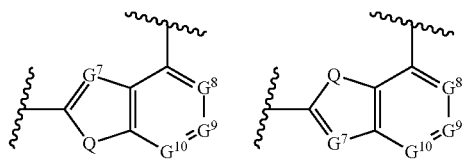

wherein Q is NH, $NR^4$, O or S; $G^7$ is CH or N; $G^8$ is CH, $CR^4$ or N; $G^9$ is CH, $CR^4$ or N; $G^{10}$ is CH, $CR^4$ or N; wherein $R^4$ is $(C_1-C_8)$alkyl. In various embodiments one of $G^7$, $G^8$, $G^9$ and $G^{10}$ is N and the remainder are each CH or $CR^4$. In various embodiments $G^7$ is N, Q is NH or $NR^4$, one of $G^8$, $G^9$ and $G^{10}$ is N and the remainder are each CH or $CR^4$. In various embodiments $G^7$ is O or S, Q is NH, $NR^4$, one of $G^8$, $G^9$ and $G^{10}$ is N and the remainder are each CH or $CR^4$. In various embodiments two of $G^7$, $G^8$, $G^9$ and $G^{10}$ is N and the remainder are each CH or $CR^4$. In various embodiments each of $G^7$, $G^8$, $G^9$ and $G^{10}$ is CH or $CR^4$. In various embodiments, at least two of $G^7$, $G^8$, $G^9$, $G^{10}$ and Q is N; Q is NH or $NR^4$ and at least one of $G^7$, $G^8$, $G^9$ and $G^{10}$ is N; Q is O or S and at least one of $G^7$, $G^8$, $G^9$ and $G^{10}$ is N.

In various embodiments of Formula (I), $Het^1$ has the structure:

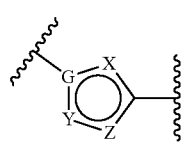

wherein G is C or N; X is N, O, S, CH or $CR^4$, wherein $R^4$ is $(C_1-C_8)$alkyl; Y is N, O, S, CH or $CR^5$, wherein $R^5$ is $(C_1-C_8)$alkyl; and Z is N, O, S, CH or $CCH_3$. In some embodiments, at least two of G, X, Y and Z is N; at least one of G, X, Y and Z is N, S or O; at least one of G, X, Y and Z is N and one of G, X, Y and Z is S or O; and/or at least two of G, X, Y and Z is N and one of G, X, Y and Z is S or O. In various embodiments, G can be C. In other various embodiments G can be N. In some embodiments, at least two of G, X, Y and Z are other than N, O and S. In further embodiments, X is $CR^4$ or Y is $CR^5$ or both. In various embodiments $R^4$ is methyl, or $R^5$ is methyl, or both. In some embodiments $R^4$ and $R^5$ are the same and in other embodiments $R^4$ and $R^5$ are different. In further embodiments, $R^4$ is ethyl, $(C_3-C_8)$alkyl, difluoromethyl or trifluoromethyl. In yet further embodiments, $R^5$ is ethyl, $(C_3-C_8)$alkyl, difluoromethyl or trifluoromethyl.

In various embodiments of Formula (I), $Het^1$ has the structure:

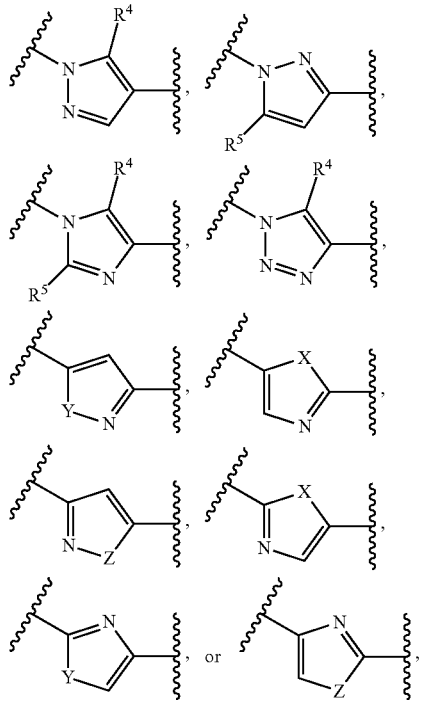

wherein $R^4$ is defined as above.

In various embodiments of Formula (I), $Cy^1$ has the structure one, pyridazin-3-one, pyrazin-2-one, pyrimidin-2-one or pyrimidin-4-one.

In various embodiments of Formula (I), $Cy^1$ has the structure

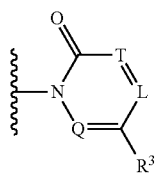

wherein: $R^3$ is H, fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido; O is N, CH, CF or $CCH_3$; L is N, CH or $CR^6$; T is N, CH or $CR^7$; and $R^6$, if present, and $R^7$, if present, is each independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In various embodiments $R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In various embodiments, $R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy. In various embodiments, $R^7$ is fluoro, chloro, bromo, iodo, cyano methyl, $(C_2-C_8)$alkyl, methoxy, $(C_2-C_8)$alkoxy, acetamido, $(C_3-C_8)$ alkylamido, $(C_2-C_8)$alkenyl, $(C_2-C_8)$alkynyl, methoxycarbonyl, $(C_2-C_8)$alkoxy-carbonyl or carboxy. In some embodiments, no more than one of Q, L and T is N. In various embodiments, Q is N. In further various embodiments, $R^3$, $R^6$ and $R^7$ are different. In further embodiments, L is $CR^6$ or T is $CR^7$, and $R^3$ is other than H. In some embodiments, L is CH or T is CH, and $R^3$ is other than H. In yet further embodiments, L is $CR^6$ or T is $CR^7$, and $R^3$ is H.

In various embodiments of Formula (I), $Cy^1$ is a substituted or unsubstituted 2-pyridone. In various embodiments of Formula (I), $Cy^1$ is a substituted or unsubstituted 3-pyridazinone.

In various embodiments of Formula (I), $Cy^1$ has the structure

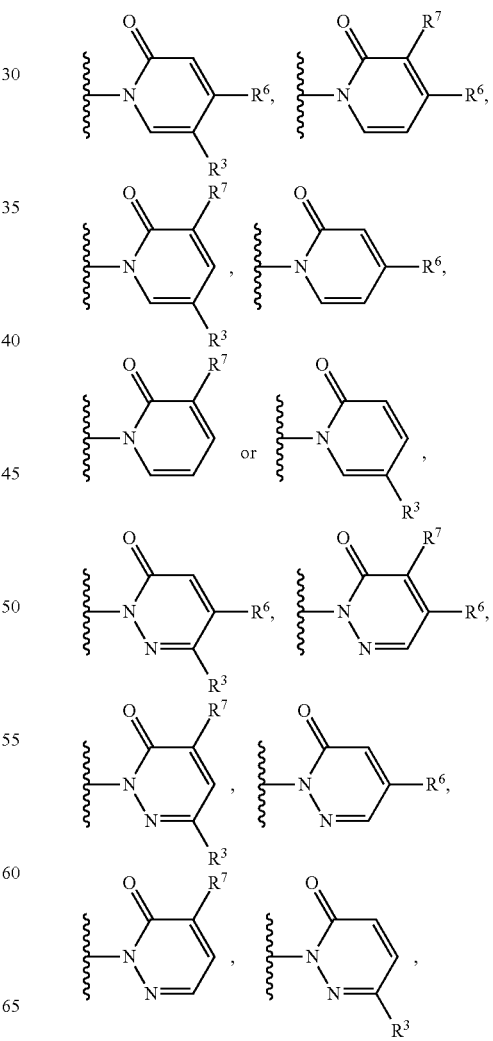

-continued

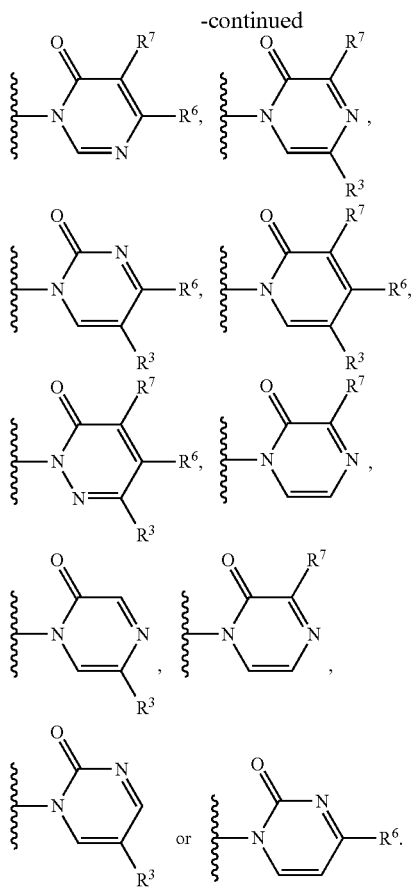

In such embodiments, $R^3$ can be fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; $R^6$ can be fluoro, chloro, bromo, iodo, cyano, methyl, $(C_2-C_8)$ alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy; and $R^7$ can be fluoro, chloro, bromo, iodo, cyano methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In various such embodiments $R^3$ can be H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In various such embodiments, $R^6$ can be fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy. In various such embodiments, $R^7$ can be fluoro, chloro, bromo, iodo, cyano methyl, $(C_2-C_8)$alkyl, methoxy, $(C_2-C_8)$ alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

In various embodiments, $R^3$ is substituted or unsubstituted $(C_1-C_8)$alkyl, $(C_2-C_8)$alkenyl) or $(C_2-C_8)$alkynyl). In some embodiments, $R^6$, if present, is substituted or unsubstituted $((C_1-C_8)$alkyl, $(C_2-C_8)$alkenyl) or $(C_2-C_8)$alkynyl). In some embodiments, $R^7$, if present, is substituted or unsubstituted $(C_1-C_8)$alkyl, $(C_2-C_8)$alkenyl) or $(C_2-C_8)$alkynyl). In some embodiments, at least one of $R^3$, $R^6$ and $R^7$, if present, is substituted or unsubstituted $(C_1-C_8)$alkyl. In some embodiments, at least one of $R^3$, $R^6$ and $R^7$, if present, is substituted or unsubstituted $(C_2-C_8)$alkenyl). In some embodiments, at least one of $R^3$, $R^6$ and $R^7$, if present, is substituted or unsubstituted $(C_2-C_8)$alkynyl).

In various embodiments of Formula (I), when $Cy^1$ is substituted with cyano, bromo or methyl and A is aryl, then A is substituted aryl. In various embodiments of Formula (I), when $Cy^1$ is mono-substituted with cyano, bromo or methyl, then A is other than aryl. In various embodiments of Formula (I), when $Cy^1$ is substituted with cyano, bromo or methyl then A is cycloalkyl or a heterocyclyl. In various embodiments of Formula (I), when $Cy^1$ is substituted with cyano, bromo or methyl then A is a nitrogen-containing heterocyclyl.

In various embodiments of Formula (I), when $Cy^1$ is substituted with t-butyl or benzodioxepinyl and A is aryl, then A is substituted aryl. In various embodiments of Formula (I), when $Cy^1$ is mono-substituted with t-butyl or benzodioxepinyl, then A is other than aryl. In various embodiments of Formula (II), when $Cy^1$ is substituted with t-butyl or benzodioxepinyl then A is cycloalkyl or a heterocyclyl. In various embodiments of Formula (I), when $Cy^1$ is substituted with t-butyl or benzodioxepinyl then A is a nitrogen-containing heterocyclyl. In various embodiments of Formula (I), when $Cy^1$ is substituted with alkyl, the alkyl is other than t-butyl or methyl. In various embodiments of Formula (I), when $Cy^1$ is mono-substituted with alkyl, the alkyl is other than t-butyl or methyl. In various embodiments of Formula (I), when $Cy^1$ is substituted with alkyl, the alkyl is linear $(C_2-C_8)$alkyl. In various embodiments of Formula (I), when $Cy^1$ is mono-substituted with aryl, the aryl is other than benzodioxepinyl.

In various embodiments of Formula (I), $Cy^1$ can be monosubstituted, disubstituted or trisubstituted.

In various embodiments of Formula (I), $L^1$ is a bond or unsubstituted alkyl. In various embodiments of Formula (I), $L^1$ is unsubstituted alkyl, alkenyl or alkynyl.

In some embodiments of Formula (I), $L^1$ is,

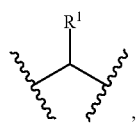

wherein $R^1$ is H, methyl or $(C_2-C_8)$alkyl. In further embodiments, $R^1$ is H so as to result in a methylene ($—CH_2—$) unit. In other embodiments $R^1$ is methyl or $(C_2-C_8)$alkyl. In yet further various embodiments, $R^1$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In another embodiment, $L^1$ is carbonyl, methylenedioxy, ethylenedioxy or $—C(R^1)_2—$, wherein each $R^1$ is independently defined or linked so as to form a ring. In some embodiments, $L^1$ is a substituted methylene.

In various embodiments of Formula (I), $L^1$ comprises at least two carbons. In some embodiments, $L^1$ comprises at least three carbon, oxygen and nitrogen atoms.

In various embodiments of Formula (I), $L^2$ has the structure

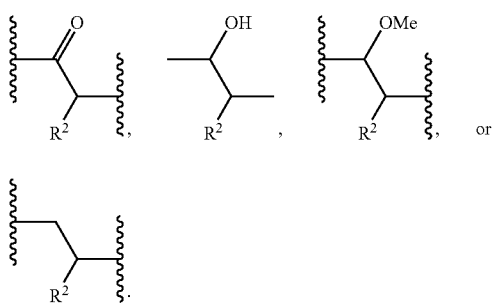

In some embodiments, $R^2$ is H or $(C_1-C_8)$alkyl. In some further embodiments $R^2$ is H, methyl, $(C_2-C_8)$alkyl, benzyl, or biphenylmethyl. In yet further various embodiments, $R^2$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido.

In various embodiments of Formula (I), $L^2$ is

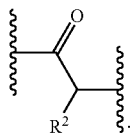

In some embodiments, $R^2$ is H or $(C_1-C_8)$alkyl. In some further embodiments $R^2$ is H, methyl, $(C_2-C_8)$alkyl, benzyl, or biphenylmethyl. In yet further various embodiments, $R^2$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In another embodiment, $L^2$ is —COC(R$^2$)$_2$—, wherein each $R^2$ is independently defined as above and optionally linked so as to form a ring. In another embodiment, $L^1$ is a

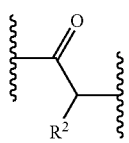

where the carbonyl group has been masked, e.g., as a methylenedioxy, a ethylenedioxy, a thial, a dithiolane, imine, or other related groups.

In various embodiments of Formula (I), $L^2$ is of the formula

-alk$^1$-C(O)—, wherein alk$^1$ is a linear or branched, substituted or unsubstituted divalent alkyl group.

In various embodiments of Formula (I), $L^2$ is

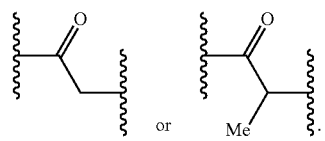 [SMILES: *CC(*)=O ; *C(=O)C(*)C]

In another embodiment, $L^2$ is a

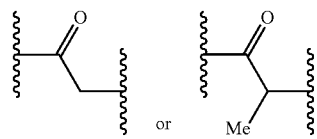 [SMILES: *CC(*)=O ; *C(=O)C(*)C]

where the carbonyl group has been masked, e.g., as a methylenedioxy, a ethylenedioxy, a thial, a dithiolane, imine, or other related groups. In some embodiments, $L^2$ is a substituted methylene.

In various embodiments, $L^2$ comprises at least three carbons. In some embodiments, $L^2$ comprises at at least four carbon, oxygen and nitrogen atoms.

In various embodiments of Formula (I), $L^2$-Cy$^1$ has the formula:

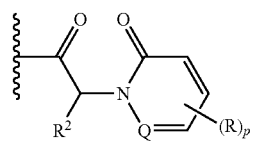

wherein
$R^2$ is H or alkyl; Q is N, CH or CCH$_3$; p is 1, 2 or 3; and
R is hydrogen, fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, where there are two or more adjacent groups, the groups can be linked to form a carbocyclic or heterocyclic ring. In various embodiments, p is 1-2. In some embodiments, when p is 1 then R is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; and when p is 2 then each instance of R is independently fluoro, chloro, bromo, iodo, cyano, methyl, $(C_2-C_8)$alkyl, $(C_2-C_8)$alkenyl, $(C_2-C_8)$alkynyl, methoxy or $(C_2-C_8)$alkoxy provided that each instance of R is not the same. In some certain embodiments, R can also be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In an alternative embodiment, $R^2$ is H or alkyl; Q is N, CH or CCH$_3$; p is 3 and R can be defined as above. In some embodiments, $R^2$ is H or (C$_1$-C$_8$)alkyl.

In various embodiments of Formula (I), $L^2$-Cy$^1$ has the formula:

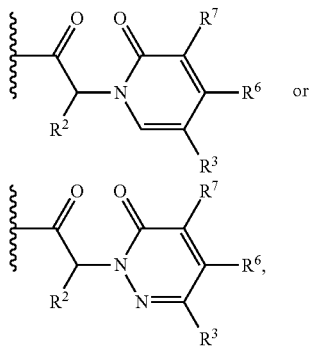

wherein $R^2$ is H, alkyl or aryl; and $R^3$, $R^6$ and $R^7$ is independently selected from hydrogen, fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, where there are two or more adjacent groups, the groups can be linked to form a carbocyclic or heterocyclic ring. In various embodiments, one of $R^3$, Re and $R^7$ is fluoro, chloro, bromo, iodo, cyano, methyl, (C$_2$-C$_8$)alkyl, methoxy, (C$_2$-C$_8$)alkoxy, acetamido, (C$_3$-C$_8$)alkylamido, (C$_2$-C$_8$)alkenyl. (C$_2$-C$_8$)alkynyl, methoxycarbonyl, (C$_2$-C$_8$)alkoxy-carbonyl or carboxy, and the remainder of $R^3$, $R^6$ and $R^7$ are H; or one of $R^3$, $R^6$ and $R^7$ is H and two of $R^3$, $R^6$ and $R^7$ is fluoro, chloro, bromo, iodo, cyano, methyl, (C$_2$-C$_8$)alkyl, (C$_2$-C$_8$)alkenyl, (C$_2$-C$_8$)alkynyl, methoxy or (C$_2$-C$_8$)alkoxy provided that the two substituents are not the same. In further various embodiments, one of $R^3$, $R^6$ and $R^7$ is fluoro, chloro, iodo, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_2$-C$_8$)alkoxy-carbonyl or carboxy, and the remainder of $R^3$, $R^6$ and $R^7$ are H; or one of $R^3$, $R^6$ and $R^7$ is H and two of $R^3$, $R^6$ and $R^7$ is fluoro, chloro, bromo, iodo, cyano, methyl, (C$_2$-C$_8$)alkyl, (C$_2$-C$_8$)alkenyl, (C$_2$-C$_8$)alkynyl, methoxy or (C$_2$-C$_8$)alkoxy provided that the two substituents are not the same. In some embodiments, $R^2$ is H, methyl, (C$_2$-C$_8$)alkyl, benzyl or biphenylmethyl.

The present disclosure further provides a compound of the Formula (II):

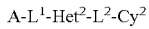 A-L$^1$-Het$^2$-L$^2$-Cy$^2$     Formula (II)

or a pharmaceutically acceptable salt, polymorph, prodrug, solvate or clathrate thereof, wherein:

A is cycloalkyl, aryl, arylalkyl or heterocyclyl containing at least one N or O;

Het$^2$ is an aromatic heterocyclyl group;

Cy$^2$ is a heterocyclyl containing one keto group and at least one nitrogen in the heterocyclyl ring, wherein the heterocyclyl is mono-substituted with fluoro, chloro, bromo, iodo, cyano, methyl, (C$_2$-C$_8$)alkyl, methoxy, (C$_2$-C$_8$)alkoxy, acetamido, (C$_3$-C$_8$)alkylamido, (C$_2$-C$_8$) alkenyl, (C$_2$-C$_8$)alkynyl, methoxycarbonyl, (C$_2$-C$_8$) alkoxy-carbonyl or carboxy or di-substituted with fluoro, chloro, bromo, iodo, cyano, methyl, (C$_2$-C$_8$) alkyl, (C$_2$-C$_8$)alkenyl, (C$_2$-C$_8$)alkynyl, methoxy or (C$_2$-C$_8$)alkoxy provided that the two substituents are not the same;

L1 is a bond, alkyl, alkenyl or alkynyl linker;

L$^2$ is an acyl or alkyl linker;

wherein A and Cy$^2$ are different;

wherein when Cy$^2$ is mono-substituted with cyano, bromo or methyl and A is aryl, then A is substituted aryl, L$^1$ comprises at least two carbons, L$^2$ comprises at least three carbons, or Cy$^2$ contains two nitrogens in the heterocyclyl ring; and when Cy$^2$ is mono-substituted with t-butyl or benzodioxepinyl and A is aryl, then A is substituted aryl, L$^1$ comprises at least two carbons, L$^2$ comprises at least three carbons or Cy$^2$ contains no more than one nitrogen in the heterocyclyl ring.

In various embodiments of Formula (II), A is substituted cycloalkyl, unsubstituted cycloalkyl, substituted aryl, unsubstituted aryl, substituted arylalkyl, unsubstituted arylalkyl, substituted nonaromatic heterocyclyl, unsubstituted nonaromatic heterocyclyl, substituted aromatic heterocyclyl or unsubstituted aromatic heterocyclyl. In further embodiments, A can be cycloalkyl, aryl, arylalkyl or heterocyclyl which is substituted by alkylsulfonyl, alkyl, alkoxy, cyano, halo, difluoromethyl or carboxy. In some embodiments, A can be other than phenyl, for example A can be cycloalkyl, arylalkyl or heterocyclyl, which is substituted by alkylsulfonyl, alkyl, alkoxy, cyano, halo, difluoromethyl or carboxy. A can also be an aryl other than phenyl. In yet further various embodiments, A can be cycloalkyl, aryl, arylalkyl or heterocyclyl which is substituted by, for example, one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. In some embodiments, A can be monosubstituted, disubstituted, trisubstituted or fully substituted.

In various embodiments of Formula (II), A is a heterocyclyl. For example, A can be tetrahydrofuranyl, tetrahydropyranyl, indole, quinoline, isoquinoline, pyrrolidinyl, piperidinyl, piperazinyl, pyrrolyl, furanyl, oxazolyl, pyrazolyl, imidazolyl, 1,2,3-oxadiazolyl, 1,2,4-oxadiazolyl, 1,25-oxadiazolyl, 1,3,4-oxadiazolyl, 1,2,3-triazolyl, 1,2,4-triazolyl, benzo[d][1,3]dioxole, pyridinyl or pyrimidinyl. In some embodiments, A can be a heterocyclyl other than pyrrolyl. In some embodiments, the heterocyclyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. As a further example, A can be heterocyclyl substituted with alkylsulfonyl, alkyl, alkoxy, cyano, halo, difluoromethyl or carboxy.

In various embodiments of Formula (II), A is cycloalkyl. For example, A can be cyclopropyl, cyclobutyl, cyclopentane, cyclohexane or bicyclo[1.1.1]pentane. In some embodiments, the cycloalkyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. As a further example, A can be cycloalkyl substituted with alkylsulfonyl, alkyl, alkoxy, cyano, halo, difluoromethyl or carboxy.

In various embodiments of Formula (II), A is aryl. For example, A can be unsubstituted phenyl or substituted phenyl. As another example, A can be unsubstituted naphthalene or substituted naphthalene. As a further example, A can be phenyl substituted with alkylsulfonyl, alkyl, alkoxy, cyano, halo, difluoromethyl or carboxy. As a further example, A can be a phenyl substituted with fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido.

In various embodiments of Formula (II), A is

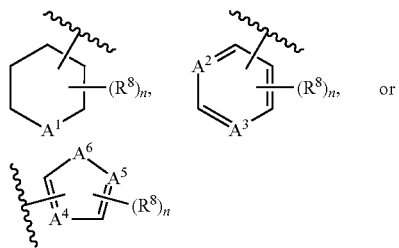

wherein:
n is 0-3; $A^1$ is O or NH, N-Alkyl; each of $A^2$ and $A^3$ is independently, CH, $CR^8$ or N; each of $A^4$, $A^5$, and $A^6$ is independently CH, C-alkyl, N, $NR^9$ or O, provided that at least one of $A^4$, $A^5$, and $A^6$ is N or $NR^9$; and $R^8$ is independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido; and $R^9$ is independently H or alkyl. In some embodiments, $R^8$ independently is alkylsulfonyl, alkyl, alkoxy, cyano, halo, difluoromethyl or carboxy.

In various embodiments of Formula (II), A is

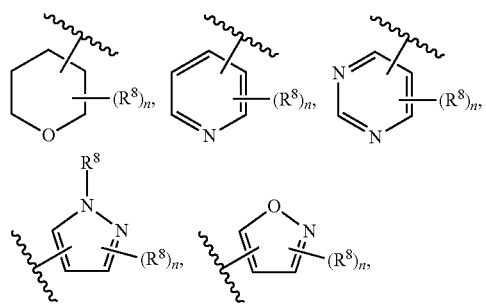

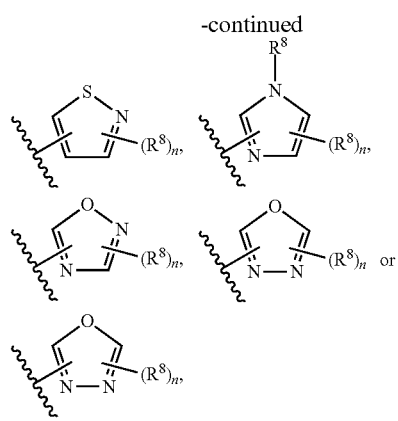

wherein: n is 0-3; $R^8$ is independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido.

In various embodiments of Formula (II), A is

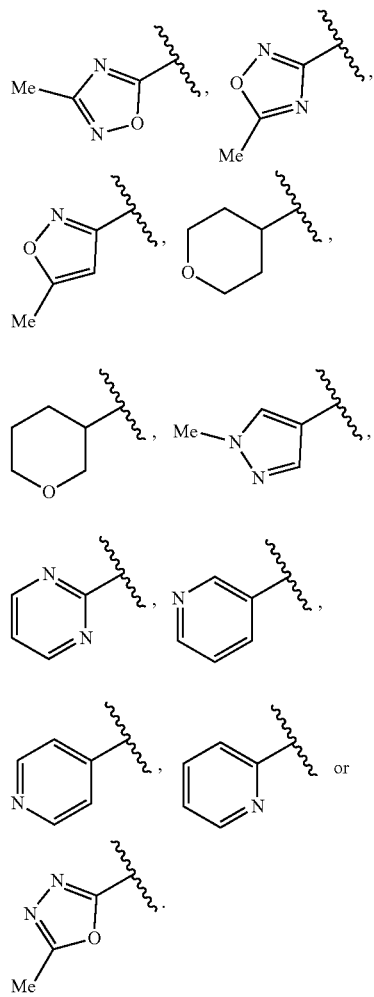

In various embodiments of Formula (II), A is
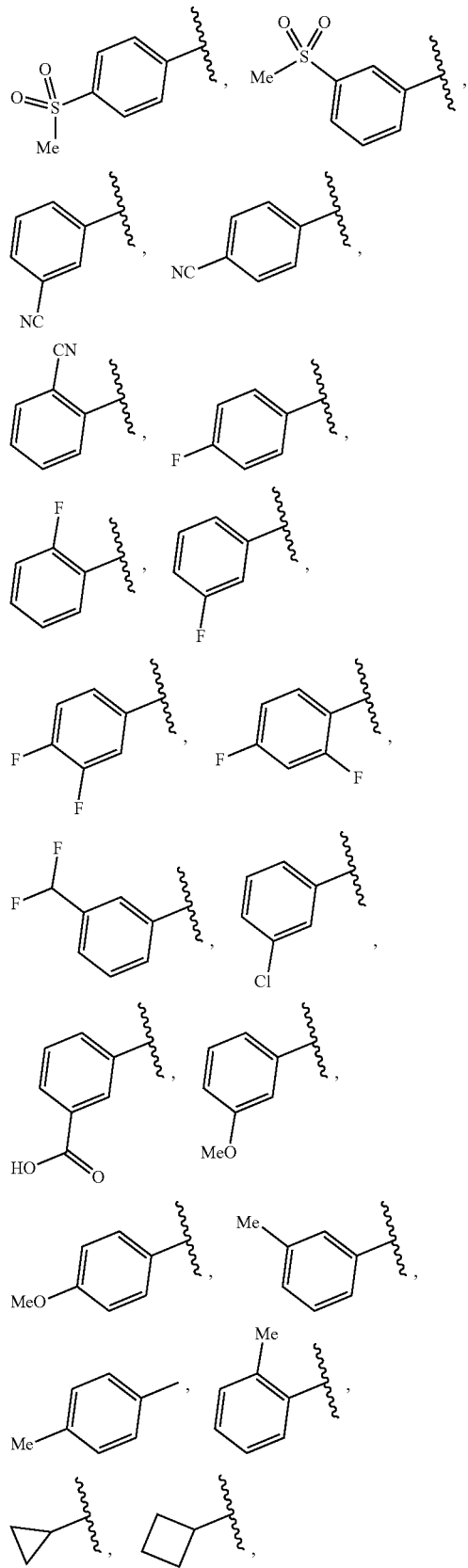
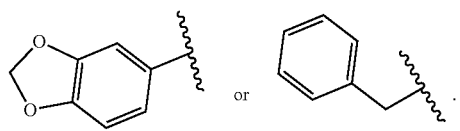
In some embodiments of Formula (II), A is a
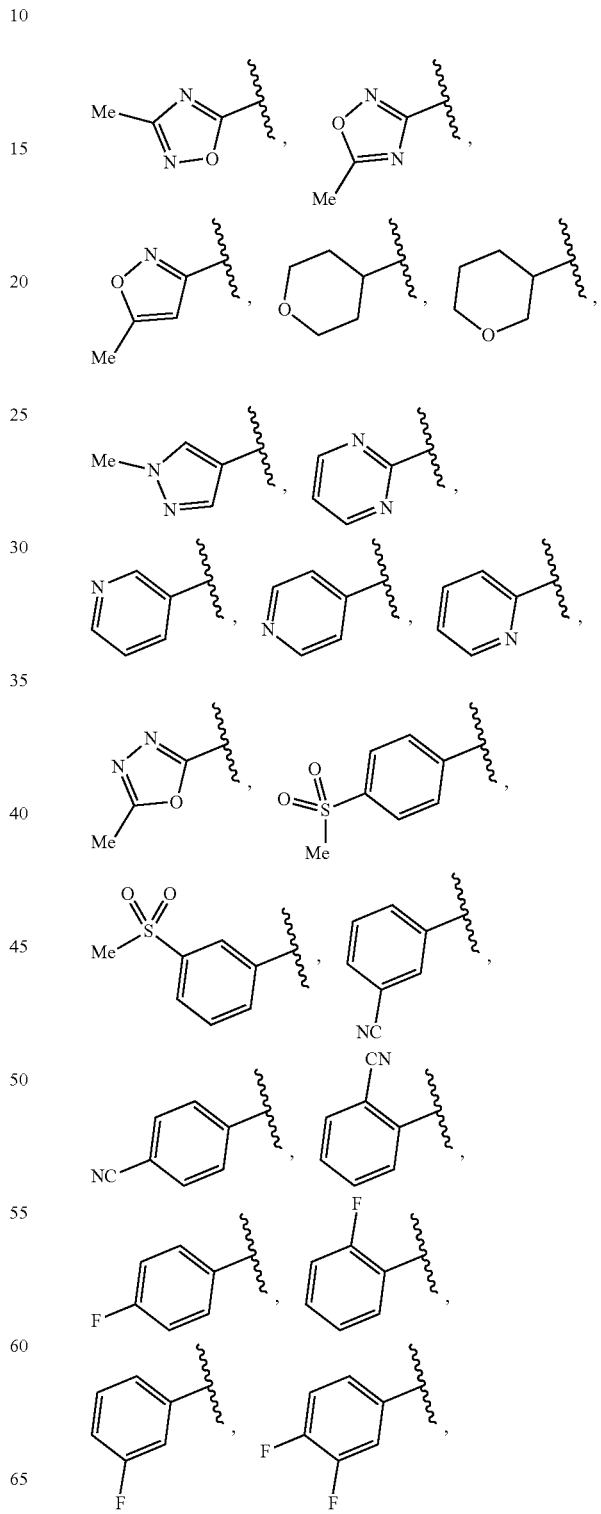

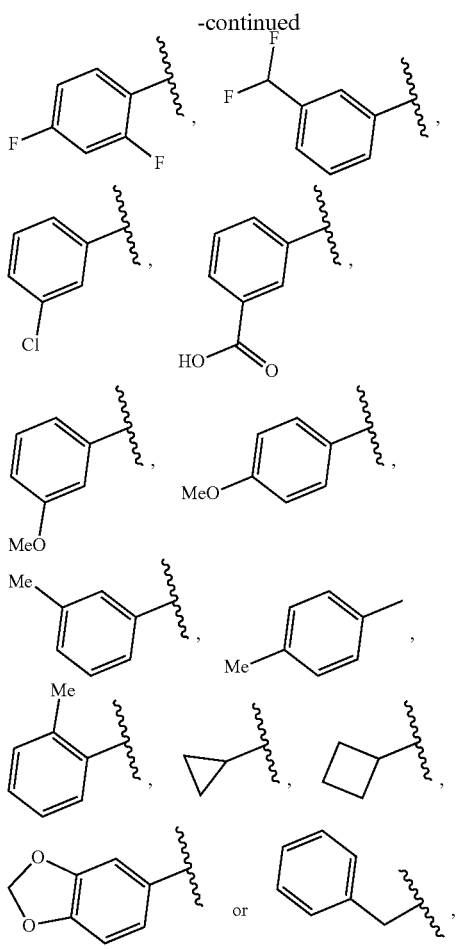

which is further substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof.

In various embodiments of Formula (II), A is cycloalkyl, aryl, arylalkyl or heterocyclyl and is unsubstituted. In certain embodiments, A is cycloalkyl, aryl, arylalkyl or heterocyclyl and is unsubstituted. In certain embodiments, A can be selected from substituted aryl and substituted or unsubstituted cycloalkyl, arylalkyl and heterocyclyl.

In various embodiments of Formula (II), $Het^2$ is a 5-membered aromatic heterocyclyl group containing at least two heteroatoms. For example, $Het^2$ can be a pyrrolyl, furanyl, oxazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-triazolyl or 1,2,4-triazolyl.

In various embodiments of Formula (II), $Het^2$ contains at least one nitrogen. In some embodiments, $Het^2$ contains two nitrogen atoms in its ring. In further various embodiments, $Het^2$ contains at least one S or O. In yet further various embodiments, $Het^2$ contains at least one nitrogen atom and one sulfur atom or one oxygen atom. $Het^2$ can contain two nitrogen atoms and one sulfur atom or one oxygen atom. $Het^2$ can contain three nitrogen atoms.

In various embodiments of Formula (II), $Het^2$ has the structure: wherein G is CH or N; $G^1$ is C or N, but when $G^1$ is N, there is not a double bond between $G^1$ and $G^2$; $G^2$ is C or N, but when $G^2$ is N, there is not a double bond between $G^1$ and $G^2$; $G^3$ is C or N; $G^4$ is CH or N; $G^5$ is CH or N; $G^6$ is CH or N; X is N, O, S, CH or $CR^4$, but when X is O or S, there is not a double bond between X and Y, wherein $R^4$ is $(C_1-C_8)$alkyl; and Y is N, O, S, CH or $CR^5$, but when Y is O or S, there is not a double bond between X and Y wherein $R^5$ is $(C_1-C_8)$alkyl. In various embodiments one of $G^1$, $G^2$, $G^3$, $G^4$, $G^5$ and $G^6$ is N and the remainder are each C. In various embodiments two of $G^1$, $G^2$, $G^3$, $G^4$, $G^5$ and $G^6$ is N and the remainder are each C. In various embodiments each of $G^1$, $G^2$, $G^3$, $G^4$, $G^5$ and $G^6$ is C. In various embodiments, at least two of G, X and Y is N; at least one of G, X, and Y and is N, S or O; at least one of G, X, and Y is N and one of G, X, and Y is S or O; and/or at least two of G, X, and Y is N and one of G, X, and Y is S or O. In various embodiments, G can be C. In other various embodiments G can be N. In some embodiments, at least two of G, X, and Y are other than N, O and S. In further embodiments, X is $CR^4$ or Y is $CR^5$ or both. In various embodiments $R^4$ is methyl, or $R^5$ is methyl, or both. In some embodiments $R^4$ and $R^5$ are the same and in other embodiments $R^4$ and $R^5$ are different. In further embodiments, $R^4$ is ethyl, $(C_3-C_8)$alkyl, difluoromethyl or trifluoromethyl. In yet further embodiments, $R^5$ is ethyl, $(C_3-C_8)$alkyl, difluoromethyl or trifluoromethyl. In various embodiments of Formula (II), $Het^2$ has the structure

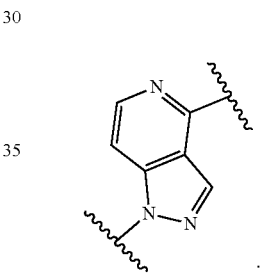

In various embodiments of Formula (II), $Het^2$ has the structure:

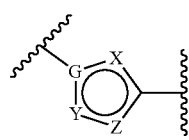

wherein G is C or N; X is N, O, S, CH or $CR^4$; Y is N, O, S, CH or $CR^5$; and Z is N, O, S, CH or $CCH_3$. In some embodiments, $R^4$ and $R^5$, if present, is each independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, $R^4$ and $R^5$, if present, is H, alkyl or aryl. In some embodiments, $R^4$ is $(C_1-C_8)$alkyl. In various embodiments, $R^5$ is $(C_1-C_8)$alkyl; In some embodiments, at least two of G, X, Y and Z is N; at least one of G, X, Y and Z is N, S or O; at least one of G, X, Y and Z is N and one of G, X, Y and Z is S or O; and/or at least two of G, X, Y and Z is N and one of G, X, Y and Z is S or O. In various embodiments, G can be C. In other various embodiments G can be N. In some embodiments, at least two of G, X, Y and Z are other than N, O and S. In further embodiments, X is $CR^4$ or Y is $CR^5$ or both. In various embodiments $R^4$ is methyl, or $R^5$ is methyl, or both. In some embodiments $R^4$ and $R^5$ are the same and in other embodiments $R^4$ and $R^5$ are different. In further embodiments, $R^4$ is ethyl, $(C_3-C_8)$alkyl, difluoromethyl or trifluoromethyl. In yet further embodiments, $R^5$ is ethyl, $(C_3-C_8)$alkyl, difluoromethyl or trifluoromethyl.

In various embodiments of Formula (II), $Het^2$ has the structure:

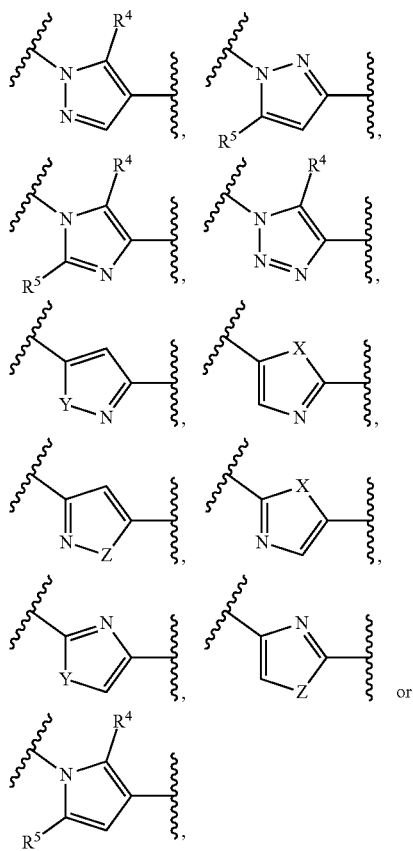

wherein $R^4$ and $R^5$ are defined as above.

In various embodiments of Formula (II), $Het^2$ is a pyrrole.

In various embodiments of Formula (II), $Het^2$ is a non-pyrrole aromatic heterocyclyl group.

In various embodiments of Formula (II), $Cy^2$ has the structure

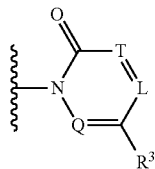

wherein: $R^3$ is H, fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido; Q is N, CH, CF or $CCH_3$; L is N, CH or $CR^6$; T is N, CH or $CR^7$; and $A^6$, if present, and $R^7$, if present, is each independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In various embodiments $R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In various embodiments, $R^6$ is fluoro, chloro, bromo, iodo, cyano, methyl, $(C_1-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy. In various embodiments, $R^3$ is methoxy, $(C_2-C_8)$alkoxy, acetamido, $(C_3-C_8)$alkylamido, vinyl, 1-fluoalklrovinyl, trifluoropropen-2-yl, $(C_3-C_8)$alkenyl, $(C_2-C_8)$alkynyl, or carboxy. In various embodiments, $R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy. In various embodiments, $R^7$ is fluoro, chloro, bromo, iodo, cyano methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In some embodiments, no more than one of Q, L and T is N. In various embodiments, Q is N. In further various embodiments, $R^3$, $R^6$ and $R^7$ are different. In further embodiments, L is $CR^6$ or T is $CR^7$, and $R^3$ is other than H. In some embodiments, L is CH or T is CH, and $R^3$ is other than H. In yet further embodiments, L is $CR^6$ or T is $CR^7$, and $R^3$ is H.

In various embodiments of Formula (II), $Cy^2$ is a substituted or unsubstituted 2-pyridone. In various embodiments of Formula (II), $Cy^2$ is a substituted or unsubstituted 3-pyridazinone.

In various embodiments of Formula (II), $Cy^2$ has the structure

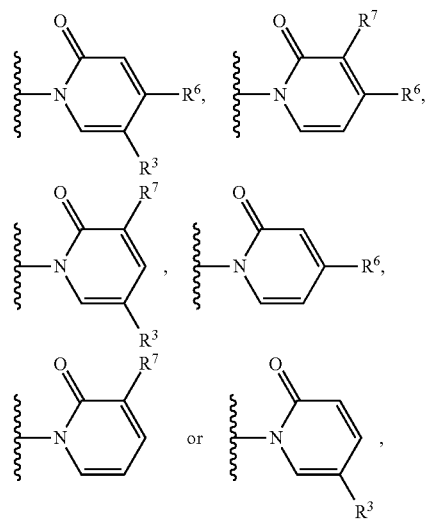

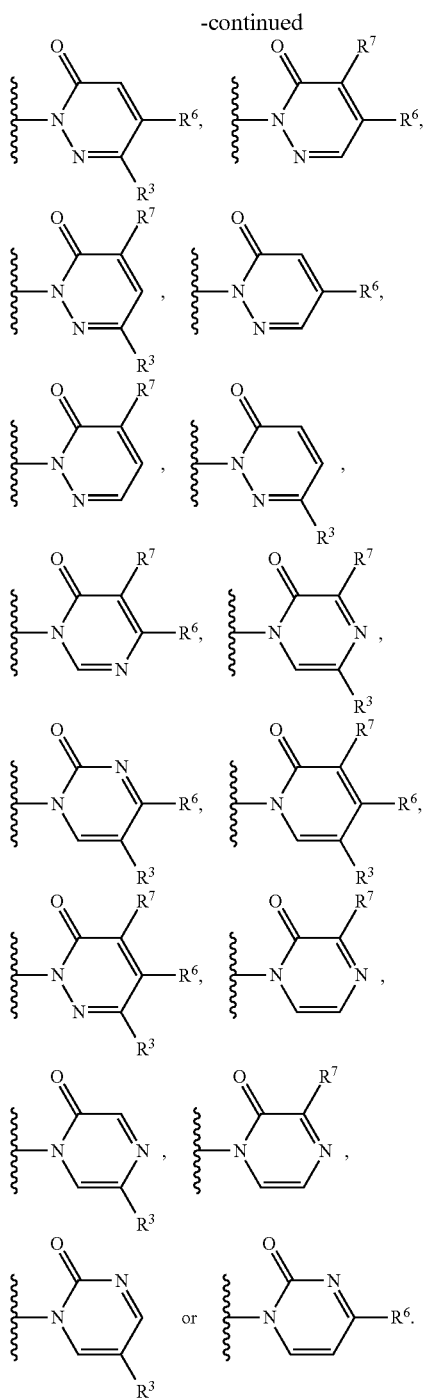

In such embodiments, $R^3$ can be fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; $R^6$ can be fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy; and $R^7$ can be fluoro, chloro, bromo, iodo, cyano methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In various such embodiments $R^3$ can be H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In various such embodiments, Re can be fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy. In various such embodiments, $R^7$ can be fluoro, chloro, bromo, iodo, cyano methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

In various embodiments of Formula (II), $R^3$ is substituted or unsubstituted $(C_1-C_8)$alkyl, $(C_2-C_8)$alkenyl) or $(C_2-C_8)$alkynyl). In some embodiments, $R^6$, if present, is substituted or unsubstituted $((C_1-C_8)$alkyl, $(C_2-C_8)$alkenyl) or $(C_2-C_8)$alkynyl). In some embodiments, $R^7$, if present, is substituted or unsubstituted $(C_1-C_8)$alkyl, $(C_2-C_8)$alkenyl) or $(C_2-C_8)$alkynyl). In some embodiments, at least one of $R^3$, $R^6$ and $R^7$, if present, is substituted or unsubstituted $(C_1-C_8)$alkyl. In some embodiments, at least one of $R^3$, $R^6$ and $R^7$, if present, is substituted or unsubstituted $(C_2-C_8)$alkenyl). In some embodiments, at least one of $R^3$, $R^6$ and $R^7$, if present, is substituted or unsubstituted $(C_2-C_8)$alkynyl).

In various embodiments of Formula (II), when $Cy^2$ is substituted with cyano, bromo or methyl and A is aryl, then A is substituted aryl. In various embodiments of Formula (II), when $Cy^2$ is mono-substituted with cyano, bromo or methyl, then A is other than aryl. In various embodiments of Formula (II), when $Cy^2$ is substituted with cyano, bromo or methyl then A is cycloalkyl or a heterocyclyl. In various embodiments of Formula (II), when $Cy^2$ is substituted with cyano, bromo or methyl then A is a nitrogen-containing heterocyclyl.

In various embodiments of Formula (II), when $Cy^2$ is substituted with t-butyl or benzodioxepinyl and A is aryl, then A is substituted aryl. In various embodiments of Formula (II), when $Cy^2$ is mono-substituted with t-butyl or benzodioxepinyl, then A is other than aryl. In various embodiments of Formula (II), when $Cy^2$ is substituted with t-butyl or benzodioxepinyl then A is cycloalkyl or a heterocyclyl. In various embodiments of Formula (II), when $Cy^2$ is substituted with t-butyl or benzodioxepinyl then A is a nitrogen-containing heterocyclyl. In various embodiments of Formula (II), when $Cy^2$ is substituted with alkyl, the alkyl is other than t-butyl or methyl. In various embodiments of Formula (II), when $Cy^2$ is mono-substituted with alkyl, the alkyl is other than t-butyl or benzodioxepinyl or methyl. In various embodiments of Formula (II), when $Cy^2$ is substituted with alkyl, the alkyl is linear $(C_1-C_8)$alkyl.

In various embodiments of Formula (II), $Cy^2$ can be monosubstituted, disubstituted or trisubstituted.

In various embodiments of Formula (II), $L^1$ is a bond or unsubstituted alkyl. In various embodiments of Formula (I), $L^1$ is unsubstituted alkyl, alkenyl or alkynyl.

In some embodiments of Formula (II), $L^1$ is

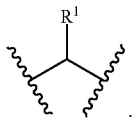

In some embodiments, $R^1$ is H, methyl or $(C_2-C_8)$alkyl. In further embodiments, $R^1$ is H so as to result in a methylene (—$CH_2$—) unit. In other embodiments $R^1$ is methyl or ($C_2$-$C_8$)alkyl. In yet further various embodiments, $R^1$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In another embodiment, $L^1$ is carbonyl, methylenedioxy, ethylenedioxy or —C($R^1$)$_2$—, wherein each $R^1$ is independently defined or linked so as to form a ring. In some embodiments, $L^1$ is a substituted methylene.

In various embodiments of Formula (II), $L^1$ comprises at least two carbons. In some embodiments, $L^1$ comprises at at least three carbon, oxygen and nitrogen atoms.

In various embodiments of Formula (II), $L^2$ has the structure

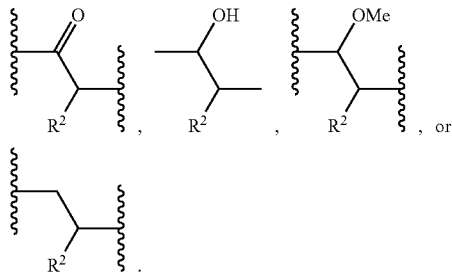

In some embodiments, $R^2$ is H or ($C_1$-$C_8$)alkyl. In some further embodiments $R^2$ is H, methyl, ($C_2$-$C_8$)alkyl, benzyl, or biphenylmethyl. In yet further various embodiments, $R^2$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido.

In various embodiments of Formula (II), $L^2$ is

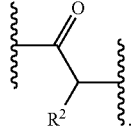

In some embodiments, $R^2$ is H or ($C_1$-$C_8$)alkyl. In some further embodiments $R^2$ is H, methyl, ($C_2$-$C_8$)alkyl, benzyl, or biphenylmethyl. In yet further various embodiments, $R^2$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In another embodiment, $L^2$ is —COC($R^2$)$_2$—, wherein each $R^2$ is independently defined as above and optionally linked so as to form a ring. In another embodiment, $L^1$ is a

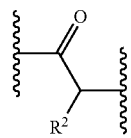

where the carbonyl group has been masked, e.g., as a methylenedioxy, a ethylenedioxy, a thial, a dithiolane, imine, or other related groups.

In various embodiments of Formula (II), $L^2$ is of the formula

-alk$^1$-C(O)—, wherein alk$^1$ is a linear or branched, substituted or unsubstituted divalent alkyl group.

In various embodiments of Formula (II), $L^2$ is

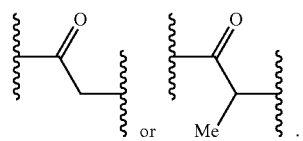 [SMILES: *CC(*)=O ; *C(=O)C(*)C]

In another embodiment, $L^2$ is a

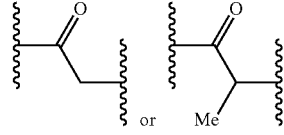 [SMILES: *CC(*)=O ; *C(=O)C(*)C]

where the carbonyl group has been masked, e.g., as a methylenedioxy, a ethylenedioxy, a thial, a dithiolane, imine, or other related groups. In some embodiments, $L^2$ is a substituted methylene.

In various embodiments, $L^2$ comprises at least three carbons. In some embodiments, $L^2$ comprises at at least four carbon, oxygen and nitrogen atoms.

In various embodiments of Formula (II), $L^2$-$Cy^2$ has the formula:

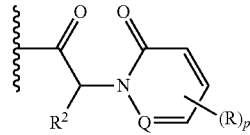

wherein
$R^2$ is H or alkyl; 0 is N, CH or CCH$_3$; p is 1, 2 or 3; and R is hydrogen, fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, where there are two or more adjacent groups, the groups can be linked to form a carbocyclic or heterocyclic ring. In various embodiments, p is 1-2. In some embodiments, when p is 1 then R is fluoro, chloro, bromo, iodo, cyano, methyl, ($C_2$-$C_8$)alkyl, methoxy, ($C_2$-$C_8$)alkoxy, acetamido, ($C_3$-$C_8$)alkylamido, ($C_2$-$C_8$) alkenyl, ($C_2$-$C_8$)alkynyl, methoxycarbonyl, ($C_2$-$C_8$) alkoxy-carbonyl or carboxy; and when p is 2 then each instance of R is independently fluoro, chloro, bromo, iodo, cyano, methyl, ($C_2$-$C_8$)alkyl, ($C_2$-$C_8$)alkenyl, ($C_2$-$C_8$)alkynyl, methoxy or ($C_2$-$C_8$)alkoxy provided that each instance of R is not the same. In some certain embodiments, R can also be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In an alternative embodiment, $R^2$ is H or alkyl; Q is N, CH or $CCH_3$; p is 3 and R can be defined as above. In some embodiments, $R^2$ is H or ($C_1$-$C_8$)alkyl.

In various embodiments of Formula (II), $L^2$-$Cy^2$ has the formula:

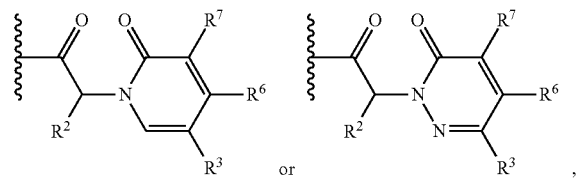

wherein $R^2$ is H, alkyl or aryl; and $R^3$, $R^6$ and $R^7$ is independently selected from hydrogen, fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, where there are two or more adjacent groups, the groups can be linked to form a carbocyclic or heterocyclic ring. In various embodiments, one of $R^3$, $R^6$ and $R^7$ is fluoro, chloro, bromo, iodo, cyano, methyl, ($C_2$-$C_8$)alkyl, methoxy, ($C_2$-$C_8$)alkoxy, acetamido, ($C_3$-$C_8$)alkylamido, ($C_2$-$C_8$)alkenyl, ($C_2$-$C_8$)alkynyl, methoxycarbonyl, ($C_2$-$C_8$)alkoxy-carbonyl or carboxy, and the remainder of $R^3$, $R^6$ and $R^7$ are H; or one of $R^3$, $R^6$ and $R^7$ is H and two of $R^3$, $R^6$ and $R^7$ is fluoro, chloro, bromo, iodo, cyano, methyl, ($C_2$-$C_8$)alkyl, ($C_2$-$C_8$)alkenyl, ($C_2$-$C_8$)alkynyl, methoxy or ($C_2$-$C_8$)alkoxy provided that the two substituents are not the same. In further various embodiments, one of $R^3$, Re and $R^7$ is fluoro, chloro, iodo, methoxy, ($C_2$-$C_8$)alkoxy, acetamido, ($C_3$-$C_8$) alkylamido, ($C_1$-$C_8$)alkenyl, ($C_2$-$C_8$)alkynyl, methoxycarbonyl, ($C_2$-$C_8$)alkoxy-carbonyl or carboxy, and the remainder of $R^3$, $A^6$ and $R^7$ are H; or one of $R^3$, $R^6$ and $R^7$ is H and two of $R^3$, $R^6$ and $R^7$ is fluoro, chloro, bromo, iodo, cyano, methyl, ($C_2$-$C_8$)alkyl, ($C_2$-$C_8$)alkenyl, ($C_2$-$C_8$)alkynyl, methoxy or ($C_2$-$C_8$)alkoxy provided that the two substituents are not the same. In some embodiments, $R^2$ is H or ($C_1$-$C_8$)alkyl.

In various embodiments of Formula (II), the compound has: A is cycloalkyl, aryl, arylalkyl or heterocyclyl containing at least one N or O; $Het^2$ is an aromatic heterocyclyl group; $Cy^2$ is a heterocyclyl containing one keto group and at least one nitrogen in the heterocyclyl ring, wherein the heterocyclyl is mono-substituted with fluoro, chloro, iodo, methoxy, ($C_2$-$C_8$)alkoxy, acetamido, ($C_3$-$C_8$)alkylamido, ($C_2$-$C_8$)alkenyl, ($C_2$-$C_8$)alkynyl, methoxycarbonyl, ($C_2$-$C_8$) alkoxy-carbonyl or carboxy or di-substituted with fluoro, chloro, bromo, iodo, cyano, methyl, ($C_2$-$C_8$)alkyl, ($C_2$-$C_8$) alkenyl, ($C_2$-$C_8$)alkynyl, methoxy or ($C_2$-$C_8$)alkoxy provided that the two substituents are not the same;

L1 is a bond, alkyl, alkenyl or alkynyl linker;
$L^2$ is an acyl or alkyl linker; and
wherein A and $Cy^2$ are different.

The present disclosure also provides a compound of the Formula (A):

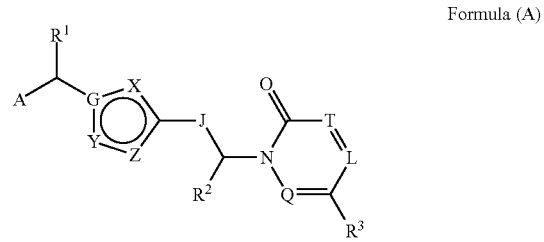

Formula (A)

or a pharmaceutically acceptable salt, polymorph, prodrug, solvate or clathrate thereof, wherein:
A is cycloalkyl, aryl, arylalkyl or heterocyclyl containing at least one N or O;
$R^1$ is H or ($C_1$-$C_8$)alkyl;
$R^2$ is H or ($C_1$-$C_8$)alkyl;
$R^3$ is hydrogen, fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido;
G is C or N;
X is N, O, S, CH or $CR^4$, wherein $R^4$ is ($C_1$-$C_8$)alkyl;
Y is N, O, S, CH or $CR^5$, wherein $R^5$ is ($C_1$-$C_8$)alkyl;
Z is N, O, S, CH or $CCH_3$;
J is CO, ($C_1$)alkyl or a bond;
O is N, CH, CF or $CCH_3$;
L is N, CH or $CR^6$, wherein $R^6$ is fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido;
T is N, CH or $CR^7$, wherein $R^7$ is fluoro, chloro, bromo, iodo, cyano, methyl, ($C_2$-$C_8$)alkyl, methoxy, ($C_2$-$C_8$) alkoxy, acetamido, ($C_3$-$C_8$)alkylamido, ($C_2$-$C_8$)alkenyl, ($C_2$-$C_8$)alkynyl, methoxycarbonyl, ($C_2$-$C_8$) alkoxy-carbonyl or carboxy; and at least two of G, X, Y and Z is independently N, O or S. In some embodiments, $R^3$ is hydrogen, fluoro, chloro, bromo, iodo, cyano, methyl, ($C_2$-$C_8$)alkyl, methoxy, ($C_2$-$C_8$)alkoxy, acetamido, ($C_3$-$C_8$)alkylamido, ($C_2$-$C_8$)alkenyl, ($C_1$-$C_8$)alkynyl, methoxycarbonyl, ($C_2$-$C_8$)alkoxy-carbonyl or carboxy; and Re, if present, and $R^7$, if present, is each independently fluoro, chloro, bromo, iodo, cyano, methyl, ($C_2$-$C_8$)alkyl, methoxy, ($C_2$-$C_8$)alkoxy, acetamido, ($C_3$-$C_8$)alkylamido, ($C_2$-$C_8$)alkenyl, ($C_2$-$C_8$) alkynyl, methoxycarbonyl, ($C_2$-$C_8$)alkoxy-carbonyl or carboxy.

The present disclosure further provides another compound of the Formula (A):

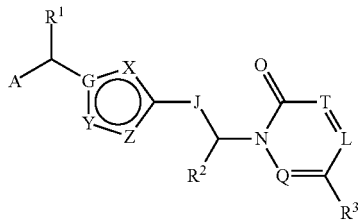

Formula (A)

or a pharmaceutically acceptable salt, polymorph, prodrug, solvate or clathrate thereof, wherein:
A is cycloalkyl, aryl, arylalkyl or heterocyclyl containing at least one N or O;
$R^1$ is H or $(C_1-C_6)$alkyl;
$R^2$ is H or $(C_1-C_6)$alkyl;
$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
at least one of G, X, Y and Z is N;
when $R^3$ is H, then L is $CR^6$ or T is $CR^7$, or both; and
when $R^3$ is cyano or bromo and A is aryl, then A is substituted aryl, $R^1$ is $(C_1-C_8)$alkyl, $R^2$ is $(C_1-C_8)$alkyl, L is $CR^6$, T is $CR^7$, G is C, or Q is N; and
when $R^3$ is t-butyl or benzodioxepinyl and A is aryl, then A is substituted aryl, $R^1$ is $(C_1-C_8)$alkyl, $R^2$ is $(C_1-C_8)$alkyl, L is $CR^6$, T is $CR^7$, G is C, or Q is CH.

The present disclosure further provides a compound of the Formula (B):

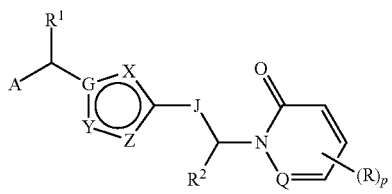

Formula (B)

or a pharmaceutically acceptable salt, polymorph, prodrug, solvate or clathrate thereof, wherein:
A is cycloalkyl, aryl, arylalkyl or heterocyclyl containing at least one N or O;
$R^1$ is H, alkyl or aryl;
$R^2$ is H, alkyl or aryl;
p is 1 or 2;
when p is 1 then R is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy
when p is 2 then each instance of R is independently fluoro, chloro, bromo, iodo, cyano, methyl, $(C_2-C_8)$alkyl, $(C_2-C_8)$alkenyl, $(C_2-C_8)$alkynyl, methoxy or $(C_2-C_8)$alkoxy provided that each instance of R is not the same;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
Q is N, CH or $CCH_3$.

The present disclosure further provides a compound of the Formula (C):

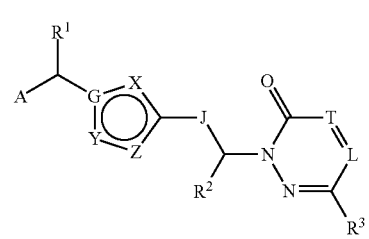

Formula (C)

or a pharmaceutically acceptable salt, polymorph, prodrug, solvate or clathrate thereof, wherein:
A is cycloalkyl, aryl, arylalkyl or heterocyclyl;
$R^1$ is H, alkyl or aryl;
$R^2$ is H, alkyl or aryl;
$R^3$ is H, fluoro, chloro, bromo, iodo, cyano, methyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
G is C or N;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
L is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy,
at least one of G, X, Y and Z is N, and
when $R^3$ is H, then L is $CR^6$ or T is $CR^7$, or both.

The present disclosure further provides a compound of the Formula (D):

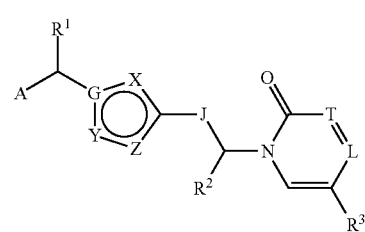

Formula (D)

or a pharmaceutically acceptable salt, polymorph, prodrug, solvate or clathrate thereof, wherein:

A is cycloalkyl, aryl, arylalkyl or heterocyclyl containing at least one N or O;

$R^1$ is H or $(C_1-C_8)$alkyl;

$R^2$ is H or $(C_1-C_8)$alkyl;

$R^3$ is H, fluoro, chloro, iodo, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

G is C or N;

X is N, O, S, CH or $CR^4$, wherein $R^4$ is $(C_1-C_8)$alkyl;

Y is N, O, S, CH or $CR^5$, wherein $R^5$ is $(C_1-C_8)$alkyl;

Z is N, O, S, CH or $CCH_3$;

J is CO, $(C_1)$alkyl or a bond;

L is N, CH or $CR^6$, wherein $R^6$ is fluoro, chloro, bromo, iodo, cyano, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

T is N, CH or $CR^7$, wherein $R^7$ is fluoro, bromo, iodo, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

at least one of G, X, Y and Z is N, and when $R^3$ is H, then L is $CR^6$ or T is $CR^7$, or both.

The present disclosure further provides a compound of the Formula E, which includes Formula (E1), Formula (E2), Formula (E3), Formula (E4), Formula (E5), Formula (E6), Formula (E7) and Formula (E8):

Formula (E1)

Formula (E2)

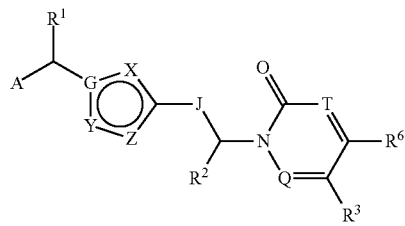

Formula (E3)

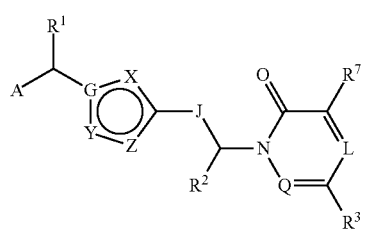

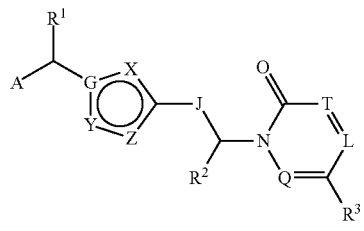

Formula (E4)

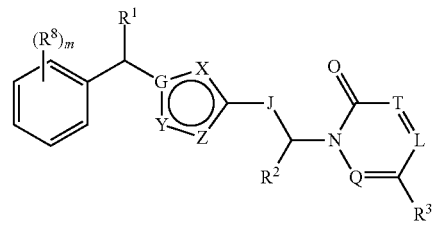

Formula (E5)

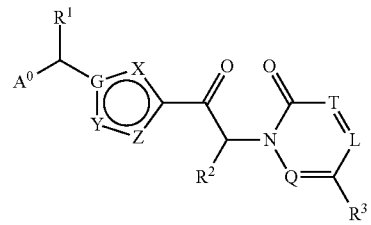

Formula (E6)

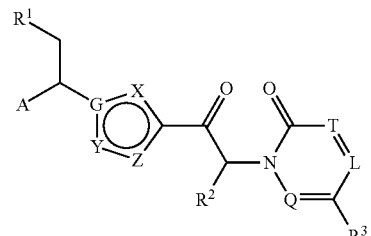

Formula (E7)

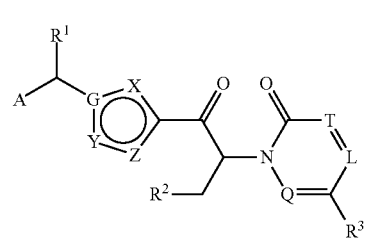

Formula (E8)

or a pharmaceutically acceptable salt, polymorph, prodrug, solvate or clathrate thereof, wherein:

A, if present, is cycloalkyl, aryl, arylalkyl or heterocyclyl;

$A^0$, if present, is cycloalkyl, arylalkyl or heterocyclyl containing at least one N or O;

$Cy^0$, if present, is a substituted heterocyclyl containing at least one S, wherein $Cy^0$ has m $R^8$ substituents;

$R^1$ is H or $(C_1-C_8)$alkyl;

$R^2$ is H or $(C_1-C_8)$alkyl;

$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

G is C or N;

X is N, O, S, CH or $CR^4$, wherein $R^4$ is $(C_1-C_8)$alkyl;

Y is N, O, S, CH or $CR^5$, wherein $R^5$ is $(C_1-C_8)$alkyl;

Z is N, O, S, CH or CCH$_3$;
J is CO, (C$_1$)alkyl or a bond;
Q is N, CH, CF or CCH$_3$;
L, if present, is N, CH or CR$^6$, wherein R$^6$ is fluoro, chloro, bromo, iodo, cyano, (C$_2$-C$_8$)alkyl, methoxy, (C$_2$-C$_8$)alkoxy, acetamido, (C$_3$-C$_8$)alkylamido, (C$_2$-C$_8$) alkenyl, (C$_2$-C$_8$)alkynyl, methoxycarbonyl, (C$_2$-C$_8$) alkoxy-carbonyl or carboxy; T, if present, is N, CH or CR$^7$, wherein R$^7$ is fluoro, bromo, iodo, (C$_2$-C$_8$)alkyl, methoxy, (C$_2$-C$_8$)alkoxy, acetamido, (C$_3$-C$_8$)alkylamido, (C$_2$-C$_8$)alkenyl, (C$_2$-C$_8$)alkynyl, methoxycarbonyl, (C$_2$-C$_8$)alkoxy-carbonyl or carboxy,
R$^8$, if present, is alkylsulfonyl, alkyl, alkoxy, cyano, halo, difluoromethyl or carboxy or two adjacent instances of R$^8$ can form a fused dioxolane ring;
n, if present, is 0-5;
m, if present, is 1-5; and
at least one of X, Y, Z and G, if present, is N.

In various embodiments of Formulae (A)-(E), A is substituted cycloalkyl, unsubstituted cycloalkyl, substituted aryl, unsubstituted aryl, substituted arylalkyl, unsubstituted arylalkyl, substituted nonaromatic heterocyclyl, unsubstituted nonaromatic heterocyclyl, substituted aromatic heterocyclyl or unsubstituted aromatic heterocyclyl. In further embodiments, A can be cycloalkyl, aryl, arylalkyl or heterocyclyl which is substituted by alkylsulfonyl, alkyl, alkoxy, cyano, halo, difluoromethyl or carboxy. In some embodiments, A can be other than phenyl, for example A can be cycloalkyl, arylalkyl or heterocyclyl, which is substituted by alkylsulfonyl, alkyl, alkoxy, cyano, halo, difluoromethyl or carboxy. A can also be an aryl other than phenyl. In yet further various embodiments, A can be cycloalkyl, aryl, arylalkyl or heterocyclyl which is substituted by, for example, one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic add, carboxylic acid, dialkylamino, dialkylamido, or combination thereof. In some embodiments, A can be monosubstituted, disubstituted, trisubstituted or fully substituted. In various embodiments A is cycloalkyl, aryl, arylalkyl or heterocyclyl containing at least one N or O.

In various embodiments of Formulae (A)-(E), A is a heterocyclyl. In various embodiments A is a heterocyclyl containing at least one N or O. For example, A can be tetrahydrofuranyl, tetrahydropyranyl, indole, quinoline, isoquinoline, pyrrolidinyl, piperidinyl, piperazinyl, pyrrolyl, furanyl, oxazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, benzo[d][1,3]dioxole, pyridinyl or pyrimidinyl. In some embodiments, A can be a heterocyclyl other than pyrrolyl. In some embodiments, the heterocyclyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. As a further example, A can be heterocyclyl substituted with alkylsulfonyl, alkyl, alkoxy, cyano, halo, difluoromethyl or carboxy.

In various embodiments of Formulae (A)-(E), A is cycloalkyl. For example, A can be cyclopropyl, cyclobutyl, cyclopentane, cyclohexane or bicyclo[1.1.1]pentane. In some embodiments, the cycloalkyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof. As a further example, A can be cycloalkyl substituted with alkylsulfonyl, alkyl, alkoxy, cyano, halo, difluoromethyl or carboxy.

In various embodiments of Formulae (A)-(E), A is aryl. For example, A can be unsubstituted phenyl or substituted phenyl. As another example, A can be unsubstituted naphthalene or substituted naphthalene. As a further example, A can be phenyl substituted with alkylsulfonyl, alkyl, alkoxy, cyano, halo, difluoromethyl or carboxy. As a further example, A can be a phenyl substituted with fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido.

In various embodiments of Formulae (A)-(E), A is

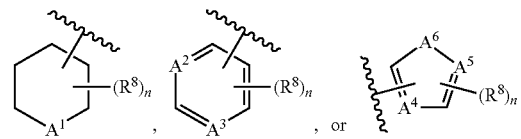

wherein:
n is 0-3; A$^1$ is O or NH, N-Alkyl; each of A$^2$ and A$^3$ is independently, CH, CR$^8$ or N; each of A$^4$, A$^5$, and A$^6$ is independently CH, C-alkyl, N, NR$^9$ or O, provided that at least one of A$^4$, A$^5$, and A$^6$ is N or NR$^9$; and R$^8$ is independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido; and R$^9$ is independently H or alkyl. In some embodiments, R$^8$ is independently alkylsulfonyl, alkyl, alkoxy, cyano, halo, difluoromethyl or carboxy.

In various embodiments of Formulae (A)-(E), A is

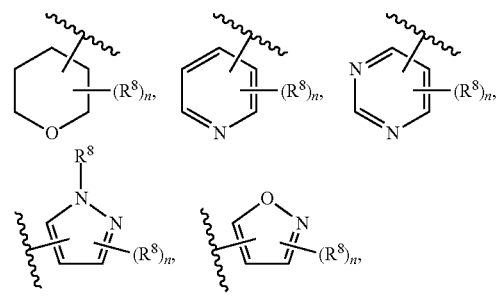

-continued

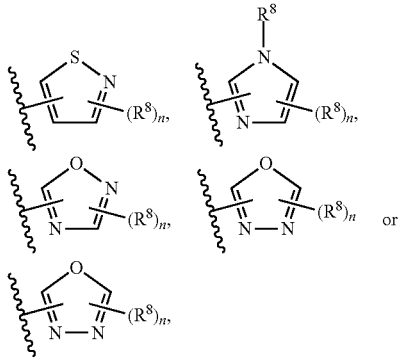

wherein: n is 0-3; $R^8$ is independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido.

In various embodiments of Formulae (A)-(E), A is

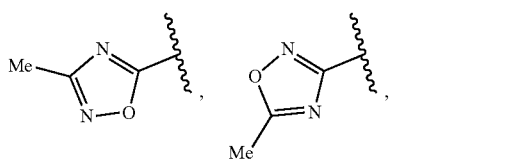

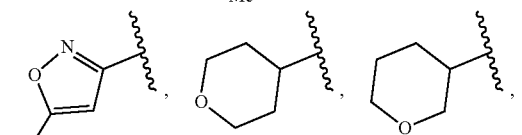

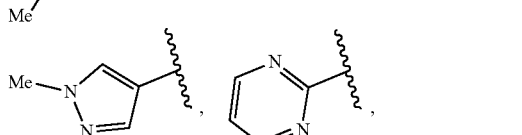

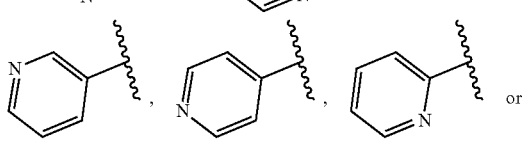

or

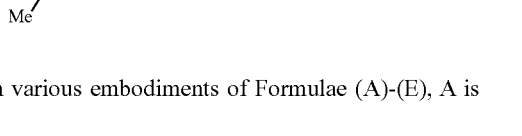

In various embodiments of Formulae (A)-(E), A is

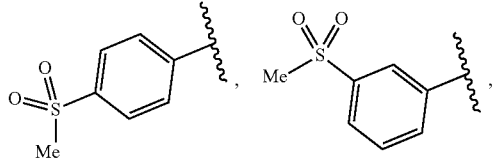

-continued

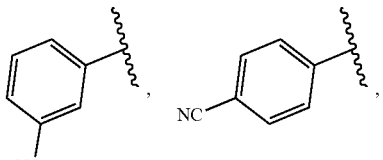

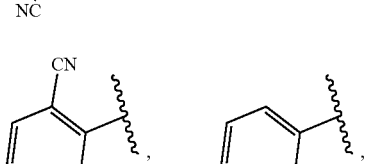

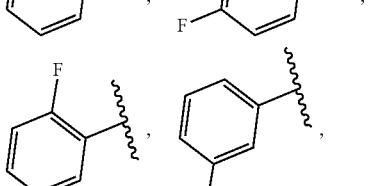

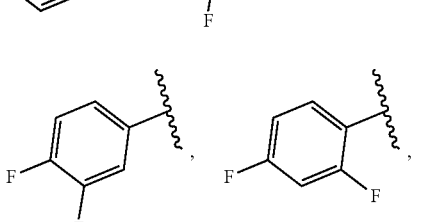

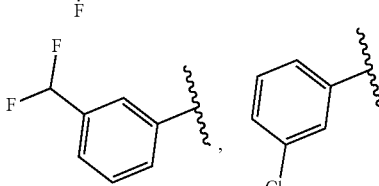

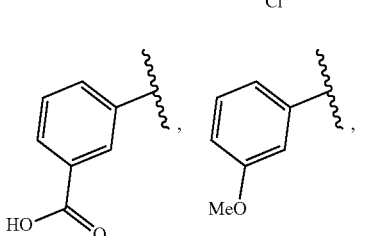

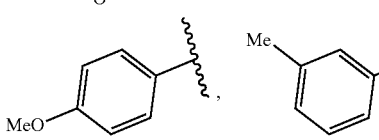

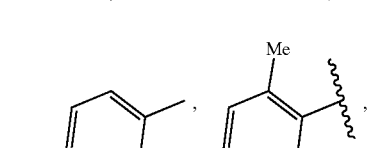

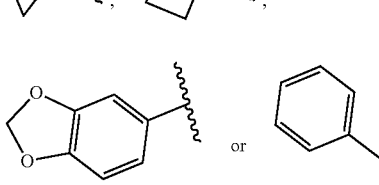

or

In some embodiments of Formulae (A)-(E), A is a

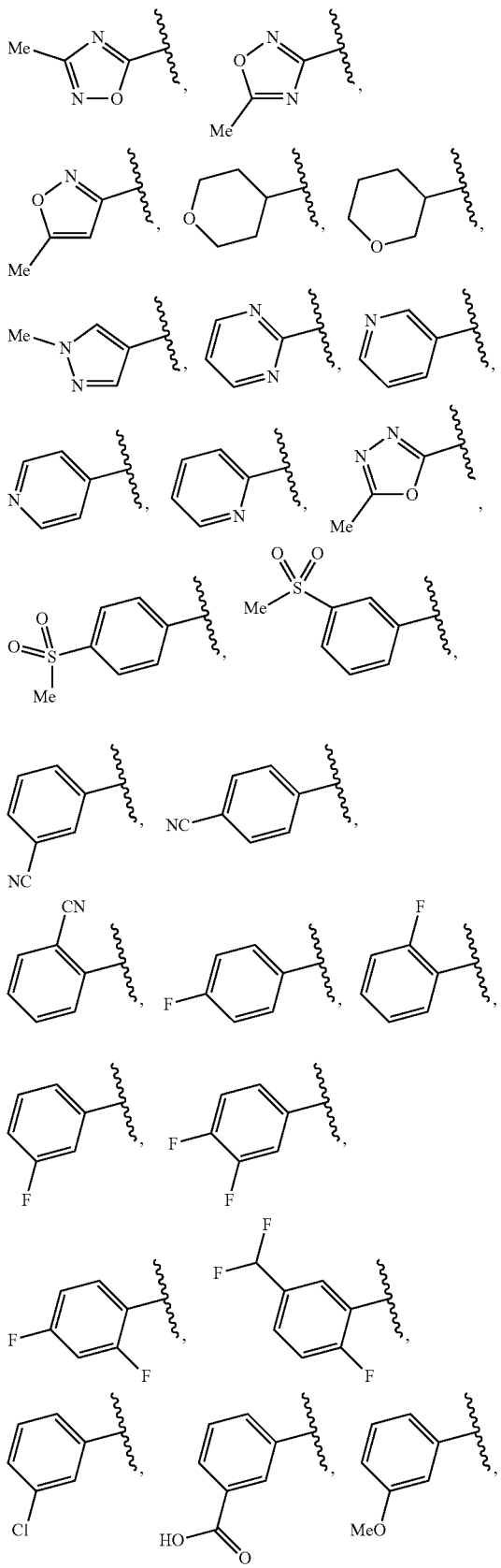

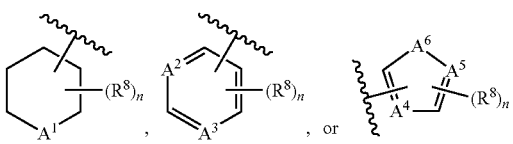

which is further substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof.

In various embodiments of Formulae (A)-(E), A is cycloalkyl, aryl, arylalkyl or heterocyclyl and is unsubstituted. In certain embodiments, A can be selected from substituted aryl and substituted or unsubstituted cycloalkyl, arylalkyl and heterocyclyl.

In various embodiments of Formulae (A)-(E), A can be defined as $A^0$. In various embodiments, $A^0$, if present, is substituted cycloalkyl, unsubstituted cycloalkyl, substituted arylalkyl, unsubstituted arylalkyl, substituted nonaromatic heterocyclyl, unsubstituted nonaromatic heterocyclyl, substituted aromatic heterocyclyl or unsubstituted aromatic heterocyclyl. In various embodiments, $A^0$, if present, can be cycloalkyl, arylalkyl or heterocyclyl and is substituted by alkylsulfonyl, alkyl, alkoxy, cyano, halo, difluoromethyl or carboxy. In various embodiments, $A^0$, if present, is tetrahydrofuranyl, tetrahydropyranyl, pyrrolidinyl, piperidinyl, piperazinyl, pyrrolyl, furanyl, oxazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, benzo[d][1,3]dioxole, pyridinyl or pyrimidinyl. In various embodiments, $A^0$, if present, can be cyclopropyl, cyclobutyl, or bicyclo[1.1.1]pentane.

In some embodiments, $A^0$, if present, is:

wherein:
n is 0-3;
$A^1$ is O or NH, N-Alkyl;
each of $A^2$ and $A^3$ is independently, CH, $CR^8$ or N provided that at least one of $A^2$ and $A^3$ is N;

each of $A^4$, $A^5$, and $A^6$ is independently CH, C-alkyl, N, $NR^9$ or O, provided that at least one of $A^4$, $A^5$, and $A^6$ is N or $NR^9$; and $R^8$ is independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido; and $R^9$ is H or alkyl. In some embodiments, Re is independently alkylsulfonyl, alkyl, alkoxy, cyano, halo, difluoromethyl or carboxy.

In some embodiments, $A^0$, if present, is:

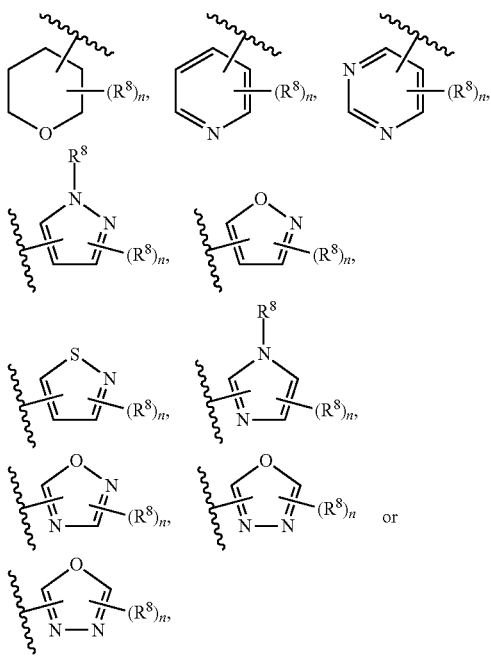

wherein: n is 0-3; and $R^8$ is independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments $R^8$ is independently alkylsulfonyl, alkyl, alkoxy, cyano, halo, difluoromethyl or carboxy.

The compound of any preceding claim, wherein $A^0$ is:

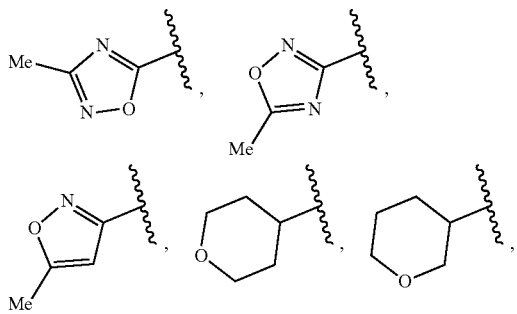

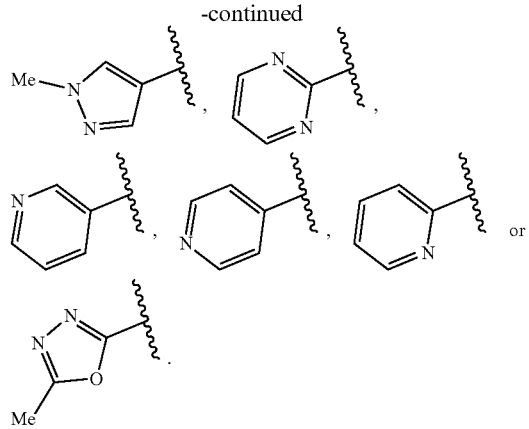

In various embodiments of Formulae (A)-(E), at least one of G, X, Y and Z is N; at least two of G, X, Y and Z is N; at least one of G, X, Y and Z is N, S or O; at least one of G, X, Y and Z is S or O; at least one of G, X, Y and Z is N and one of G, X, Y and Z is S or O; or at least two of G, X, Y and Z is N and one of G, X, Y and Z is S or O; or a combination thereof.

In various embodiments of Formulae (A)-(E), G can be C. In other embodiments G can be N.

In some embodiments of Formulae (A)-(E), at least two of G, X, Y and Z are other than N, O and S.

In further embodiments of Formulae (A)-(E), X is $CR^4$ or Y is $CR^5$ or both. In various embodiments $R^4$ is methyl, or $R^5$ is methyl, or both. In some embodiments $R^4$ and $R^5$ are the same and in other embodiments $R^4$ and $R^5$ are different. In further embodiments, $R^4$ is ethyl, $(C_3-C_8)$alkyl, difluoromethyl or trifluoromethyl. In yet further embodiments, $R^5$ is ethyl, $(C_3-C_8)$alkyl, difluoromethyl or trifluoromethyl.

In various embodiments of Formulae (A), (B) and (E), Q is N.

In various embodiments of Formulae (A), (B) and (E), Q is CH.

In further embodiments of Formulae (A) and (C)-(E), no more than one of Q, if present, L and T is N.

In various embodiments of Formulae (A) and (C)-(E), $R^3$, $R^6$ and $R^7$, if present, are each different.

In various embodiments of Formulae (A) and (C)-(E), L is $CR^6$ or T is $CR^7$, and $R^3$ is other than H.

In various embodiments of Formulae (A) and (C)-(E), L is $CR^6$, T is $CR^7$, and $R^3$ is H.

In various embodiments of Formulae (A) and (C)-(E), L is CH or T is CH, and $R^3$ is other than H.

In various embodiments of Formulae (A) and (C)-(E), L is $CR^6$ or T is $CR^7$, and $R^3$ is H.

In certain embodiments of Formulae (A) and (C)-(E), $R^3$ is H, fluoro, chloro, bromo, iodo, cyano, methyl, $(C_2-C_8)$ alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; Q is N, CH, CF or $CCH_3$; L is N, CH or $CR^6$, wherein $R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, $(C_2-C_8)$alkoxy-carbonyl or carboxy; T is N, CH or $CR^7$, wherein $R^7$ is fluoro, chloro, bromo, iodo, cyano methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy. In some embodiments, no more than one of Q, L and T is N. In various embodiments, Q is N. In further various embodiments, $R^3$, $R^6$ and $R^7$ are different. In further embodiments, L is $CR^6$ or T is $CR^7$, and $R^3$ is other than H. In some embodiments, L is CH or T is CH, and $R^3$ is other than H. In yet further embodiments, L is $CR^6$ or T is $CR^7$, and $R^3$ is H.

In further embodiments of Formulae (A) and (C)-(E), $R^3$ is H, fluoro, chloro, bromo, iodo, cyano, methyl, ($C_2$-$C_8$) alkyl, methoxy, ($C_2$-$C_8$)alkoxy, acetamido, ($C_3$-$C_8$)alkylamido, ($C_2$-$C_8$)alkenyl, ($C_2$-$C_8$)alkynyl, methoxycarbonyl, ($C_2$-$C_8$)alkoxy-carbonyl or carboxy; $R^6$ is fluoro, chloro, bromo, iodo, cyano, methyl, ($C_2$-$C_8$)alkyl, methoxy, ($C_2$-$C_8$)alkoxy, acetamido, ($C_3$-$C_8$)alkylamido, ($C_2$-$C_8$)alkenyl, ($C_2$-$C_8$)alkynyl, ($C_2$-$C_8$)alkoxy-carbonyl or carboxy; and $R^7$ is fluoro, chloro, bromo, iodo, cyano methyl, ($C_2$-$C_8$)alkyl, methoxy, ($C_2$-$C_8$)alkoxy, acetamido, ($C_3$-$C_8$)alkylamido, ($C_2$-$C_8$)alkenyl, ($C_2$-$C_8$)alkynyl, methoxycarbonyl, ($C_2$-$C_8$) alkoxy-carbonyl or carboxy. In some embodiments, $R^3$ can be substituted or unsubstituted ($C_1$-$C_8$)alkyl. In some embodiments, Re can be substituted or unsubstituted ($C_1$-$C_8$)alkyl. In some embodiments, $R^7$ can be substituted or unsubstituted ($C_1$-$C_8$)alkyl.

In some certain embodiments of Formulae (A) and (C)-(E), $R^3$, $R^6$ and $R^7$ is each independently a substituent selected from fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, where there are two or more adjacent groups, the groups can be linked to form a carbocyclic or heterocyclic ring.

In various embodiments, $R^3$ is substituted or unsubstituted ($C_1$-$C_8$)alkyl, ($C_2$-$C_8$)alkenyl) or ($C_2$-$C_8$)alkynyl). In some embodiments, $R^6$, if present, is substituted or unsubstituted (($C_1$-$C_8$)alkyl, ($C_2$-$C_8$)alkenyl) or ($C_2$-$C_8$)alkynyl). In some embodiments, $R^7$, if present, is substituted or unsubstituted ($C_1$-$C_8$)alkyl, ($C_2$-$C_8$)alkenyl) or ($C_2$-$C_8$)alkynyl). In some embodiments, at least one of $R^3$, $R^6$ and $R^7$, if present, is substituted or unsubstituted ($C_1$-$C_8$)alkyl. In some embodiments, at least one of $R^3$, $R^6$ and $R^7$, if present, is substituted or unsubstituted ($C_2$-$C_8$)alkenyl). In some embodiments, at least one of $R^3$, $R^6$ and $R^7$, if present, is substituted or unsubstituted ($C_2$-$C_8$)alkynyl).

In some certain embodiments of Formulae (A) and (C)-(E), $R^3$, $R^6$ and $R^7$ is each independently an alkyl other than haloalkyl or an alkyl other than fluoro-substituted alkyl. In some certain embodiments of Formulae (A) and (C)-(E), $R^3$, $R^6$ and $R^7$ is each independently a substituent other than cyano, other than tert-butyl, other than trifluoromethyl, other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or a substituent which meets a combination of such descriptions.

In some embodiments of Formulae (A)-(E), $R^1$ is H or alkyl. In further embodiments, $R^1$ is H so as to result in a methylene (—$CH_2$—) unit. In other embodiments $R^1$ is methyl or ($C_2$-$C_8$)alkyl. In yet further various embodiments, $R^1$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluorom- ethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In specific embodiments, $R^2$ forms a spiro ring with the carbon to which it is attached.

In various embodiments of Formulae (A)-(E), $R^2$ is H, alkyl, aryl or arylalkyl. In some further embodiments $R^2$ is H, methyl, ($C_2$-$C_8$)alkyl, benzyl, or biphenylmethyl. In yet further various embodiments, $R^2$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In specific embodiments, $R^2$ forms a spiro ring with the carbon to which it is attached. In other specific embodiments, $R^2$ forms a ring with J.

In various embodiments of Formulae (A) and (C)-(E), J is

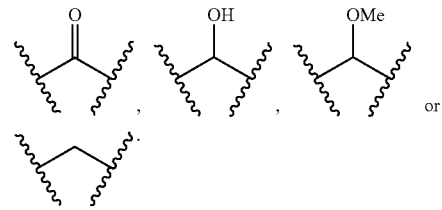

In another embodiment, J is a

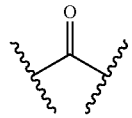 [SMILES: *C(*)=O]

where the carbonyl group has been masked, e.g., as a methylenedioxy, a ethylenedioxy, a thial, a dithiolane, imine or other related groups. In various embodiments, J is a substituted methylene.

In various embodiments of Formula (A),
A is cycloalkyl, aryl, arylalkyl or heterocyclyl containing at least one N or O;
$R^1$ is H or ($C_1$-$C_8$)alkyl;
$R^2$ is H or ($C_1$-$C_8$)alkyl;
$R^3$ is H, fluoro, chloro, iodo, methyl, methoxy, ($C_1$-$C_8$) alkoxy, acetamido, ($C_3$-$C_8$)alkylamido, ($C_2$-$C_8$)alkenyl, ($C_2$-$C_8$)alkynyl, methoxycarbonyl, ($C_2$-$C_8$) alkoxy-carbonyl or carboxy;
G is C or N;
X is N, O, S, CH or $CR^4$, wherein $R^4$ is ($C_1$-$C_8$)alkyl;
Y is N, O, S, CH or $CR^5$, wherein $R^5$ is ($C_1$-$C_8$)alkyl;
Z is N, O, S, CH or $CCH_3$;
J is CO, ($C_1$)alkyl or a bond;
Q is N, CH, CF or $CCH_3$;
L is N, CH or $CR^6$, wherein $R^6$ is fluoro, chloro, bromo, iodo, cyano, ($C_2$-$C_8$)alkyl, methoxy, ($C_2$-$C_8$)alkoxy, acetamido, ($C_3$-$C_8$)alkylamido, ($C_2$-$C_8$)alkenyl, ($C_2$-$C_8$)alkynyl, methoxycarbonyl, ($C_2$-$C_8$)alkoxy-carbonyl or carboxy;
T is N, CH or $CR^7$, wherein $R^7$ is fluoro, bromo, iodo, ($C_2$-$C_8$)alkyl, methoxy, ($C_2$-$C_8$)alkoxy, acetamido, ($C_3$-

$C_8$)alkylamido, ($C_2$-$C_8$)alkenyl, ($C_2$-$C_8$)alkynyl, methoxycarbonyl, ($C_2$-$C_8$)alkoxy-carbonyl or carboxy;
at least one of G, X, Y and Z is N; and
when $R^3$ is H, then L is $CR^6$ or T is $CR^7$, or both.
In various embodiments of the preceding formulae, such as Formulae (I), (II) and (A), the compound has the structure:
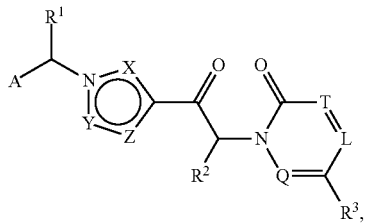
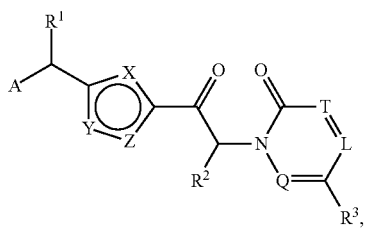
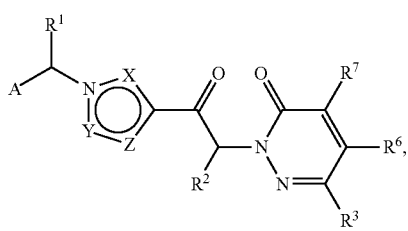
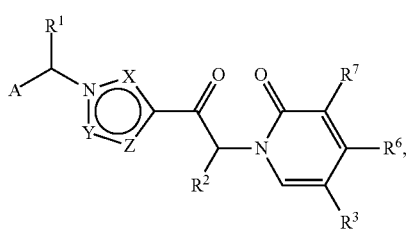
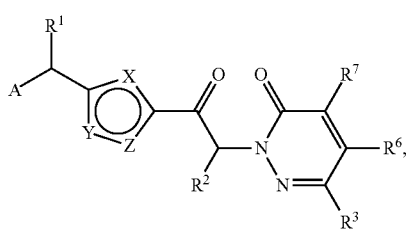
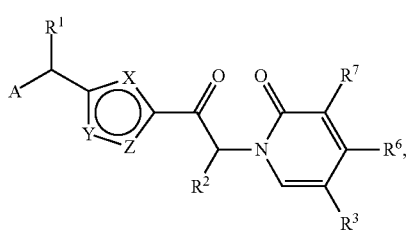
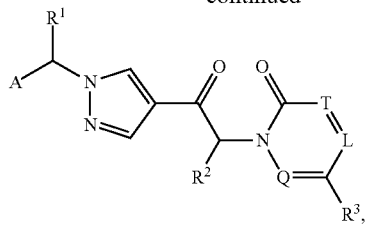
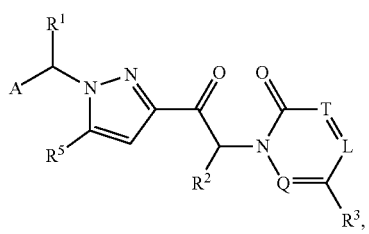
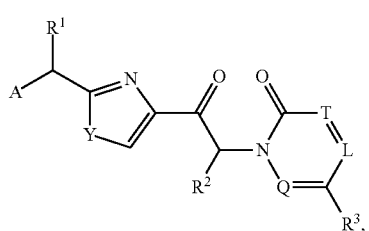
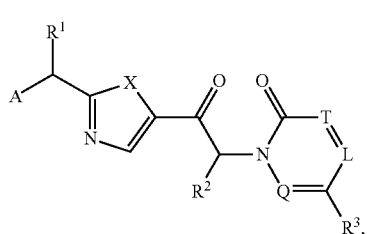
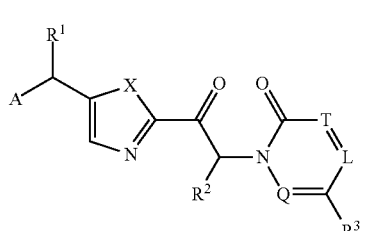
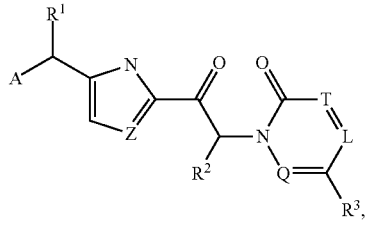
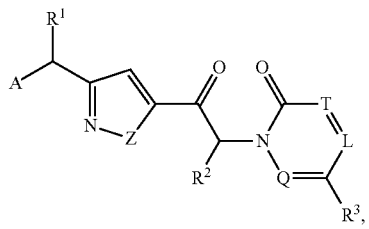

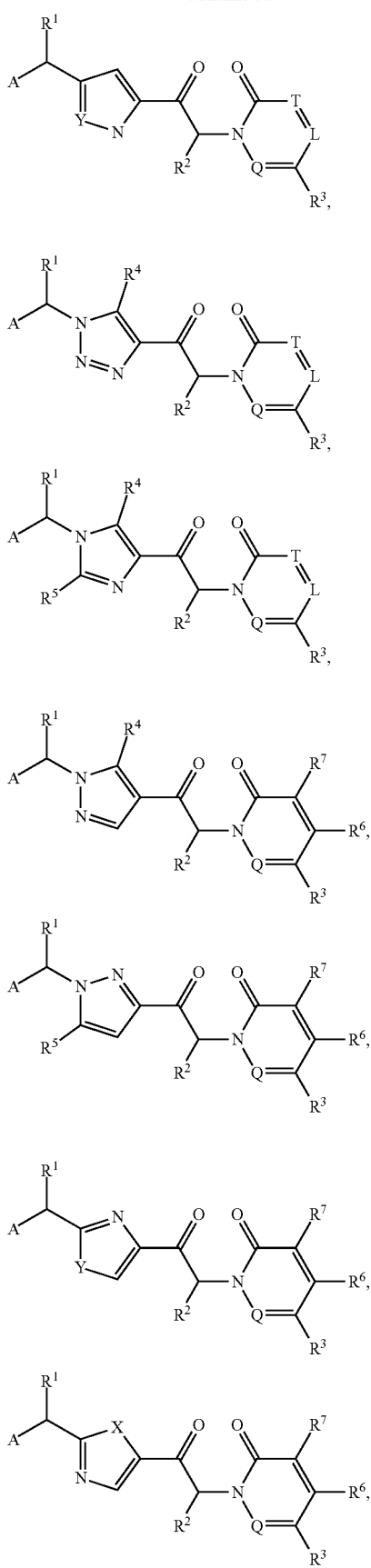
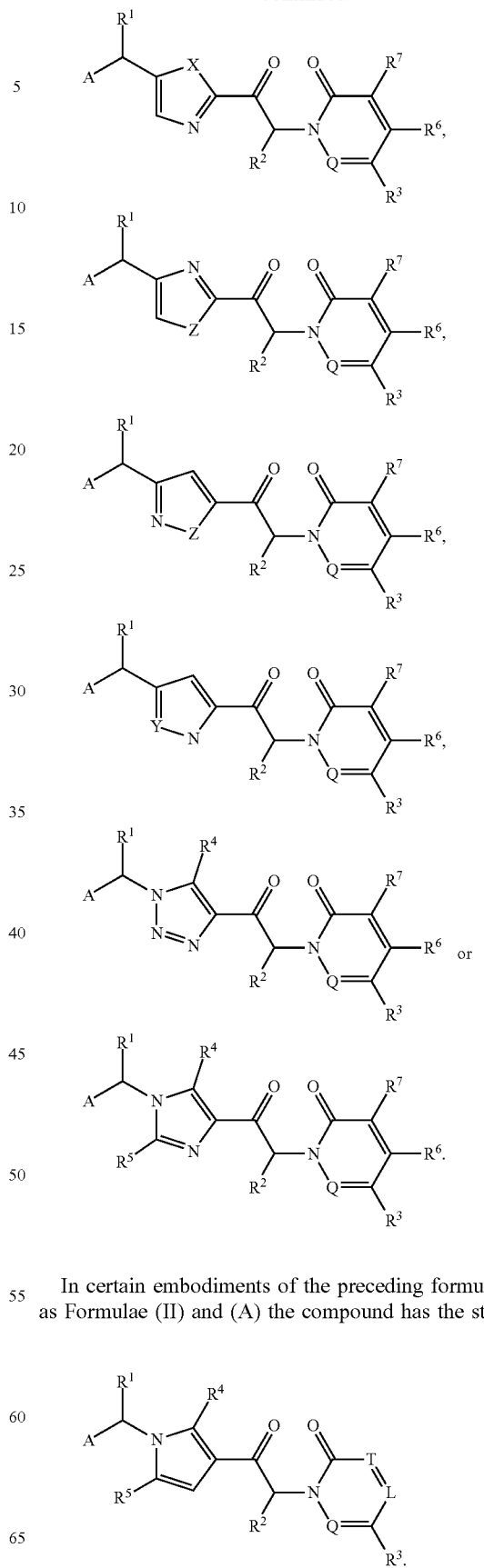
In certain embodiments of the preceding formulae, such as Formulae (II) and (A) the compound has the structure:
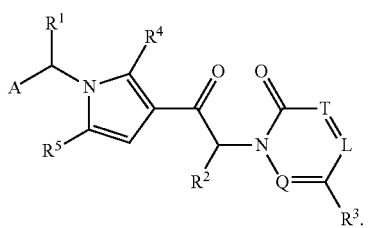

In embodiments, A, Q, T, L, $R^1$, $R^2$, $R^3$, $R^4$, and $R^5$, if present, can be defined in any such manner as described hereinabove.

The present disclosure also provides a compound of the Formula (F):

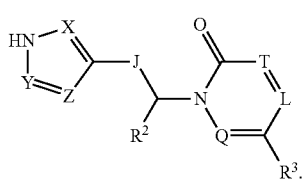

Formula (F)

or a pharmaceutically acceptable salt, polymorph, prodrug, solvate or clathrate thereof, wherein:

$R^2$ is H or alkyl;
X is N, O, S, CH or $CR^4$, wherein $R^4$ is alkyl;
Y is N, O, S, CH or $CR^5$, wherein $R^5$ is alkyl;
Z is N, O, S, CH or $CCH_3$;
J is CO, $(C_1)$alkyl or a bond;
Q is N, CH, CF or $CCH_3$;
L is N, CH or $CR^6$;
T is N, CH or $CR^7$; and
$R^3$, $R^6$ and $R^7$ is each independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido; and $R^9$ is H or alkyl. In some embodiments, $R^8$ is alkylsulfonyl, alkyl, alkoxy, cyano, halo, difluoromethyl or carboxy.

In various embodiments of Formula (F), $R^2$ is H, methyl, $(C_2-C_8)$alkyl or arylalkyl. In further embodiments of Formula (F), $R^2$ is H, methyl, benzyl or biphenylmethyl.

In various embodiments of Formula (F), $R^4$, if present, and $R^5$, if present, is each independently (C1-C8)alkyl.

In various embodiments of Formula (F), $R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

In various embodiments of Formula (F), $R^7$, if present, and $R^8$, if present, is each independently is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

In various embodiments of Formula (F), the compound, or a pharmaceutically acceptable salt, polymorph, prodrug, solvate or clathrate thereof, has the structure of the Formula (F):

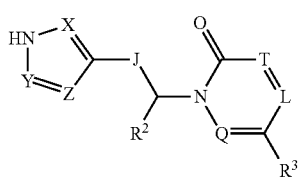

Formula (F)

wherein:
$R^2$ is H or $(C_1-C_8)$alkyl;
$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
X is N, O, S, CH or $CR^4$, wherein $R^4$ is $(C_1-C_8)$alkyl;
Y is N, O, S, CH or $CR^5$, wherein $R^5$ is $(C_1-C_8)$alkyl;
Z is N, O, S, CH or $CCH_3$;
J is CO, $(C_1)$alkyl or a bond;
Q is N, CH, CF or $CCH_3$;
L is N, CH or $CR^6$, wherein $R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;
T is N, CH or $CR^7$, wherein $R^7$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

In various embodiments of Formula (F), at least one of G, X, Y and Z is N; at least two of G, X, Y and Z is N; at least one of G, X, Y and Z is N, S or O; at least one of G, X, Y and Z is S or O; at least one of G, X, Y and Z is N and one of G, X, Y and Z is S or O; or at least two of G, X, Y and Z is N and one of G, X, Y and Z is S or O; or a combination thereof.

In various embodiments of Formula (F), G can be C. In other embodiments G can be N.

In some embodiments of Formula (F), at least two of G, X, Y and Z are other than N, O and S.

In further embodiments of Formula (F), X is $CR^4$ or Y is $CR^5$ or both. In various embodiments $R^4$ is methyl, or $R^5$ is methyl, or both. In some embodiments $R^4$ and $R^5$ are the same and in other embodiments $R^4$ and $R^5$ are different. In further embodiments, $R^4$ is ethyl, $(C_3-C_8)$alkyl, difluoromethyl or trifluoromethyl. In yet further embodiments, $R^5$ is ethyl, $(C_3-C_8)$alkyl, difluoromethyl or trifluoromethyl.

In further embodiments of Formula (F), Q is N or CH.

In various embodiments of Formula (F), $R^3$, $R^6$ and $R^7$, if present, are each different.

In various embodiments of Formula (F), L is $CR^6$ or T is $CR^7$, and $R^3$ is other than H.

In various embodiments of Formula (F), L is $CR^6$, T is $CR^7$, and $R^3$ is H.

In various embodiments of Formula (F), L is CH or T is CH, and $R^3$ is other than H.

In various embodiments of Formula (F), L is $CR^6$ or T is $CR^7$, and $R^3$ is H.

In various embodiments of Formula (F), $R^2$ is H or $(C_1-C_8)$alkyl. In some further embodiments $R^2$ is H, methyl, $(C_2-C_8)$alkyl, benzyl, or biphenylmethyl. In yet further various embodiments, $R^2$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfinyl, dialkylaminosulfonyl, sulfonic acid, carboxylic acid, dialkylamino or dialkylamido. In specific embodiments, $R^2$ forms a spiro ring with the carbon to which it is attached. In other specific embodiments, $R^2$ forms a ring with J.

In various embodiments of Formula (F), J is

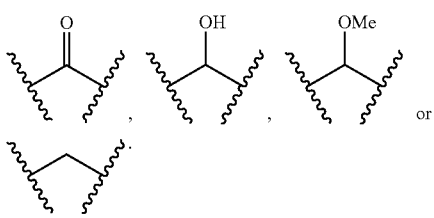

In another embodiment, J is a

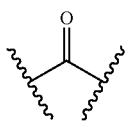

where the carbonyl group has been masked, e.g., as a methylenedioxy, a ethylenedioxy, a thial, a dithiolane, imine or other related groups.

The present disclosure further provides a compound of the Formula (G):

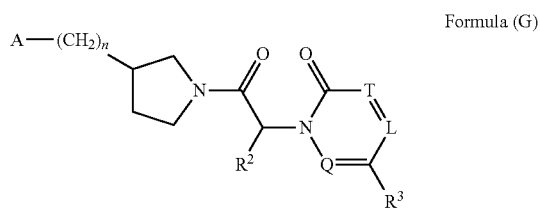

Formula (G)

or a pharmaceutically acceptable salt, polymorph, prodrug, solvate or clathrate thereof, wherein:

A is cycloalkyl, aryl, arylalkyl or heterocyclyl;
n is 0-6;
$R^2$ is H, alkyl or aryl;
Q is N, CH, CF or $CCH_3$;
L is N, CH or $CR^6$; and
T is N, CH or $CR^7$; and
$R^3$, $R^6$ and $R^7$ is each independently fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthio, alkylsulfonyl, alkylsulfinyl, dialkylaminosulfonyl, sulfonic acid, carboxylic acid, dialkylamino or dialkylamido; and $R^9$ is H or alkyl. In some embodiments, $R^8$ is alkylsulfonyl, alkyl, alkoxy, cyano, halo, difluoromethyl or carboxy.

In various embodiments of Formula (G), A is substituted cycloalkyl, unsubstituted cycloalkyl, substituted aryl, unsubstituted aryl, substituted arylalkyl, unsubstituted arylalkyl, substituted nonaromatic heterocyclyl, unsubstituted nonaromatic heterocyclyl, substituted aromatic heterocyclyl or unsubstituted aromatic heterocyclyl. In further embodiments, A can be cycloalkyl, aryl, arylalkyl or heterocyclyl which is substituted by alkylsulfonyl, alkyl, alkoxy, cyano, halo, difluoromethyl or carboxy. In some embodiments, A can be other than phenyl, for example A can be cycloalkyl, arylalkyl or heterocyclyl, which is substituted by alkylsulfonyl, alkyl, alkoxy, cyano, halo, difluoromethyl or carboxy. A can also be an aryl other than phenyl. In yet further various embodiments, A can be cycloalkyl, aryl, arylalkyl or heterocyclyl which is substituted by, for example, one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthio, alkylsulfonyl, alkylsulfinyl, dialkylaminosulfonyl, sulfonic acid, carboxylic acid, dialkylamino, dialkylamido, or combination thereof. In some embodiments, A can be monosubstituted, disubstituted, trisubstituted or fully substituted.

In various embodiments of Formula (G), A is a heterocyclyl. For example, A can be tetrahydrofuranyl, tetrahydropyranyl, indole, quinoline, isoquinoline, pyrrolidinyl, piperidinyl, piperazinyl, pyrrolyl, furanyl, oxazolyl, pyrazolyl, imidazolyl, 1,2,3-oxadiazol yl, 1,2,4-oxadiazolyl, 1,2,5-oxadiazolyl, 1,3,4-oxadiazolyl, 1,2,3-triazolyl, 1,2,4-triazolyl, benzo[d][1,3]dioxole, pyridinyl or pyrimidinyl. In some embodiments, A can be a heterocyclyl other than pyrrolyl. In some embodiments, the heterocyclyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthio, alkylsulfonyl, alkylsulfinyl, dialkylaminosulfonyl, sulfonic acid, carboxylic acid, dialkylamino, dialkylamido, or combination thereof. As a further example, A can be heterocyclyl substituted with alkylsulfonyl, alkyl, alkoxy, cyano, halo, difluoromethyl or carboxy.

In various embodiments of Formula (G), A is cycloalkyl. For example, A can be cyclopropyl, cyclobutyl, cyclopentane, cyclohexane or bicyclo[1.1.1]pentane. In some embodiments, the cycloalkyl can be substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthio, alkylsulfonyl, alkylsulfinyl, dialkylaminosulfonyl, sulfonic acid, carboxylic acid, dialkylamino, dialkylamido, or combination thereof. As a further example, A can be cycloalkyl substituted with alkylsulfonyl, alkyl, alkoxy, cyano, halo, difluoromethyl or carboxy.

In various embodiments of Formula (G), A is aryl. For example, A can be unsubstituted phenyl or substituted phenyl. As another example, A can be unsubstituted naphthalene or substituted naphthalene. As a further example, A can be phenyl substituted with alkylsulfonyl, alkyl, alkoxy, cyano, halo, difluoromethyl or carboxy. As a further example, A can be a phenyl substituted with fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthio, alkylsulfonyl, alkylsulfinyl, dialkylaminosulfonyl, sulfonic acid, carboxylic acid, dialkylamino or dialkylamido.

In various embodiments of Formula (G), A is

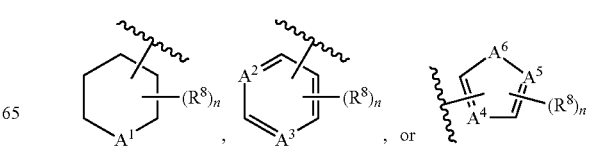

wherein:

n is 0-3; $A^1$ is O or NH, N-Alkyl; each of $A^2$ and $A^3$ is independently, CH, $CR^8$ or N; each of $A^4$, $A^5$, and $A^6$ is independently CH, C-alkyl, N, $NR^9$ or O, provided that at least one of $A^4$, $A^5$, and $A^6$ is N or $NR^9$; and $R^8$ is fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido; and $R^9$ is H or alkyl. In some embodiments, $R^8$ is alkylsulfonyl, alkyl, alkoxy, cyano, halo, difluoromethyl or carboxy.

In various embodiments of Formula (G), A is

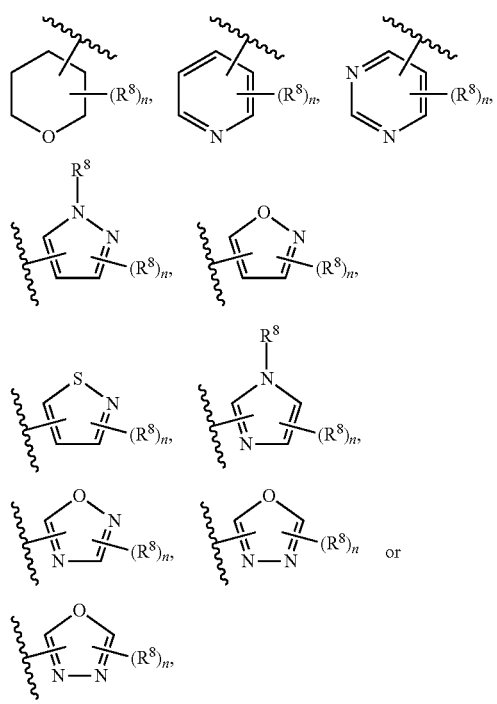

wherein: n is 0-3; $R^8$ is fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, $R^8$ is alkylsulfonyl, alkyl, alkoxy, cyano, halo, difluoromethyl or carboxy.

In various embodiments of Formula (G), A is

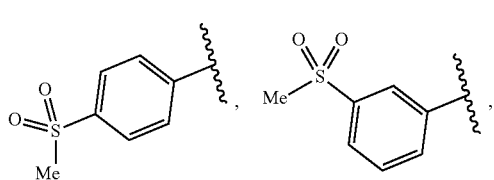

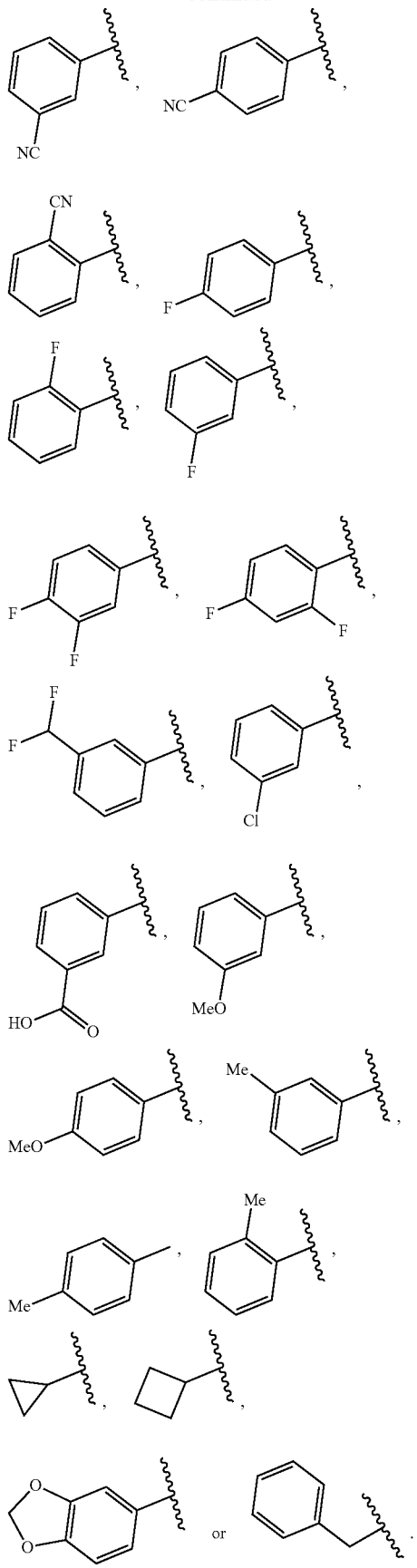

In various embodiments of Formula (G), A is

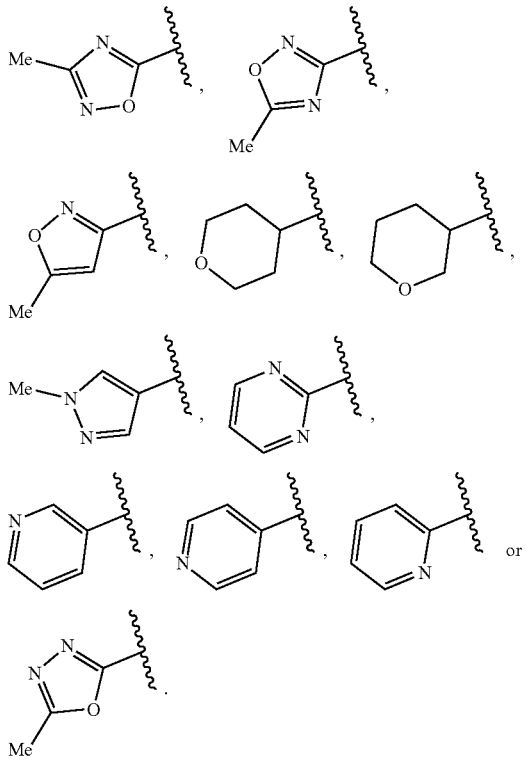

In some embodiments of Formula (G), A is a

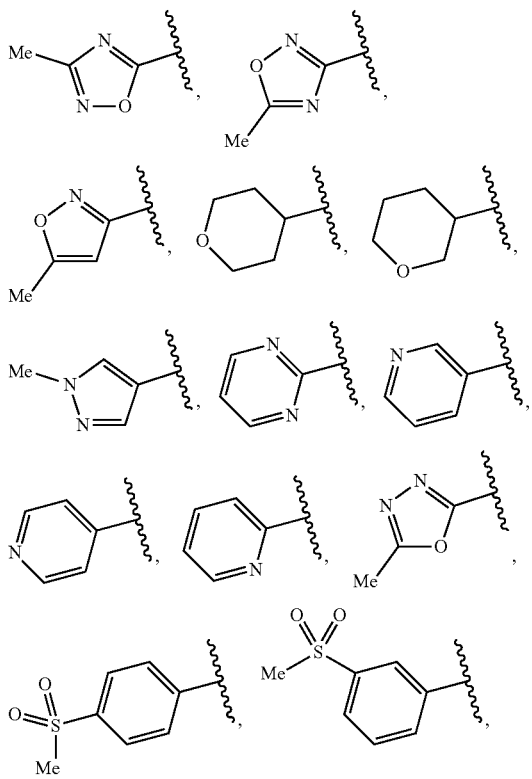

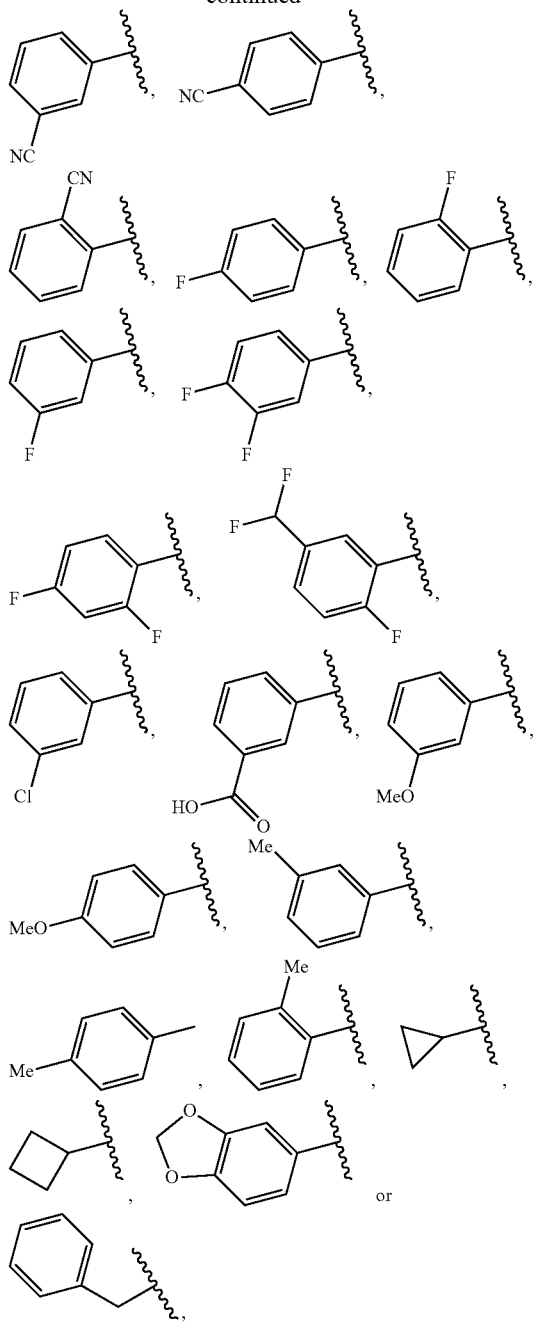

which is further substituted with one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino, dialkylamido, or combination thereof.

In various embodiments of Formula (G), A is cycloalkyl, aryl, arylalkyl or heterocyclyl and is unsubstituted. In certain embodiments, A can be selected from substituted aryl and substituted or unsubstituted cycloalkyl, arylalkyl and heterocyclyl.

In various embodiments of Formula (G), $R^2$ is H or $(C_1-C_8)$alkyl. In some further embodiments $R^2$ is H, methyl, $(C_2-C_8)$alkyl, benzyl, or biphenylmethyl. In yet further various embodiments, $R^2$ can be fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino or dialkylamido. In specific embodiments, $R^2$ forms a spiro ring with the carbon to which it is attached.

In various embodiments of Formula (G), $R^3$ is $R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

In various embodiments of Formula (G), $R^6$, if present, and $R^7$, if present, is each independently fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy.

In various embodiments of Formula (G), n is 1.

In various embodiments of Formula (G),

A is cycloalkyl, aryl, arylalkyl or heterocyclyl;

n is 0-6; $R^2$ is H or $(C_1-C_8)$alkyl;

$R^3$ is H, fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy;

Q is N, CH, CF or $CCH_3$;

L is N, CH or $CR^6$, wherein $R^6$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy; and T is N, CH or $CR^7$, wherein $R^7$ is fluoro, chloro, bromo, iodo, cyano, methyl, $(C_2-C_8)$alkyl, methoxy, $(C_2-C_8)$alkoxy, acetamido, $(C_3-C_8)$alkylamido, $(C_2-C_8)$alkenyl, $(C_2-C_8)$alkynyl, methoxycarbonyl, $(C_2-C_8)$alkoxy-carbonyl or carboxy A is cycloalkyl, aryl, arylalkyl or heterocyclyl;

In various embodiments of Formula (G), the compound has the structure:

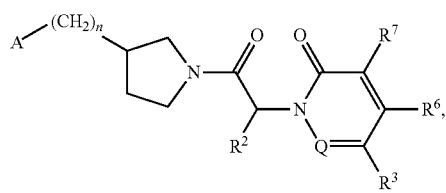

wherein Q is N or CH.

In various embodiments of Formula (G), the compound has the structure:

The compound of any of the preceding formulae, wherein the compound is other than The instant disclosure also relates to the compounds shown in Table A:

TABLE A

| A | L¹ | Het¹ | L² | Cy¹ |
|---|---|---|---|---|
| cyclohexane with A¹, (R⁸)ₙ | Alkyl | fused bicyclic with G¹–G⁶, X=Y | Alkyl | pyridinone with R⁶, R³ |
| 6-membered ring with A², A³, (R⁸)ₙ | Alkyl | fused bicyclic with G¹–G⁶, X=Y | Alkyl | pyridinone with R⁶, R³ |
| 5-membered ring with A⁴, A⁵, A⁶, (R⁸)ₙ | Alkyl | fused bicyclic with G¹–G⁶, X=Y | Alkyl | pyridinone with R⁶, R³ |
| pyridine with (R⁸)ₙ | Alkyl | indole | Alkyl | pyridinone with R⁶, R³ |
| benzene with (R⁸)ₙ | Alkyl | indole | Alkyl | pyridinone with R⁶, R³ |
| cyclohexene with (R⁸)ₙ | Alkyl | indole | Alkyl | pyridinone with R³ |
| phenyl | Alkyl | indole | Alkyl | pyridinone with R³ |

TABLE A-continued

| A | L¹ | Het¹ | L² | Cy¹ |
|---|---|---|---|---|
| pyridinyl (R⁸)ₙ | Alkyl | indazolyl (4-linked, N1-linked) | Alkyl | pyridin-2(1H)-one with R⁶ and R³ |
| phenyl (R⁸)ₙ | Alkyl | indazolyl (4-linked, N1-linked) | Alkyl | pyridin-2(1H)-one with R⁶ and R³ |
| phenyl (R⁸)ₙ | Alkyl | indazolyl (4-linked, N1-linked) | Alkyl | pyridin-2(1H)-one with R³ |
| phenyl | Alkyl | indazolyl (4-linked, N1-linked) | Alkyl | pyridin-2(1H)-one with R³ |
| pyridinyl (R⁸)ₙ | Alkyl | pyrrolo[3,2-b]pyridinyl | Alkyl | pyridin-2(1H)-one with R⁶ and R³ |
| phenyl (R⁸)ₙ | Alkyl | pyrrolo[3,2-b]pyridinyl | Alkyl | pyridin-2(1H)-one with R⁶ and R³ |

TABLE A-continued

| A | L¹ | Het¹ | L² | Cy¹ |
|---|---|---|---|---|
| phenyl-(R⁸)ₙ | Alkyl | pyrrolo[3,2-c]pyridine | Alkyl | pyridin-2(1H)-one with R³ |
| phenyl | Alkyl | pyrrolo[3,2-c]pyridine | Alkyl | pyridin-2(1H)-one with R³ |
| pyridyl-(R⁸)ₙ | Alkyl | pyrazolo[4,3-c]pyridine | Alkyl | pyridin-2(1H)-one with R⁶, R³ |
| phenyl-(R⁸)ₙ | Alkyl | pyrazolo[4,3-c]pyridine | Alkyl | pyridin-2(1H)-one with R⁶, R³ |
| phenyl-(R⁸)ₙ | Alkyl | pyrazolo[4,3-c]pyridine | Alkyl | pyridin-2(1H)-one with R³ |
| phenyl | Alkyl | pyrazolo[4,3-c]pyridine | Alkyl | pyridin-2(1H)-one with R³ | wherein alkyl, $A^1$-$A^6$, X, Y, $G^1$-$G^6$, $R^3$, $R^8$, and $R^8$ are each defined herein. Alkyl can be 1 to 6 carbon atoms such as —$CH_2$—, —$CH_2CH_2$—, —$CH_2CH_2CH_2$—, —$CH_2CH_2CH_2CH_2$—, and —$CH_2CH_2CH_2CH_2CH_2$—, each of which can be substituted or unsubstituted. $L^1$ and $L^2$ in Table A can each be the same or different. $L^1$ and $L^2$ in Table A can each be the same and can be —$CH_2$—.

In various embodiments of the compound, the compound can meet the requirements of more than one of Formulae (I), (II) and (A)-(G). For example, the compound can have the structure of Formulae (I) and Formula (A) or the compound can have the structure of Formula (II) and Formula (B).

In some examples, compounds of the Formulae (I), (II) and (A)-(G) exhibit sphingosine 1-phosphate receptor 2 antagonistic ($S1P_2$) activity. In some examples, compounds of the Formulae (I), (II) and (A)-(G) exhibit $S1P_2$ antagonistic activity at concentrations of from about 100 nM to about 100 μM (e.g., from about 100 nM to about 10 μM; about 100 nM to about 900 nM; about 250 nM to about 1 μM; or about 750 nM to about 100 μM).

The present invention also provides a pharmaceutical composition comprising a compound of any of the preceding formulae and a pharmaceutically acceptable carrier. The present invention also provides a pharmaceutical composition comprising a therapeutically effective amount of a compound of one of Formulae (I), (II) and (A)-(G), and a pharmaceutically acceptable carrier.

Various embodiments of the present invention also contemplate pharmaceutical compositions comprising one or more compounds of the various embodiments of the present invention and one or more pharmaceutically acceptable excipients. A "pharmaceutical composition" refers to a chemical or biological composition suitable for administration to a subject (e.g., mammal). Such compositions can be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" is a carrier, sometimes a liquid, in which an active therapeutic agent is formulated. The excipient generally does not provide any pharmacological activity to the formulation, though it can provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes, but is not limited to, any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions can be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention can be orally administered as a capsule (hard or soft), tablet (film coated, enteric coated or uncoated), powder or granules (coated or uncoated) or liquid (solution or suspension). The formulations can be conveniently prepared by any of the methods well-known in the art. The pharmaceutical compositions of the present invention can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal days; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention can vary according to factors such as the disease state, age, gender, weight, patient history, risk factors, predisposition to disease, administration route, pre-existing treatment regime (e.g., possible interactions with other medications), and weight of the subject. Dosage regimens can be adjusted to provide the optimum therapeutic response. For example, a single bolus can be administered, several divided doses can be administered over time, or the dose can be proportionally reduced or increased as indicated by the exigencies of therapeutic situation.

A "dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in subjects. In therapeutic use for treatment of conditions in mammals (e.g., humans) for which the compounds of the present invention or an appropriate pharmaceutical composition thereof are effective, the compounds of the present invention can be administered in an effective amount. The dosages as suitable for this invention can be a composition, a pharmaceutical composition or any other compositions described herein.

For each of the recited embodiments, the dosage is typically administered once, twice, or thrice a day, although more frequent dosing intervals are possible. The dosage can be administered every day, every 2 days, every 3 days, every 4 days, every 5 days, every 6 days, and/or every 7 days (once a week). In one embodiment, the dosage can be administered daily for up to and including 30 days, preferably between 7-10 days. In another embodiment, the dosage can be administered twice a day for 10 days. If the patient requires treatment for a chronic disease or condition, the dosage can be administered for as long as signs and/or symptoms persist. The patient can require "maintenance treatment" where the patient is receiving dosages every day for months, years, or the remainder of their lives. In addition, the composition of this invention can be to effect prophylaxis of recurring symptoms. For example, the dosage can be administered once or twice a day to prevent the onset of symptoms in patients at risk, especially for asymptomatic patients.

The compositions described herein can be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to, for example, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (nonlocal), composition is given via the digestive tract. Administration can be parenteral, where the desired effect is systemic, composition is given by other routes than the digestive tract.

$S1PR_2$ is one of five S1P receptor subtypes and is a member of the GPCR superfamily. $S1PR_2$ is abundantly expressed in the endothelium, in addition to fibrogenic and immune cells, and is potently upregulated in the endothelium by inflammation.

$S1PR_2$ activation disrupts adherens junctions and is essential for pathological angiogenesis in the mouse retina, leading to defective neovascularization (Skoura A. et al. J Clin Invest. 2007 September; 117(9):2506-16). It has been shown that the angiogenic process proceeds normally in $S1PR_2$ knockout (KO) mice during normal retinal development. However, when $S1PR_2$ KO mice were exposed to ischemic stress, their retinas showed increased physiological intraretinal angiogenesis and reduced pathological intravitreal neovascularization. It was further demonstrated that $S1PR_2$ is required for the inflammatory cell infiltration, induction of the proinflammatory and pro-angiogenic enzyme cyclooxygenase (COX)-2 and the suppression of the endothelial nitric oxide synthase (eNOS) which produces the vasodilator nitric oxide (NO). The $S1PR_2$-driven inflammatory process is therefore an important molecular event in pathological retinal angiogenesis, and $S1PR_2$ antagonists should have utility in the prevention and treatment of abnormal angiogenesis in retinal degenerative diseases such as age-related macular degeneration and diabetic retinopathy.

$S1PR_2$ has been shown to be an important mediator of fibrotic diseases. In a chronic mouse carbon tetrachloride (CCl4) model of liver disease, $S1PR_2$ KO mice showed reduced proliferation in hepatic myofibroblasts, the cell type implicated in pathology associated with liver fibrosis (Serriere-Lanneau V. et al. FASEB J=2007 July; 21(9):2005-13). Additionally, a role for $S1PR_2$ in several models of liver disease in mice has been identified (Ikeda H. et al. J Lipid Res. 2009 March; 50(3):556-64). In a single-dose CCl model, $S1PR_2$ KO mice were shown to have an increased regenerative response compared with WT control mice.

S1PR$_2$ KO mice also exhibited a higher survival rate in a dimethylnitrosamine-induced liver injury mode. Histological examination revealed significantly less liver pathology in a chronic CCl$_4$ model of liver disease for the S1PR$_2$ KO mice. The S1PR$_2$-specific antagonist JTE-013 was shown to protect against liver injury in multiple studies in bile duct ligation (BDL) murine models of liver disease (Wang Y. et al. Hepatology. 2017 June; 65(6):2005-2018. Yang L. Sci Rep. 2015 Sep. 1; 5:13423). In support of the specific role of S1PR$_2$ in the BDL model, mice lacking S1PR$_2$ also demonstrated decreased liver pathology. Therefore S1PR$_2$ receptor antagonists are expected to have utility for the treatment of liver fibrosis.

S1PR$_2$ has also been identified as a driver of lung fibrosis ((Zhao J. et al. PLoS ONE 2018 13(5): e0197604). S1PR2 KO mice manifest significantly attenuated lung fibrosis induced by bleomycin. S1PR$_2$ was found to be expressed in alveolar macrophages, vascular endothelial cells and alveolar epithelial cells in the lung, and S1PR$_2$-expressing cells accumulated in the fibrotic regions. Bleomycin administration stimulated the mRNA expression of the profibrotic cytokines IL-13 and IL-4 and inflammatory macrophage markers in cells collected from broncho-alveolar lavage fluids (BALF), and S1PR$_2$ deletion markedly diminished the stimulated expression of these markers. In bleomycin administered S1PR$_2$ KO mice, STAT6 phosphorylation in BALF cells was substantially diminished compared with WT mice. S1PR$_2$ blockade in WT mice with an S1PR$_2$ antagonist alleviated bleomycin-induced lung fibrosis. Thus, S1PR$_2$ facilitates lung fibrosis via augmentation of IL-13 expression and its signaling in BALF cells, and antagonists of S1PR$_2$ are expected to have clinical utility for the treatment of lung fibrosis.

S1P signaling plays a role in the permeability function of the blood brain barrier (BBB); consequently, S1PR$_2$ modulation of SIP signaling has been studied in the context of MS, stroke, and sepsis. For instance, S1PR$_2$ KO mice show a dramatic decrease in infarct volume and cerebral edema compared with WT counterparts in mouse models of stroke (Kim G. S. et al. Nat Commun. 2015 Aug. 5; 6:7893). It was also shown that inhibition of S1PR$_2$ by administration of the S1PR$_2$ antagonist JTE-013 to WT mice subjected to ischemia/reperfusion (I/R) similarly resulted in a dramatic decrease in infarct ratio and edema ratio as well as improved neurological scores.

Breakdown of the blood-brain barrier (BBB) has also been demonstrated during septic infections, with sepsis shown to induce activation of cerebral endothelial cells, resulting in increased permeability of the BBB due to inflammation (Sonneville R. et al. Ann Intensive Care. 2013 May 29; 3(1):15). This increased permeability has been demonstrated in an animal model of cecal ligation (Yokoo H. et al. PLoS One. 2012; 7(12):e51539.). Increased vascular leakage and inflammatory signaling in sepsis suggests that antagonism of S1PR$_2$ may lessen brain injury and improve prognosis.

Enhanced S1PR$_2$ expression at the BBB has been implicated as a key factor in susceptibility to the development of multiple sclerosis (MS) (Cruz-Orengo L. et al. J Clin Invest. 2014 June; 124(6):2571-84). The incidence of MS is 4-fold higher in the female population and S1PR$_2$ expression was shown to be correspondingly increased in disease-susceptible regions of the CNS of female patients with MS compared with their male counterparts. This striking gender difference to disease susceptibility and S1PR$_2$ expression was recapitulated in an SJL mouse strain with experimental autoimmune encephalomyelitis (SJL EAE) mouse model of MS. Pharmacological blockade of S1PR$_2$ or genetic deletion of S1PR$_2$ in female SJL EAE mice significantly reduced BBB permeability and seventy of EAE compared with that of WT controls. Therefore S1PR$_2$ antagonists are expected to have utility for the treatment of MS.

Chimeric antigen receptor T-cell (CAR-T) therapy represents an important treatment paradigm in oncology. CAR-T therapy is associated with significant toxicity, including cytokine release syndrome with concomitant neurologic side effects in a sub-set of patients as a consequence of inflammation and blood-brain barrier disruption (Gust, J. et al. Cancer Discov. 2017, 7(12); 1404-19). These side effects can be fatal, limiting the potential utility of CAR-T. Consequently, there is a significant unmet need for effective treatment (or prevention) of these adverse neurological effects. In principle, an S1PR$_2$ functional antagonist could, by protecting the blood-brain barrier from vascular leakage, abrogate this significant CAR-T risk without eliminating its effectiveness.

The present disclosure therefore provides a method for treating a fibrotic disease, abnormal vascular leak and pathological angiogenesis, and tumor-associated angiogenesis comprising administering a therapeutically effective amount of any of the preceding compounds, e.g., a compound of any of Formula (I)—(II) and (A)-(G), or a pharmaceutical composition comprising said compound, to a subject in need thereof. In various embodiments, the abnormal vascular leak and pathological angiogenesis is associated with the wet form of age-related macular degeneration. In various embodiments, the fibrotic disease is fibrosis of the lung, liver, kidney, retina, skin or heart.

The present disclosure also provides a method for treating multiple sclerosis comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for treating highly vascular tumors comprising administering a therapeutically effective amount of any of the preceding compounds, e.g., a compound of any of Formula (I)—(II) and (A)-(G), or a pharmaceutical composition comprising said compound, to a subject in need thereof. In various embodiments, the highly vascular tumors are renal carcinoma, glioblastoma, and neuroblastoma. The tumors can be highly fibrotic such as in the case of pancreatic cancer.

The present disclosure also provides a method for chimeric antigen receptor T-cell (CAR-T) therapy, comprising administering a therapeutically effective amount of any of the preceding compounds, e.g., a compound of any of Formula (I)—(II) and (A)-(G), or a pharmaceutical composition comprising said compound, to the subject.

The present disclosure also provides a method for treating cytokine release syndrome, comprising administering a therapeutically effective amount of any of the preceding compounds, e.g., a compound of any of Formula (I)—(II) and (A)-(G), or a pharmaceutical composition comprising said compound, to the subject.

The present disclosure also provides a method for treating pathological angiogenesis in a subject, comprising administering a therapeutically effective amount of any of the preceding compounds, e.g., a compound of any of Formula (I)—(II) and (A)-(G), or a pharmaceutical composition comprising said compound, to the subject.

The present disclosure also provides a method for treating atherosclerosis comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for treating diabetes comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for treating stroke (e.g., ischemic stroke and stroke related conditions, such as cerebral vasogenic edema) comprising administering a therapeutically effective amount of any of the preceding compounds, e.g., a compound of any of Formula (I)—(II) and (A)-(G), or a pharmaceutical composition comprising said compound, to a subject in need thereof. Antagonism of $S1PR_2$ may be a useful approach to ameliorate the brain damage associated with stroke and reperfusion by preserving neurovascular integrity, thereby reducing the entry of toxic plasma proteins and blood cells into the brain parenchyma and diminishing downstream inflammatory and mechanical injury.

The present disclosure also provides a method for preventing or treating sepsis-induced changes in blood-brain barrier permeability (e.g., decreasing BBB permeability during septic infections) comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for treating nonalcoholic steatohepatitis (NASH) comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for treating nonalcoholic steatohepatitis (NASH) comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for treating hepatobiliary conditions, including cholangiocarcinoma, as well as glucose and lipid management, comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for at least one of regulating proliferation of cholangiocytes and promoting ductular reaction comprising administering a therapeutically effective amount of any of the preceding compounds, e.g., a compound of any of Formula (I)—(II) and (A)-(G), or a pharmaceutical composition comprising said compound, to a subject in need thereof.

The present disclosure also provides a method for ameliorating blood brain barrier dysfunction and brain damage associated with chronic traumatic encephalopathy; and at least one of traumatic brain injury, hypertensive encephalopathy, neurodegenerative diseases, vascular dementias, and multiple sclerosis, comprising administering a therapeutically effective amount of any of the preceding compounds, e.g., a compound of any of Formula (I)—(II) and (A) (G), or a pharmaceutical composition comprising said compound, to a subject in need thereof.

The present disclosure also provides a method for at least one of treating inflammatory response syndrome and sepsis; restoring endothelial function, preventing vascular leak, disseminated intravascular coagulation, and multi-organ dysfunction; treating or preventing vascular complications of diabetes, such as cardiovascular disease, coronary artery disease, stroke, retinopathy, nephropathy and neuropathy, the method comprising administering a therapeutically effective amount of any of the preceding compounds, e.g., a compound of any of Formula (I)—(II) and (A)-(G), or a pharmaceutical composition comprising said compound, to a subject in need thereof.

Various compounds disclosed herein have GLISA-determined $IC_{50}$ values of less than 1 µM, less than 500 nM, less than 200 nM, less than 100 nM, less than 60 nM, less than 50 nM, less than 40 nM, less than 30 nM, less than 20 nM or less than 10 nM; for example, GLISA-determined $IC_{50}$ values of from about 10 nM to about 100 nM, about 100 nM to about 1 µM, about 1 µM to about 5 µM or between about 5 µM and 10 µM.

Various compounds disclosed herein at 1 µM give GLISA-determined percent inhibition of over 50%, over 60%, over 70% or over 80% inhibition. Some tested compounds produced GLISA % inhibition results over 60%. Various compounds of the present invention (at 1 µM) produce GLISA % inhibition results between about 30% and 80%. Various compounds of the present invention (at 1 µM) produce GLISA % inhibition results between about 40% and 70%. Various compounds of the present invention (at 1 µM) produce GLISA % inhibition results between about 50% and 80%. Various compounds of the present invention (at 1 µM) produce GLISA % inhibition results between about 60% and 80%. Various compounds of the present invention (at 1 µM) produce GLISA % inhibition results of 1-20%, 20-40%, 40-60%, 60-80% or 80-100%.

Various compounds of the present invention produce FLIPR $IC_{50}$ (nM) results under 10, 20, 30, 40, 50 or 60. Some tested compounds produced FLIPR $IC_{50}$ (nM) results under 30. Various compounds of the present invention produce GLISA $IC_{50}$ (nM) results under 100, 200, 500 or 1000. Various compounds of the present invention produce GLISA $IC_{50}$ (nM) results between about 10 and 100, between about 100 and 1000, between about 1000 and 5000 or between about 5000 and 10,000.

The term "therapeutically effective amount" as used herein, refers to that amount of one or more compounds of the various examples of the present invention that elicits a biological or medicinal response in a tissue system, animal or human, that is being sought by a researcher, veterinarian, medical doctor or other clinician, which includes alleviation of the symptoms of the disease or disorder being treated. In some examples, the therapeutically effective amount is that which can treat or alleviate the disease or symptoms of the disease at a reasonable benefit/risk ratio applicable to any medical treatment. However, it is to be understood that the total daily usage of the compounds and compositions described herein can be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

The term "alkyl" as used herein refers to substituted or unsubstituted straight chain, branched and cyclic, saturated mono- or bi-valent groups having from 1 to 20 carbon atoms, 10 to 20 carbon atoms, 12 to 18 carbon atoms, 6 to about 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of straight chain mono-valent ($C_1$-$C_{20}$)-alkyl groups include those with from 1 to 8 carbon atoms such as methyl (i.e., $CH_3$), ethyl, n-propyl, n-butyl, n-pentyl, n-hexyl, n-heptyl, n-octyl groups. Examples of branched mono-valent ($C_1$-$C_{20}$)-alkyl groups include isopropyl, iso-butyl, sec-butyl, t-butyl, neopentyl, and isopentyl. Examples of straight chain bi-valent ($C_1$-$C_{20}$)alkyl groups include those with from 1 to 6 carbon atoms such as —$CH_2$—, —$CH_2CH_2$—, —$CH_2CH_2CH_2$—, —$CH_2CH_2CH_2CH_2$—, and —$CH_2CH_2CH_2CH_2CH_2$—. Examples of branched bi-valent alkyl groups include —$CH(CH_3)CH_2$— and —$CH_2CH(CH_3)CH_2$—. Examples of cyclic alkyl groups include cyclopropyl, cyclobutyl, cyclopentyl, cyclohexyl, cyclooctyl, bicyclo[1.1.1]pentyl, bicyclo[2.1.1]hexyl, and bicyclo[2.2.1]heptyl. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. In some embodiments, alkyl includes a combination of substituted and unsubstituted alkyl. As an example, alkyl, and also ($C_1$)alkyl, includes methyl and substituted methyl. As a particular example, ($C_1$)alkyl includes benzyl. As a further example, alkyl can include methyl and substituted ($C_2$-$C_8$)alkyl. Alkyl can also include substituted methyl and unsubstituted ($C_2$-$C_8$)alkyl. In some embodiments, alkyl can be methyl and $C_2$-$C_8$ linear alkyl. In some embodiments, alkyl can be methyl and $C_2$-$C_8$ branched alkyl. The term methyl is understood to be —$CH_3$, which is not substituted. The term methylene is understood to be —$CH_2$—, which is not substituted. For comparison, the term ($C_1$)alkyl is understood to be a substituted or an unsubstituted —$CH_3$ or a substituted or an unsubstituted —$CH_2$—. Representative substituted alkyl groups can be substituted one or more times with any of the groups listed herein, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkyl groups can be substituted from a set of groups including amino, hydroxy, cyano, carboxy, nitro, thio and alkoxy, but not including halogen groups. Thus, in some embodiments alkyl can be substituted with a non-halogen group. For example, representative substituted alkyl groups can be substituted with a fluoro group, substituted with a bromo group, substituted with a halogen other than bromo, or substituted with a halogen other than fluoro. In some embodiments, representative substituted alkyl groups can be substituted with one, two, three or more fluoro groups or they can be substituted with one, two, three or more non-fluoro groups. For example, alkyl can be trifluoromethyl, difluoromethyl, or fluoromethyl, or alkyl can be substituted alkyl other than trifluoromethyl, difluoromethyl or fluoromethyl. Alkyl can be haloalkyl or alkyl can be substituted alkyl other than haloalkyl.

The term "alkenyl" as used herein refers to substituted or unsubstituted straight chain, branched and cyclic, saturated mono- or bi-valent groups having at least one carbon-carbon double bond and from 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. The double bonds can be trans or as orientation. The double bonds can be terminal or internal. The alkenyl group can be attached via the portion of the alkenyl group containing the double bond, e.g., vinyl, propen-1-yl and buten-1-yl, or the alkenyl group can be attached via a portion of the alkenyl group that does not contain the double bond, e.g., penten-4-yl. Examples of mono-valent ($C_2$-$C_{20}$)-alkenyl groups include those with from 1 to 8 carbon atoms such as vinyl, propenyl, propen-1-yl, propen-2-yl, butenyl, buten-1-yl, buten-2-yl, sec-buten-1-yl, sec-buten-3-yl, pentenyl, hexenyl, heptenyl and octenyl groups. Examples of branched mono valent ($C_2$-$C_{20}$)-alkenyl groups include isopropenyl, iso-butenyl, sec-butenyl, t-butenyl, neopentenyl, and isopentenyl. Examples of straight chain bi-valent ($C_2$-$C_{20}$)alkenyl groups include those with from 2 to 6 carbon atoms such as —CHCH—, —CHCHCH$_2$—, —CHCHCH$_2$CH$_2$—, and —CHCHCH$_2$CH$_2$CH$_2$—. Examples of branched bi-valent alkyl groups include —C(CH$_3$)CH— and —CHC(CH$_3$)CH$_2$—. Examples of cyclic alkenyl groups include cyclopentenyl, cyclohexenyl and cyclooctenyl. It is envisaged that alkenyl can also include masked alkenyl groups, precursors of alkenyl groups or other related groups. As such, where alkenyl groups are described it, compounds are also envisaged where a carbon-carbon double bond of an alkenyl is replaced by an epoxide or aziridine ring. Substituted alkenyl also includes alkenyl groups which are substantially tautomeric with a non-alkenyl group. For example, substituted alkenyl can be 2-aminoalkenyl, 2-alkylaminoalkenyl, 2-hydroxyalkenyl, 2-hydroxyvinyl, 2-hydroxypropenyl, but substituted alkenyl is also understood to include the group of substituted alkenyl groups other than alkenyl which are tautomeric with non-alkenyl containing groups. In some embodiments, alkenyl can be understood to include a combination of substituted and unsubstituted alkenyl. For example, alkenyl can be vinyl and substituted vinyl. For example, alkenyl can be vinyl and substituted ($C_3$-$C_8$) alkenyl. Alkenyl can also include substituted vinyl and unsubstituted ($C_3$-$C_8$)alkenyl. Representative substituted alkenyl groups can be substituted one or more times with any of the groups listed herein, for example, monoalkylamino, dialkylamino, cyano, acetyl, amido, carboxy, nitro, alkylthio, alkoxy, and halogen groups. As further example, representative substituted alkenyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkenyl groups can be substituted from a set of groups including monoalkylamino, dialkylamino, cyano, acetyl, amido, carboxy, nitro, alkylthio and alkoxy, but not including halogen groups. Thus, in some embodiments alkenyl can be substituted with a non-halogen group. In some embodiments, representative substituted alkenyl groups can be substituted with a fluoro group, substituted with a bromo group, substituted with a halogen other than bromo, or substituted with a halogen other than fluoro. For example, alkenyl can be 1-fluorovinyl, 2-fluorovinyl, 1,2-difluorovinyl, 1,2,2-trifluorovinyl, 2,2-difluorovinyl, trifluoropropen-2-yl, 3,3,3-trifluoropropenyl, 1-fluoropropenyl, 1-chlorovinyl, 2-chlorovinyl, 1,2-dichlorovinyl, 1,2,2-trichlorovinyl or 2,2-dichlorovinyl. In some embodiments, representative substituted alkenyl groups can be substituted with one, two, three or more fluoro groups or they can be substituted with one, two, three or more non-fluoro groups.

The term "alkynyl" as used herein, refers to substituted or unsubstituted straight and branched chain alkyl groups, except that at least one triple bond exists between two carbon atoms. Thus, alkynyl groups have from 2 to 50 carbon atoms, 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. Examples include, but are not limited to ethynyl, propynyl, propyn-1-yl, propyn-2-yl, butynyl, butyn-1-yl, butyn-2-yl, butyn-3-yl, butyn-4-yl, pentynyl, pentyn-1-yl, hexynyl, Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to about 10 carbon atoms or 6 to 8 carbon atoms. Examples of (C$_6$-C$_{20}$)aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. Examples include substituted phenyl, substituted napthalenyl, substituted azulenyl, substituted biphenylyl, substituted indacenyl, substituted fluorenyl, substituted phenanthrenyl, substituted triphenylenyl, substituted pyrenyl, substituted naphthacenyl, substituted chrysenyl, and substituted anthracenyl groups. Examples also include unsubstituted phenyl, unsubstituted napthalenyl, unsubstituted azulenyl, unsubstituted biphenylyl, unsubstituted indacenyl, unsubstituted fluorenyl, unsubstituted phenanthrenyl, unsubstituted triphenylenyl, unsubstituted pyrenyl, unsubstituted naphthacenyl, unsubstituted chrysenyl, and unsubstituted anthracenyl groups. Aryl includes phenyl groups and also non-phenyl aryl groups. From these examples, it is clear that the term (C$_6$-C$_{20}$)aryl encompasses mono- and polycyclic (C$_6$-C$_{20}$)aryl groups, including fused and non-fused polycyclic (C$_6$-C$_{20}$)aryl groups.

The term "heterocyclyl" as used herein refers to substituted aromatic, unsubstituted aromatic, substituted non-aromatic, and unsubstituted non-aromatic rings containing 3 or more atoms in the ring, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms (C$_3$-C$_8$), 3 to 6 carbon atoms (C$_3$-C$_6$) or 6 to 8 carbon atoms (C$_6$-C$_8$). A heterocyclyl group designated as a C$_2$-heterocyclyl can be a 5-membered ring with two carbon atoms and three heteroatoms, a 6-membered ring with two carbon atoms and four heteroatoms and so forth. Likewise a C$_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups. For example, heterocyclyl groups include, without limitation:

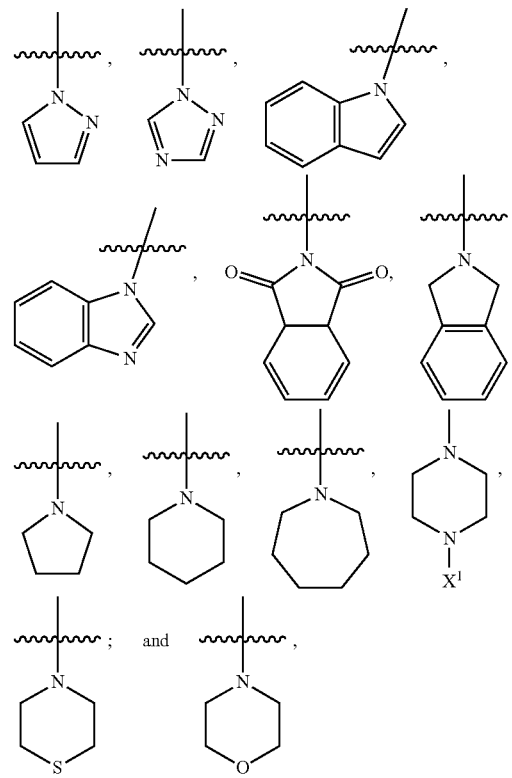

wherein X$^1$ represents H, (C$_1$-C$_{20}$)alkyl, (C$_6$-C$_{20}$)aryl or an amine protecting group (e.g., a t-butyloxycarbonyl group) and wherein the heterocyclyl group can be substituted or unsubstituted. A nitrogen-containing heterocyclyl group is a heterocyclyl group containing a nitrogen atom as an atom in the ring. In some embodiments, the heterocyclyl is other than thiophene or substituted thiophene. In some embodiments, the heterocyclyl is other than furan or substituted furan.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. Thus, alkyoxy also includes an oxygen atom connected to an alkyenyl group and oxygen atom connected to an alkynyl group. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "aryloxy" as used herein refers to an oxygen atom connected to an aryl group as are defined herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl, biphenylmethyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The terms "halo," "halogen," or "halide" group, as used herein, by themselves or as part of another substituent, mean, unless otherwise stated, a fluorine, chlorine, bromine, or iodine atom.

The term "amino" as used herein refers to a substituent of the form $-NH_2$, $-NHR$, $-NR_2$, $-NR_3^+$, wherein each R is independently selected, and protonated forms of each, except for $-NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, alkenyl, alkynyl, alkoxy, aryl, cycloalkyl, heterocyclyl, group or the like.

The term "formyl" as used herein refers to a group containing a carbonyl moiety wherein the group is bonded via the carbonyl carbon atom. The carbonyl carbon atom is also bonded to a hydrogen atom.

The term "alkoxycarbonyl" as used herein refers to a group containing a carbonyl moiety wherein the group is bonded via the carbonyl carbon atom. The carbonyl carbon atom is also bonded to an oxygen atom which is further bonded to an alkyl group. Alkoxycarbonyl also includes the group where a carbonyl carbon atom is also bonded to an oxygen atom which is further bonded to an alkyenyl group. Alkoxycarbonyl also includes the group where a carbonyl carbon atom is also bonded to an oxygen atom which is further bonded to an alkynyl group. In a further case, which is included in the definition of alkoxycarbonyl as the term is defined herein, and is also included in the term "aryloxycarbonyl," the carbonyl carbon atom is bonded to an oxygen atom which is bonded to an aryl group instead of an alkyl group.

The term "arylcarbonyl" as used herein refers to a group containing a carbonyl moiety wherein the group is bonded via the carbonyl carbon atom. The carbonyl carbon atom is also bonded to an aryl group.

The term "alkylamido" as used herein refers to a group containing a carbonyl moiety wherein the group is bonded via the carbonyl carbon atom. The carbonyl carbon atom is also bonded to a nitrogen group which is bonded to one or more alkyl groups. In a further case, which is also an alkylamido as the term is defined herein, the carbonyl carbon atom is bonded to an nitrogen atom which is bonded to one or more aryl group instead of, or in addition to, the one or more alkyl group. In a further case, which is also an alkylamido as the term is defined herein, the carbonyl carbon atom is bonded to an nitrogen atom which is bonded to one or more alkenyl group instead of, or in addition to, the one or more alkyl and or/aryl group. In a further case, which is also an alkylamido as the term is defined herein, the carbonyl carbon atom is bonded to an nitrogen atom which is bonded to one or more alkynyl group instead of, or in addition to, the one or more alkyl, alkenyl and/or aryl group.

The term "carboxy" as used herein refers to a group containing a carbonyl moiety wherein the group is bonded via the carbonyl carbon atom. The carbonyl carbon atom is also bonded to a hydroxy group or oxygen anion so as to result in a carboxylic acid or carboxylate. Carboxy also includes both the protonated form of the carboxylic acid and the salt form. For example, carboxy can be understood as COOH or $CO_2H$.

The term "alkylthio" as used herein refers to a sulfur atom connected to an alkyl, alkenyl, or alkynyl group as defined herein.

The term "arylthio" as used herein refers to a sulfur atom connected to an aryl group as defined herein.

The term "alkylsulfonyl" as used herein refers to a sulfonyl group connected to an alkyl, alkenyl, or alkynyl group as defined herein.

The term "alkylsulfinyl" as used herein refers to a sulfinyl group connected to an alkyl, alkenyl, or alkynyl group as defined herein.

The term "dialkylaminosulfonyl" as used herein refers to a sulfonyl group connected to a nitrogen further connected to two alkyl groups, as defined herein, and which can optionally be linked together to form a ring with the nitrogen. This term also includes the group where the nitrogen is further connected to one or two alkenyl groups in place of the alkyl groups.

The term "dialkylamino" as used herein refers to an amino group connected to two alkyl groups, as defined herein, and which can optionally be linked together to form a ring with the nitrogen. This term also includes the group where the nitrogen is further connected to one or two alkenyl groups in place of the alkyl groups.

The term "dialkylamido" as used herein refers to an amido group connected to two alkyl groups, as defined herein, and which can optionally be linked together to form a ring with the nitrogen. This term also includes the group where the nitrogen is further connected to one or two alkenyl groups in place of the alkyl groups.

The term "substituted" as used herein refers to a group that is substituted with one or more groups including, but not limited to, the following groups: deuterium (D), halogen (e.g., F, Cl, Br, and I), R, OR, OC(O)N(R)$_2$, CN, NO, $NO_2$, $ONO_2$, azido, $CF_3$, $OCF_3$, methylenedioxy, ethylenedioxy, ($C_3$-$C_{20}$)heteroaryl, $N(R)_2$, $Si(R)_3$, SR, SOR, $SO_2R$, $SO_2N(R)_2$, $SO_2R$, $P(O)(OR)_2$, $OP(O)(OR)_2$, $C(O)R$, $C(O)C(O)R$, $C(O)CH_2C(O)R$, $C(S)R$, $C(O)OR$, $OC(O)R$, $C(O)N(R)_2$, $C(O)N(R)OH$, $OC(O)N(R)_2$, $C(S)N(R)_2$, $(CH_2)_{0-2}N(R)C(O)R$, $(CH_2)_{0-2}N(R)N(R)_2$, $N(R)N(R)C(O)R$, $N(R)N(R)C(O)OR$, $N(R)N(R)CON(R)_2$, $N(R)SO_2R$, $N(R)SO_2N(R)_2$, $N(R)C(O)OR$, $N(R)C(O)R$, $N(R)C(S)R$, $N(R)C(O)N(R)_2$, $N(R)C(S)N(R)_2$, N(COR)COR, N(OR)R, $C(=NH)N(R)_2$, $C(O)N(OR)R$, or $C(=NOR)R$ wherein R can be hydrogen, ($C_1$-$C_{20}$)alkyl or ($C_6$-$C_{20}$)aryl. Substituted also includes a group that is substituted with one or more groups including, but not limited to, the following groups: fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic ring. Such adjacent groups can have a vicinal or germinal relationship, or they can be adjacent on a ring in, e.g., an ortho-arrangement. Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxycarbonyl, alkoxycarbonyl, thiophenyl, and nitrophenyl groups.

In some instances, the compounds described herein (e.g., the compounds of the Formulae (I), (II) and (A)-(G) can contain chiral centers. All diastereomers of the compounds described herein are contemplated herein, as well as racemates.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric (or larger) amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

As used herein, the term "subject" or "patient" refers to any organism to which a composition described herein can be administered, e.g., for experimental, diagnostic, prophylactic and/or therapeutic purposes. Subject refers to a mammal receiving the compositions disclosed herein or subject to disclosed methods. It is understood and herein contemplated that "mammal" includes but is not limited to humans, non-human primates, cows, horses, dogs, cats, mice, rats, rabbits, and guinea pigs.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

Each embodiment described above is envisaged to be applicable in each combination with other embodiments described herein. For example, embodiments corresponding to Formula (I) are equally envisaged as being applicable to Formulae (II) and (A)-(G). As another example, embodiments corresponding to Formula (II) are equally envisaged as being applicable to Formulae (I) and (A)-(G).

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed can be resorted to by those of ordinary skill in the art, and that such modifications and variations are considered to be within the scope of embodiments of the present disclosure The invention is now described with reference to the following Examples. The following working examples therefore, are provided for the purpose of illustration only and specifically point out certain embodiments of the present invention, and are not to be construed as limiting in any way the remainder of the disclosure. Therefore, the examples should be construed to encompass any and all variations which become evident as a result of the teaching provided herein.

EXAMPLES

The present invention can be better understood by reference to the following examples which are offered by way of illustration. The present invention is not limited to the examples given herein.

General Methods

The activity of the compounds described herein was evaluated using one or more of the various methods described herein.

GLISA RhoA Activation—Antagonist Assay

GLISA assays were performed using RhoA (BK124) activation kit purchased from Cytoskeleton Inc., Denver, CO Doxycycline-inducible Flag-tag $S1P_2$ expressing Chinese hamster ovary (CHO) cells (CHO-$S1P_2$-FL) were seeded in a 6-well plate, $1.5 \times 10^5$ cells per well. Cells were stimulated with 1 mg/ml of Doxycycline to induce $S1P_2$ expression in serum free IMDM media with 0.1% BSA/PBS. Following day, cells were stimulated with the compounds described herein (1 nM-10 μM) or 1 μM JTE-013 for 1 hour at 37° C. Following compound incubation, cells were washed with PBS×3 and induced with 100 nM $S1P_2$ for 5 min. Immediately after $S1P_2$ incubation, cells were harvested and lysed in GLISA-lysis buffer, 150 μl/well, as suggested by the manufacturer. Protein concentration was examined using GLISA—Precision Red Advanced Protein assay reagent as described in assay manual. Lysates were immobilized on GTP-bound capture plate and GLISA assay was performed based on manufacture recommendations as reported previously.

GLISA RhoA Activation—Agonist Assay

Agonist assay was performed the same way as antagonist above. The only difference occurred in cell stimulation. After Doxycycline induction in SFM, cells were stimulated with either 100 nM $S1P_2$ or compounds (1 nM-10 μM) for 5 min. For negative controls, cells were pre-treated with 1 μM JTE-013 for 1 hour prior to $S1P_2$ stimulation. Following $S1P_2$ or compound stimulation, cell harvest, lysis and GLISA RhoA assay was performed in the same way as in Antagonist assay described herein.

GLISA Results

Compounds were tested according to the GLISA RhoA activation (antagonist) assay. Tested compounds produced GLISA $IC_{50}$ (nM) results ranging from around 10 nM to over 10,000 nM. Some tested compounds produced GLISA $IC_{50}$ (nM) results under 30. Some tested compounds produced GLISA $IC_{50}$ (nM) results under 60. Some tested compounds produced GLISA $IC_{50}$ (nM) results under 100. Some tested compounds produced GLISA $IC_{50}$ (nM) results under 200. Some tested compounds produced GLISA $IC_{50}$ (nM) results under 500. Some tested compounds produced GLISA $IC_{50}$ (nM) results under 1000. Some tested compounds produced GLISA $IC_{50}$ (nM) results between 10 and 100. Some tested compounds produced GLISA $IC_{50}$ (nM) results between 100 and 1000. Some tested compounds produced GLISA $IC_{50}$ (nM) results between 1000 and 5000. Some tested compounds produced GLISA $IC_{50}$ (nM) results between 5000 and 10000.

Tested compounds produced GLISA % inhibition (at 1 μM) at results ranging from around 1% to around 90%. Some tested compounds produced GLISA % inhibition results over 50%. Some tested compounds produced GLISA % inhibition results over 60%. Some tested compounds produced GLISA % inhibition results over 70%. Some tested compounds produced GLISA % inhibition results over 80%. Some tested compounds produced GLISA % inhibition results between about 30% and 80%. Some tested compounds produced GLISA % inhibition results between about 40% and 70%. Some tested compounds produced GLISA % inhibition results between about 50% and 80%. Some tested compounds produced GLISA % inhibition results between about 60% and 80%. Some tested compounds produced GLISA % inhibition results of 1-20%, 20-40%, 40-60%, 60-80% and 80-100%.

FLIPR Calcium Activation—Antagonist Assay

An assay was performed using Fluo-4 NW Calcium activation kit (#F36206) purchased from Molecular Probes/ Life Technologies, Grand Island, NY. Calcium assay was performed according to the manufacturer's instructions. Briefly, CHO-S1PR$_2$ FL cells ($5 \times 10^4$ cells (for 384 well plate) or $7.5 \times 10^4$ cells (for 96 well plate)) were seeded 24 hours prior to experiment in serum free IMDM media supplemented with 0.1% fatty acid free BSA/PBS (SFM). After starvation, cells were stimulated with the compounds described herein (1 nM-10 µM) for 1 hour in SFM at room temperature. Cells were then washed with PBS and prepared for Calcium induction assay as instructed in Fluo-4 NW Calcium activation kit protocol. For calcium induction, 100 nM S1P$_2$ or 1 µM ATP were added in ligand plate places in the Hamamatsu FDSS6000 drug screening system. Ligand was added in 15 seconds intervals for 15 min and signal ratio of 480/540 nM was measured using the Hamamatsu FDSS6000 instrument.

FLIPR Calcium Activation—Agonist Assay

Cells were seeded and starved as described in antagonist assay. For calcium induction, the compounds described herein were diluted in assay buffer in 5 concentrations 10 µM, 1 µM, 100 nM, 10 nM and 1 nM on the ligand plate. 1 µM ATP and 100 nM S1P were added to separate wells on the ligand plate. For calcium induction, 100 nM S1P$_2$, 1 µM ATP or compounds were added in 15 seconds intervals for 15 min and signal ratio of 480/540 nM was measured using the Hamamatsu FDSS6000 instrument.

FLIPR Results

Compounds were tested according to the FLIPR calcium activation (antagonist) assay. Tested compounds produced FLIPR IC$_{50}$ (nM) results ranging from around 10 nM to around 10,000 nM. Some tested compounds produced FLIPR IC$_{50}$ (nM) results under 20. Some tested compounds produced FLIPR IC$_{50}$ (nM) results under 30. Some tested compounds produced FLIPR IC$_{50}$ (nM) results under 60. Some tested compounds produced FLIPR IC$_{50}$ (nM) results under 100. Some tested compounds produced FLIPR IC$_{50}$ (nM) results under 1000. Some tested compounds produced FLIPR IC$_{50}$ (nM) results between 10 and 100. Some tested compounds produced FLIPR IC$_{50}$ (nM) results between 100 and 1000. Some tested compounds produced FLIPR IC$_{50}$ (nM) results between 1000 and 5000. Some tested compounds produced FLIPR IC$_{50}$ (nM) results between 5000 and 10000.

CAMP Measurement—Antagonist Assay

Assay was performed using Direct CAMP ELISA kit (#ADI-900-066) purchased from Enzo life sciences, Farmingdale, NY All assays were performed according to manufacture instructions and as previously reported 5. Briefly, CHO-SP1R2-FL cells were seeded in 6 well plate, $2.5 \times 10^5$ cells/well. Cells were cultured overnight in IMDM with 10% Serum. To induce S1P$_2$, cells were stimulated with 1 mg/ml doxycycline in serum free IMDM supplemented with 0.1% BSA/PBS for 36 hours. Following Dox induction, cells were treated with 10 µM phosphodiesterase inhibitor IBMX (Tocris) for 2 hours at 37° C. To test compounds, the compounds were incubated with cells (1 nM-10 µM) in serum free media for 1 hour at 37° C. 1 µM JTE-013 was added as a negative control. Following, cells were washed with PBS and stimulated with 1 µM 51P for 30 min at 37° C. Cells were harvested according to Direct cAMP ELISA kit instructions using 0.1 M HCl. Elisa assay was performed as instructed in the manual.

CAMP Measurement—Agonist Assay

After Doxycycline induction, cells were treated with 10 µM isobutyl methyl xanthine (IBMX) (Tocris) for 2 hours at 37° C. To test agonist activity, compounds at concentration range of 1 nM-10 µM or 1 µM S1P$_2$ was incubated with cells for 30 min at 37° C. Cells were harvested and lysed as previously according to manufacturer's instructions. ELISA CAMP assay was performed as in antagonist assay, following manufacturer instructions.

S1PR$_2$ Protein Degradation—Dose Response

CHO-S1P$_2$ expressing cells were seeded in 6 well plates and allowed to grow overnight in IMDM with 10% serum. After 24 hours, compounds described herein were added at 100 nM-10 µM concentrations and incubated with cells for 3 hours at 37° C. protein lysates were harvested immediately after as described herein.

S1PR$_2$ Protein Degradation—Time Course

CHO-S1P$_2$ expressing cells were seeded in 6 well plates and allowed to grow overnight in IMDM with 10% serum. After 24 hours, 1 µM or 100 nM concentrations of the compounds described herein were added to cells and incubated for 30 min, 1 hour, 3 hours and 6 hours. Lysates were harvested at each time point as described below in western blot procedure.

S1P$_2$ Protein Degradation—MG132 Rescue Experiment

Experimental set up was identical to S1P$_2$ dose response degradation experiments. Cells were seeded in 6 well plates and stimulated for 3 hours with compounds described herein at 100 nM-10 µM. To test the effect of MG132 proteasome inhibitor, cells were pre-incubated with 10 µM MG132 (Sigma) for 2 hours prior to stimulation with the compounds described herein.

Western Blotting

CHO cells were washed with 1× with ice cold PBS and lysed with modified RIPA buffer (containing 1 mM EDTA, 50 Mm Tris, 0.5% sodium deoxycholate, 0.1% SDS, 1% TritonX and 0.5% Fos Choline) containing 1 mM Na$_3$VO$_4$, 1 mM NaF and protease inhibitor cocktail. Cells were lysed for 30 min on ice. Protein concentration was assessed using precision red protein reagent (Cytoskeleton) and concentrations calculated based on absorbance at 600 nm. Protein samples were denatured at 95° C. for 5 min after addition of 10% mercaptoethanol. Equal amounts of protein were separated into 10% polyacrylamide gel and transblotted on nitrocellulose membrane.

For S1P$_2$, membrane was blocked in 1% milk 1% BSA in PBST for 1 hour at room temperature. After blocking, membrane was blotted with S1P$_2$ antibody (Protein Tech Inc., Rosemont, IL; 21180-1-AP) 1:1000 overnight at 4° C.

For Flagmembranes were blocked in 5% milk/PBST for 1 hour at room temperature. After blocking, membrane was blotted with Flag 2H8 clone antibody (TransGenic Inc., Fukuoka, Japan KO602-M) 1:500 overnight at 4° C.

Loading controls were blotted with β-actin 1:10000 (Sigma A-1978).

Immunofluorescence Analysis $5 \times 10^5$ S1P$_2$-YFP CHO cells, CHO-S1P$_2$-GFP or CHO-S1P$_2$-FL were seeded in 35 mm glass bottom dishes. Cells were starved for 24 h in serum free IMDM supplemented with 0.1% fatty acid free BSA/PBS. Cells were induced with 100 nM S1P$_2$ for 30 min, 1 h and 3 h. 100 nM of the compounds described herein were incubated for 30 min, 1 h, 3 h, 6 h, and 12 h. After each time point, cells were fixed with 4% PFA/PBS for 10 min in room temperature and washed three times with PBS immediately thereafter. For immunostaining-cells were permeabilized with 0.1% TritonX/PBS for 10 min and blocked in 2% BSA/PBS for 30 min.

For FLAG Immunofluorescence—incubated 1250 with Flag 2H8 clone antibody (Tra TransGenic Inc., Fukuoka, Japan KO602-M) for 3 hours at room temperature. Secondary Antibody: Goat anti mouse alexa 488 1:1000 1 hour, RT.

For GFP Immunofluorescence—incubated 1:1000 with GFP antibody (Abcam 6556) for 3 hours at room temperature. Secondary Antibody: Donkey anti Rabbit alexa 488 1:1000 1 hour, RT.

Bile Duct Ligation (BDL) Liver Fibrosis Model

Six to eight-week-old mice were subjected to bile duct ligation to induce mouse cirrhotic liver injury model. To perform BDL, mice were subjected to a mid-abdominal incision, under general anesthesia. The common bile duct was ligated in two adjacent positions approximately 1 cm from the porta hepatis. The duct was then severed by incision between the two sites of ligation. One day after surgery, mice were administered compounds described herein at 30 mg/ml once daily. Drug delivery was performed by gavage in 0.5% methylcellulose with 0.1 Tween 80. Eight days after BDL surgery mice were harvested, though the harvesting can be performed at any suitable period of time, including 14 days after BDL surgery. Blood serum was collected for liver enzyme analysis and livers were harvested and were either snap frozen or fixed with 4% PFA and cryopreserved in OCT for sectioning and immunohistochemical analysis.

Examples 1-141

Compounds 1-156, listed in Table 1, can be synthesized, for example, according to the general synthetic methods depicted in Schemes 1-18. Compounds 1-156 can also be produced using the specific methods described in Examples 1-146 herein.

TABLE 1

| Compound ID | Chemical name | Structure | Observed MS |
|---|---|---|---|
| 1 | 1-(2-(1-benzyl-2,5-dimethyl-1H-pyrrol-3-yl)-2-oxoethyl)-5-bromopyridin-2(1H)-one | 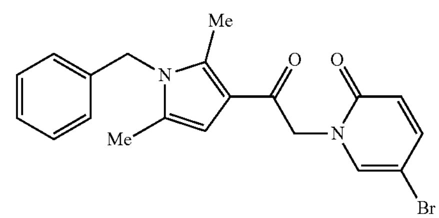 [SMILES: Cc1cc(C(=O)Cn2cc(Br)ccc2=O)c(C)n1Cc1ccccc1] | 401.27 |
| 2 | 1-(2-(1-benzyl-2,5-dimethyl-1H-pyrrol-3-yl)-2-oxoethyl)-5-iodopyridin-2(1H)-one | 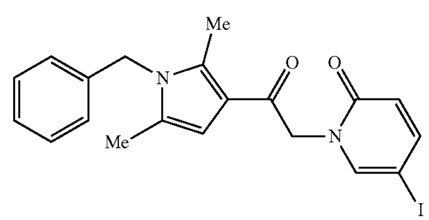 [SMILES: Cc1cc(C(=O)Cn2cc(I)ccc2=O)c(C)n1Cc1ccccc1] | 447.3 |
| 3 | 1-(2-(1-benzyl-2,5-dimethyl-1H-pyrrol-3-yl)-2-oxoethyl)-5-ethynylpyridin-2(1H)-one | 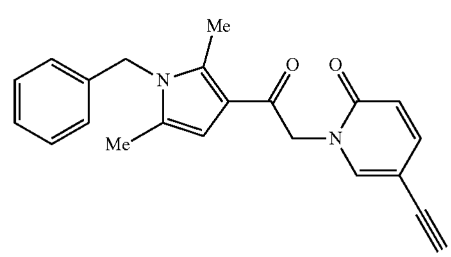 [SMILES: C#Cc1ccc(=O)n(CC(=O)c2cc(C)n(Cc3ccccc3)c2C)c1] | 345.34 |
| 4 | 1-(1-(1-benzyl-2,5-dimethyl-1H-pyrrol-3-yl)-1-oxopropan-2-yl)-5-bromopyridin-2(1H)-one | 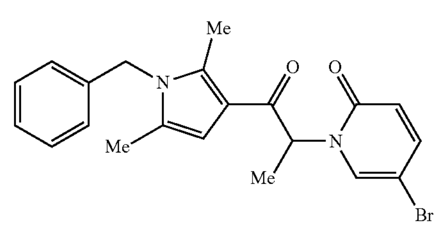 [SMILES: Cc1cc(C(=O)C(C)n2cc(Br)ccc2=O)c(C)n1Cc1ccccc1] | 415.28 |

TABLE 1-continued

| Compound ID | Chemical name | Observed MS |
|---|---|---|
| 5 | 5-bromo-1-(1-(2,5-dimethyl-1-((5-methyl-1,2,4-oxadiazol-3-yl)methyl)-1H-pyrrol-3-yl)-1-oxopropan-2-yl)pyridin-2(1H)-one | 419.1 |
| 6 | 5-bromo-1-(1-(2,5-dimethyl-1-((3-methyl-1,2,4-oxadiazol-5-yl)methyl)-1H-pyrrol-3-yl)-1-oxopropan-2-yl)pyridin-2(1H)-one | 419.1 |
| 7 | 5-bromo-1-(1-(2,5-dimethyl-1-(pyrimidin-2-ylmethyl)-1H-pyrrol-3-yl)-1-oxopropan-2-yl)pyridin-2(1H)-one | 415.1 |
| 8 | 5-bromo-1-(1-(2,5-dimethyl-1-((1-methyl-1H-pyrazol-4-yl)methyl)-1H-pyrrol-3-yl)-1-oxopropan-2-yl)pyridin-2(1H)-one | 417.1 |
| 9 | 5-bromo-1-(1-(2,5-dimethyl-1-((5-methylisoxazol-3-yl)methyl)-1H-pyrrol-3-yl)-1-oxopropan-2-yl)pyridin-2(1H)-one | 418.1 |
| 10 | 5-bromo-1-(1-(2,5-dimethyl-1-((tetrahydro-2H-pyran-4-yl)methyl)-1H-pyrrol-3-yl)-1-oxopropan-2-yl)pyridin-2(1H)-one | 421.1 |
| 11 | 5-bromo-1-(1-(2,5-dimethyl-1-((tetrahydro-2H-pyran-3-yl)methyl)-1H-pyrrol-3-yl)-1-oxopropan-2-yl)pyridin-2(1H)-one | 421.1 |

TABLE 1-continued

| Compound ID | Chemical name | Observed MS |
|---|---|---|
| 12 | 5-bromo-1-(1-(2,5-dimethyl-1-((1-methyl-1H-pyrazol-3-yl)methyl)-1H-pyrrol-3-yl)-1-oxopropan-2-yl)pyridin-2(1H)-one | 417.1 |
| 13 | 5-bromo-1-(1-(2,5-dimethyl-1-(4-(methylsulfonyl)benzyl)-1H-pyrrol-3-yl)-1-oxopropan-2-yl)pyridin-2(1H)-one | 491.1 |
| 14 | 5-bromo-1-(1-(2,5-dimethyl-1-(3-(methylsulfonyl)benzyl)-1H-1-pyrrol-3-yl)-1-oxopropan-2-yl)pyridin-2(1H)-one | 491.1 |
| 15 | 3-((3-(2-(5-bromo-2-oxopyridin-1(2H)-yl)propanoyl)-2,5-dimethyl-1H-pyrrol-1-yl)methyl)benzonitrile | 438.1 |
| 16 | 4-((3-(2-(5-bromo-2-oxopyridin-1(2H)-yl)propanoyl)-2,5-dimethyl-1H-pyrrol-1-yl)methyl)benzonitrile | 438.1 |
| 17 | 2-((3-(2-(5-bromo-2-oxopyridin-1(2H)-yl)propanoyl)-2,5-dimethyl-1H-pyrrol-1-yl)methyl)benzonitrile | 438.1 |
| 18 | 5-bromo-1-(1-(1-(4-fluorobenzyl)-2,5-dimethyl-1H-pyrrol-3-yl)-1-oxopropan-2-yl)pyridin-2(1H)-one | 431.1 |

TABLE 1-continued

| Compound ID | Chemical name | Structure | Observed MS |
|---|---|---|---|
| 19 | 5-bromo-1-(1-(1-(2-fluorobenzyl)-2,5-dimethyl-1H-pyrrol-3-yl)-1-oxopropan-2-yl)pyridin-2(1H)-one | 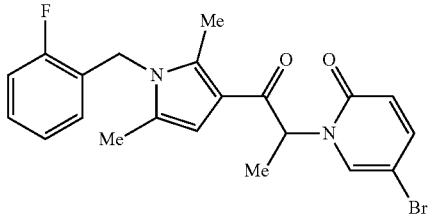 [SMILES: Cc1cc(C(=O)C(C)n2cc(Br)ccc2=O)c(C)n1Cc1ccccc1F] | 431.1 |
| 20 | 5-bromo-1-(1-(1-(3,4-difluorobenzyl)-2,5-dimethyl-1H-pyrrol-3-yl)-1-oxopropan-2-yl)pyridin-2(1H)-one | 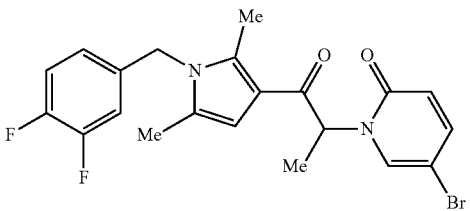 [SMILES: Cc1cc(C(=O)C(C)n2cc(Br)ccc2=O)c(C)n1Cc1ccc(F)c(F)c1] | 449.1 |
| 21 | 5-bromo-1-(1-(1-(3-(difluoromethyl)benzyl)-2,5-dimethyl-1H-pyrrol-3-yl)-1-oxopropan-2-yl)pyridin-2(1H)-one | 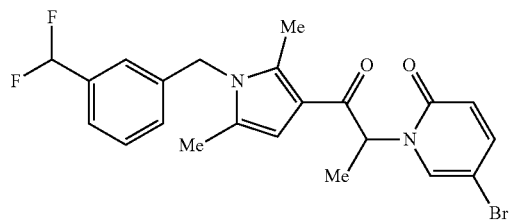 [SMILES: Cc1cc(C(=O)C(C)n2cc(Br)ccc2=O)c(C)n1Cc1cccc(C(F)F)c1] | 463.1 |
| 22 | 5-bromo-1-(1-(1-(3-chlorobenzyl)-2,5-dimethyl-1H-pyrrol-3-yl)-1-oxopropan-2-yl)pyridin-2(1H)-one | 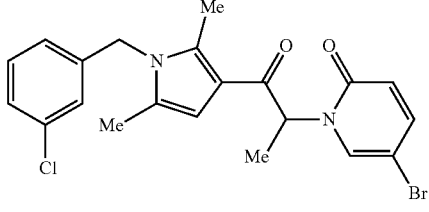 [SMILES: Cc1cc(C(=O)C(C)n2cc(Br)ccc2=O)c(C)n1Cc1cccc(Cl)c1] | 447.1 |
| 23 | 3-((3-(2-(5-bromo-2-oxopyridin-1(2H)-yl)propanoyl)-2,5-dimethyl-1H-pyrrol-1-yl)methyl)benzoic acid | 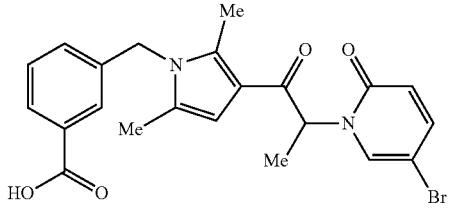 [SMILES: Cc1cc(C(=O)C(C)n2cc(Br)ccc2=O)c(C)n1Cc1cccc(C(=O)O)c1] | 457.1 |
| 24 | 5-bromo-1-(1-(2,5-dimethyl-1-(pyridin-3-ylmethyl)-1H-pyrrol-3-yl)-1-oxopropan-2-yl)pyridin-2(1H)-one | 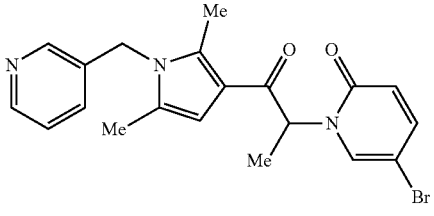 [SMILES: Cc1cc(C(=O)C(C)n2cc(Br)ccc2=O)c(C)n1Cc1cccnc1] | 416.28 |
| 25 | 5-bromo-1-(1-(2,5-dimethyl-1-(pyridin-4-ylmethyl)-1H-pyrrol-3-yl)-1-oxopropan-2-yl)pyridin-2(1H)-one | 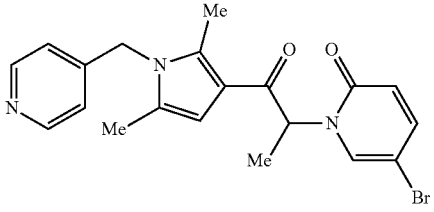 [SMILES: Cc1cc(C(=O)C(C)n2cc(Br)ccc2=O)c(C)n1Cc1ccncc1] | 416.28 |

TABLE 1-continued

| Compound ID | Chemical name | Structure | Observed MS |
|---|---|---|---|
| 26 | 1-(2-(1-benzyl-2,5-dimethyl-1H-pyrrol-3-yl)-2-oxoethyl)-5-(prop-1-yn-1-yl)pyridin-2(1H)-one | 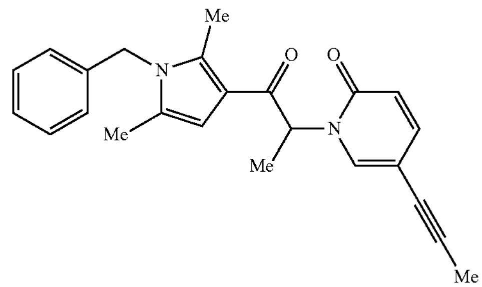 [SMILES: CC#Cc1ccc(=O)n(C(C)C(=O)c2cc(C)n(Cc3ccccc3)c2C)c1] | 359.35 |
| 27 | 1-(2-(1-benzyl-5-methyl-1H-pyrazol-4-yl)-2-oxoethyl)-5-bromopyridin-2(1H)-one | 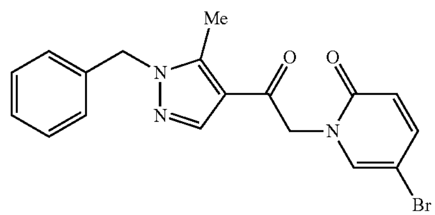 [SMILES: Cc1c(C(=O)Cn2cc(Br)ccc2=O)cnn1Cc1ccccc1] | 386.22 |
| 28 | 5-bromo-1-(2-(1-(4-fluorobenzyl)-2,5-dimethyl-1H-pyrrol-3-yl)-2-oxoethyl)pyridin-2(1H)-one | 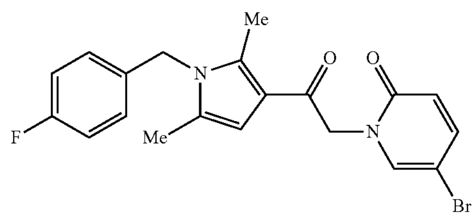 [SMILES: Cc1cc(C(=O)Cn2cc(Br)ccc2=O)c(C)n1Cc1ccc(F)cc1] | 419.26 |
| 29 | 1-(2-(1-benzyl-5-methyl-1H-pyrazol-4-yl)-2-oxoethyl)-5-ethynylpyridin-2(1H)-one | 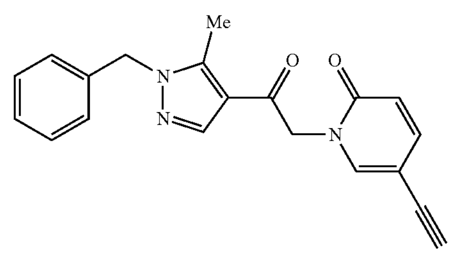 [SMILES: C#Cc1ccc(=O)n(CC(=O)c2cnn(Cc3ccccc3)c2C)c1] | 332.24 |
| 30 | 5-bromo-1-(2-(1-(4-fluorobenzyl)-2,5-dimethyl-1H-imidazol-4-yl)-2-oxoethyl)pyridin-2(1H)-one | 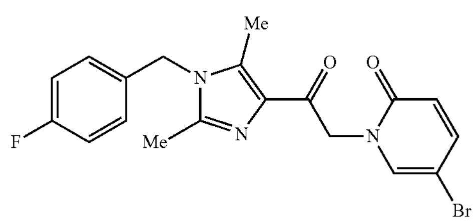 [SMILES: Cc1nc(C(=O)Cn2cc(Br)ccc2=O)c(C)n1Cc1ccc(F)cc1] | 420.0 |
| 31 | 5-ethynyl-1-(2-(1-(4-fluorobenzyl)-5-methyl-1H-pyrazol-3-yl)-2-oxoethyl)pyridin-2(1H)-one | 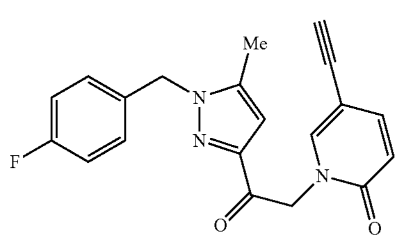 [SMILES: C#Cc1ccc(=O)n(CC(=O)c2cc(C)n(Cc3ccc(F)cc3)n2)c1] | 350.1 |

TABLE 1-continued

| Compound ID | Chemical name | Observed MS |
|---|---|---|
| 32 | 3-((4-(2-(5-bromo-2-oxopyridin-1(2H)-yl)acetyl)-5-methyl-1H-pyrazol-1-yl)methyl)benzoic acid | 430.0 |
| 33 | 5-bromo-1-(2-(5-methyl-1-(pyridin-3-ylmethyl)-1H-pyrazol-4-yl)-2-oxoethyl)pyridin-2(1H)-one | 389.2 |
| 34 | 1-(2-(1-benzyl-5-methyl-1H-pyrazol-4-yi)-2-oxoethyl)-5-vinylpyridin-2(1H)-one | 334.3 |
| 35 | 5-ethynyl-1-(2-(5-methyl-1-(pyridin-3-ylmethyl)-1H-pyrazol-4-yl)-2-oxoethyl)pyridin-2(1H)-one | 333.2 |
| 36 | 3-((4-(2-(5-ethynyl-2-oxopyridin-1(2H)-yl)acetyl)-5-methyl-1H-pyrazol-1-yl)methyl)benzoic acid | 376.1 |
| 37 | 1-(2-(1-benzyl-5-methyl-1H-pyrazol-4-yl)-2-oxoethyl)-4-bromopyridin-2(1H)-one | 388.0 |
| 38 | 1-(2-(1-benzyl-5-methyl-1H-pyrazol-4-yl)-2-oxoethyl)-4-ethynylpyridin-2(1H)-one | 332.2 |

TABLE 1-continued

| Compound ID | Chemical name | Structure | Observed MS |
|---|---|---|---|
| 39 | 1-(2-(1-benzyl-5-methyl-1H-pyrazol-4-yl)-2-oxoethyl)-5-bromo-3-methylpyridin-2(1H)-one | 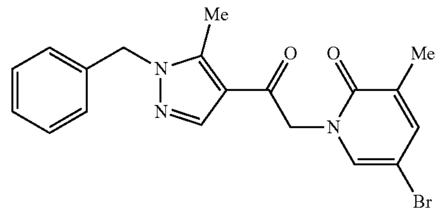 [SMILES: Cc1cc(Br)cn(CC(=O)c2cnn(Cc3ccccc3)c2C)c1=O] | 402.18 |
| 40 | 1-(2-(1-benzyl-5-methyl-1H-pyrazol-4-yl)-2-oxoethyl)-5-bromo-4-methylpyridin-2(1H)-one | 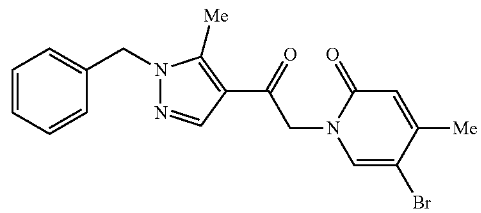 [SMILES: Cc1cc(=O)n(CC(=O)c2cnn(Cc3ccccc3)c2C)cc1Br] | 402.21 |
| 41 | 1-(2-(1-benzyl-5-methyl-1H-pyrazol-4-yl)-2-oxoethyl)-5-bromo-3-methoxypyridin-2(1H)-one | 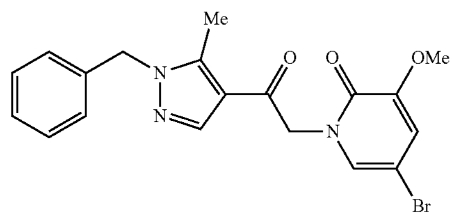 [SMILES: COc1cc(Br)cn(CC(=O)c2cnn(Cc3ccccc3)c2C)c1=O] | 418.19 |
| 42 | 1-(2-(1-benzyl-5-methyl-1H-pyrazol-4-yl)-2-oxoethyl)-5-ethynyl-3-methylpyridin-2(1H)-one | 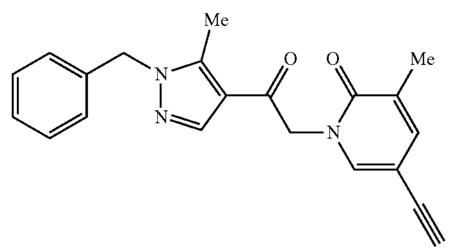 [SMILES: C#Cc1cc(C)c(=O)n(CC(=O)c2cnn(Cc3ccccc3)c2C)c1] | 346.3 |
| 43 | 2-(2-(1-benzyl-5-methyl-1H-pyrazol-4-yl)-2-oxoethyl)-6-ethynylpyridazin-3(2H)-one | 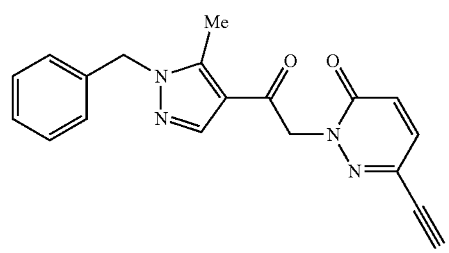 | 333.25 |
| 44 | 1-(2-(1-benzyl-2,5-dimethyl-1H-pyrrol-3-yl)-2-oxoethyl)-2-methyl-6-oxo-1,6-dihydropyridine-3-carbonitrile | 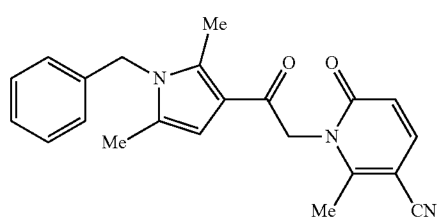 [SMILES: Cc1cc(C(=O)Cn2c(C)c(C#N)ccc2=O)c(C)n1Cc1ccccc1] | 360.38 |
| 45 | 1-(2-(1-benzyl-2,5-dimethyl-1H-pyrrol-3-yl)-2-oxoethyl)-5-chloropyridin-2(1H)-one | 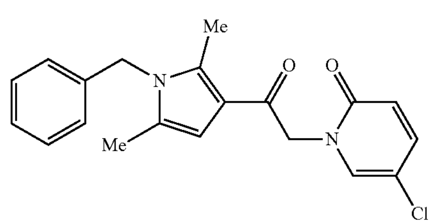 [SMILES: Cc1cc(C(=O)Cn2cc(Cl)ccc2=O)c(C)n1Cc1ccccc1] | 355.29 |

TABLE 1-continued

| Compound ID | Chemical name | Structure | Observed MS |
|---|---|---|---|
| 46 | 1-(2-(1-benzyl-2,5-dimethyl-1H-pyrrol-3-yl)-2-oxoethyl)-6-oxo-1,6-dihydropyridine-3-carboxylic acid | 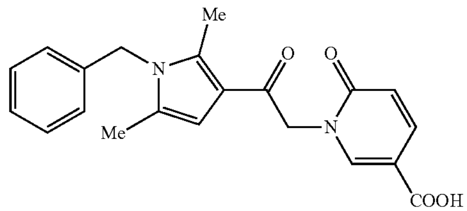 [SMILES: Cc1cc(C(=O)Cn2cc(C(=O)O)ccc2=O)c(C)n1Cc1ccccc1] | 365.38 |
| 47 | 1-(2-(2,5-dimethyl-1H-pyrrol-3-yl)-2-oxoethyl)-6-oxo-1,6-dihydropyridine-3-carbonitrile | 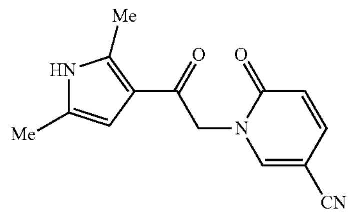 [SMILES: Cc1cc(C(=O)Cn2cc(C#N)ccc2=O)c(C)[nH]1] | 256.28 |
| 48 | 1-(3-([1,1'-biphenyl]-4-yl)-1-(2,5-dimethyl-1H-pyrrol-3-yl)-1-oxopropan-2-yl)-6-oxo-1,6-dihydropyridine-3-carbonitrile | 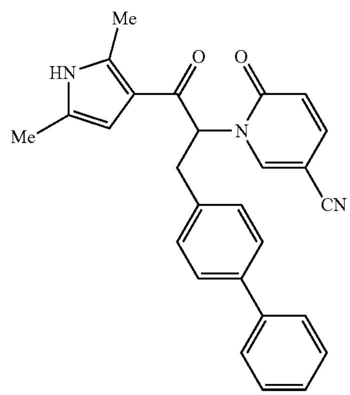 [SMILES: Cc1cc(C(=O)C(Cc2ccc(-c3ccccc3)cc2)n2cc(C#N)ccc2=O)c(C)[nH]1] | 422.46 |
| 49 | 1-(2-(1-benzyl-2,5-dimethyl-1H-pyrrol-3-yl)-2-oxoethyl)-4-methyl-6-oxo-1,6-dihydropyridine-3-carbonitrile | 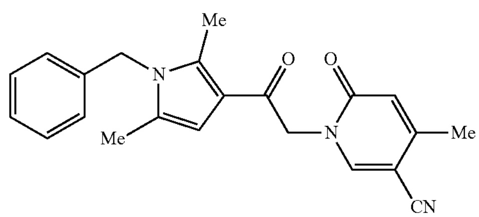 [SMILES: Cc1cc(=O)n(CC(=O)c2cc(C)n(Cc3ccccc3)c2C)cc1C#N] | 360.33 |
| 50 | 1-(2-(1-benzyl-dimethyl-1H-1-pyrrol-3-yl)-2-oxoethyl)-5-methoxypyridin-2(1H)-one | 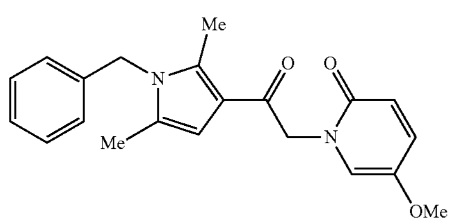 [SMILES: COc1ccc(=O)n(CC(=O)c2cc(C)n(Cc3ccccc3)c2C)c1] | 351.39 |
| 51 | 1-(1-(1-benzyl-2,5-dimethyl-1H-pyrrol-3-yl)-1-oxo-3-phenylpropan-2-yl)-6-oxo-1,6-dihydropyridine-3-carbonitrile | 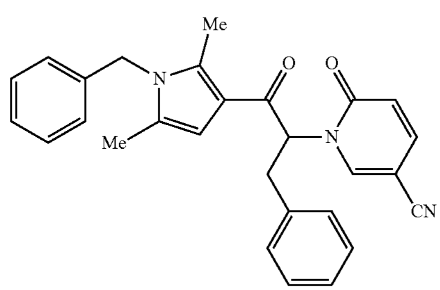 [SMILES: Cc1cc(C(=O)C(Cc2ccccc2)n2cc(C#N)ccc2=O)c(C)n1Cc1ccccc1] | 436.38 |

TABLE 1-continued

| Compound ID | Chemical name | Structure | Observed MS |
|---|---|---|---|
| 52 | 1-1-(1-benzyl-2,5-dimethyl-1H-pyrrol-3-yl)-1-oxopropan-2-yl)-6-oxo-1,6-dihydropyridine-3-carbonitrile | 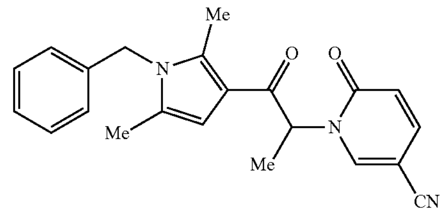 [SMILES: Cc1cc(C(=O)C(C)n2cc(C#N)ccc2=O)c(C)n1Cc1ccccc1] | 360.32 |
| 53 | 1-(2-(1-benzyl-2,5-dimethyl-1H-pyrrol-3-yl)-2-oxoethyl)-5-(tert-butyl)pyridin-2(1H)-one | 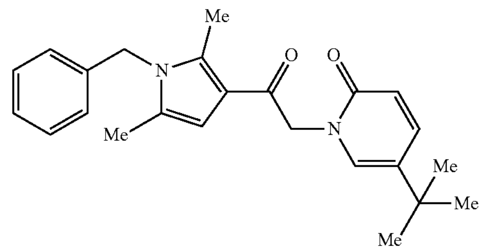 [SMILES: Cc1cc(C(=O)Cn2cc(C(C)(C)C)ccc2=O)c(C)n1Cc1ccccc1] | 377.44 |
| 54 | N-(1-(2-(1-benzyl-2,5-dimethyl-1H-pyrrol-3-yl)-2-oxoethyl)-6-oxo-1,6-dihydropyridin-3-yl)acetamide | 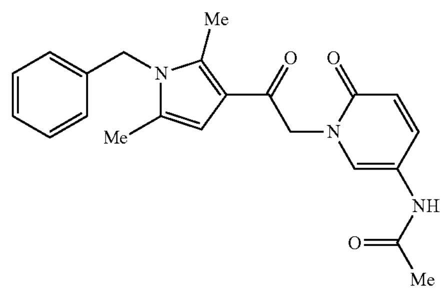 [SMILES: CC(=O)Nc1ccc(=O)n(CC(=O)c2cc(C)n(Cc3ccccc3)c2C)c1] | 378.38 |
| 55 | 2-(2-(1-benzyl-5-methyl-1H-pyrazol-4-yl)-2-oxoethyl)-6-bromopyridazin-3(2H)-one | 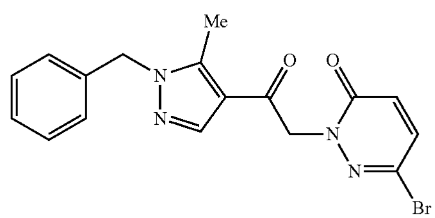 [SMILES: Cc1c(C(=O)Cn2nc(Br)ccc2=O)cnn1Cc1ccccc1] | 389.18 |
| 56 | 1-(2-(1-benzyl-5-methyl-1H-pyrazol-4-yl)-2-oxoethyl)-5-bromopyrimidin-2(1H)-one | 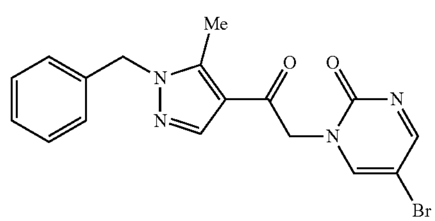 [SMILES: Cc1c(C(=O)Cn2cc(Br)cnc2=O)cnn1Cc1ccccc1] | 389.18 |
| 57 | 5-bromo-1-(1-(2,5-dimethyl-1-((5-methyl-1,3,4-oxadiazol-2-yl)methyl)-1H-pyrrol-3-yl)-1-oxopropan-2-yl)pyridin-2(1H)-one | 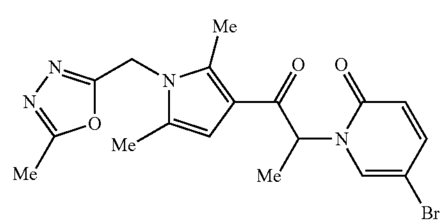 [SMILES: Cc1nnc(Cn2c(C)cc(C(=O)C(C)n3cc(Br)ccc3=O)c2C)o1] | 419.1 |

TABLE 1-continued

| Compound ID | Chemical name | Structure | Observed MS |
|---|---|---|---|
| 58 | 5-bromo-1-(1-(1-(cyclopropylmethyl)-2,5-dimethyl-1H-pyrrol-3-yl)-1-oxopropan-2-yl)pyridn-2(1H)-one | 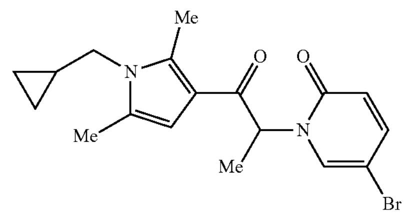 [SMILES: Cc1cc(C(=O)C(C)n2cc(Br)ccc2=O)c(C)n1CC1CC1] | 377.1 |
| 59 | 5-bromo-1-(1-(1-(cyclobutylmethyl)-2,5-dimethyl-1H-pyrrol-3-yl)-1-oxopropan-2-yl)pyridin-2(1H)-one | 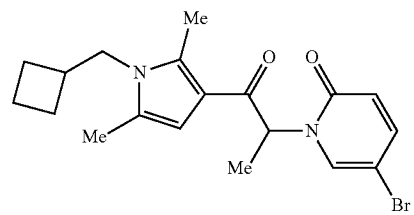 [SMILES: Cc1cc(C(=O)C(C)n2cc(Br)ccc2=O)c(C)n1CC1CCC1] | 391.1 |
| 60 | 5-bromo-1-(1-(1-(3-methoxybenzyl)-2,5-dimethyl-1H-pyrrol-3-yl)-1-oxopropan-2-yl)pyridin-2(1H)-one | 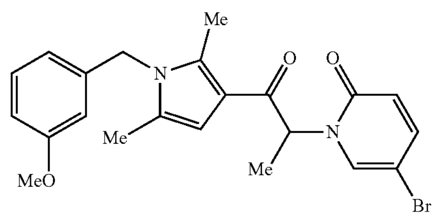 [SMILES: COc1cccc(Cn2c(C)cc(C(=O)C(C)n3cc(Br)ccc3=O)c2C)c1] | 443.1 |
| 61 | 5-bromo-1-(1-(1-(4-methoxybenzyl)-2,5-dimethyl-1H-pyrrol-3-yl)-1-oxopropan-2-yl)pyridin-2(1H)-one | 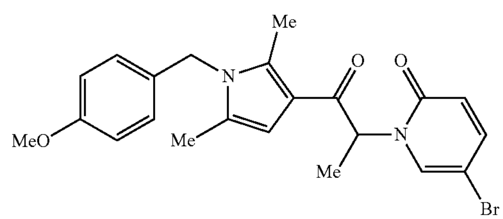 [SMILES: COc1ccc(Cn2c(C)cc(C(=O)C(C)n3cc(Br)ccc3=O)c2C)cc1] | 443.2 |
| 62 | 5-bromo-1-(1-(1-(3-fluorobenzyl)-2,5-dimethyl-1H-pyrrol-3-yl)-1-oxopropan-2-yl)pyridin-2(1H)-one | 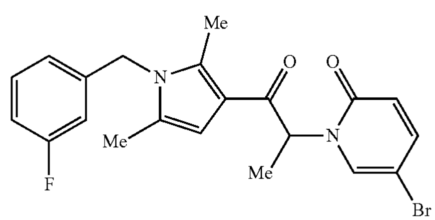 | 431.1 |
| 63 | 5-bromo-1-(1-(2,5-dimethyl-1-(3-methylbenzyl)-1H-pyrrol-3-yl)-1-oxopropan-2-yl)pyridin-2(1H)-one | 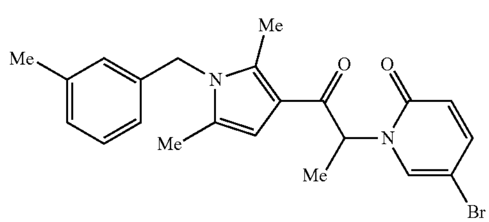 [SMILES: Cc1cccc(Cn2c(C)cc(C(=O)C(C)n3cc(Br)ccc3=O)c2C)c1] | 427.1 |
| 64 | 5-bromo-1-(1-(2,5-dimethyl-1-(2-methylbenzyl)-1H-pyrrol-3yl)-1-oxopropan-2-yl)pyridin-2(1H)-one | 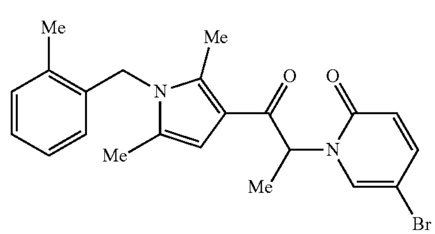 [SMILES: Cc1ccccc1Cn1c(C)cc(C(=O)C(C)n2cc(Br)ccc2=O)c1C] | 427.1 |

TABLE 1-continued

| Compound ID | Chemical name | Structure | Observed MS |
|---|---|---|---|
| 65 | 5-bromo-1-(1-(2,5-dimethyl-1-(4-methylbenzyl)-1H-pyrrol-3-yl)-1-oxopropan-2-yl)pyridin-2(1H)-one | 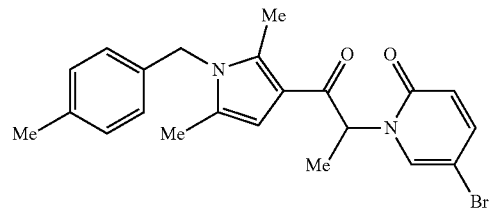 [SMILES: Cc1ccc(Cn2c(C)cc(C(=O)C(C)n3cc(Br)ccc3=O)c2C)cc1] | 427.1 |
| 66 | 5-bromo-1-(2-(3-(4-fluorobenzyl)pyrrolidin-1-yl)-2-oxoethyl)pyridin-2(1H)-one | 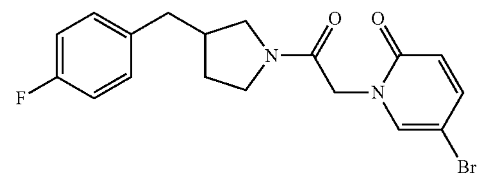 [SMILES: O=C(Cn1cc(Br)ccc1=O)N1CCC(Cc2ccc(F)cc2)C1] | 395.0 |
| 67 | 5-bromo-1-(2-(3-(4-fluorophenyl)pyrrolidin-1-yl)-2-oxoethyl)pyridin-2(1H)-one | 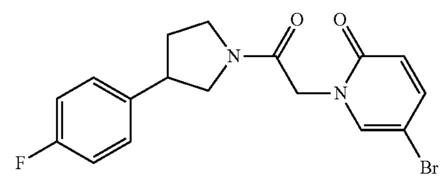 [SMILES: O=C(Cn1cc(Br)ccc1=O)N1CCC(c2ccc(F)cc2)C1] | 381.0 |
| 68 | 5-bromo-1-(2-(1-(4-fluorobenzyl)-5-methyl-1H-pyrazol-3-yl)-2-oxoethyl)pyridin-2(1H)-one | 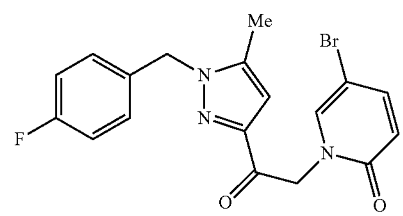 [SMILES: Cc1cc(C(=O)Cn2cc(Br)ccc2=O)nn1Cc1ccc(F)cc1] | 404.1 |
| 69 | 1-(2-(1-benzyl-5-methyl-1H-pyrazol-4-yl)-2-oxoethyl)-2-oxo-1,2-dihydropyridine-3,5-dicarbonitrile | 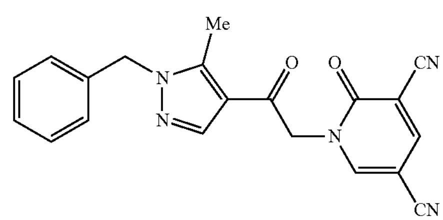 [SMILES: Cc1c(C(=O)Cn2cc(C#N)cc(C#N)c2=O)cnn1Cc1ccccc1] | 357.1 |
| 70 | 1-(2-(1-benzyl-5-methyl-1H-pyrazol-4-yl)-2-oxoethyl)-5-bromopyrazin-2(1H)-one | 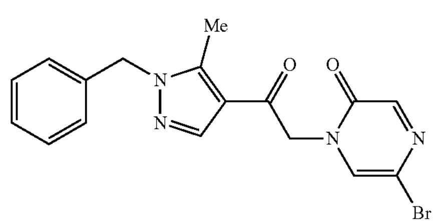 [SMILES: Cc1c(C(=O)Cn2cc(Br)ncc2=O)cnn1Cc1ccccc1] | 405.88 |
| 71 | 1-(2-(1-benzyl-5-methyl-1H-pyrazol-4-yl)-2-oxoethyl)-5-bromo-6-fluoropyridin-2(1H)-one | 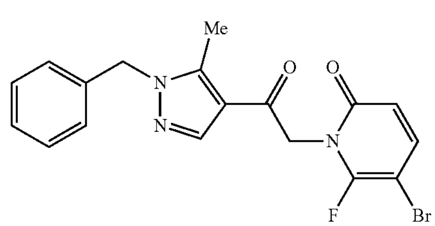 [SMILES: Cc1c(C(=O)Cn2c(F)c(Br)ccc2=O)cnn1Cc1ccccc1] | 405.88 |

TABLE 1-continued

| Compound ID | Chemical name | Structure | Observed MS |
|---|---|---|---|
| 72 | 1-(2-(1-benzyl-5-methyl-1H-pyrazol-4-yl)-2-oxoethyl)-5-bromo-4-fluoropyridin-2(1H)-one | 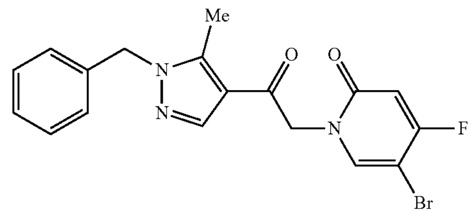 [SMILES: Cc1c(C(=O)Cn2cc(Br)c(F)cc2=O)cnn1Cc1ccccc1] | 406.2 |
| 73 | 2-(1-(1-benzyl-5-methyl-1H-pyrazol-4-yl)-1-oxopropan-2-yl)-6-ethynylpyridazin-3(2H)-one | 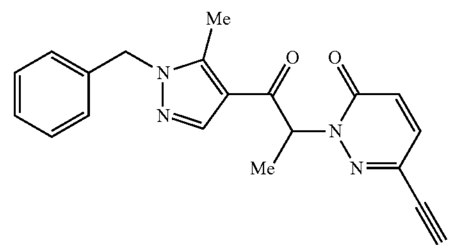 [SMILES: C#Cc1ccc(=O)n(C(C)C(=O)c2cnn(Cc3ccccc3)c2C)n1] | 347.1 |
| 74 | 6-ethynyl-2-(1-(1-(4-fluorobenzyl)-5-methyl-1H-pyrazol-4-yl)-1-oxopropan-2-yl)pyridazin-3(2H)-one | 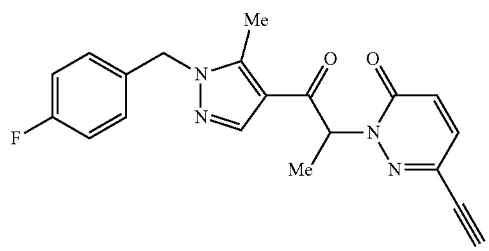 [SMILES: C#Cc1ccc(=O)n(C(C)C(=O)c2cnn(Cc3ccc(F)cc3)c2C)n1] | 365.2 |
| 75 | 2-(1-(1-(2,4-difluorobenzyl)-5-methyl-1H-pyrazol-4-yl)-1-oxopropan-2-yl)-6-ethynylpyridazin-3(2H)-one | 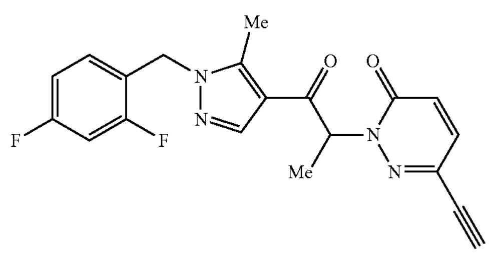 [SMILES: C#Cc1ccc(=O)n(C(C)C(=O)c2cnn(Cc3ccc(F)cc3F)c2C)n1] | 373.1 |
| 76 | 2-(1-(1-benzyl-5-methyl-1H-pyrazol-4-yl)-1-oxopropan-2-yl)-6-vinylpyridazin-3(2H)-one | 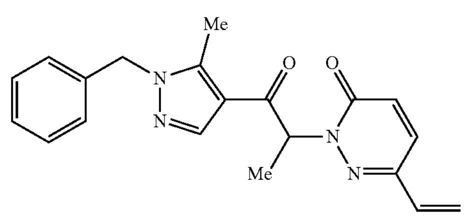 [SMILES: C=Cc1ccc(=O)n(C(C)C(=O)c2cnn(Cc3ccccc3)c2C)n1] | 349.1 |
| 77 | 1-(1-(5-methyl-1-(pyridin-2-ylmethyl)-1H-pyrazol-4-yl)-1-oxopropan-2-yl)-5-vinylpyridin-2(1H)-one | 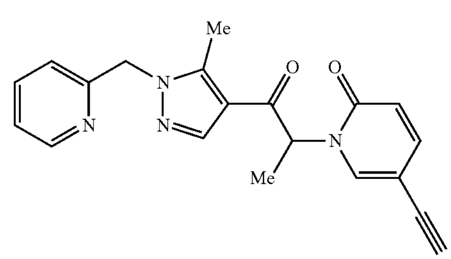 [SMILES: C#Cc1ccc(=O)n(C(C)C(=O)c2cnn(Cc3ccccn3)c2C)c1] | 347.2 |

TABLE 1-continued

| Compound ID | Chemical name | Observed MS |
|---|---|---|
| 78 | 1-(1-(5-ethyl-1-(pyridin-2-ylmethyl)-1H-pyrazol-4-yl)-1-oxopropan-2-yl)-5-ethynylpyridin-2(1H)-one | 347.2 |
| 79 | 1-(1-(5-methyl-1-(pyridin-2-ylmethyl)-1H-pyrazol-4-yl)-1-oxopropan-2-yl)-5-vinylpyridin-2(1H)-one | 349.1 |
| 80 | 1-(2-(5-ethyl-1-(pyridin-2-ylmethyl)-1H-pyrazol-4-yl)-2-oxoethyl)-5-vinylpyridin-2(1H)-one | 349.1 |
| 81 | 1-(2-(1-benzyl-5-methyl-1H-pyrazol-4yl)-2-oxoethyl)-5-(prop-1-en-2-yl)pyridin-2(1H)-one | 348.2 |
| 82 | 1-(2-(1-benzyl-5-(trifluoromethyl)-1H-pyrazol-4-yl)-2-oxoethyl)-5-vinylpyridin-2(1H)-one | 388.2 |
| 83 | 1-(2-(1-benzyl-5-methyl-1H-pyrazol-4-yl)-2-oxoethyl)-5-(1-fluorovinyl)pyridin-2(1H)-one | 352.1 |

TABLE 1-continued

| Compound ID | Chemical name | Structure | Observed MS |
|---|---|---|---|
| 84 | 1-(2-(1-benzyl-5-methyl-1H-pyrazol-4-yl)-2-oxoethyl)-5-(3,3,3-trifluoroprop-1-en-2-yl)pyridin-2(1H)-one | 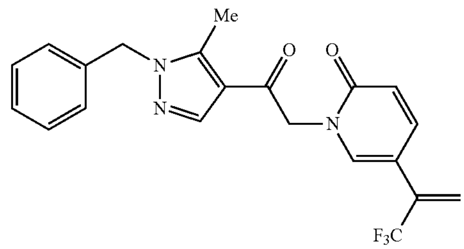 [SMILES: C=C(c1ccc(=O)n(CC(=O)c2cnn(Cc3ccccc3)c2C)c1)C(F)(F)F] | 402.1 |
| 85 | 1-(2-(1-benzyl-5-ethyl-1H-pyrazol-4-yl)-2-oxoethyl)-5-vinylpyridin-2(1H)-one | 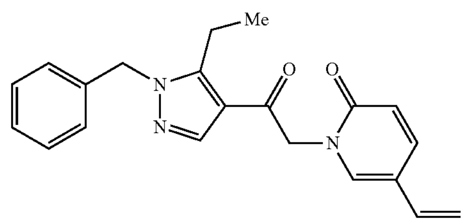 [SMILES: C=Cc1ccc(=O)n(CC(=O)c2cnn(Cc3ccccc3)c2CC)c1] | 348.1 |
| 86 | 1-(2-(1-benzyl-3,5-dimethyl-1H-pyrazol-4-yl)-2-l oxoethyl)-5-vinylpyridin-2(1H)-one | 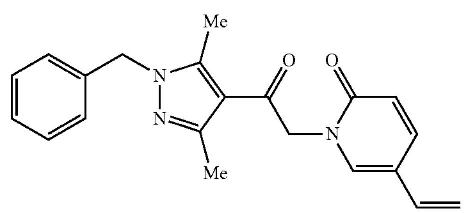 [SMILES: C=Cc1ccc(=O)n(CC(=O)c2c(C)nn(Cc3ccccc3)c2C)c1] | 348.1 |
| 87 | 1-(2-(1-benzyl-5-(difluoromethyl)-1H-pyrazol-4-yl)-2-oxoethyl)-5-vinylpyridin-2(1H)-one | 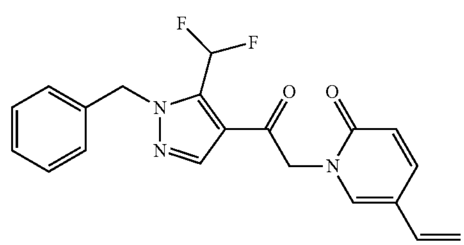 [SMILES: C=Cc1ccc(=O)n(CC(=O)c2cnn(Cc3ccccc3)c2C(F)F)c1] | 370.1 |
| 88 | 1(2-(1-benzyl-5-ethyl-1H-1,2,3-triazol-4-yl)-2-oxoethyl)-5-ethynylpyridin-2(1H)-one | 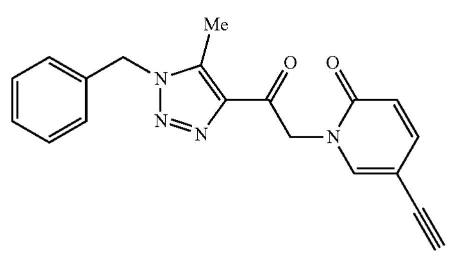 | 333.1 |
| 89 | 1-(2-(1-benzyl-5-methyl-1H-1,2,3-triazo-4-yl)-2-oxoethyl)-5-vinylpyridin-2(1H)-one | 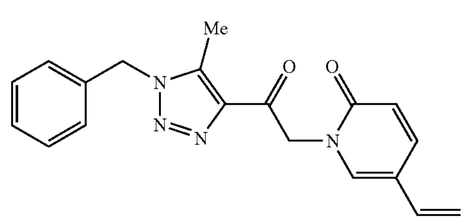 [SMILES: C=Cc1ccc(=O)n(CC(=O)c2nnn(Cc3ccccc3)c2C)c1] | 335.1 |

TABLE 1-continued

| Compound ID | Chemical name | Observed MS |
|---|---|---|
| 90 | methyl 1-(2-(1-benzyl-2,5-dimethyl-1H-pyrrol-3-yl)-2-oxoethyl)-6-oxo-1,6-dihydropyridine-3-carboxylate | 379.32 |
| 91 | 1-(2-(2,5-dimethyl-1-phenethyl-1H-pyrrol-3-yl)-2-oxoethyl)-6-oxo-1,6-dihydropyridine-3-carbonitrile | 360.36 |
| 92 | 1-(2-(2,5-dimethyl-1-(1-phenylethyl)-1H-pyrrol-3-yl)-2-oxoethyl)-6-oxo-1,6-dihydropyridine-3-carbonitrile | 360.35 |
| 93 | 1-(2-(1-(benzo[d][1,3]dioxol-5-ylmethyl)-2,5-dimethyl-1H-pyrrol-3-yl)-2-oxoethyl)-6-oxo-1,6-dihydropyridine-3-carbonitrile | 390.37 |
| 94 | 1-(2-(2-benzyloxazol-4-yl)-2-oxoethyl)-5-vinylpyridin-2(1H)-one | 321.1 |
| 95 | 1-(2-(2-benzyloxazol-4-yl)-2-oxoethyl)-5-ethynylpyridin-2(1H)-one | 319.0 |
| 96 | 1-(2-(2-benzylthiazol-4-yl)-2-oxoethyl)-5-vinylpyridin-2(1H)-one | 337.1 |

TABLE 1-continued

| Compound ID | Chemical name | Structure | Observed MS |
|---|---|---|---|
| 97 | 1-(2-(2-benzylthiazol-4-yl)-2-oxoethyl)-5-ethynylpyridin-2(1H)-one | 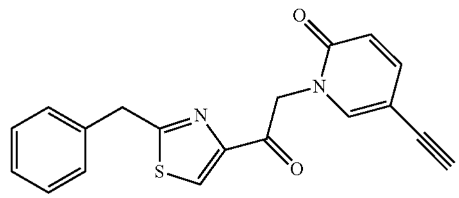 [SMILES: C#Cc1ccc(=O)n(CC(=O)c2coc(Cc3ccccc3)n2)c1] | 335.0 |
| 98 | 1-(2-(2-benzyloxazol-5-yl)-2-oxoethyl)-5-vinylpyridin-2(1H)-one | 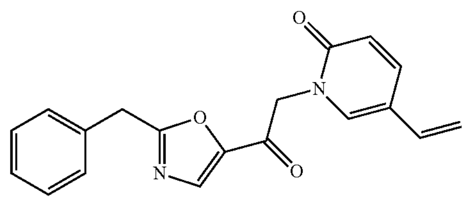 | 321.1 |
| 99 | 1-(2-(2-benzyloxazol-5-yl)-2-oxoethyl)-5-ethynylpyridin-2(1H)-one | 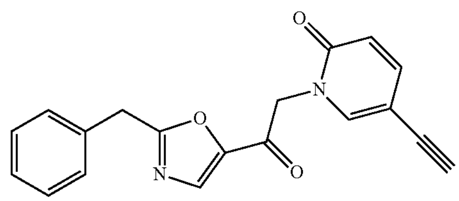 | 319.0 |
| 100 | 1-(2-(2-benzylthiazol-5-yl)-2-oxoethyl)-5-vinylpyridin-2(1H)-one | 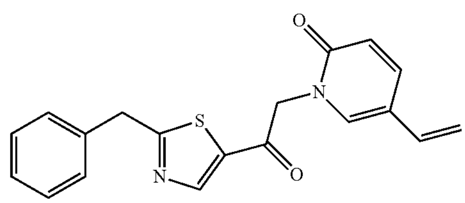 [SMILES: C=Cc1ccc(=O)n(CC(=O)c2cnc(Cc3ccccc3)s2)c1] | 337.0 |
| 101 | 1-(2-(2-benzylthiazol-5-yl)-2-oxoethyl)-5-ethynylpyridin-2(1H)-one | 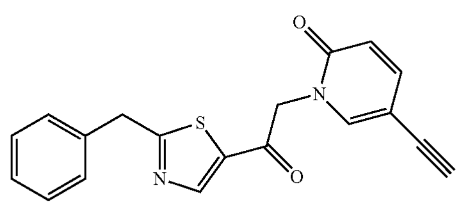 | 335.0 |
| 102 | 1-(2-(4-benzyloxazol-2-yl)-2-oxoethyl)-5-vinylpyridin-2(1H)-one | 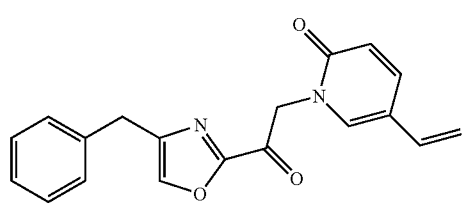 [SMILES: C=Cc1ccc(=O)n(CC(=O)c2nc(Cc3ccccc3)co2)c1] | 321.1 |
| 103 | 1-(2-(4-benzyloxazol-2-yl)-2-oxoethyl)-5-ethynylpyridin-2(1H)-one | 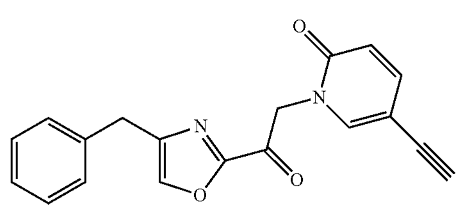 [SMILES: C#Cc1ccc(=O)n(CC(=O)c2nc(Cc3ccccc3)cs2)c1] | 319.1 |

TABLE 1-continued

| Compound ID | Chemical name | Structure | Observed MS |
|---|---|---|---|
| 104 | 1-(2-(4-benzylthiazol-2-yl)-2-oxoethyl)-5-vinylpyridin-2(1H)-one | 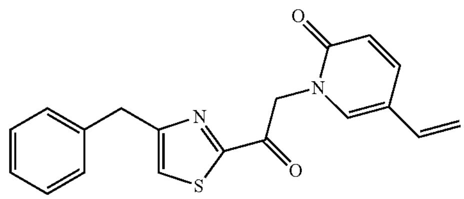 | 337.1 |
| 105 | 1-(2-(4-benzylthiazol-2-yl)-2-oxoethyl)-5-ethynylpyridin-2(1H)-one | 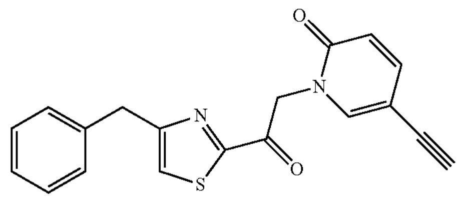 | 335 |
| 106 | 1-(2-(1-benzyl-5-(methyl-d3)-1H-pyrazol-4-yl)-2-oxoethyl)-5-vinylpyridin-2(1H)-one | 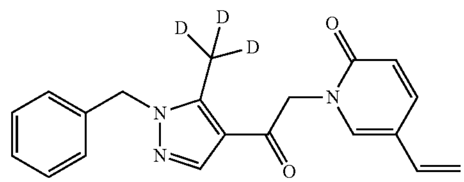 [SMILES: [2H]C([2H])([2H])c1c(C(=O)Cn2cc(C=C)ccc2=O)cnn1Cc1ccccc1] | 337.2 |
| 107 | 1-(2-(1-benzyl-2,5-dimethyl-1H-pyrrol-3-yl)-2-oxoethyl)-5-vinylpyridin-2(1H)-one | 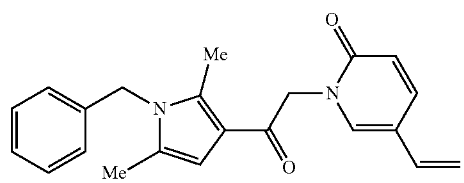 [SMILES: C=Cc1ccc(=O)n(CC(=O)c2cc(C)n(Cc3ccccc3)c2C)c1] | 347.1 |
| 108 | 5-acetyl-1-(2-(1-benzyl-5-methyl-1H-pyrazol-4-yl)-2-oxoethyl)pyridin-2(1H)-one | 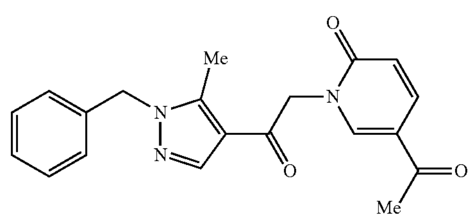 [SMILES: CC(=O)c1ccc(=O)n(CC(=O)c2cnn(Cc3ccccc3)c2C)c1] | 350.1 |
| 109 | 1-(2-(1-benzyl-5-methyl-1H-pyrazol-4-yl)-2-oxoethyl)-2-oxo-5-vinyl-1,2-dihydropyridine-3-carbonitrile | 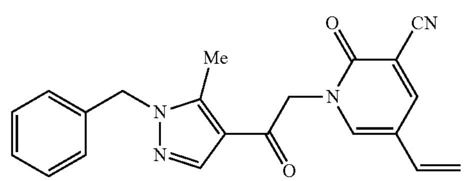 [SMILES: C=Cc1cc(C#N)c(=O)n(CC(=O)c2cnn(Cc3ccccc3)c2C)c1] | 359.1 |
| 110 | 1-(2-(3-benzyl-4-methylisoxazol-5-yl)-2-oxoethyl)-5-vinylpyridin-2(1H)-one | 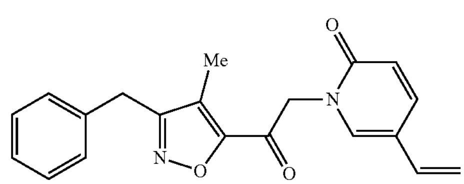 [SMILES: C=Cc1ccc(=O)n(CC(=O)c2onc(Cc3ccccc3)c2C)c1] | 335.1 |
| 111 | 1-(2-(3-benzyl-4-methylisoxazol-5-yl)-2-oxoethyl)-5-ethynylpyridin-2(1H)-one | 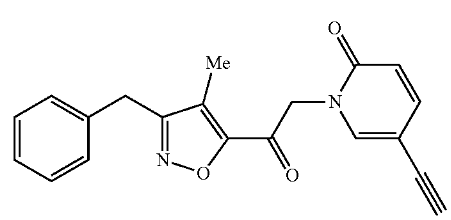 [SMILES: C#Cc1ccc(=O)n(CC(=O)c2onc(Cc3ccccc3)c2C)c1] | 333.1 |

TABLE 1-continued

| Compound ID | Chemical name | Structure | Observed MS |
|---|---|---|---|
| 112 | 1-(2-(1-benzyl-5-methyl-1H-pyrazol-4-yl)-2-oxoethyl)-3-vinylpyridin-2(1H)-one | 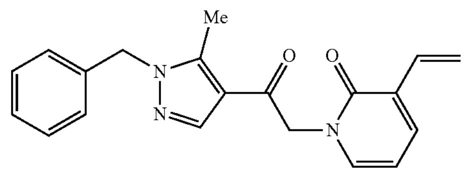 [SMILES: C=Cc1cccn(CC(=O)c2cnn(Cc3ccccc3)c2C)c1=O] | 334.1 |
| 113 | 1-(2-(1-benzyl-5-methyl-1H-pyrazol-4-yl)-2-oxoethyl)-3-fluoro-5-vinylpyridin-2(1H)-one | 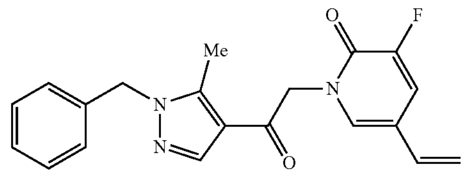 | 352.1 |
| 114 | 2-(2-(1-benzyl-5-methyl-1H-pyrazol-4-yl)ethoxy)-5-vinylpyridine | 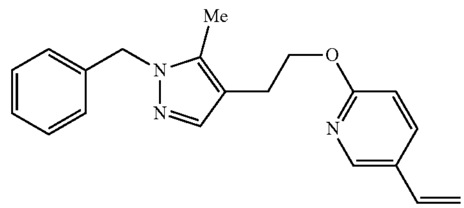 [SMILES: C=Cc1ccc(OCCc2cnn(Cc3ccccc3)c2C)nc1] | 320.1 |
| 115 | 1-(2-(1-benzyl-5-methyl-1H-pyrazol-4-yl)-2-oxoethyl)-2-oxo-5-(3,3,3-trifluoroprop-1-en-2-yl)-1,2-dihydropyridine-3-carbonitrile | 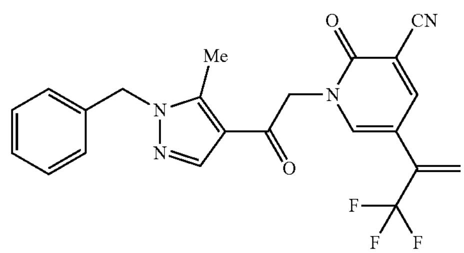 [SMILES: C=C(c1cc(C#N)c(=O)n(CC(=O)c2cnn(Cc3ccccc3)c2C)c1)C(F)(F)F] | 427.1 |
| 116 | 1-(2-(1-benzyl-5-methyl-1H-pyrazol-4-yl)-2-oxoethyl)-2-oxo-5-vinyl-1,2-dihydropyridine-4-carbonitrile | 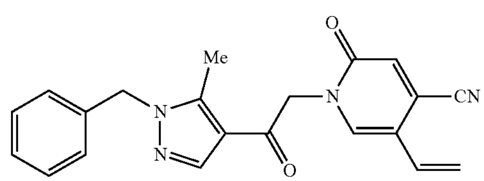 [SMILES: C=Cc1cn(CC(=O)c2cnn(Cc3ccccc3)c2C)c(=O)cc1C#N] | 359.2 |
| 117 | 1-(1-(1-benzyl-5-methyl-1H-pyrazol-4-yl)-1-oxopropan-2-yl)-5-vinylpyrazin-2(1H)-one | 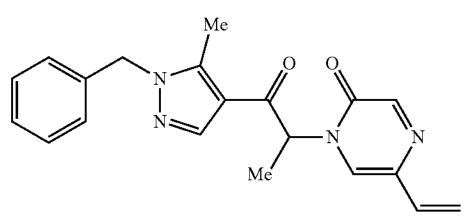 [SMILES: C=Cc1cn(C(C)C(=O)c2cnn(Cc3ccccc3)c2C)c(=O)cn1] | 349.1 |
| 118 | 1-(2-(1-benzyl-5-methyl-1H-pyrazol-4-yl)-2-hydroxyethyl)-5-vinylpyridin-2(1H)-one | 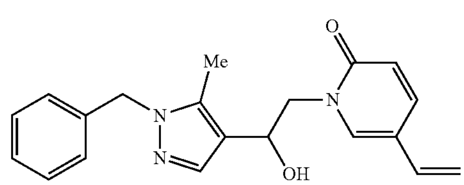 [SMILES: C=Cc1ccc(=O)n(CC(O)c2cnn(Cc3ccccc3)c2C)c1] | 336.1 |
| 119 | 1-(2-(1-benzyl-5-methyl-1H-pyrazol-4-yl)-2-methoxyethyl)-5-vinylpyridin-2(1H)-one | 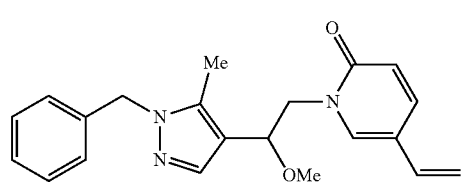 [SMILES: C=Cc1ccc(=O)n(CC(OC)c2cnn(Cc3ccccc3)c2C)c1] | 350.2 |

TABLE 1-continued

| Compound ID | Chemical name | Structure | Observed MS |
|---|---|---|---|
| 120 | 1-(2-(1-benzyl-5-methyl-1H-pyrazol-4-yl)ethyl)-5-vinylpyridin-2(1H)-one | 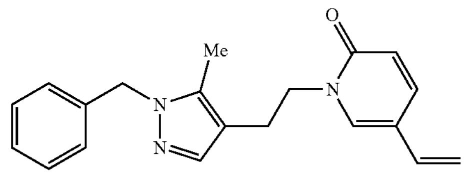 [SMILES: C=Cc1ccc(=O)n(CCc2cnn(Cc3ccccc3)c2C)c1] | 320.1 |
| 121 | 1-((1-benzyl-5-methyl-1H-pyrazol-4-yl)methyl)-5-vinylpyridin-2(1H)-one | 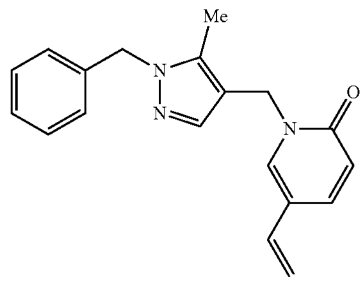 [SMILES: C=Cc1ccc(=O)n(Cc2cnn(Cc3ccccc3)c2C)c1] | 306.1 |
| 122 | 1-(2-(1-benzyl-5-methyl-1H-pyrazol-4-yl)-2-oxoethyl)-4-fluoro-5-vinylpyridin-2(1H)-one | 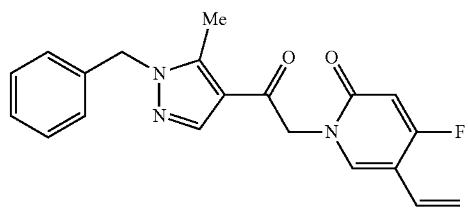 [SMILES: C=Cc1cn(CC(=O)c2cnn(Cc3ccccc3)c2C)c(=O)cc1F] | 352.1 |
| 123 | 1-(1-(1-benzyl-5-methyl-1H-pyrazol-4-yl)-1-oxopropan-2-yl)-5-vinylpyrimidin-2(1H)-one | 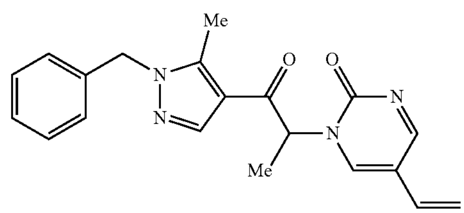 [SMILES: C=Cc1cnc(=O)n(C(C)C(=O)c2cnn(Cc3ccccc3)c2C)c1] | 349.1 |
| 124 | 1-(1-benzyl-5-methyl-1H-pyrazol-4-yl)-2-((5-vinylpyrazin-2-yl)oxy)propan-1-one | 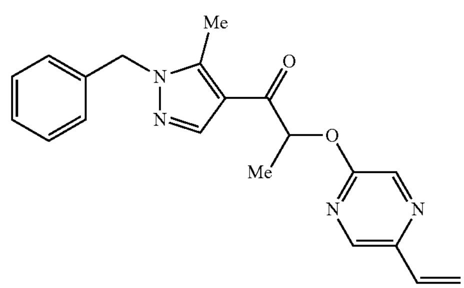 [SMILES: C=Cc1cnc(OC(C)C(=O)c2cnn(Cc3ccccc3)c2C)cn1] | 349.2 |
| 125 | 1-(2-(1-benzyl-5-methyl-1H-pyrazol-4-yl)-2-oxoethyl)-6-fluoro-5-vinylpyridin-2(1H)-one | 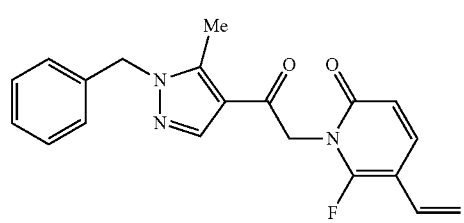 [SMILES: C=Cc1ccc(=O)n(CC(=O)c2cnn(Cc3ccccc3)c2C)c1F] | 352.1 |

TABLE 1-continued

| Compound ID | Chemical name | Structure | Observed MS |
|---|---|---|---|
| 126 | (E)-1-(2-(1-benzyl-5-methyl-1H-pyrazol-4-yl)-2-oxoethyl)-5-(3-(dimethylamino)prop-1-en-1-yl)pyridin-2(1H)-one | 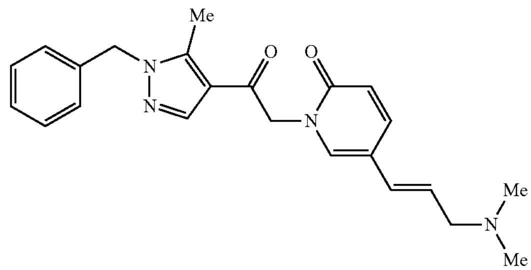 [SMILES: Cc1c(C(=O)Cn2cc(/C=C/CN(C)C)ccc2=O)cnn1Cc1ccccc1] | 391.1 |
| 127 | (Z)-1-(2-(1-benzyl-5-methyl-1H-pyrazol-4-yl)-2-oxoethyl)-5-(3-(dimethylamino)prop-1-en-1-yl)pyridin-2(1H)-one | 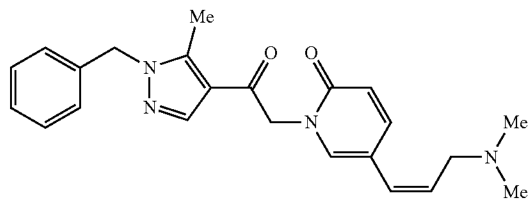 [SMILES: Cc1c(C(=O)Cn2cc(/C=C\CN(C)C)ccc2=O)cnn1Cc1ccccc1] | 391.1 |
| 128 | (E)-(2-(1-benzyl-5-methyl-1H-pyrazol-4-yl)-2-oxoethyl)-5-(3-morpholinoprop-1-en-1-yl)pyridin-2(1H)-one | 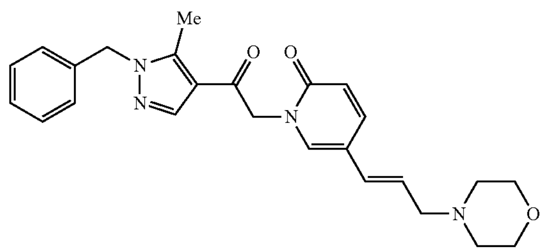 [SMILES: Cc1c(C(=O)Cn2cc(/C=C/CN3CCOCC3)ccc2=O)cnn1Cc1ccccc1] | 433.2 |
| 129 | (Z)-1-(2-(1-benzyl-5-methyl-1H-pyrazol-4-y1)-2-oxoethyl)-5-(3-morpholinoprop-1-en-1-yl)pyridin-2(1H)-one | 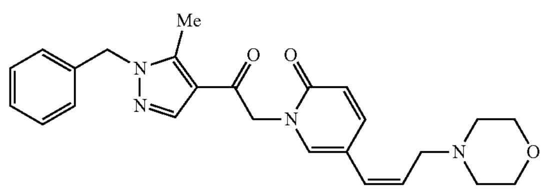 [SMILES: Cc1c(C(=O)Cn2cc(/C=C\CN3CCOCC3)ccc2=O)cnn1Cc1ccccc1] | 433.2 |
| 130 | 1-((1-Benzyl-1H-pyrazolo[4,3-c]pyridin-4-y)methyl)-5-bromopyridin-2(1H)-one hydrochloride | 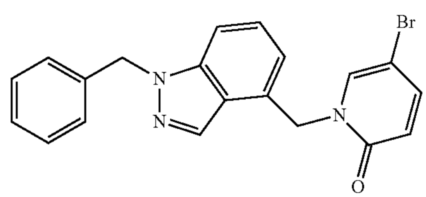 [SMILES: O=c1ccc(Br)cn1Cc1cccc2c1cnn2Cc1ccccc1] | 397.0 |
| 131 | 1-((1-benzyl-1H-pyrazolo[4,3-c]pyridin-4-yl)methyl)-5-ethynylpyridin-2(1H)one hydrochloride | 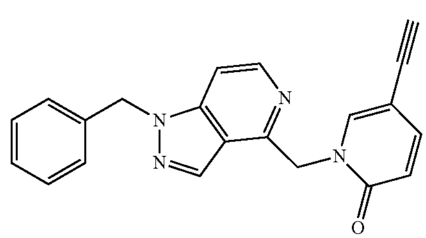 [SMILES: C#Cc1ccc(=O)n(Cc2nccc3c2cnn3Cc2ccccc2)c1] | 341.1 |
| 132 | 1-((2-benzyl-1-methyl-1H-imidazo1[4,5-c]pyridin-4-yl)methyl)-5-bromopyridin-2(1H)-one | 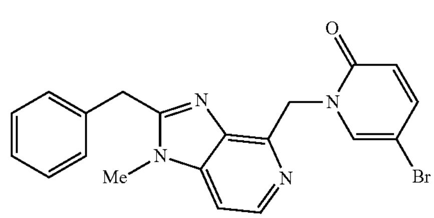 [SMILES: Cn1c(Cc2ccccc2)nc2c(Cn3cc(Br)ccc3=O)nccc21] | 409.0 |

TABLE 1-continued

| Compound ID | Chemical name | Structure | Observed MS |
|---|---|---|---|
| 133 | 1-((2-benzyl-1-methyl-1H-imidazo[4,5-c]pyridin-4-yl)methyl)-5-ethynylpyridin-2(1H)-one | 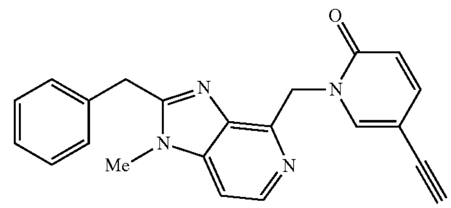 [SMILES: C#Cc1ccc(=O)n(Cc2nccc3c2nc(Cc2ccccc2)n3C)c1] | 355.1 |
| 134 | 1-(2-(1-benzyl-5-methyl-1H-pyrazol-4-yl)-2-oxoethyl)-5-ethynyl-3-fluoropyridin-2(1H)-one | 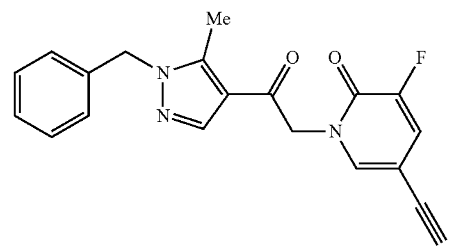 [SMILES: C#Cc1cc(F)c(=O)n(CC(=O)c2cnn(Cc3ccccc3)c2C)c1] | 350.2 |
| 135 | 1-(2-(1-benzyl-2,5-dimethyl-1H-imidazol-4-yl)-2-oxoethyl)-5-bromopyridin-2(1H)-one | 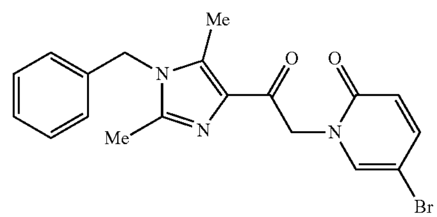 [SMILES: Cc1nc(C(=O)Cn2cc(Br)ccc2=O)c(C)n1Cc1ccccc1] | 400.0 |
| 136 | 5-ethynyl-1-(2-(1-(4-fluorobenzyl)-2,5-dimethyl-1H-1-imidazol-4-yl)-2-oxoethyl)pyridin-2(1H)-one | 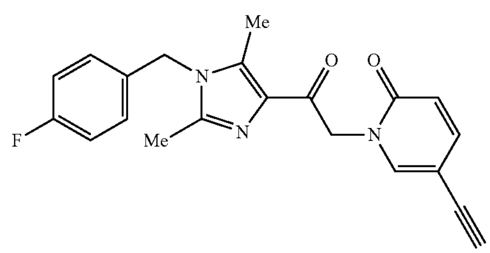 [SMILES: C#Cc1ccc(=O)n(CC(=O)c2nc(C)n(Cc3ccc(F)cc3)c2C)c1] | 364.1 |
| 137 | 5-bromo-1-(2-(1-(4-fluorobenzyl)-5-methyl-1H-pyrazol-4-yl)-2-oxoethyl)pyridin-2(1H)-one | 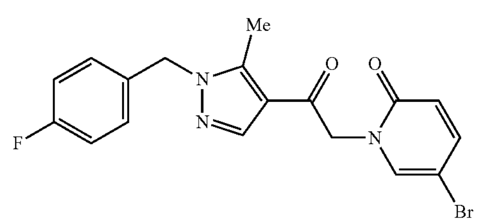 [SMILES: Cc1c(C(=O)Cn2cc(Br)ccc2=O)cnn1Cc1ccc(F)cc1] | 404.0 |
| 138 | 3-((4-(2-(5-bromo-2-oxopyridin-1(2H)-yl)acetyl)-5-methyl-1H-pyrazol-1-yl)methyl)benzonitrile | 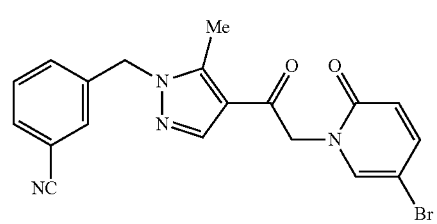 [SMILES: Cc1c(C(=O)Cn2cc(Br)ccc2=O)cnn1Cc1cccc(C#N)c1] | 411.1 |

TABLE 1-continued

| Compound ID | Chemical name | Observed MS |
|---|---|---|
| 139 | 3-((4-(2-(5-ethynyl-2-oxopyridin-1(2H)-yl)acetyl)-5-methyl-1H-pyrazol-1-yl)methyl)benzonitrile | 357.1 |
| 140 | 5-ethynyl-1-(2-(1-(4-fluorobenzyl)-5-methyl-1H-pyrazol-4-yl)-2-oxoethyl)pyridin-2(1H)-one | 350.1 |
| 141 | 1-(2-(1-benzyl-5-methyl-1H-pyrazol-4-yl)-2-oxoethyl)-5-bromo-3-fluoropyridin-2(1H)-one | 404.0 |
| 142 | 1-(2-(1-benzyl-5-methyl-1H-pyrazol-4-yl)-2-oxoethyl)-5-bromo-2-oxo-1,2-dihydropyridine-3-carbonitrile | 413.0 |
| 143 | 1-(2-(1-benzyl-5-methyl-1H-pyrazol-4-yl)-2-oxoethyl)-4-vinylpyridin-2(1H)-one | 334.1 |
| 144 | 1-(2-(1-(4-fluorobenzyl)-5-methyl-1H-pyrazol-3-yl)-2-oxoethyl)-5-(prop-1-yn-1-yl)pyridin-2(1H)-one | 364.2 |
| 145 | 1-(2-(1-benzyl-5-methyl-1H-pyrazol-3-yl)-2-oxoethyl)-5-ethynylpyridin-2(1H)-one | 332.1 |

TABLE 1-continued

| Compound ID | Chemical name | Structure | Observed MS |
|---|---|---|---|
| 146 | 1-(2-(1-benzyl-5-methyl-1H-pyrazol-3-yl)-2-oxoethyl)-5-bromopyridin-2(1H)-one | 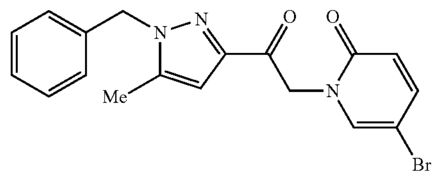 [SMILES: Cc1cc(C(=O)Cn2cc(Br)ccc2=O)nn1Cc1ccccc1] | 386.1 |
| 147 | 1-(2-(5-benzyloxazol-2-yl)-2-oxoethyl)-5-vinylpyridin-2(1H)-one | 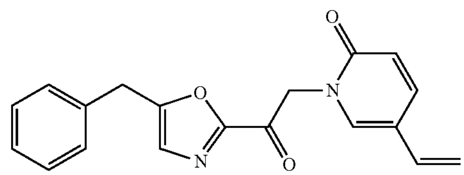 [SMILES: C=Cc1ccc(=O)n(CC(=O)c2ncc(Cc3ccccc3)o2)c1] | |
| 148 | 1-(2-(5-benzyloxazol-2-yl)-2-oxoethyl)-5-ethynylpyridin-2(1H)-one | 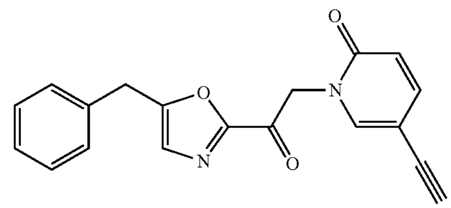 [SMILES: C#Cc1ccc(=O)n(CC(=O)c2ncc(Cc3ccccc3)o2)c1] | |
| 149 | 1-(2-(5-benzylthiazol-2-yl)-2-oxoethyl)-5-vinylpyridin-2(1H)-one | 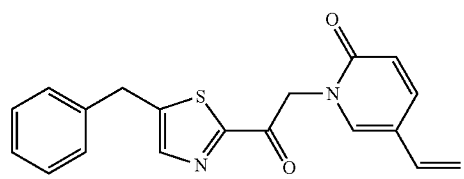 | |
| 150 | 1-(2-(5-benzylthiazol-2-yl)-2-oxoethyl)-5-ethynylpyridin-2(1H)-one | 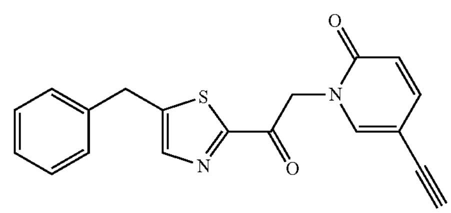 | |
| 151 | 1-(2-(3-benzyl-4-methylisothiazol-5-yl)-2-oxoethyl)-5-vinylpyridin-2(1H)-one | 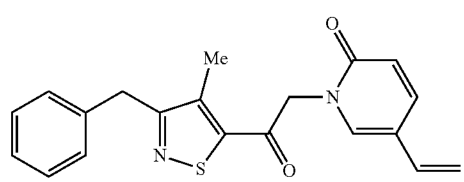 | |
| 152 | 1-(2-(3-benzyl-4-methylisothiazol-5-yl)-2-oxoethyl)-5-ethynylpyridin-2(1H)-one | 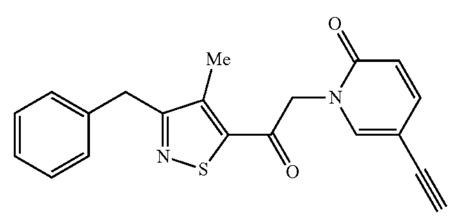 | |
| 153 | 1-(2-(5-benzyl-4-methylisoxazol-3-yl)-2-oxoethyl)-5-vinylpyridin-2(1H)-one | 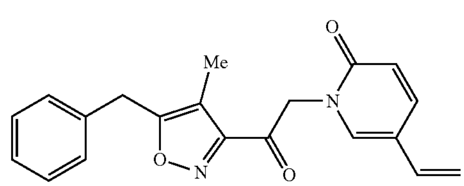 | |

TABLE 1-continued
| Compound ID | Chemical name | Structure | Observed MS |
|---|---|---|---|
| 154 | 1-(2-(5-benzyl-4-methylisoxazol-3-yl)-2-oxoethyl)-5-ethynylpyridin-2(1H)-one | 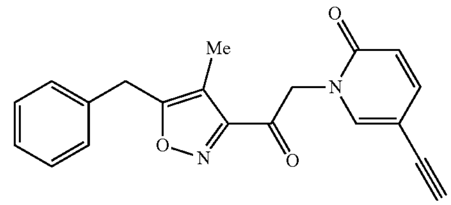 [SMILES: C#Cc1ccc(=O)n(CC(=O)c2noc(Cc3ccccc3)c2C)c1] | |
| 155 | 1-(2-(5-benzyl-4-methylisothiazol-3-yl)-2-oxoethyl)-5-vinylpyridin-2(1H)-one | 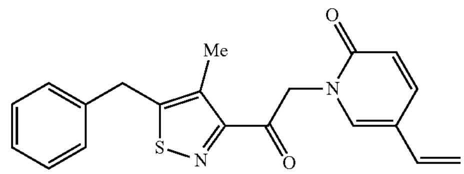 [SMILES: C=Cc1ccc(=O)n(CC(=O)c2nsc(Cc3ccccc3)c2C)c1] | |
| 156 | 1-(2-(5-benzyl-4-methylisothiazol-3-yl)-2-oxoethyl)-5-ethynylpyridin-2(1H)-one | 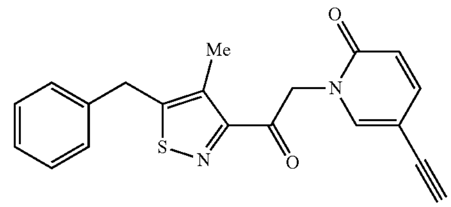 | |
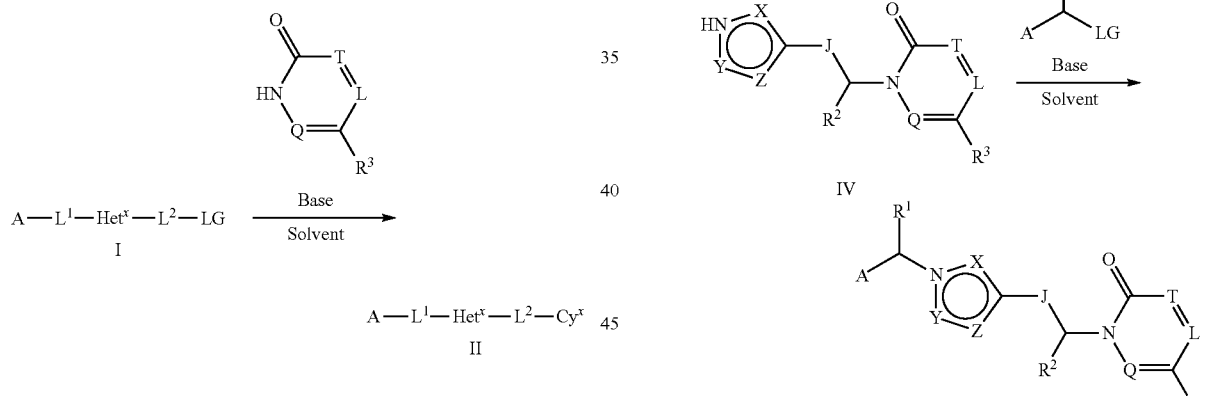
In addition, compounds of the formula (IIa) can generally be produced as shown in Schemes 2 and 3.
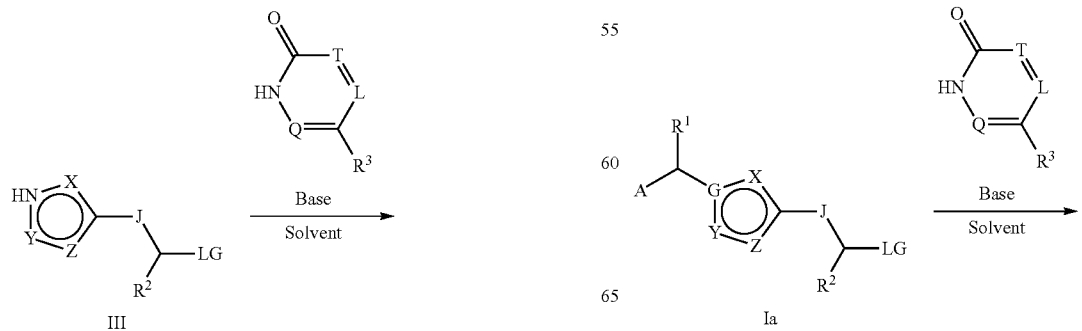

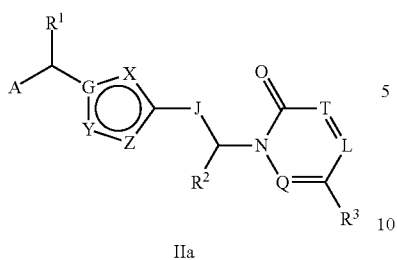

IIa

Further, compounds of the formula (IIIa) can generally be produced as shown in Scheme 4.

Scheme 4-Generic synthetic scheme for intermediate IIIa

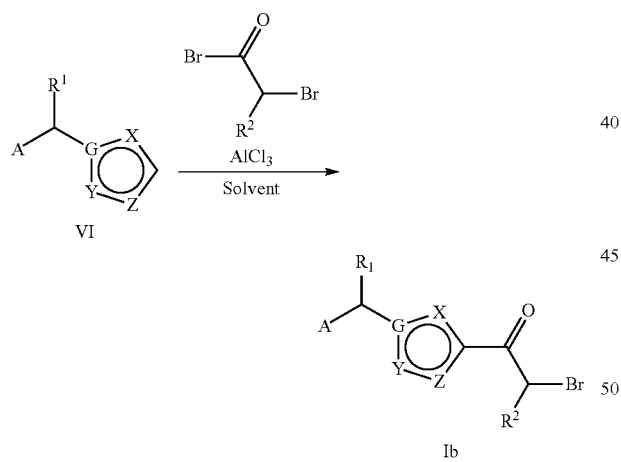

Then, compounds of the formula (Ib) can generally be produced as shown in Schemes 5 and 6.

Scheme 5-Generic synthetic scheme for intermediate Ib

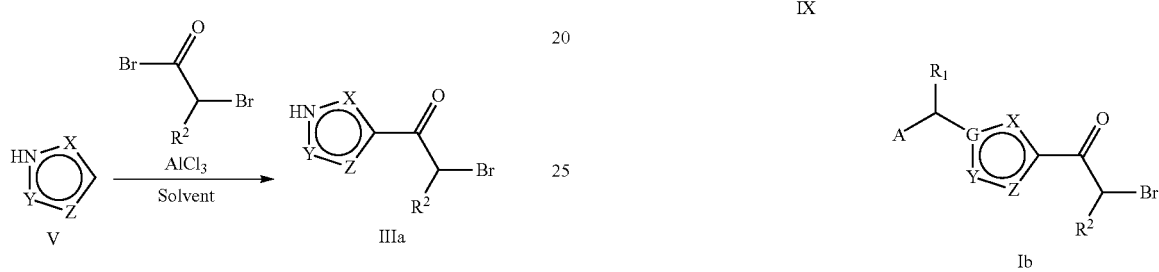

Scheme 6-Generic synthetic scheme for iontermediate Ib

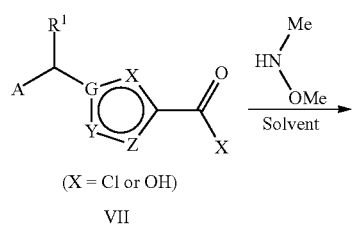

VII

Further still, compounds of the formulae A4 and A5 can generally be produced as shown in Schemes 7 and 8.

Scheme 7-Synthetic scheme for pyrrole derivatives A4 and A5

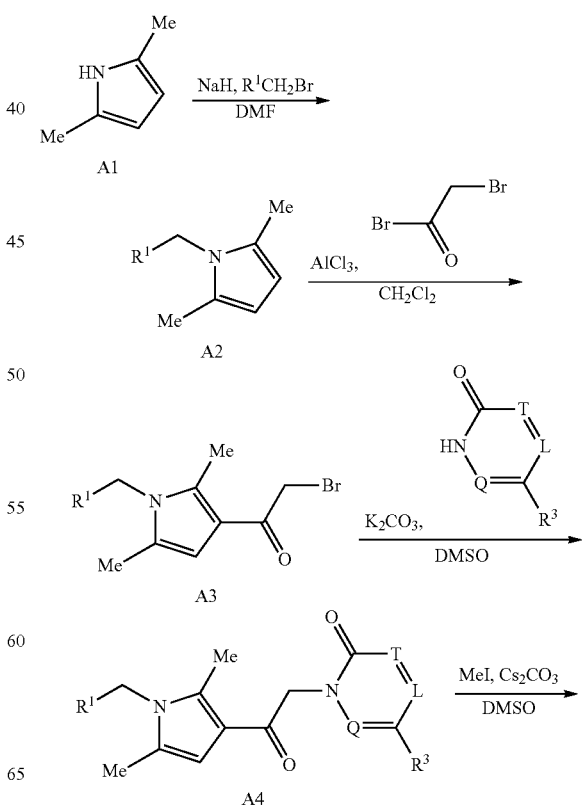

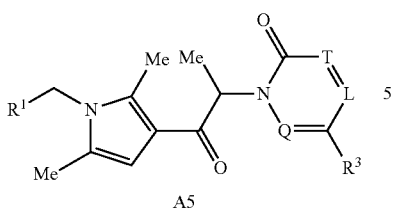
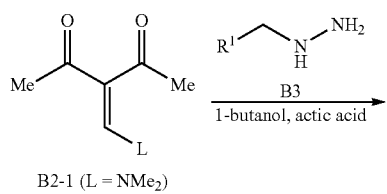
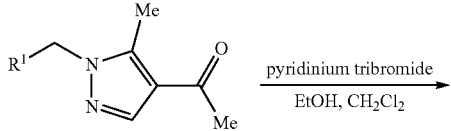
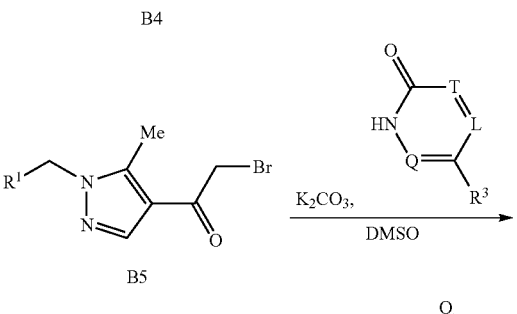
Scheme 8-Synthetic scheme for pyrrole derivatives A5
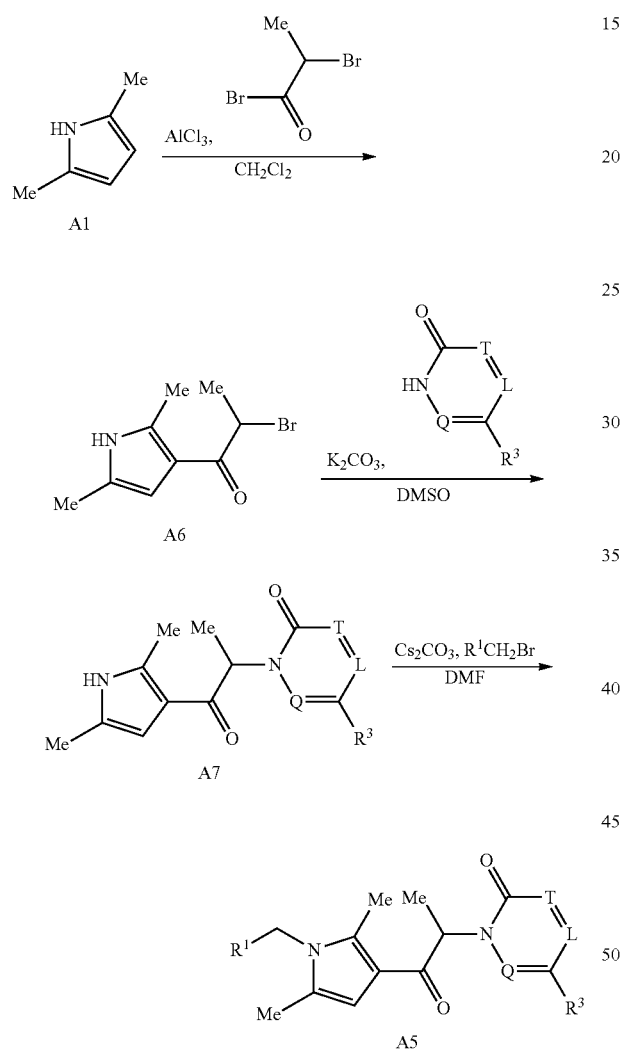
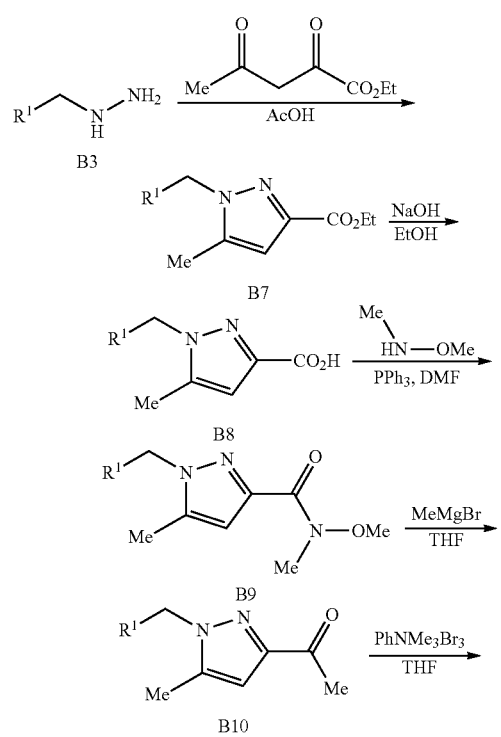
Compounds of the formulae (B6), (B12), and (C9) can be produced as shown in Schemes 9-11, respectively.
Scheme 9-Synthetic scheme for pyrazole derivatives B6
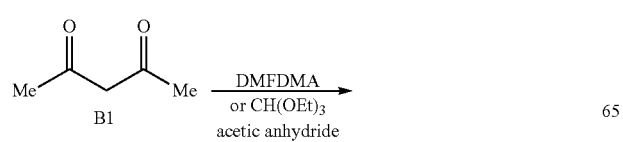

-continued
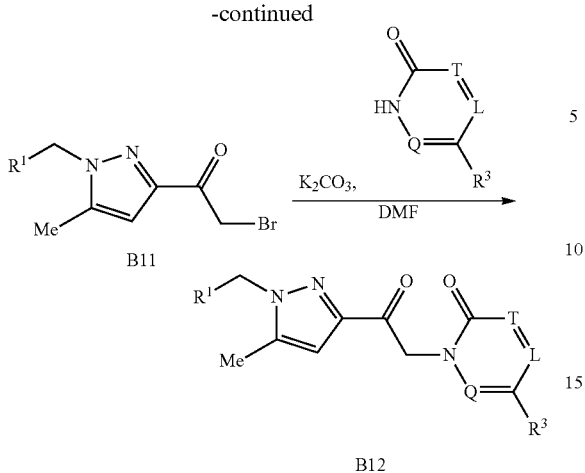
Scheme 11-Synthetic scheme for imidazole derivatives C9
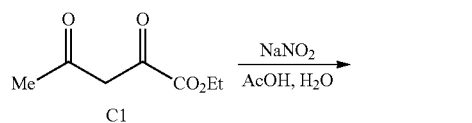
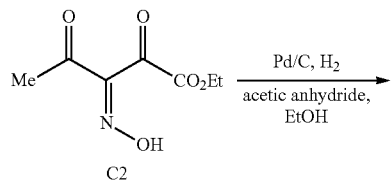
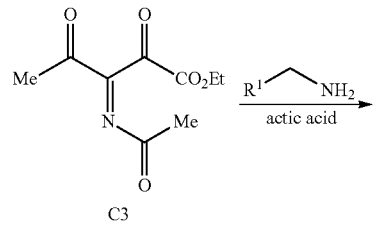
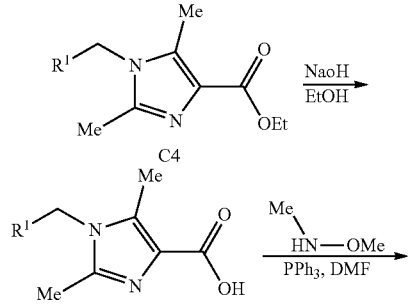
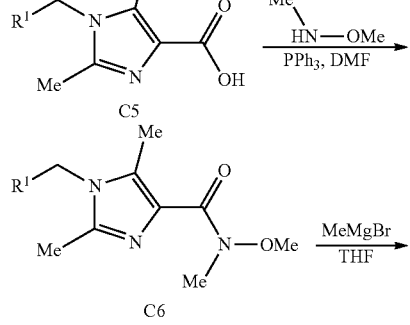
-continued
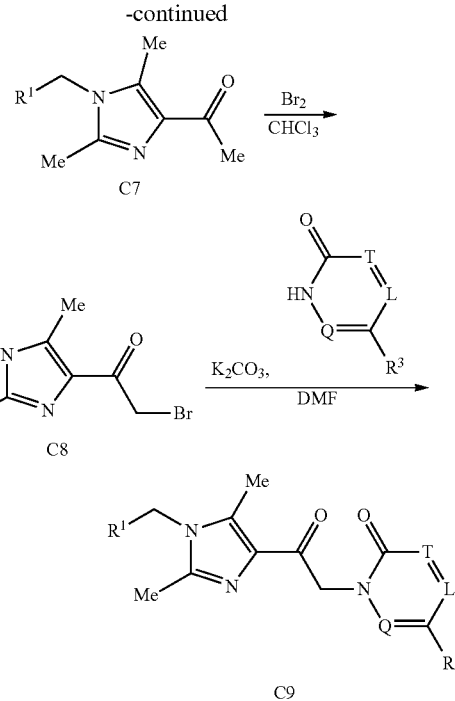
Finally, compounds of the formulae (D2), (E4), (F8), (F13), (G7), (H6), and (19) can be produced as shown in Schemes 12-18, respectively.
Scheme 12-Synthetic scheme for imidazole derivatives D2
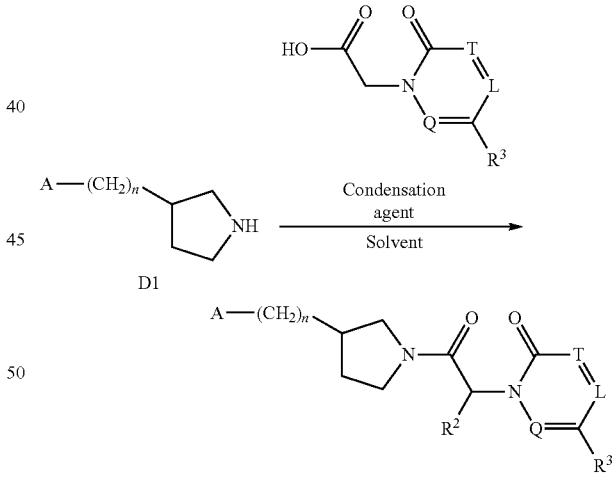
Scheme 13-Synthetic scheme for triazole derivatives E4
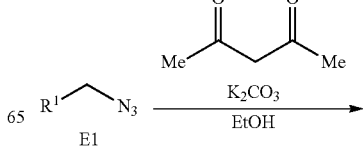

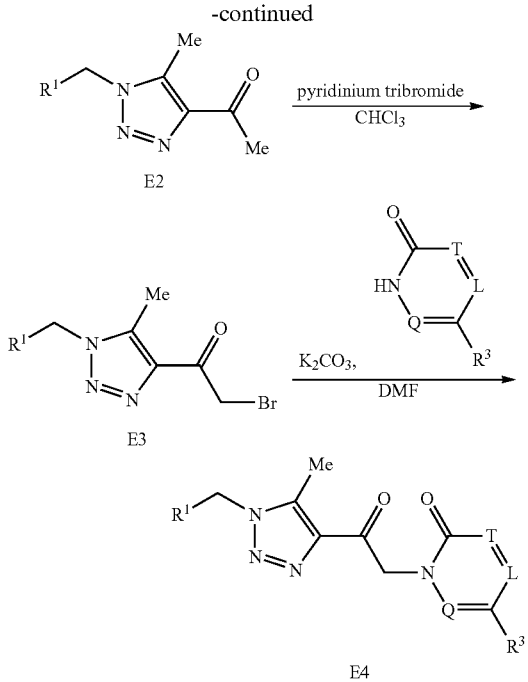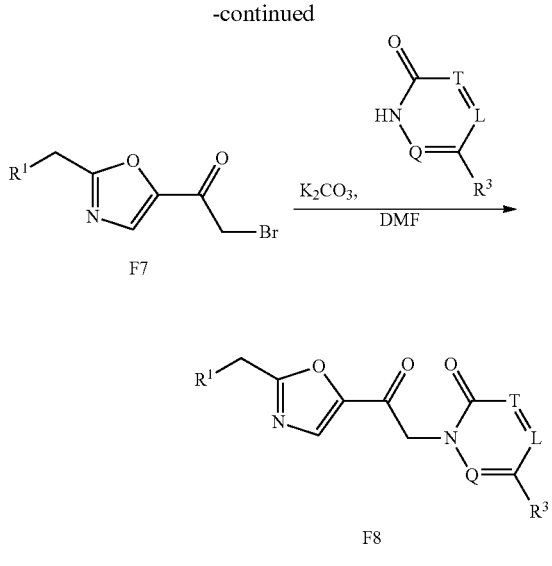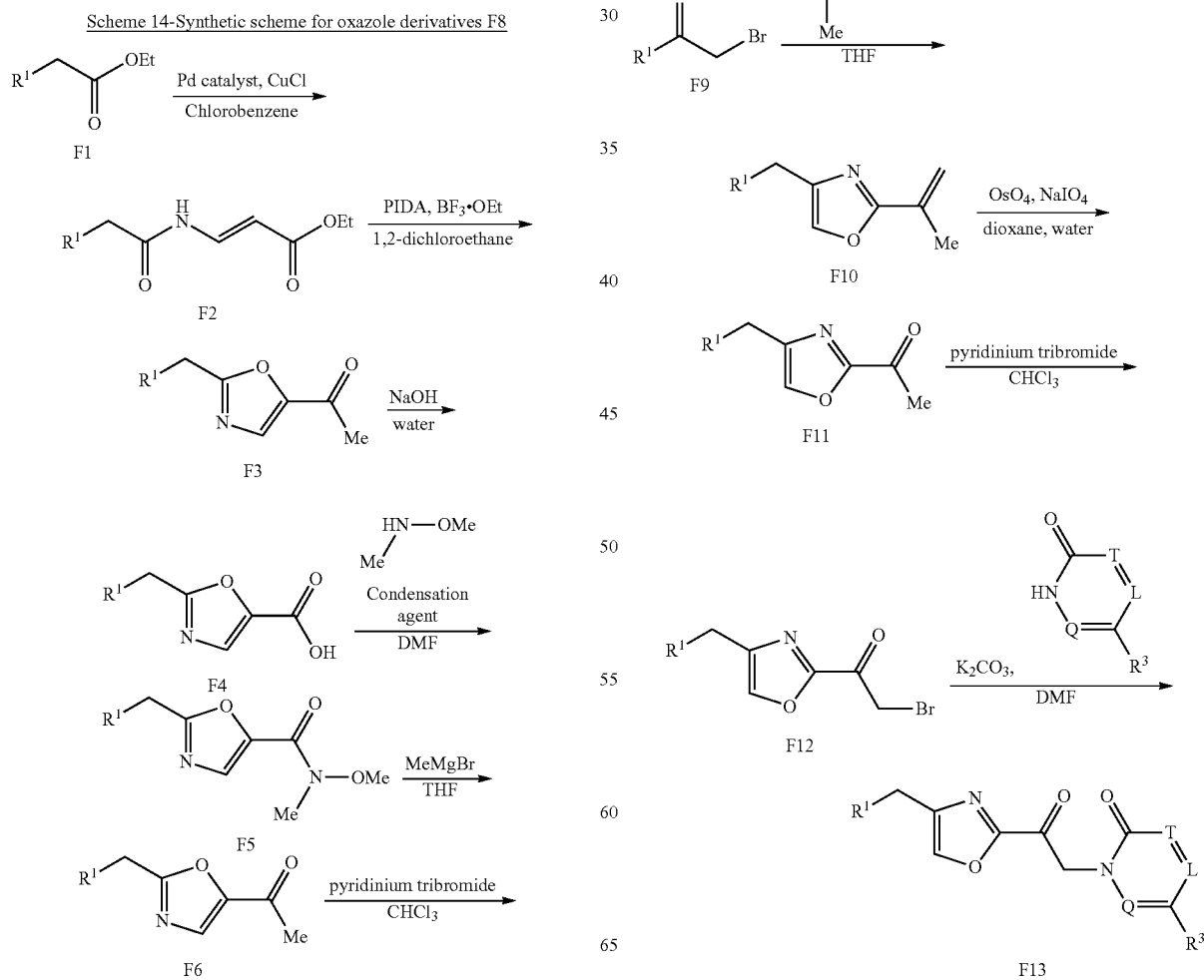

Scheme 16-Synthetic scheme for isooxazole derivatives G7
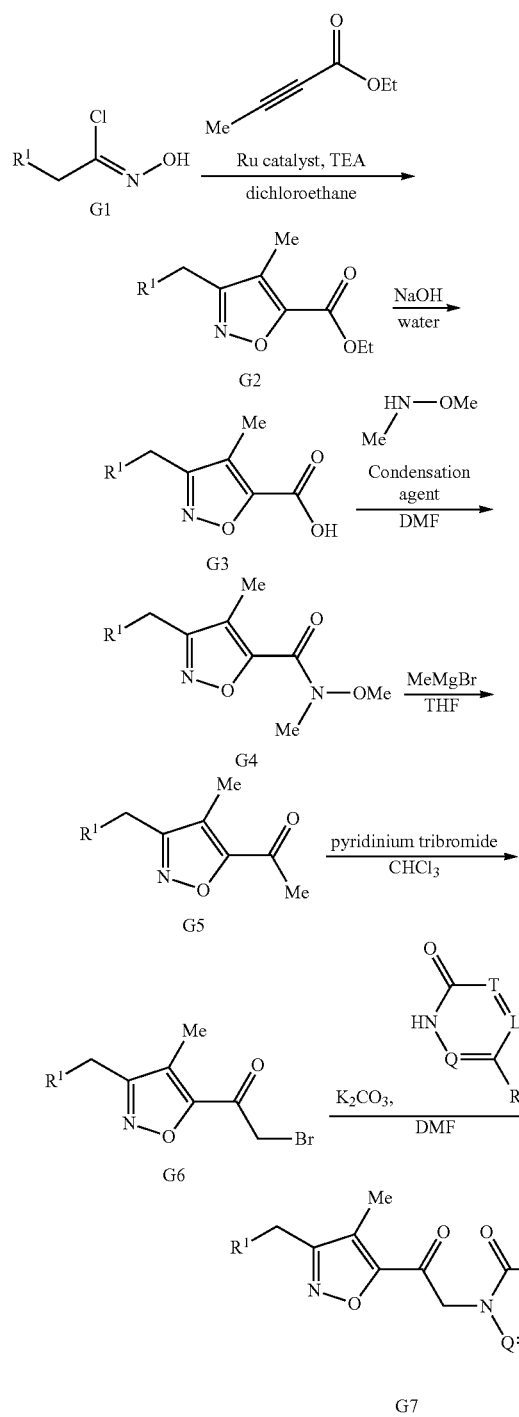
Scheme 17-Synthetic scheme for indazole derivatives H6
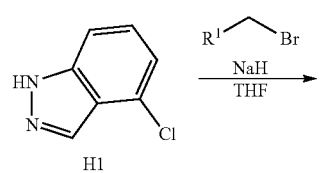
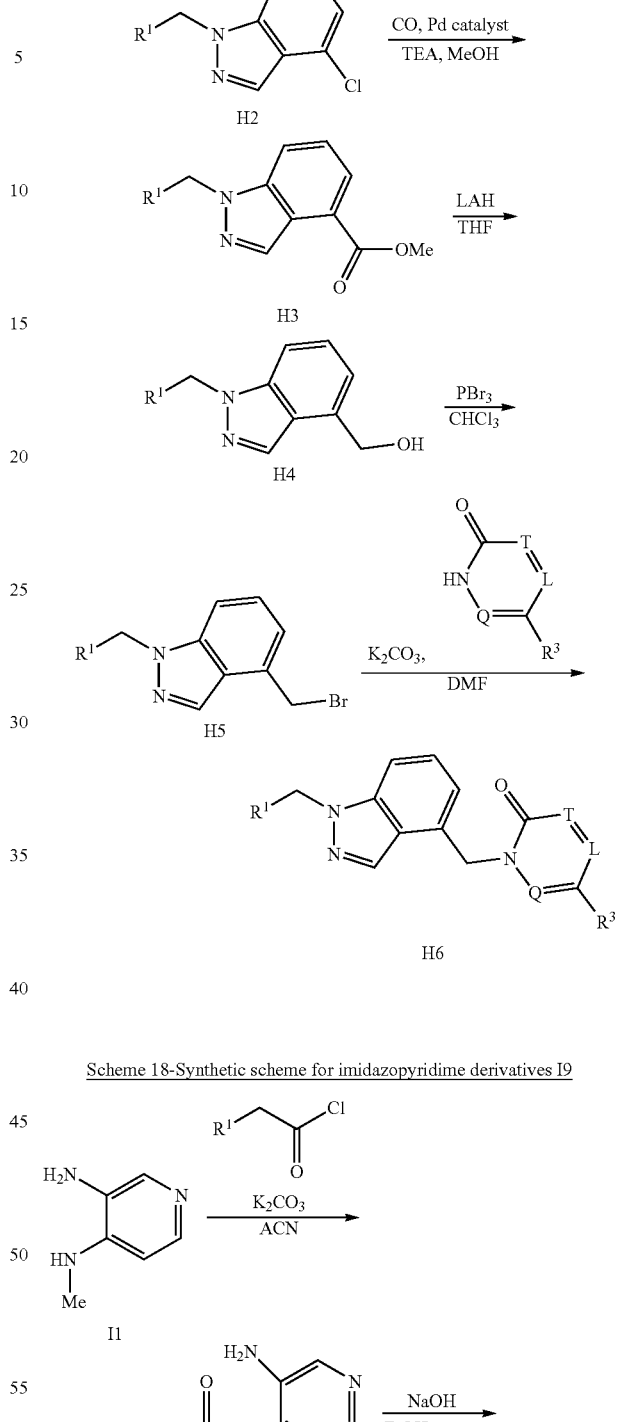
Scheme 18-Synthetic scheme for imidazopyridime derivatives I9
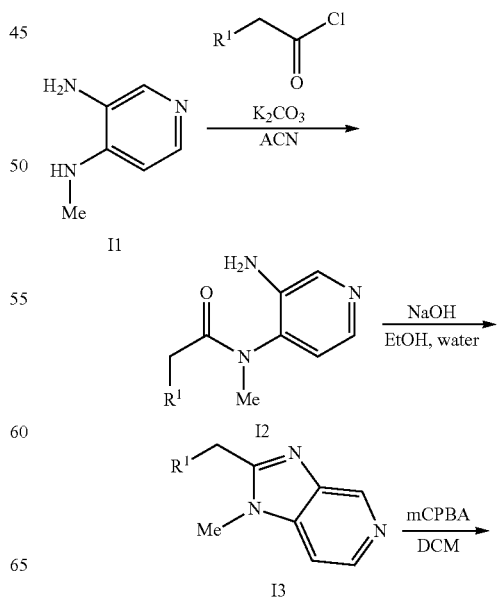

-continued

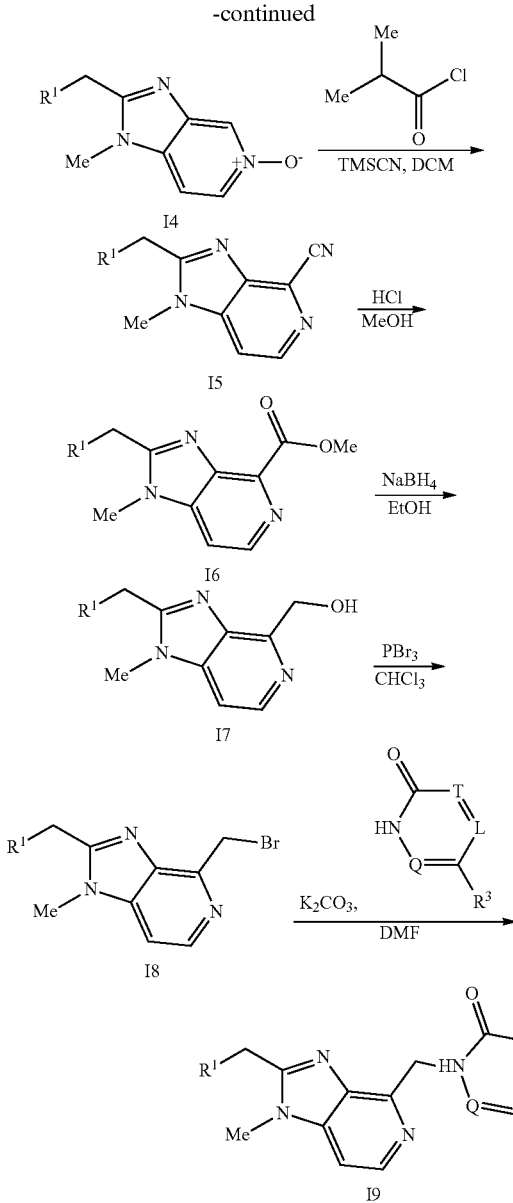

Compounds 1-141 can be produced using the specific methods described in Examples 1-131.

Example 1

1-(2-(1-Benzyl-2,5-dimethyl-1H-pyrrol-3-yl)-2-oxoethyl)-5-bromopyridin-2(1H)-one A mixture of 1-(1-benzyl-2,5-dimethyl-1H-pyrrol-3-yl)-2-chloroethan-1-one (350 mg), 5-bromopyridin-2(1H)-one (466 mg), DIPEA (468 uL), and DMF (30 mL) was stirred at 100° C. for 2 days. The mixture was allowed to cool to room temperature. The mixture was quenched with brine, and extracted with ethyl acetate, washed with brine, and concentrated in vacuo. The residue was purified by NH silica gel chromatography (ethyl acetate:hexane=1:25 to 3:5) to give the target compound (284 mg) as a solid.

$^1$H NMR (500 MHz, CDCl$_3$): δ 7.44-7.37 (m, 2H), 7.34 (d, J=7.8 Hz, 2H), 7.29 (s, 1H), 6.98-6.87 (m, 2H), 6.55 (dd, J=9.6, 0.8 Hz, 1H), 6.42 (d, J=1.1 Hz, 1H), 5.15 (s, 2H), 5.08 (s, 2H), 2.50 (s, 3H), 2.18 (d, J=1.0 Hz, 3H).

Example 2

1-(2-(1-Benzyl-2,5-dimethyl-1H-pyrrol-3-yl)-2-oxoethyl)-5-ethynylpyridin-2(1H)-one A target compound was synthesized in a similar manner as example 1 using 1-(1-benzyl-2,5-dimethyl-1H-pyrrol-3-yl)-2-chloroethan-1-one and 5-iodopyridin-2(1H)-one.

$^1$H NMR (500 MHz, CDCl$_3$): δ 7.51-7.45 (m, 2H), 7.38-7.28 (m, 3H), 6.94-6.88 (m, 2H), 6.49-6.39 (m, 2H), 5.13 (s, 2H), 5.08 (s, 2H), 2.50 (s, 3H), 2.17 (d, J=1.1 Hz, 3H).

Example 3

1-(2-(1-Benzyl-2,5-dimethyl-1H-pyrrol-3-yl)-2-oxoethyl)-5-ethynylpyridin-2(1H)-one K$_2$CO$_3$ (158 mg) was added to the solution of 1-(1-benzyl-2,5-dimethyl-1H-pyrrol-3-yl)-2-chloroethan-1-one (150 mg) and 5-ethynylpyridin-2(1H)-one (68.3 mg) in DMSO (2.0 mL) at room temperature. The mixture was stirred at room temperature for 5 h. The mixture was poured into water (8 mL), and the resulting precipitate was collected by filtration, washed with hexane, and dried in vacuo. The solid was washed with MeOH and ethyl acetate, and dried in vacuo to give the target compound (125 mg) as a solid.

$^1$H NMR (500 MHz, CDCl$_3$): δ 7.51 (d, J=2.4 Hz, 1H), 7.41 (dd, J=9.5, 2.4 Hz, 1H), 7.37-7.29 (m, 3H), 6.91 (d, J=7.4 Hz, 2H), 6.57 (d, J=9.4 Hz, 1H), 6.42 (s, 1H), 5.16 (s, 2H), 5.08 (s, 2H), 3.01 (s, 1H), 2.50 (s, 3H), 2.18 (s, 3H).

Example 4

1-(1-(1-Benzyl-2,5-dimethyl-1H-pyrrol-3-yl)-1-oxopropan-2-yl)-5-bromopyridin-2(1H)-one Iodomethane (247 mg) was added portion-wise to a mixture of 1-(2-(1-benzyl-2,5-dimethyl-1H-pyrrol-3-yl)-2-oxoethyl)-5-bromopyridin-2(1H)-one (116 mg) and Cs$_2$CO$_3$ (189 mg) in DMSO (1.0 mL). The mixture was stirred at room temperature for 2 days. The mixture was purified by silica gel chromatography (ethyl acetate:hexane=1:10 to 3:2) to give the target compound (17.0 mg) as a solid.

$^1$H NMR (500 MHz, DMSO-d$_6$): δ 7.83 (d, J=2.8 Hz, 1H), 7.57 (dt, J=9.7, 2.6 Hz, 1H), 7.36 (td, J=7.6, 2.3 Hz, 2H), 7.28 (dd, J=8.5, 6.1 Hz, 1H), 6.95 (d, J=7.5 Hz, 2H), 6.50 (d, J=2.8 Hz, 1H), 6.41 (dd, J=9.6, 2.6 Hz, 1H), 6.15-6.01 (m, 1H), 5.18 (d, J=2.8 Hz, 2H), 2.40 (d, J=2.7 Hz, 3H), 2.13 (d, J=2.7 Hz, 3H), 1.58 (dd, J=7.5, 2.6 Hz, 3H).

Example 5

5-Bromo-1-(1-(2,5-dimethyl-1-((5-methyl-1,2,4-oxadiazol-3-yl)methyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 6

5-Bromo-1-(1-(2,5-dimethyl-1-((3-methyl-1,2,4-oxadiazol-5-yl)methyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 7

5-Bromo-1-(1-(2,5-dimethyl-1-(pyrimidin-2-ylmethyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 8

5-Bromo-1-(1-(2,5-dimethyl-1-((1-methyl-1H-pyrazol-4-yl)methyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 9

5-Bromo-1-(1-(2,5-dimethyl-1-((5-methylisoxazol-3-yl)methyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 10

5-Bromo-1-(1-(2,5-dimethyl-1-((tetrahydro-2H-pyran-4-yl)methyl)-1H-pyrrol-3-1)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 11

5-Bromo-1-(1-(2,5-dimethyl-1-((tetrahydro-2H-pyran-3-yl)methyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 12

5-Bromo-1-(1-(2,5-dimethyl-1-((1-methyl-1H-pyrazol-3-yl)methyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 13

5-Bromo-1-(1-(2,5-dimethyl-1-(4-(methylsulfonyl)benzyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-1)-1-oxopropan-2-yl)pyridin-2(1H)-one.

Example 14

5-Bromo-1-(1-(2,5-dimethyl-1-(3-(methylsulfonyl)benzyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 15

3-((3-(2-(5-Bromo-2-oxopyridin-1(2H)-yl)propanoyl)-2,5-dimethyl-1H-pyrrol-1-yl)methyl)benzonitrile A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 16

4-((3-(2-(5-Bromo-2-oxopyridin-1(2H)-yl)propanoyl)-2,5-dimethyl-1H-pyrrol-1-yl)methyl)benzonitrile A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 17

2-((3-(2-(5-Bromo-2-oxopyridin-1(2H)-yl)propanoyl)-2,5-dimethyl-1H-pyrrol-1-yl)methyl)benzonitrile A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 18

5-Bromo-1-(1-(1-(4-fluorobenzyl)-2,5-dimethyl-1H-pyrrol-3-yl)-1-oxopropan-2-yl)pyridin-2(1H)-one A target compound was synthesized in a similar manner as step C in example 3.

Example 19

5-Bromo-1-(1-(1-(2-fluorobenzyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 20

5-Bromo-1-(1-(1-(3,4-difluorobenzyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 21

5-Bromo-1-(1-(1-(3-(difluoromethyl)benzyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 22

5-Bromo-1-(1-(1-(3-chlorobenzyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 23

3-((3-(2-(5-Bromo-2-oxopyridin-1(2H)-yl)propanoyl)-2,5-dimethyl-1H-pyrrol-1-yl)methyl)benzoic Acid A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 24

5-Bromo-1-(1-(2,5-dimethyl-1-(pyridin-3-ylmethyl)-1H-pyrrol-3-yl)-1-oxopropan-2-yl)pyridin-2(1H)-one A) 2-Bromo-1-(2,5-dimethyl-1H-pyrrol-3-yl)propan-1-one To the mixture of 2,5-dimethyl-1H-pyrrole (5.0 g), AlCl$_3$ (7.7 g) and dichloroethane (100 mL) was added 2-bromopropanoyl bromide (5.5 mL), which was stirred at 0° C. for 3 hours. The mixture was quenched with brine at room temperature and extracted with dichloromethane. The organic layer was separated, washed with brine, dried over MgSO$_4$, and concentrated in vacuo. The residue was purified by silica gel chromatography (ethyl acetate:hexane=0:100 to 2:5) to give the target compound (3.0 g) as a solid.
MS: (M+H$^+$): 230.14

B) 5-Bromo-1-(1-(2,5-dimethyl-1H-pyrrol-3-yl)-1-oxopropan-2-yl)pyridin-2(1H)-one A mixture of 2-bromo-1-(2,5-dimethyl-1H-pyrrol-3-yl)propan-1-one (3.50 g), 5-bromopyridin-2(1H)-one (2.65 g), K$_2$CO$_3$ (3.15 g) and DMSO (2.0 mL) was stirred at 25° C. for 4 hours. The mixture was quenched with water. The resulting solid was collected by filtration and washed with water. Recrystallization from MeOH/water gave the target compound (3.6 g) as a solid.
MS: (M+H$^+$): 323.17

C) 5-Bromo-1-(1-(2,5-dimethyl-1-(pyridin-3-ylmethyl)-1H-pyrrol-3-yl)-1-oxopropan-2-yl)pyridin-2(1H)-one A mixture of 5-bromo-1-(1-(2,5-dimethyl-1H-pyrrol-3-yl)-1-oxopropan-2-yl)pyridin-2(1H)-one (60.0 mg), NaH (14.9 mg, 60% purity) and DMF (1.0 mL) was stirred at room temperature for 20 min. To the mixture was added 3-(bromomethyl)pyridine (51.7 mg) and the mixture was stirred at room temperature for 3 h. The mixture was quenched with water and extracted with ethyl acetate. The organic layer was separated, washed with water and brine, dried with MgSO$_4$, and concentrated in vacuo. The residue was purified by silica gel chromatography (MeOH:ethyl acetate=0:100 to 2:3) to give the target compound (5.3 mg) as a solid.
$^1$H NMR (500 MHz, DMSO-d$_6$): δ 8.50 (dd, J=4.8, 1.5 Hz, 1H), 8.29 (d, J=2.2 Hz, 1H), 7.83 (d, J=2.6 Hz, 1H), 7.57 (dd, J=9.6, 2.7 Hz, 1H), 7.39 (dd, J=7.9, 4.7 Hz, 1H), 7.27 (dt, J=8.0, 1.9 Hz, 1H), 6.51 (s, 1H), 6.41 (d, J=9.6 Hz, 1H), 6.06 (d, J=7.4 Hz, 1H), 5.25 (s, 2H), 2.42 (s, 3H), 2.15 (s, 3H), 1.58 (d, J=7.4 Hz, 3H).

Example 25

5-Bromo-1-(1-(2,5-dimethyl-1-(pyridin-4-ylmethyl)-1H-pyrrol-3-yl)-1-oxopropan-2-yl)pyridin-2(1H)-one A mixture of 5-bromo-1-(1-(2,5-dimethyl-1H-pyrrol-3-yl)-1-oxopropan-2-yl)pyridin-2(1H)-one (150 mg), NaH (37.1 mg, 60% purity) and DMF (2.0 mL) was stirred at room temperature for 20 min. To the mixture was added 4-(bromomethyl)pyridine (234 mg) and the mixture was stirred at room temperature for 3 h. The mixture was quenched with water and extracted with ethyl acetate. The organic layer was separated, washed with water and brine, dried with MgSO$_4$, and concentrated in vacuo. The residue was purified by silica gel chromatography (MeOH:ethyl acetate=0:100 to 2:3) to give the target compound (48.5 mg) as a solid.
$^1$H NMR (500 MHz, DMSO-d$_6$): δ 8.60-8.49 (m, 2H), 7.84 (d, J=2.6 Hz, 1H), 7.57 (dd, J=9.7, 2.7 Hz, 1H), 6.98-6.87 (m, 2H), 6.53 (s, 1H), 6.41 (d, J=9.7 Hz, 1H), 6.07 (q, J=7.3 Hz, 1H), 5.25 (s, 2H), 2.38 (s, 3H), 2.11 (s, 3H), 1.59 (d, J=7.4 Hz, 3H).

Example 26

1-(2-(1-Benzyl-2,5-dimethyl-1H-pyrrol-3-yl)-2-oxoethyl)-5-(prop-1-yn-1-yl)pyridin-2(1H)-one A mixture of 1-(2-(1-benzyl-2,5-dimethyl-1H-pyrrol-3-yl)-2-oxoethyl)-5-bromopyridin-2(1H)-one (300 mg), trimethyl(prop-1-yn-1-yl)silane (222 μL), CuI (14.3 mg) and DMA (1.5 mL) was stirred at 80° C. for 2 days. The mixture was quenched with water and extracted with ethyl acetate. The organic layer was separated, washed with water and brine, dried with MgSO$_4$, and concentrated in vacuo. The residue was purified by silica gel chromatography (ethyl acetate:hexane=2:3 to 100:0) to give the target compound (116 mg) as a solid.

$^1$H NMR (500 MHz, DMSO-d$_6$): δ 7.83 (d, J=2.4 Hz, 1H), 7.43 (dd, J=9.4, 2.5 Hz, 1H), 7.37 (dd, J=8.3, 6.9 Hz, 2H), 7.29 (d, J=7.3 Hz, 1H), 7.00-6.82 (m, 2H), 6.52 (d, J=1.1 Hz, 1H), 6.39 (d, J=9.4 Hz, 1H), 5.20 (s, 2H), 5.14 (s, 2H), 2.41 (s, 3H), 2.15 (s, 3H), 2.01 (s, 3H).

Example 27

1-(2-(1-Benzyl-5-methyl-1H-pyrazol-4-yl)-2-oxoethyl)-5-bromopyridin-2(1H)-one

A mixture of 1-(1-benzyl-5-methyl-1H-pyrazol-4-yl)-2-bromoethan-1-one (590 mg), 5-bromopyridin-2(1H)-one (350 mg), K$_2$CO$_3$ (556 mg), and DMSO (10 mL) was stirred at room temperature overnight. The mixture was quenched with water and extracted with ethyl acetate. The organic layer was separated, washed with water and brine, dried with MgSO$_4$, and concentrated in vacuo to give the target compound (313 mg) as a solid.
$^1$H NMR (500 MHz, DMSO-d$_6$): δ 8.29 (s, 1H), 7.96 (d, J=2.8 Hz, 1H), 7.60 (dd, J=9.7, 2.8 Hz, 1H), 7.41-7.27 (m, 3H), 7.21-7.13 (m, 2H), 6.43 (d, J=9.7 Hz, 1H), 5.43 (s, 2H), 5.22 (s, 2H), 2.50 (s, 3H).

Example 28

5-Bromo-1-(2-(1-(4-fluorobenzyl)-2,5-dimethyl-1H-pyrrol-3-yl)-2-oxoethyl)pyridin-2(1H)-one A) 2-Bromo-1-(1-(4-fluorobenzyl)-2,5-dimethyl-1H-pyrrol-3-yl)ethan-1-one To a mixture of 1-(4-fluorobenzyl)-2,5-dimethyl-1H-pyrrole (200 mg), AlCl$_3$ (144 mg) and dichloromethane (2.0 mL) was added 2-bromoacetyl bromide (85.7 μL) at 0° C., and the mixture was stirred at the same temperature for 1 hour. The mixture was quenched with water and extracted with ethyl acetate. The organic layer was separated, washed with diluted NaHCO$_3$ solution and brine, dried with MgSO$_4$, and concentrated in vacuo to give the target compound.
MS: (M+H$^+$): 324.14

B) 5-Bromo-1-(2-(1-(4-fluorobenzyl)-2,5-dimethyl-1H-pyrrol-3-yl)-2-oxoethyl)pyridin-2(1H)-one A mixture of 2-bromo-1-(1-(4-fluorobenzyl)-2,5-dimethyl-1H-pyrrol-3-yl)ethan-1-one (250 mg), 5-bromopyridin-2(1H)-one (134 mg), K$_2$CO$_3$ (213 mg) in DMSO (4.0 mL) was stirred at room temperature overnight. The mixture was quenched with water and extracted with ethyl acetate. The organic layer was separated, washed with water and brine, dried with MgSO$_4$, and concentrated in vacuo. The residue was purified by silica gel chromatography (ethyl acetate:hexane=2:3 to 100:0) to give the target compound (59.1 mg) as a solid.
$^1$H NMR (500 MHz, DMSO-d$_6$): δ 7.95 (d, J=2.8 Hz, 1H), 7.58 (dd, J=9.7, 2.8 Hz, 1H), 7.20 (t, J=8.8 Hz, 2H), 6.99 (dd, J=8.5, 5.4 Hz, 2H), 6.52 (s, 1H), 6.41 (d, J=9.6 Hz, 1H), 5.19 (s, 2H), 5.14 (s, 2H), 2.41 (s, 3H), 2.15 (s, 3H).

Example 29

1-(2-(1-Benzyl-5-methyl-1H-pyrazol-4-yl)-2-oxoethyl)-5-ethynylpyridin-2(1H)-one

A solution of 1-(1-benzyl-5-methyl-1H-pyrazol-4-yl)-2-bromoethan-1-one (25.5 g), 5-ethynylpyridin-2(1H)-one (10.4 g) and K$_2$CO$_3$ (24.0 g) in DMSO (257 mL) was stirred at 25° C. for 16 h. Three batches (each of 8.5 g) were carried out in parallel and then combined. Ice water was added dropwise to the mixture and the mixture was stirred for 30 min. The resulting precipitate was collected by filtration and washed repeatedly with hexane. This solid was then dissolved in dichloromethane (1.5 L), dried over Na$_2$SO$_4$, and concentrated to get the crude compound. This crude compound was purified by silica gel chromatography (MeOH:dichloromethane=1.5:98.5 to 2:98) to afford the target compound (20.8 g) as a solid.
$^1$H NMR (400 MHz, DMSO-d$_6$): δ 8.30 (s, 1H), 7.99 (s, 1H), 7.52-7.50 (m, 1H), 7.37-7.31 (m, 3H), 7.18-7.17 (m, 2H), 6.44-6.42 (m, 1H), 5.43 (s, 2H), 5.25 (s, 2H), 4.11 (s, 1H), 2.51 (s, 3H).

Example 30

5-Bromo-1-(2-(1-(4-fluorobenzyl)-2,5-dimethyl-1H-imidazol-4-yl)-2-oxoethyl)pyridin-2(1H)-one A) Ethyl 1-(4-fluorobenzyl)-2,5-dimethyl-1H-imidazole-4-carboxylate To a solution of ethyl 2-acetamido-3-oxo-butanoate (22.0 g) in acetic acid (150 mL) was added (4-fluorophenyl)methanamine (44.1 g). The mixture was stirred at 120° C. for 12 hours. The reaction mixture was concentrated, poured into saturated sodium carbonate solution, and extracted with dichloromethane. The organic phase was washed with brine, dried over anhydrous Na$_2$SO$_4$, concentrated, and purified by silica gel chromatography (petroleum ether:ethyl acetate=1:1 to 1:2) to give the target compound as a solid.
MS: (M+H$^+$): 277.2

B) 1-(4-Fluorobenzyl)-2,5-dimethyl-1H-imidazole-4-carboxylic Acid

To a stirred solution of ethyl 1-(4-fluorobenzyl)-2,5-dimethyl-1H-imidazole-4-carboxylate (7.0 g) in EtOH (100 mL) was added 2M NaOH solution (25.3 mL). The reaction mixture was heated to 50° C., and stirred for 2 hours. The reaction mixture was poured into water and washed with ethyl acetate. The aqueous phase was concentrated in vacuum to give the residue. The residue was dissolved in dichloromethane and the insoluble material was removed by filtration. The filtrate was concentrated in vacuum to give the target compound as a solid.
MS: (M+H$^+$): 249.2

C) 1-(4-Fluorobenzyl)-N-methoxy-N,2,5-trimethyl-1H-imidazole-4-carboxamide

A target compound was synthesized in a similar manner as step A in example 68 using 1-(4-fluorobenzyl)-2,5-dimethyl-1H-imidazole-4-carboxylic acid.
$^1$H NMR (400 MHz, CDCl$_3$): δ 7.04-6.96 (m, 2H), 6.95-6.88 (m, 2H), 4.99 (s, 2H), 3.80 (s, 3H), 3.49 (s, 3H), 2.35 (s, 3H), 229 (s, 3H).

D) 1-(1-(4-Fluorobenzyl)-2,5-dimethyl-1H-imidazol-4-yl)ethan-1-one

A target compound was synthesized in a similar manner as step B in example 68 using 1-(4-fluorobenzyl)-N-methoxy-N,2,5-trimethyl-1H-imidazole-4-carboxamide ¹H NMR (400 MHz, CDCl₃): δ 7.04 (t, J=8.6 Hz, 2H), 6.96-6.88 (m, 2H), 5.03 (s, 2H), 2.57 (s, 3H), 2.48 (s, 3H), 2.34 (s, 3H).

E) 2-Bromo-1-(1-(4-fluorobenzyl)-2,5-dimethyl-1H-imidazol-4-yl)ethan-1-one

A target compound was synthesized in a similar manner as step C in example 68 using 1-(1-(4-fluorobenzyl)-2,5-dimethyl-1H-imidazol-4-yl)ethan-1-one
MS: (M+H⁺): 325.1

F) 5-Bromo-1-(2-(1-(4-fluorobenzyl)-2,5-dimethyl-1H-imidazol-4-yl)-2-oxoethyl)pyridin-2(1H)-one A target compound was synthesized in a similar manner as step D in example 68 using 2-bromo-1-(1-(4-fluorobenzyl)-2,5-dimethyl-1H-imidazol-4-yl)ethan-1-one and 5-bromopyridin-2(1H)-one.
¹H NMR (400 MHz, CDCl₃): δ 7.40 (d, J=9.7 Hz, 1H), 7.32 (s, 1H), 7.06 (t, J=8.4 Hz, 2H), 6.97-6.88 (m, 2H), 6.54 (d, J=9.7 Hz, 1H), 5.39 (s, 2H), 5.05 (s, 2H), 2.46 (s, 3H), 2.35 (s, 3H).

Example 31

5-Ethynyl-1-(2-(1-(4-fluorobenzyl)-5-methyl-1H-pyrazol-3-yl)-2-oxoethyl)pyridin-2(1H)-one A target compound was synthesized in a similar manner as step D in example 68 using 2-bromo-1-(1-(4-fluorobenzyl)-5-methyl-1H-pyrazol-3-yl)ethan-1-one and 5-ethynylpyridin-2(1H)-one.
¹H NMR (400 MHz, CDCl₃): δ 7.47 (s, 1H), 7.41 (d, J=9.5 Hz, 1H), 7.17-7.09 (m, 2H), 7.09-7.01 (m, 2H), 6.64 (s, 1H), 6.57 (d, J=9.3 Hz, 1H), 5.39 (s, 2H), 5.32 (s, 2H), 3.01 (s, 1H), 2.24 (s, 3H).

Example 32

3-((4-(2-(5-Bromo-2-oxopyridin-1(2H)-yl)acetyl)-5-methyl-1H-pyrazol-1-yl)methyl)benzoic Acid

A) Methyl 3-((4-acetyl-5-methyl-1H-pyrazol-1-yl)methyl)benzoate

To a solution of methyl 3-(hydrazinomethyl)benzoate dihydrochloride (9 g) in n-BuOH (190 mL) and acetic acid (5.7 mL) was added 3-((dimethylamino)methylene)pentane-2,4-dione (8.28 g). The mixture was stirred at 100° C. for 3 hours. The mixture was adjusted to pH=8 with NaHCO₃ solution. The reaction mixture was poured into water, extracted with ethyl acetate, washed with brine, dried over Na₂SO₄, concentrated, and purified by silica gel chromatography (petroleum ether:ethyl acetate=10:1 to 5:1) to give the target compound (1.8 g) as an oil.
¹H NMR (400 MHz, DMSO-d₆): δ 8.58 (s, 1H), 7.93-7.87 (m, 2H), 7.60-7.50 (m, 2H), 5.36 (s, 2H), 3.88-3.82 (m, 3H), 2.34 (s, 3H), 2.30 (s, 3H).

B) Methyl 3-((4-(2-bromoacetyl)-5-methyl-1H-pyrazol-1-yl)methyl)benzoate

A target compound was synthesized in a similar manner as step C in example 34 using methyl 3-((4-acetyl-5-methyl-1H-pyrazol-1-yl)methyl)benzoate.

C) Methyl 3-((4-(2-(5-bromo-2-oxopyridin-1(2H)-yl)acetyl)-5-methyl-1H-pyrazol-1-yl)methyl)benzoate A target compound was synthesized in a similar manner as step D in example 34 using methyl 3-((4-(2-bromoacetyl)-5-methyl-1H-pyrazol-1-yl)methyl)benzoate and 5-bromopyridin-2(1H)-one and 5-bromopyridin-2(1H)-one.
MS: (M+H⁺): 446.0

D) 3-((4-(2-(5-Bromo-2-oxopyridin-1(2H)-yl)acetyl)-5-methyl-1H-pyrazol-1-yl)methyl)benzoic Acid To a solution of methyl 3-((4-(2-(5-bromo-2-oxopyridin-1(2H)-yl)acetyl)-5-methyl-1H-pyrazol-1-yl)methyl)benzoate (120 mg) in THF (2 mL) and MeOH (2 mL) was added 4M lithium hydroxide solution (203 µL). The mixture was stirred at 10° C. for 16 hours. The reaction mixture was concentrated and purified by HPLC to give the target compound (25.8 mg) as a solid.
¹H NMR (400 MHz, Methanol-d₄): δ 8.30 (s, 1H), 7.96 (d, J=2.7 Hz, 1H), 7.90-7.79 (m, 1H), 7.79-7.70 (m, 1H), 7.58 (dd, J=9.7, 2.8 Hz, 1H), 7.47-7.34 (m, 1H), 7.34-7.27 (m, 1H), 6.42 (d, J=9.8 Hz, 1H), 5.47 (s, 2H), 5.23 (s, 2H), 2.49 (s, 3H).

Example 33

5-Bromo-1-(2-(5-methyl-1-(pyridin-3-ylmethyl)-1H-pyrazol-4-yl)-2-oxoethyl)pyridin-2(1H)-one

A) 1-(5-Methyl-1-(pyridin-3-ylmethyl)-1H-pyrazol-4-yl)ethan-1-one

A target compound was synthesized in a similar manner as step A in example 32 using 3-(hydrazinylmethyl)pyridine.
¹H NMR (400 MHz, CDCl₃): δ 8.41-8.55 (m, 2H), 7.85 (s, 1H), 7.41 (d, J=7.7 Hz, 1H), 7.23 (dd, J=5.0, 7.8 Hz, 1H), 5.28 (s, 2H), 2.50 (s, 3H), 2.40 (s, 3H).

B) 2-Bromo-1-(5-methyl-1-(pyridin-3-ylmethyl)-1H-pyrazol-4-yl)ethan-1-one

A target compound was synthesized in a similar manner as step C in example 34 using 1-(5-methyl-1-(pyridin-3-ylmethyl)-1H-pyrazol-4-yl)ethan-1-one.
MS: (M+H⁺): 294.0

C) 5-Bromo-1-(2-(5-methyl-1-(pyridin-3-ylmethyl)-1H-pyrazol-4-yl)-2-oxoethyl)pyridin-2(1H)-one A target compound was synthesized in a similar manner as step D in example 34 using 2-bromo-1-(5-methyl-1-(pyridin-3-ylmethyl)-1H-pyrazol-4-yl)ethan-1-one and 5-bromopyridin-2(1H)-one.
¹H NMR (400 MHz, CDCl₃): δ 8.59 (d, J=4.0 Hz, 1H), 8.52 (br s, 1H), 8.05 (s, 1H), 7.45 (d, J=7.8 Hz, 1H), 7.41 (dd, J=2.6, 9.8 Hz, 1H), 7.35 (d, J=2.6 Hz, 1H), 7.29 (dd, J=5.0, 7.9 Hz, 1H), 6.53 (d, J=9.7 Hz, 1H), 5.35 (s, 2H), 5.10 (s, 2H), 2.55 (s, 3H).

Example 34

1-(2-(1-Benzyl-5-methyl-1H-pyrazol-4-yl)-2-oxo-ethyl)-5-vinylpyridin-2(1H)-one

A) 3-(Ethoxymethylene)pentane-2,4-dione

A solution of compound pentane-2,4-dione (120 g) and triethyl orthoformate (311 g) in acetic anhydride (320 mL) was refluxed with stirring for 3 h at 130° C. The mixture was concentrated under vacuum to give the target compound (758 g) as an oil, which was used to next step without purification.

B) 1-(1-Benzyl-5-methyl-1H-pyrazol-4-yl)ethan-1-one

A solution of 3-(ethoxymethylene)pentane-2,4-dione (127 g) and benzylhydrazine dihydrochloride (60.0 g) in n-butyl alcohol (1200 mL) and acetic acid (96.0 mL) was stirred at 100° C. for 3 h. Five batches were carried out in parallel and then combined. The mixture was neutralized with saturated aqueous NaHCO$_3$ until pH=8. Then the aqueous layer was extracted with ethyl acetate. The combined organic layer was washed with brine, dried over Na$_2$SO$_4$, filtered and the filtrate was concentrated under vacuum. The residue was purified by silica gel column chromatography (petroleum ether:ethyl acetate=20:1 to 5:1) to give the target compound (242 g) as a solid.

$^1$H NMR (400 MHz, DMSO-d$_6$): δ 8.05 (s, 1H), 7.27-7.35 (m, 3H), 7.14 (d, J=7.2 Hz, 2H), 5.36 (s, 2H), 2.47 (s, 3H), 2.37 (s, 3H).

C) 1-(1-Benzyl-5-methyl-1H-pyrazol-4-yl)-2-bromoethan-1-one

To a solution of 1-(1-benzyl-5-methyl-1H-pyrazol-4-yl)ethan-1-one (18.0 g) in CHCl$_3$ (240 mL) was added pyridinium tribromide (26.9 g). The mixture was stirred at 70° C. for 1 hour. Another batch with 3.0 g of the starting material was combined, diluted with water, and extracted with dichloromethane. The combined organic layers were washed with brine, dried over Na$_2$SO$_4$, concentrated, and purified by silica gel chromatography (petroleum ether:ethyl acetate=20:1 to 15:2) to afford the target compound (16 g) as a solid.

$^1$H NMR (400 MHz, Methanol-d$_4$): δ 8.10 (s, 1H), 7.33 (d, J=7.6 Hz, 3H), 7.15 (d, J=7.1 Hz, 2H), 5.39 (s, 2H), 4.40 (s, 2H), 2.52 (s, 3H).

D) 1-(2-(1-Benzyl-5-methyl-1H-pyrazol-4-yl)-2-oxoethyl)-5-bromopyridin-2(1H)-one A mixture of 1-(1-benzyl-5-methyl-1H-pyrazol-4-yl)-2-bromoethan-1-one (590 mg), 5-bromopyridin-2(1H)-one (350 mg), K$_2$CO$_3$ (556 mg), and DMSO (10 mL) was stirred at room temperature overnight. The mixture was quenched with water and extracted with ethyl acetate. The organic layer was separated, washed with water and brine, dried with MgSO$_4$, and concentrated in vacuo to give the target compound (313 mg) as a solid.

$^1$H NMR (500 MHz, DMSO-d$_6$): δ 8.29 (s, 1H), 7.96 (d, J=2.8 Hz, 1H), 7.60 (dd, J=9.7, 2.8 Hz, 1H), 7.41-7.27 (m, 3H), 7.21-7.13 (m, 2H), 6.43 (d, J=9.7 Hz, 1H), 5.43 (s, 2H), 5.22 (s, 2H), 2.50 (s, 3H).

E) 1-(2-(1-Benzyl-5-methyl-1H-pyrazol-4-yl)-2-oxoethyl)-5-vinylpyridin-2(1H)-one A mixture of 1-(2-(1-benzyl-5-methyl-1H-pyrazol-4-yl)-2-oxoethyl)-5-bromopyridin-2(1H)-one (0.4 g), potassium vinyltrifluoroborate (694 mg), Pd(OAc)$_2$ (116 mg), bis(1-adamantyl)-butylphosphane (371 mg), and Cs$_2$CO$_3$ (674 mg), toluene (10 mL), and water (2 mL) was stirred under nitrogen atmosphere at 110° C. for 12 hours. The reaction mixture was partitioned between ethyl acetate and water. The organic layer was dried over Na$_2$SO$_4$, concentrated, and purified by HPLC to give the target compound (32.5 mg) as a white solid.

$^1$H NMR (400 MHz, DMSO-d$_6$): δ 8.29 (s, 1H), 7.79 (dd, J=2.8, 9.6 Hz, 1H), 7.69 (d, J=2.4 Hz, 1H), 7.29-7.37 (m, 3H), 7.16 (d, J=6.8 Hz, 2H), 6.42-6.49 (m, 2H), 5.57 (d, J=17.6 1H), 5.42 (s, 2H), 5.22 (s, 2H), 5.09 (d, J=10.8 Hz, 1H), 2.48 (s, 3H).

Example 35

5-Ethynyl-1-(2-(5-methyl-1-(pyridin-3-ylmethyl)-1H-pyrazol-4-yl)-2-oxoethyl)pyridin-2(1H)-one A target compound was synthesized in a similar manner as step D in example 34 using 2-bromo-1-(5-methyl-1-(pyridin-3-ylmethyl)-1H-pyrazol-4-yl)ethan-1-one and 5-ethynylpyridin-2(1H)-one.

$^1$H NMR (400 MHz, CDCl$_3$): δ 8.59 (d, J=3.9 Hz, 1H), 8.53 (s, 1H), 8.06 (s, 1H), 7.48-7.44 (m, 2H), 7.42 (dd, J=2.4, 9.4 Hz, 1H), 7.30 (dd, J=5.3, 7.9 Hz, 1H), 6.57 (d, J=9.6 Hz, 1H), 5.35 (s, 2H), 5.12 (s, 2H), 3.01 (s, 1H), 2.55 (s, 3H).

Example 36

3-((4-(2-(5-Ethynyl-2-oxopyridin-1(2H)-yl)acetyl)-5-methyl-1H-pyrazol-1-yl)methyl)benzoic acid

A) Methyl 3-((5-methyl-4-(2-(2-oxo-5-((trimethylsilyl)ethynyl)pyridin-1(2H)-yl)acetyl)-1H-pyrazol-1-yl)methyl)benzoate A mixture of methyl 3-((4-(2-(5-bromo-2-oxopyridin-1(2H)-yl)acetyl)-5-methyl-1H-pyrazol-1-yl)methyl)benzoate (200 mg), ethynyltrimethylsilane (623 μL), N-cyclohexyl-N-methyl-cyclohexanamine (190 μL) and MeCN (8 mL) was degassed and purged with nitrogen for 3 times. XPhos-Pd-G2 (80 mg) was added to the mixture and the mixture was stirred at 80° C. for 12 hours under nitrogen atmosphere. The reaction mixture was concentrated under reduced pressure and purified by prep-TLC to give the target compound (150 mg) as a solid.

MS: (M+H$^+$): 462.0

B) 3-((4-(2-(5-Ethynyl-2-oxopyridin-1(2H)-yl)acetyl)-5-methyl-1H-pyrazol-1-yl)methyl)benzoic Acid A target compound was synthesized in a similar manner as step D in example 32 using methyl 3-((5-methyl-4-(2-(2-oxo-5-((trimethylsilyl)ethynyl)pyridin-1(2H)-yl)acetyl)-1H-pyrazol-1-yl)methyl)benzoate.

$^1$H NMR (400 MHz, DMSO-d$_6$): δ 8.31 (s, 1H), 7.98 (d, J=2.2 Hz, 1H), 7.87 (d, J=7.3 Hz, 1H), 7.76 (s, 1H), 7.53-7.46 (m, 2H), 7.44-7.38 (m, 1H), 6.42 (d, J=9.3 Hz, 1H), 5.50 (s, 2H), 5.24 (s, 2H), 4.09 (s, 1H), 2.51 (m, 3H).

Example 37

1-(2-(1-Benzyl-5-methyl-1H-pyrazol-4-yl)-2-oxoethyl)-4-bromopyridin-2(1H)-one

A target compound was synthesized in a similar manner as step D in example 34 using 1-(1-benzyl-5-methyl-1H-pyrazol-4-yl)-2-bromoethan-1-one and 4-bromopyridin-2(1H)-one.

$^1$H NMR (400 MHz, DMSO-d$_6$): δ 8.27 (s, 1H), 7.60 (d, J=7.3 Hz, 1H), 7.40-7.25 (m, 3H), 7.19-7.12 (m, 2H), 6.75 (d, J=2.2 Hz, 1H), 6.51 (dd, J=2.2, 7.2 Hz, 1H), 5.43-5.31 (m, 2H), 5.25-5.15 (m, 2H), 2.48 (s, 3H).

Example 38

1-(2-(1-Benzyl-5-methyl-1H-pyrazol-4-yl)-2-oxoethyl)-4-bromopyridin-2(1H)-one

A target compound was synthesized in a similar manner as step D in example 34 using 1-(1-benzyl-5-methyl-1H-pyrazol-4-yl)-2-bromoethan-1-one and 4-ethynylpyridin-2(1H)-one.

$^1$H NMR (400 MHz, Methanol-d$_4$): δ 8.21 (s, 1H), 7.55 (d, J=7.0 Hz, 1H), 7.37-7.27 (m, 3H), 7.16 (d, J=7.2 Hz, 2H), 6.65 (s, 1H), 6.41 (dd, J. 1.5, 6.9 Hz, 1H), 5.41 (s, 2H), 5.29 (s, 2H), 4.01 (s, 1H), 2.52 (s, 3H).

Example 39

1-(2-(1-Benzyl-5-methyl-1H-pyrazol-4-yl)-2-oxoethyl)-5-bromo-3-methylpyridin-2(1H)-one A mixture of 1-(1-benzyl-5-methyl-1H-pyrazol-4-yl)-2-bromoethan-1-one (590 mg), 5-bromo-3-methylpyridin-2-ol (378 mg), K$_2$CO$_3$ (555.60 mg, 4.02 mmol) and DMSO (10 mL) was stirred at room temperature overnight. The mixture was quenched with water and the resulting solid was collected by filtration and washed with water. The solid was recrystallized from DMSO/water to give the target compound (460 mg) as a solid.

$^1$H NMR (500 MHz, DMSO-d$_6$): δ 8.29 (s, 1H), 7.83 (dd, J=2.7, 0.9 Hz, 1H), 7.53 (dq, J=2.3, 1.1 Hz, 1H), 7.40-7.35 (m, 2H), 7.34-7.29 (m, 1H), 7.19-7.15 (m, 2H), 5.43 (s, 2H), 5.22 (s, 2H), 2.50 (s, 3H), 2.01 (t, J=0.9 Hz, 3H).

Example 40

1-(2-(1-Benzyl-5-methyl-1H-pyrazol-4-yl)-2-oxoethyl)-5-bromo-4-methylpyridin-2(1H)-one A mixture of 1-(1-benzyl-5-methyl-1H-pyrazol-4-yl)-2-bromoethan-1-one (200 mg), 5-bromo-4-methylpyridin-2(1H)-one (153 mg), K$_2$CO$_3$ (283 mg), and DMSO (3.0 mL) was stirred at room temperature overnight. The mixture was quenched with water, and the resulting solid was collected by filtration and washed by DMSO/water (2:1), water, and isopropyl ether successively. The solid was recrystallized from DMSO/water to give the target compound (114 mg) as a solid.

$^1$H NMR (500 MHz, CDCl$_3$): δ 8.05 (s, 1H), 7.39-7.30 (m, 4H), 7.16-7.12 (m, 2H), 6.55 (d, J=1.2 Hz, 1H), 5.35 (s, 2H), 5.12 (s, 2H), 2.53 (s, 3H), 2.28 (d, J=1.1 Hz, 3H).

Example 41

1-(2-(1-Benzyl-5-methyl-1H-pyrazol-4-yl)-2-oxoethyl)-5-bromo-3-methoxypyridin-2(1H)-one A mixture of 1-(1-benzyl-5-methyl-1H-pyrazol-4-yl)-2-bromoethan-1-one (200 mg), 5-bromo-3-methoxypyridin-2(1H)-one (139 mg), K$_2$CO$_3$ (189 mg), and DMSO (3.0 mL) was stirred at room temperature overnight. The mixture was quenched with water, and the resulting solid was collected by filtration and washed with DMSO/water (1:1), water, and isopropyl ether successively. The solid was recrystallized from DMSO/water to give the target compound (156 mg) as a solid.

$^1$H NMR (500 MHz, CDCl$_3$): δ 8.05 (s, 1H), 7.39-7.30 (m, 3H), 7.17-7.12 (m, 2H), 7.00 (d, J=2.3 Hz, 1H), 6.71 (d, J=2.3 Hz, 1H), 5.35 (s, 2H), 5.16 (s, 2H), 3.85 (s, 3H), 2.53 (s, 3H).

Example 42

1-(2-(1-Benzyl-5-methyl-1H-pyrazol-4-yl)-2-oxoethyl)-5-ethynyl-3-methylpyridin-2(1H)-one To a mixture of 1-(2-(1-benzyl-5-methyl-1H-pyrazol-4-yl)-2-oxoethyl)-5-bromo-3-methylpyridin-2(1H)-one (200 mg), ethynyl(trimethyl)silane (147 mg), and MeCN (10 mL) was added XPhos-Pd-G2 (39.3 mg) and N-cyclohexyl-N-methyl-cyclohexanamine (195 mg). Then the mixture was de gassed and stirred at 80° C. under nitrogen atmosphere for 12 hours. The reaction mixture was filtered through a pad of Celite and the filter cake was washed with ethyl acetate. The filtrate was concentrated and purified by silica gel chromatography (ethyl acetate:hexane=4:1 to 9:1) to give an intermediate 1-(2-(1-benzyl-5-methyl-1H-pyrazol-4-yl)-2-oxoethyl)-3-methyl-5-((trimethylsilyl)ethynyl)pyridin-2(1H)-one.

This intermediate was dissolved in MeOH (10 mL) and K$_2$CO$_3$ (138 mg) was added, and the mixture was stirred at room temperature for 0.5 hours. The mixture was concentrated and purified by silica gel chromatography (ethyl acetate:hexane=95:5 to 100:0) to give the target compound (80 mg) as a solid.

$^1$H NMR (500 MHz, CDCl$_3$): δ 8.06 (s, 1H), 7.42-7.30 (m, 5H), 7.17-7.11 (m, 2H), 5.35 (s, 2H), 5.12 (s, 2H), 2.99 (s, 1H), 2.53 (s, 3H), 2.15 (t, J=0.8 Hz, 3H).

Example 43

2-(2-(1-Benzyl-5-methyl-1H-pyrazol-4-yl)-2-oxoethyl)-6-ethynylpyridazin-3(2H)-one To a mixture of 2-(2-(1-benzyl-5-methyl-1H-pyrazol-4-yl)-2-oxoethyl)-6-bromopyridazin-3(2H)-one (250 mg), ethynyl(trimethyl)silane (188 mg) and MeCN (10 mL) was added XPhos-Pd-G2 (50.3 mg) and N-cyclohexyl-N-methyl-cyclohexanamine (249 mg). Then the mixture was de-gassed and stirred at 80° C. under nitrogen atmosphere for 12 hours. The reaction mixture was filtered through a pad of Celite and the filter cake was washed with ethylacetate. The filtrate was concentrated and purified by silica gel chromatography (ethyl acetate:hexane=4:1 to 9:1) to give an intermediate 2-(2-(1-benzyl-5-methyl-1H-pyrazol-4-yl)-2-oxoethyl)-6-((trimethylsilyl)ethynyl)pyridazin-3(2H)-one.

This intermediate was dissolved in MeOH (10 mL) and K$_2$CO$_3$ (177 mg) was added, and the mixture was stirred at room temperature for 0.5 hours. The mixture was concentrated and purified by silica gel chromatography (ethyl acetate:hexane=95:5 to 100:0) to give the target compound (91 mg) as a solid.

$^1$H NMR (500 MHz, CDCl$_3$): δ 8.00 (s, 1H), 7.38-7.30 (m, 4H), 7.15-7.10 (m, 2H), 6.97 (d, J=9.6 Hz, 1H), 5.40 (s, 2H), 5.35 (s, 2H), 3.22 (s, 1H), 2.53 (s, 3H).

Example 44

1-(2-(1-Benzyl-2,5-dimethyl-1H-pyrrol-3-yl)-2-oxoethyl)-2-methyl-6-oxo-1,6-dihydropyridine-3-carbonitrile A target compound was synthesized in a similar manner as example 1 using 1-(1-benzyl-2,5-dimethyl-1H-pyrrol-3-yl)-2-chloroethan-1-one and 2-methyl-6-oxo-1,6-dihydropyridine-3-carbonitrile.

$^1$H NMR (500 MHz, CDCl$_3$): δ 7.43 (d, J=9.5 Hz, 1H), 7.36 (t, J. 7.4 Hz, 2H), 7.31 (d, J=7.2 Hz, 1H), 6.93 (d, J=7.6 Hz, 2H), 6.54 (d, J=9.5 Hz, 1H), 6.43 (s, 1H), 5.37 (s, 2H), 5.09 (s, 2H), 2.55 (s, 3H), 2.50 (s, 3H), 2.19 (s, 3H).

Example 45

1-(2-(1-Benzyl-2,5-dimethyl-1H-pyrrol-3-yl)-2-oxoethyl)-5-chloropyridin-2(1H)-one A target compound was synthesized in a similar manner as example 1 using 1-(1-benzyl-2,5-dimethyl-1H-pyrrol-3-yl)-2-chloroethan-1-one and 5-chloropyridin-2(1H)-one.

$^1$H NMR (500 MHz, CDCl$_3$): δ 7.38-7.29 (m, 5H), 6.91 (d, J=7.5 Hz, 2H), 6.60 (d, J=9.7 Hz, 1H), 6.42 (s, 1H), 5.17-5.13 (m, 2H), 5.08 (s, 2H), 2.52-2.48 (m, 3H), 2.18 (s, 3H).

Example 46

1-(2-(1-Benzyl-2,5-dimethyl-1H-pyrrol-3-yl)-2-oxoethyl)-6-oxo-1,6-dihydropyridine-3-carboxylic Acid A target compound was synthesized in a similar manner as example 1 using 1-(1-benzyl-2,5-dimethyl-1H-pyrrol-3-yl)-2-chloroethan-1-one and 6-oxo-1,6-dihydropyridine-3-carboxylic acid.

$^1$H NMR (500 MHz, DMSO-d$_6$): δ 12.19 (s, 1H), 8.12 (d, J=2.6 Hz, 1H), 7.85 (dd, J=9.6, 2.6 Hz, 1H), 7.36 (t, J=7.5 Hz, 2H), 7.28 (t, J=7.3 Hz, 1H), 6.95 (d, J=7.6 Hz, 2H), 6.46-6.40 (m, 2H), 5.28 (s, 2H), 5.19 (s, 2H), 2.41 (s, 3H), 2.13 (s, 3H).

Example 47

1-(2-(2,5-Dimethyl-1H-pyrrol-3-yl)-2-oxoethyl)-6-oxo-1,6-dihydropyridine-3-carbonitrile A solution of 2-chloro-1-(2,5-dimethyl-1H-pyrrol-3-yl)ethan-1-one (400 mg) in DMF (20 mL) was added to DIPEA (814 μL) and 6-oxo-1,6-dihydropyridine-3-carbonitrile (279 mg) at room temperature. The mixture was stirred at 70° C. for 24 hours. The mixture was poured into water and extracted with ethyl acetate. The organic layer was separated, washed with brine, dried over MgSO$_4$, and concentrated in vacuo. The residue was purified by silica gel chromatography (ethyl acetate:hexane=4:1 to 100:0) to give the target compound (272 mg) as a solid.

$^1$H NMR (500 MHz, DMSO-d$_6$): δ 11.29 (s, 1H), 8.50 (d, J=2.4 Hz, 1H), 7.74 (dd, J=9.6, 2.5 Hz, 1H), 6.53 (d, J=9.4 Hz, 1H), 6.28 (d, J=2.4 Hz, 1H), 5.13 (s, 2H), 2.39 (s, 3H), 2.17 (s, 3H).

Example 48

1-(3-((1,1'-Biphenyl)-4-yl)-1-(2,5-dimethyl-1H-pyrrol-3-yl)-1-oxopropan-2-yl)-6-oxo-1,6-dihydropyridine-3-carbonitrile NaH (47.0 mg, 60% purity) was added to the solution of 1-(2-(2,5-dimethyl-1H-pyrrol-3-yl)-2-oxoethyl)-6-oxo-1,6-dihydropyridine-3-carbonitrile (200 mg), 4-(bromomethyl)-1,1'-biphenyl (193 mg) in DMF (8.0 mL) at 0° C. Then the mixture was stirred at 60° C. for 5 hours. The mixture was poured into water and extracted with ethyl acetate. The organic layer was separated, washed with brine, dried over MgSO$_4$, and concentrated in vacuo. The residue was purified by silica gel chromatography (ethyl acetate:hexane=1:3 to 7:3) to give the target compound (52.8 mg) as a solid.

$^1$H NMR (500 MHz, CDCl$_3$): δ 8.17-8.09 (m, 2H), 7.58-7.55 (m, 2H), 7.52-7.49 (m, 2H), 7.44 (dd, J=8.4, 6.9 Hz, 2H), 7.37-7.30 (m, 2H), 7.28-7.26 (m, 2H), 6.72 (dd, J=9.2, 6.4 Hz, 1H), 6.51 (d, 9.5 Hz, 1H), 6.38 (dd, J=2.6, 1.2 Hz, 1H), 3.58 (dd, J=14.6, 6.4 Hz, 1H), 3.13 (dd, J=14.6, 9.3 Hz, 1H), 2.55 (s, 3H), 2.22 (d, J=1.1 Hz, 3H).

Example 49

1-(2-(1-Benzyl-2,5-dimethyl-1H-pyrrol-3-yl)-2-oxoethyl)-4-methyl-6-oxo-1,6-dihydropyridine-3-carbonitrile A target compound was synthesized in a similar manner as example 1 using 1-(1-benzyl-2,5-dimethyl-1H-pyrrol-3-yl)-2-chloroethan-1-one and 4-methyl-6-oxo-1,6-dihydropyridine-3-carbonitrile.

$^1$H NMR (500 MHz, CDCl$_3$): δ 7.72 (s, 1H), 7.38-7.28 (m, 3H), 6.94-6.88 (m, 2H), 6.48 (d, J=1.4 Hz, 1H), 6.41 (d, J=1.1 Hz, 1H), 5.18 (s, 2H), 5.09 (s, 2H), 2.50 (s, 3H), 2.37 (d, J=1.2 Hz, 3H), 2.18 (d, J=1.0 Hz, 3H).

Example 50

1-(2-(1-Benzyl-2,5-dimethyl-1H-pyrrol-3-yl)-2-oxoethyl)-5-methoxypyridin-2(1H)-one A target compound was synthesized in a similar manner as example 1 using 1-(1-benzyl-2,5-dimethyl-1H-pyrrol-3-yl)-2-chloroethan-1-one and 5-methoxypyridin-2(1H)-one.

$^1$H NMR (500 MHz, CDCl$_3$): δ 7.34 (s, 2H), 7.29 (s, 2H), 6.94-6.89 (m, 2H), 6.76 (s, 1H), 6.61 (d, J=9.9 Hz, 1H), 6.45 (s, 1H), 5.16 (s, 2H), 5.08 (s, 2H), 3.70 (s, 3H), 2.50 (s, 3H), 2.17 (s, 3H).

Example 51

1-(1-(1-Benzyl-2,5-dimethyl-1H-pyrrol-3-yl)-1-oxo-3-phenylpropan-2-yl)-6-oxo-1,6-dihydropyridine-3-carbonitrile A) 1-(2-((tert-Butyldimethylsilyl)oxy)-2-(2,5-dimethyl-1H-pyrrol-3-yl)vinyl)-6-oxo-1,6-dihydropyridine-3-carbonitrile A mixture of 1-(2-(2,5-dimethyl-1H-pyrrol-3-yl)-2-oxoethyl)-6-oxo-1,6-dihydropyridine-3-carbonitrile (100 mg), (tert-butyl(dimethyl)silyl]trifluoromethanesulfonate (134 mg), triethylamine (54.3 μL), and dichloromethane (5 mL) was stirred at 25° C. for 4 hours. The mixture was quenched with brine at room temperature and extracted with ethyl acetate. The organic layer was separated, washed with brine, dried over MgSO$_4$, and concentrated in vacuo. The residue was purified by silica gel chromatography (ethyl acetate: hexane=1:19 to 3:2) to give the title compound (66.0 mg) as a solid.

MS: (M+H$^+$): 370.3

B) 1-(1-(1-Benzyl-2,5-dimethyl-1H-pyrrol-3-yl)-1-oxo-3-phenylpropan-2-yl)-6-oxo-1,6-dihydropyridine-3-carbonitrile A mixture of 1-(2-((tert-butyldimethylsilyl)oxy)-2-(2,5-dimethyl-1H-pyrrol-3-yl)vinyl)-6-oxo-1,6-dihydropyridine-3-carbonitrile (66.0 mg), TBAF (51.4 mg), benzyl bromide (23.3 μL), and THF (1.0 mL) was stirred at 0° C. for 2 hours. The mixture was quenched with brine at room temperature and extracted with ethyl acetate. The organic layer was separated, washed with brine, dried over MgSO$_4$, and concentrated in vacuo. The residue was purified by silica gel chromatography (ethyl acetate:hexane=0:100 to 100:0) to give the target compound (18.0 mg) as a solid.

$^1$H NMR (500 MHz, CDCl$_3$): δ 8.17 (d, J=2.4 Hz, 1H), 7.37-7.29 (m, 5H), 7.27-7.19 (m, 4H), 6.92-6.86 (m, 2H), 6.74 (dd, J=9.5, 6.4 Hz, 1H), 6.54-6.47 (m, 2H), 5.06 (s, 2H), 3.56 (dd, J=14.6, 6.3 Hz, 1H), 3.12 (dd, J=145, 9.5 Hz, 1H), 2.51 (s, 3H), 2.14 (d, J=0.9 Hz, 3H).

Example 52

1-(1-(1-Benzyl-2,5-dimethyl-1H-pyrrol-3-yl)-1-oxopropan-2-yl)-6-oxo-1,6-dihydropyridine-3-carbonitrile A) 1-(2-(1-Benzyl-2,5-dimethyl-1H-pyrrol-3-yl)-2-oxoethyl)-6-oxo-1,6-dihydropyridine-3-carbonitrile A target compound was synthesized in a similar manner as example 1 using 1-(1-benzyl-2,5-dimethyl-1H-pyrrol-3-yl)-2-chloroethan-1-one and 6-oxo-1,6-dihydropyridine-3-carbonitrile.

$^1$H NMR (500 MHz, DMSO-d$_6$): δ 8.51 (d, J=2.5 Hz, 1H), 7.74 (dd, J=9.5, 2.5 Hz, 1H), 7.36 (dd, J=8.3, 6.9 Hz, 2H), 7.28 (s, 1H), 6.99-6.90 (m, 2H), 6.58-6.50 (m, 2H), 5.20 (d, J=1.5 Hz, 4H), 2.40 (s, 3H), 2.14 (d, J=1.0 Hz, 3H).

B) 1-(1-(1-Benzyl-2,5-dimethyl-1H-pyrrol-3-yl)-1-oxopropan-2-yl)-6-oxo-1,6-dihydropyridine-3-carbonitrile Iodomethane (54 μL) was added portion-wise to a mixture of 1-(2-(1-benzyl-2,5-dimethyl-1H-pyrrol-3-yl)-2-oxoethyl)-6-oxo-1,6-dihydropyridine-3-carbonitrile (100 mg), Cs$_2$CO$_3$ (188 mg) and DMSO (1.0 mL). The mixture was stirred at room temperature overnight. The mixture was purified by silica gel chromatography (ethyl acetate: hexane=1:4 to 9:1) to give the target compound (19.0 mg) as a solid.

$^1$H NMR (500 MHz, DMSO-d$_6$): δ 8.54 (d, J=2.4 Hz, 1H), 7.73 (dd, J=9.5, 2.4 Hz, 1H), 7.36 (t, J=7.6 Hz, 2H), 7.28 (t, J=7.4 Hz, 1H), 6.98-6.93 (m, 2H), 6.58-6.48 (m, 2H), 6.10 (q, J=7.4 Hz, 1H), 2.40 (s, 3H), 2.14 (s, 3H), 1.64 (d, J=7.5 Hz, 3H).

Example 53

1-(2-(1-Benzyl-2,5-dimethyl-1H-pyrrol-3-yl)-2-oxoethyl)-5-(tert-butyl)pyridin-2(1H)-one A target compound was synthesized in a similar manner as example 1 using 1-(1-benzyl-2,5-dimethyl-1H-pyrrol-3-yl)-2-chloroethan-1-one and 5-(tert-butyl)pyridin-2(1H)-one.

$^1$H NMR (500 MHz, DMSO-d$_6$): δ 7.61 (dd, J=9.5, 2.8 Hz, 1H), 7.43 (d, J=2.7 Hz, 1H), 7.37 (dd, J=8.2, 7.0 Hz, 2H), 7.28 (s, 1H), 7.02-6.88 (m, 2H), 6.51 (d, J=1.2 Hz, 1H), 6.38 (d, J=9.5 Hz, 1H), 5.20 (s, 2H), 5.14 (s, 2H), 2.41 (s, 3H), 2.15 (d, J=0.9 Hz, 3H), 1.21 (s, 9H).

Example 54

N-(1-(2-(1-Benzyl-2,5-dimethyl-1H-pyrrol-3-0)-2-oxoethyl)-6-oxo-1,6-dihydropyridin-3-yl)acetamide A target compound was synthesized in a similar manner as example 1 using 1-(1-benzyl-2,5-dimethyl-1H-pyrrol-3-yl)-2-chloroethan-1-one and N-(6-oxo-1,6-dihydropyridin-3-yl)acetamide.

$^1$H NMR (500 MHz, CDCl$_3$): δ 8.60 (t, J=7.2 Hz, 1H), 8.13 (d, J=2.8 Hz, 1H), 7.38 (t, J=7.5 Hz, 2H), 7.31 (t, J=7.3 Hz, 1H), 7.10 (dd, J=9.7, 2.8 Hz, 1H), 6.94 (d, J=7.5 Hz, 2H), 6.50 (d, J=9.6 Hz, 1H), 6.44 (s, 1H), 5.24 (s, 2H), 5.11 (s, 2H), 2.53 (s, 3H), 2.19 (s, 3H), 2.03 (s, 3H).

Example 55

2-(2-(1-Benzyl-5-methyl-1H-pyrazol-4-yl)-2-oxoethyl)-6-bromopyridazin-3(2H)-one

A mixture of 1-(1-benzyl-5-methyl-1H-pyrazol-4-yl)-2-bromoethan-1-one (590 mg), 6-bromopyridazin-3(2H)-one (351 mg), K$_2$CO$_3$ (556 mg, 4.02 mmol), and DMSO (10 mL) was stirred at room temperature overnight. The mixture was quenched with water, and the resulting solid was collected by filtration and washed with water. The solid recrystallized from DMSO/water to give the target compound (500 mg) as a solid.

$^1$H NMR (500 MHz, DMSO-d$_6$): δ 8.27 (s, 1H), 7.70 (d, J=9.7 Hz, 1H), 7.37 (dd, J=8.1, 6.6 Hz, 2H), 7.34-7.29 (m, 1H), 7.21-7.15 (m, 2H), 7.03 (d, J=9.7 Hz, 1H), 5.43 (s, 2H), 5.39 (s, 2H), 2.50 (s, 3H).

Example 56

1-(2-(1-Benzyl-5-methyl-1H-pyrazol-4-yl)-2-oxoethyl)-5-bromopyrimidin-2(1H)-one

To a suspension of 1-(1-benzyl-5-methyl-1H-pyrazol-4-yl)-2-bromoethan-1-one (680 mg) in dichloromethane (150 mL) was added triethylamine (3.86 mL) at room temperature to give a clear solution, to which was added a solution of 5-bromopyrimidin-2-ol (405 mg) in dichloromethane (150 mL) at room temperature, and the mixture was stirred at room temperature overnight. The mixture was quenched with water and extracted with CH$_2$Cl$_2$. The organic layer was separated, dried with Na$_2$SO$_4$, and concentrated in vacuo. The residue was purified by silica gel chromatography (ethyl acetate:hexane=2:3 to 1:1) and recrystallized from ethyl acetate to give the target compound (80 mg) as a solid.

¹H NMR (500 MHz, CDCl₃): δ 8.66-8.60 (m, 1H), 8.04 (s, 1H), 7.72 (d, J=3.3 Hz, 1H), 7.43-7.30 (m, 3H), 7.17-7.13 (m, 2H), 5.36 (s, 2H), 5.13 (s, 2H), 2.54 (s, 3H).

Example 57

5-Bromo-1-(1-(2,5-dimethyl-1-((5-methyl-1,3,4-oxadiazol-2-yl)methyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 58

5-Bromo-1-(1-(1-(cyclopropylmethyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 59

5-Bromo-1-(1-(1-(cyclobutylmethyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 60

5-Bromo-1-(1-(1-(3-methoxybenzyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 61

5-Bromo-1-(1-(1-(4-methoxybenzyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 62

5-Bromo-1-(1-(1-(3-fluorobenzyl)-2,5-dimethyl-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 63

5-Bromo-1-(1-(2,5-dimethyl-1-(3-methylbenzyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 64

5-Bromo-1-(1-(2,5-dimethyl-1-(2-methylbenzyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 65

5-Bromo-1-(1-(2,5-dimethyl-1-(4-methylbenzyl)-1H-pyrrol-3-yl)-1-oxopropan-2-yl)pyridin-2(1H)-one A target compound was synthesized in a similar manner as step C in example 24 using 5-bromo-1-(1-(2,5-dimethyl-1H-pyrrol-3-yl)-1-oxopropan-2-yl)pyridin-2(1H)-one.

Example 66

5-Bromo-1-(2-(3-(4-fluorobenzyl)pyrrolidin-1-yl)-2-oxoethyl)pyridin-2(1H)-one

To a mixture of 2-(5-bromo-2-oxopyridin-1(2H)-yl)acetic acid (200 mg), 3-(4-fluorobenzyl)pyrrolidine (232 mg), and DMF (10.0 mL) was added HATU (491 mg) and DIPEA (451 μL) in one portion at 12° C. The mixture was stirred at the same temperature for 2 hours. The reaction mixture was diluted with water and extracted with ethyl acetate. The combined organic layers were washed with water and brine, dried over Na₂SO₄, and concentrated under reduced pressure to give a residue. The residue was purified by HPLC to give the target compound (199 mg) as a solid.

¹H NMR (500 MHz, Methanol-d₄): δ 7.80 (t, J=3.2 Hz, 1H), 7.61 (dd, J=2.4, 9.7 Hz, 1H), 7.29-7.19 (m, 2H), 7.02 (q, J=8.5 Hz, 2H), 6.50 (d, J=9.7 Hz, 1H), 4.82-4.67 (m, 2H), 3.79-3.57 (m, 2H), 3.56-3.33 (m, 1H), 3.28-3.06 (m, 1H), 2.8 (dd, J=8.3, 11.6 Hz, 2H), 2.5 (dd, J=7.5, 15.9 Hz, 1H), 2.15-1.90 (m, 1H), 1.85-1.59 (m, 1H).

Example 67

5-Bromo-1-(2-(3-(4-fluorophenyl)pyrrolidin-1-yl)-2-oxoethyl)pyridin-2(1H)-one

A target compound was synthesized in a similar manner as example 66 using 3-(4-fluorophenyl)pyrrolidine.

¹H NMR (500 MHz, Methanol-d₄): δ 7.88 (br s, 1H), 7.66 (d, J=9.7 Hz, 1H), 7.41-7.29 (m, 2H), 7.07 (q, J=8.4 Hz, 2H), 6.55 (d, J=9.5 Hz, 1H), 4.90-4.78 (m, 2H), 4.11-3.92 (m, 1H), 3.89-3.72 (m, 1H), 3.71-3.33 (m, 3H), 2.48-2.28 (m, 1H), 2.21-2.00 (m, 1H).

Example 68

5-Bromo-1-(2-(1-(4-fluorobenzyl)-5-methyl-1H-pyrazol-3-yl)-2-oxoethyl)pyridin-2(1H)-one A) 1-(4-Fluorobenzyl)-N-methoxy-N,5-dimethyl-1H-pyrazole-3-carboxamide To a stirred solution of 1-(4-fluorobenzyl)-5-methyl-1H-pyrazole-3-carboxylic acid (3.60 g) and N,O-dimethylhydroxylamine hydrochloride (1.5 g) in DMF (30 mL) was added triphenylphosphine (14.7 g) and DIPEA (5.37 mL). Then the mixture was stirred at 15° C. for 3 hours. Another batch of the reaction was combined, diluted with water and extracted with ethyl acetate. The organic layer was washed with brine, dried over $Na_2SO_4$, concentrated, and purified by silica gel chromatography (petroleum ether:ethyl acetate=5:1 to 3:1) to give the target compound (4 g) as an oil.
$^1$H NMR (400 MHz, $CDCl_3$): δ 7.10 (dd, J=5.3, 8.6 Hz, 2H), 7.02-6.95 (m, 2H), 6.55 (s, 1H), 5.35-5.26 (m, 2H), 3.75 (s, 3H), 3.42 (s, 3H), 2.19 (s, 3H).

B) 1-(1-(4-Fluorobenzyl)-5-methyl-1H-pyrazol-3-yl)ethan-1-one

To a stirred solution of 1-(4-fluorobenzyl)-N-methoxy-N,5-dimethyl-1H-pyrazole-3-carboxamide (3.6 g) in THF (50 mL) was added MeMgBr (3.0 M, 8.65 mL) drop-wise at 0° C. Then the reaction mixture was allowed to warm to 15° C., and stirred for 2 hours. Another batch of the reaction was combined, quenched by saturated $NH_4Cl$ solution, and extracted with ethyl acetate. The organic layer was washed with brine, dried over $Na_2SO_4$, concentrated, and purified by silica gel chromatography (petroleum ether:ethyl acetate=5:1 to 3:1) to give the target compound (4 g) as a oil.
$^1$H NMR (400 MHz, $CDCl_3$): δ 7.13-7.07 (m, 2H), 7.06-6.99 (m, 2H), 6.58 (s, 1H), 5.31 (s, 2H), 2.57 (s, 3H), 2.21 (s, 3H).

C) 2-Bromo-1-(1-(4-fluorobenzyl)-5-methyl-1H-pyrazol-3-yl)ethan-1-one

To a stirred solution of 1-(1-(4-fluorobenzyl)-5-methyl-1H-pyrazol-3-yl)ethan-1-one (1.0 g) in THF (15 mL) was added trimethylphenylammonium tribromide (1.78 g) in portions. Then the reaction mixture was stirred at 15° C. for 12 hours. The reaction mixture was filtered, concentrated, and purified by column chromatography (petroleum ether:ethyl acetate=10:1 to 5:1 to 3:1) to give the target compound (850 mg) as a solid.
$^1$H NMR (400 MHz, $CDCl_3$): δ 7.16-7.09 (m, 2H), 7.07-7.00 (m, 2H), 6.65 (s, 1H), 5.31 (s, 2H), 4.58 (s, 2H), 2.23 (s, 3H).

D) 5-Bromo-1-(2-(1-(4-fluorobenzyl)-5-methyl-1H-pyrazol-3-yl)-2-oxoethyl)pyridin-2(1H)-one A target compound was synthesized in a similar manner as step D in example 34 using 2-bromo-1-(1-(4-fluorobenzyl)-5-methyl-1H-pyrazol-3-yl)ethan-1-one and 5-bromopyridin-2(1H)-one.
$^1$H NMR (400 MHz, $CDCl_3$): δ 7.40 (d, J=9.5 Hz, 1H), 7.35 (s, 1H), 7.17-7.10 (m, 2H), 7.09-7.01 (m, 2H), 6.64 (s, 1H), 6.54 (d, J=9.8 Hz, 1H), 5.38 (s, 2H), 5.32 (s, 2H), 2.24 (s, 3H).

Example 69

1-(2-(1-Benzyl-5-methyl-1H-pyrazol-4-yl)-2-oxoethyl)-2-oxo-1,2-dihydropyridine-3,5-dicarbonitrile A target compound was synthesized in a similar manner as step D in example 34 using 1-(1-benzyl-5-methyl-1H-pyrazol-4-yl)-2-bromoethan-1-one and 2-oxo-1,2-dihydropyridine-3,5-dicarbonitrile.
$^1$H NMR (500 MHz, DMSO-$d_6$): δ 8.39 (d, J=5.1 Hz, 2H), 8.31 (s, 1H), 7.35 (d, J=7.5 Hz, 3H), 7.16 (d, J=7.0 Hz, 2H), 5.42 (s, 2H), 5.33 (s, 2H), 4.26 (s, 1H), 2.52 (br s, 3H).

Example 70

1-(2-(1-Benzyl-5-methyl-1H-pyrazol-4-yl)-2-oxoethyl)-5-bromopyrazin-2(1H)-one

A mixture of 1-(1-benzyl-5-methyl-1H-pyrazol-4-yl)-2-bromoethan-1-one (770 mg), 5-bromopyrazin-2(1H)-one (460 mg), $K_2CO_3$ (726.98 mg, 5.26 mmol) and DMSO (10.0 mL) was stirred at room temperature overnight. The mixture was quenched with water, and the resulting solid was collected by filtration and washed with water. The solid was purified by silica gel chromatography (ethyl acetate:hexane=100:0) followed by recrystallization form ethyl acetate/hexane to give the target compound (40 mg) as a solid.
$^1$H NMR (500 MHz, $CDCl_3$): δ 8.07-8.02 (m, 2H), 7.41-7.24 (m, 4H), 7.19-7.11 (m, 2H), 5.36 (s, 2H), 5.10 (s, 2H), 2.54 (s, 3H).

Example 71

1-(2-(1-Benzyl-5-methyl-1H-pyrazol-4-yl)-2-oxoethyl)-5-bromo-6-fluoropyridin-2(1H)-one A mixture of 1-(1-benzyl-5-methyl-1H-pyrazol-4-yl)-2-bromoethan-1-one (540 mg), 5-bromo-6-fluoropyridin-2-ol (354 mg), $K_2CO_3$ (509.16 mg, 3.68 mmol), and DMSO (10 mL) was stirred at room temperature overnight. The mixture was quenched with water, and the resulting solid was collected by filtration and washed with water. The solid was recrystallized from DMSO/water to give the target compound (550 mg) as a solid.
$^1$H NMR (500 MHz, DMSO-$d_6$): δ 8.21 (s, 1H), 8.18 (t, J=8.9 Hz, 1H), 7.34 (dt, J=28.6, 7.4 Hz, 3H), 7.19 (d, J=7.4 Hz, 2H), 6.92 (d, J=8.4 Hz, 1H), 5.45 (s, 2H), 5.41 (s, 2H), 2.49 (s, 3H).

Example 72

1-(2-(1-Benzyl-5-methyl-1H-pyrazol-4-yl)-2-oxoethyl)-5-bromo-4-fluoropyridin-2(1H)-one A mixture of 1-(1-benzyl-5-methyl-1H-pyrazol-4-yl)-2-bromoethan-1-one (450 mg), 5-bromo-4-fluoropyridin-2-ol (294 mg), $K_2CO_3$ (424 mg), and DMSO (10 mL) was stirred at room temperature overnight. The mixture was quenched with water, and the resulting solid was collected by filtration and washed with water. The solid was recrystallized from DMSO/water to give the target compound (360 mg) as a solid.

$^{1}$H NMR (500 MHz, DMSO-d$_6$): δ 8.30 (s, 1H), 8.23 (d, J=9.0 Hz, 1H), 7.37 (dd, J=8.1, 6.5 Hz, 2H), 7.34-7.29 (m, 1H), 7.20-7.16 (m, 2H), 6.51 (d, J=11.0 Hz, 1H), 5.43 (s, 2H), 5.25 (s, 2H), 2.50 (s, 3H).

Example 73

2-(1-(1-Benzyl-5-methyl-1H-pyrazol-4-yl)-1-oxopropan-2-yl)-6-ethynylpyridazin-3(2H)-one A) Ethyl 1-benzyl-5-methyl-1H-pyrazole-4-carboxylate To a solution of benzylhydrazine dihydrochloride (5.0 g) and ethyl 2-((dimethylamino)methylene)-3-oxobutanoate (4.75 g) in EtOH (10 mL) was added DIPEA (13.4 mL). The mixture was stirred at 25° C. for 12 hours. The reaction mixture was poured into water, extracted with ethyl acetate, washed with brine, dried with anhydrous Na$_2$SO$_4$, and concentrated under reduced pressure to give the crude product. The residue was purified by silica gel chromatography (petroleum ether:ethyl acetate=8:1) to give the target compound (6 g) as an oil.

B) 1-Benzyl-5-methyl-1H-pyrazole-4-carboxylic Acid

To a solution of ethyl 1-benzyl-5-methyl-1H-pyrazole-4-carboxylate (2 g) in EtOH (20 mL) was added 2M NaOH solution (8.19 mL). The mixture was stirred at 50° C. for 2 hours. The reaction mixture was poured into water and washed with dichloromethane. The aqueous phase was adjusted to pH=3 with 1M HCl solution and extracted with ethyl acetate. The combined organic layers were washed with brine, dried with anhydrous Na$_2$SO$_4$, and concentrated to give the target compound (900 mg) as a solid.

MS: (M+H$^+$): 217.0

C) 1-Benzyl-N-methoxy-N,5-dimethyl-1H-pyrazole-4-carboxamide

A target compound was synthesized in a similar manner as step A in example 68 using 1-benzyl-5-methyl-1H-pyrazole-4-carboxylic acid $^{1}$H NMR (400 MHz, CDCl$_3$): δ 7.95 (s, 1H), 7.34-7.27 (m, 3H), 7.15-7.08 (m, 2H), 5.32 (s, 2H), 3.69 (s, 3H), 3.32 (s, 3H), 2.50 (s, 3H).

D) 1-(1-Benzyl-5-methyl-1H-pyrazol-4-yl)propan-1-one

A target compound was synthesized in a similar manner as step B in example 68 using 1-benzyl-N-methoxy-N,5-dimethyl-1H-pyrazole-4-carboxamide and EtMgBr.

$^{1}$H NMR (400 MHz, CDCl$_3$): δ 7.82 (s, 1H), 7.29-7.20 (m, 3H), 7.06-7.02 (m, 2H), 5.23 (s, 2H), 2.73 (q, J=7.3 Hz, 2H), 2.45 (s, 3H), 1.10 (t, J=7.3 Hz, 3H).

E) 1-(1-Benzyl-5-methyl-1H-pyrazol-4-yl)-2-bromopropan-1-one

To a mixture of 1-(1-benzyl-5-methyl-1H-pyrazol-4-yl)propan-1-one (180 mg) in chloroform (2 mL) was added pyridinium tribromide (252 mg). The mixture was stirred at 62° C. for 12 hours. The reaction mixture was diluted with water, concentrated, adjusted to pH=8 with saturated NaHCO$_3$ solution, and extracted with ethyl acetate. The combined organic layers were washed with brine, dried over Na$_2$SO$_4$, and concentrated to give the target compound (290 mg) as an oil.

MS: (M+H$^+$): 309.1

F) 2-(1-(1-Benzyl-5-methyl-1H-pyrazol-4-yl)-1-oxopropan-2-yl)-6-bromopyridazin-3 (2H)-one A target compound was synthesized in a similar manner as step D in example 34 using 1-(1-benzyl-5-methyl-1H-pyrazol-4-yl)-2-bromopropan-1-one and 6-bromopyridazin-3(2H)-one.

$^{1}$H NMR (400 MHz, CDCl$_3$): δ 7.91 (s, 1H), 7.35-7.24 (m, 4H), 7.11 (d, J=7.1 Hz, 2H), 6.80 (d, J=9.7 Hz, 1H), 5.94 (q, J=7.1 Hz, 1H), 5.28 (s, 2H), 2.50 (s, 3H), 1.68 (d, J=7.1 Hz, 3H).

G) 2-(1-(1-Benzyl-5-methyl-1H-pyrazol-4-yl)-1-oxopropan-2-yl)-6-((trimethylsilyl)ethynyl)pyridazin-3(2H)-one A target compound was synthesized in a similar manner as step A in example 36 using 2-(1-(1-benzyl-5-methyl-1H-pyrazol-4-yl)-1-oxopropan-2-yl)-6-bromopyridazin-3(2H)-one.

MS: (M+H$^+$): 419.3

H) 2-(1-(1-Benzyl-5-methyl-1H-pyrazol-4-yl)-1-oxopropan-2-yl)-6-ethynylpyridazin-3(2H)-one To a mixture of 2-(1-(1-benzyl-5-methyl-1H-pyrazol-4-yl)-1-oxopropan-2-yl)-6-((trimethylsilyl)ethynyl)pyridazin-3(2H)-one (1.0 g) in MeOH (10 mL) was added K$_2$CO$_3$ (990 mg). The mixture was stirred at 25° C. for 2 hours. The reaction mixture was diluted with water and extracted with ethyl acetate. The combined organic layers were washed with brine, dried over Na$_2$SO$_4$, concentrated, and purified by silica gel chromatography (petroleum ether:ethyl acetate=9:1 to 5:1 to 4:1 to 11:9) followed by HPLC to give the target compound (70.5 mg) as a solid.

$^{1}$H NMR (400 MHz, Methanol-d$_4$): δ 8.05 (s, 1H), 7.51 (d, J=9.7 Hz, 1H), 7.36-7.26 (m, 3H), 7.13 (d, J=6.8 Hz, 2H), 6.96 (d, J=9.7 Hz, 1H), 6.05 (q, J=7.1 Hz, 1H), 5.39 (s, 2H), 3.85 (s, 1H), 2.50 (s, 3H), 1.66 (d, J=7.1 Hz, 3H).

Example 74

6-Ethynyl-2-(1-(1-(4-fluorobenzyl)-5-methyl-1H-pyrazol-4-yl)-1-oxopropan-2-yl)pyridazin-3(2H)-one A) Ethyl 1-(4-fluorobenzyl)-5-methyl-1H-pyrazole-4-carboxylate A target compound was synthesized in a similar manner as step A in example 73 using (4-fluorobenzyl)hydrazine dihydrochloride.

B) 1-(4-Fluorobenzyl)-5-methyl-1H pyrazole-4-carboxylic Acid

A target compound was synthesized in a similar manner as step B in example 73 using ethyl 1-(4-fluorobenzyl)-5-methyl-1H-pyrazole-4-carboxylate.

¹H NMR (400 MHz, DMSO-d₆): δ 7.82 (s, 1H), 7.2-7.13 (m, 4H), 5.35 (s, 2H), 2.47 (s, 3H).

C) 1-(4-Fluorobenzyl)-N-methoxy-N,5-dimethyl-1H-pyrazole-4-carboxamide

A target compound was synthesized in a similar manner as step A in example 68 using 1-(4-fluorobenzyl)-5-methyl-1H-pyrazole-4-carboxylic acid.
¹H NMR (400 MHz, CDCl₃): δ 7.95 (s, 1H), 7.27 (s, 1H), 7.14-7.09 (m, 2H), 7.05-6.99 (m, 2H), 528 (s, 2H), 3.69 (s, 3H), 3.32 (s, 3H), 2.51 (s, 3H).

D) 1-(1-(4-Fluorobenzyl)-5-methyl-1H-pyrazol-4-yl)propan-1-one

A target compound was synthesized in a similar manner as step B in example 68 using 1-(4-fluorobenzyl)-N-methoxy-N,5-dimethyl-1H-pyrazole-4-carboxamide and EtMgBr.
¹H NMR (400 MHz, CDCl₃): δ 7.89 (s, 1H), 7.14-7.09 (m, 2H), 7.05-6.98 (m, 2H), 5.27 (s, 2H), 2.80 (q, J=7.3 Hz, 2H), 2.53 (s, 3H), 1.18 (t, J=7.3 Hz, 3H).

E) 2-Bromo-1-(1-(4-fluorobenzyl)-5-methyl-1H-pyrazol-4-yl)propan-1-one

A target compound was synthesized in a similar manner as step E in example 73 using 1-(1-(4-fluorobenzyl)-5-methyl-1H-pyrazol-4-yl)propan-1-one.
MS: (M+H⁺): 325.3

F) 6-Bromo-2-(1-(1-(4-fluorobenzyl)-5-methyl-1H-pyrazol-4-yl)-1-oxopropan-2-yl)pyridazin-3(2H)-one A target compound was synthesized in a similar manner as step D in example 34 using 2-bromo-1-(1-(4-fluorobenzyl)-5-methyl-1H-pyrazol-4-yl)propan-1-one and 6-bromopyridazin-3(2H)-one.
¹H NMR (400 MHz, CDCl₃): δ 7.90 (s, 1H), 7.30-7.25 (m, 2H), 7.15-7.07 (m, 2H), 7.04-6.98 (m, 2H), 6.81 (d, J=9.7 Hz, 1H), 5.93 (q, J=7.1 Hz, 1H), 5.25 (s, 2H), 2.50 (s, 3H), 1.68 (d, J=7.3 Hz, 3H).

G) 2-(1-(1-(4-Fluorobenzyl)-5-methyl-1H-pyrazol-4-yl)-1-oxopropan-2-yl)-6-((trimethylsilyl)ethynyl)pyridazin-3(2H)-one A target compound was synthesized in a similar manner as step A in example 36 using 6-bromo-2-(1-(1-(4-fluorobenzyl)-5-methyl-1H-pyrazol-4-yl)-1-oxopropan-2-yl)pyridazin-3(2H)-one.
MS: (M+H⁺): 437.4

H) 6-Ethynyl-2-(1-(1-(4-fluorobenzyl)-5-methyl-1H-pyrazol-4-yl)-1-oxopropan-2-yl)pyridazin-3(2H)-one A target compound was synthesized in a similar manner as step H in example 73 using 2-(1-(1-(4-fluorobenzyl)-5-methyl-1H-pyrazol-4-yl)-1-oxopropan-2-yl)-6-((trimethylsilyl)ethynyl)pyridazin-3(2H)-one.
¹H NMR (400 MHz, CDCl₃): δ 7.87 (s, 1H), 7.24 (d, J=0.9 Hz, 1H), 7.14-7.05 (m, 2H), 7.04-6.96 (m, 2H), 6.86 (d, J=9.6 Hz, 1H), 5.97 (q, J=7.0 Hz, 1H), 523 (s, 2H), 3.16 (s, 1H), 2.49 (s, 3H), 1.68 (d, J=7.0 Hz, 3H).

Example 75

2-(1-(1-(2,4-Difluorobenzyl)-5-methyl-1H-pyrazol-4-yl)-1-oxopropan-2-yl)-6-ethynylpyridazin-3(2H)-one

A) Ethyl 1-(2,4-difluorobenzyl)-5-methyl-1H-pyrazole-4-carboxylate

A target compound was synthesized in a similar manner as step A in example 73 using (2,4-difluorobenzyl)hydrazine dihydrochloride.
MS: (M+H⁺): 281.2

B) 1-(2,4-Difluorobenzyl)-5-methyl-1H-pyrazole-4 carboxylic Acid

A target compound was synthesized in a similar manner as step B in example 73 using ethyl 1-(2,4-difluorobenzyl)-5-methyl-1H-pyrazole-4-carboxylate.
MS: (M+H⁺): 253.2

C) 1-(2,4-Difluorobenzyl)-N-methoxy-N,5-dimethyl-1H-pyrazole-4-carboxamide

A target compound was synthesized in a similar manner as step A in example 68 using 1-(2,4-Difluorobenzyl)-5-methyl-1H-pyrazole-4-carboxylic acid.
¹H NMR (400 MHz, CDCl₃): δ 7.94 (s, 1H), 6.95-7.05 (m, 1H), 6.80-6.88 (m, 2H), 5.30 (s, 2H), 3.68 (s, 3H), 3.32 (s, 3H), 2.55 (s, 3H).

D) 1-(1-(2,4-Difluorobenzyl)-5-methyl-1H-pyrazol-4-yl)propan-1-one

A target compound was synthesized in a similar manner as step B in example 68 using 1-(2,4-Difluorobenzyl)-N-methoxy-N,5-dimethyl-1H-pyrazole-4-carboxamide and EtMgBr.
¹H NMR (400 MHz, CDCl₃): δ 7.89 (s, 1H), 6.97-7.10 (m, 1H), 6.79-6.89 (m, 2H), 5.29 (s, 2H), 2.80 (q, J=7.3 Hz, 2H), 2.57 (s, 3H), 1.18 (t, J=7.3 Hz, 3H).

E) 2-Bromo-1-(1-(2,4-difluorobenzyl)-5-methyl-1H-pyrazol-4-yl)propan-1-one

A target compound was synthesized in a similar manner as step E in example 73 using 1-(1-(2,4-difluorobenzyl)-5-methyl-1H-pyrazol-4-yl)propan-1-one.

F) 6-Bromo-2-(1-(1-(2,4-difluorobenzyl)-5-methyl-1H-pyrazol-4-yl)-1-oxopropan-2-yl)pyridazin-3(2H)-one A target compound was synthesized in a similar manner as step D in example 34 using 2-Bromo-1-(1-(2,4-difluorobenzyl)-5-methyl-1H-pyrazol-4-yl)propan-1-one and 6-bromopyridazin-3(2H)-one.
¹H NMR (400 MHz, CDCl₃): δ 7.88 (s, 1H), 7.25 (d, J=1.5 Hz, 1H), 7.00-7.09 (m, 1H), 6.76-6.89 (m, 3H), 5.91 (q, J=7.2 Hz, 1H), 5.26 (s, 2H), 2.49-2.59 (m, 3H), 1.67 (d, J=7.2 Hz, 3H).

G) 2-(1-(1-(2,4-Difluorobenzyl)-5-methyl-1H-pyrazol-4-yl)-1-oxopropan-2-yl)-6-((trimethylsilyl)ethynyl)pyridazin-3(2H)-one A target compound was synthesized in a similar manner as step A in example 36 using 6-bromo-2-(1-(1-(2,4-difluorobenzyl)-5-methyl-1H-pyrazol-4-yl)-1-oxopropan-2-yl)pyridazin-3(2H)-one.

H) 2-(1-(1-(2,4-Difluorobenzyl)-5-methyl-1H-pyrazol-4-yl)-1-oxopropan-2-yl)-6-ethynylpyridazin-3(2H)-one A target compound was synthesized in a similar manner as step H in example 73 using 2-(1-(1-(2,4-difluorobenzyl)-5-methyl-1H-pyrazol-4-yl)-1-oxopropan-2-yl)-6-((trimethylsilyl)ethynyl)pyridazin-3(2H)-one $^1$H NMR (400 MHz, DMSO-d$_6$): δ 8.11 (s, 1H), 7.57 (d, J=9.7 Hz, 1H), 7.29 (td, J=2.6, 9.5, 10.6 Hz, 1H), 7.17-7.24 (m, 1H), 7.08 (dt, J=2.2, 8.55 Hz, 1H), 6.99 (d, J=9.7 Hz, 1H), 6.01 (q, J=7.0 Hz, 1H), 5.37 (s, 2H), 4.55 (s, 1H), 2.51 (s, 3H), 1.53 (d, J=7.0 Hz, 3H).

Example 76

2-(1-(1-Benzyl-5-methyl-1H-pyrazol-4-yl)-1-oxopropan-2-yl)-6-vinylpyridazin-3(2H)-one To a solution of 2-(1-(1-benzyl-5-methyl-1H-pyrazol-4-yl)-1-oxopropan-2-yl)-6-bromopyridazin-3(2H)-one (51 mg) in THF (2 mL) and water (0.4 mL) were added potassium vinyltrifluoroborate (85.1 mg) and K$_3$PO$_4$ (54.0 mg). After that XPhos-Pd-G1 (5.63 mg) was added to the mixture and the mixture was stirred at 80° C. for 12 hours. The reaction mixture was diluted with water and extracted with ethyl acetate. The combined organic layers were washed with brine, dried over Na$_2$SO$_4$, concentrated, and purified by preparative TLC (petroleum ether:ethyl acetate=1:1) to give the target compound (49.7 mg) as a solid.

$^1$H NMR (400 MHz, CDCl$_3$): δ 7.81 (s, 1H), 7.42 (d, J=9.7 Hz, 1H), 7.26-7.19 (m, 3H), 7.03 (d, J=6.4 Hz, 2H), 6.86 (d, J=9.7 Hz, 1H), 6.57 (d, J=11.1, 18.0 Hz, 1H), 5.97 (q, J=7.1 Hz, 1H), 5.70 (d, J=17.9 Hz, 1H), 5.43 (d, J=11.0 Hz, 1H), 5.21 (s, 2H), 2.44 (5, 3H), 1.61 (d, J=7.1 Hz, 3H).

Example 77

1-(1-(5-Methyl-1-(pyridin-2-ylmethyl)-1H-pyrazol-4-yl)-1-oxopropan-2-yl)-5-vinylpyridin-2(1H)-one A) 1-(1-(5-Methyl-1-(pyridin-2-ylmethyl)-1H-pyrazol-4-yl)-1-oxopropan-2-yl)-5-((trimethylsilyl)ethynyl)pyridin-2(1H)-one A target compound was synthesized in a similar manner as step A in example 36 using 5-bromo-1-(1-(5-methyl-1-(pyridin-2-ylmethyl)-1H-pyrazol-4-yl)-1-oxopropan-2-yl)pyridin-2(1H)-one.

B) 1-(1-(5-Methyl-1-(pyridin-2-ylmethyl)-1H-pyrazol-4-yl)-1-oxopropan-2-yl)-5-vinylpyridin-2(1H)-one A target compound was synthesized in a similar manner as step H in example 73 using 1-(1-(5-methyl-1-(pyridin-2-ylmethyl)-1H-pyrazol-4-yl)-1-oxopropan-2-yl)-5-((trimethylsilyl)ethynyl)pyridin-2(1H)-one.

$^1$H NMR (400 MHz, CDCl$_3$): δ 8.57 (d, J=4.4 Hz, 1H), 8.12 (s, 1H), 7.62-7.69 (m, 2H), 7.36 (dd, J=2.2, 9.7 Hz, 1H), 7.23 (dd, J=5.3, 7.5 Hz, 1H), 6.99 (d, J=7.9 Hz, 1H), 6.54 (d, J=9.7 Hz, 1H), 6.33 (q, J=7.3 Hz, 1H), 5.35-5.47 (m, 2H), 3.02 (s, 1H), 2.57 (s, 3H), 1.61 (d, J=7.5 Hz, 3H).

Example 78

1-(1-(5-Ethyl-1-(pyridin-2-ylmethyl)-1H-pyrazol-4-yl)-1-oxopropan-2-yl)-5-ethynylpyridin-2(1H)-one A) 1-(2-(5-Ethyl-1-(pyridin-2-ylmethyl)-1H-pyrazol-4-yl)-2-oxoethyl)-5-((trimethylsilyl)ethynyl)pyridin-2(1H)-one A target compound was synthesized in a similar manner as step A in example 36 using 5-bromo-1-(2-(5-ethyl-1-(pyridin-2-ylmethyl)-1H-pyrazol-4-yl)-2-oxoethyl)pyridin-2(1H)-one.

B) 1-(1-(5-Ethyl-1-(pyridin-2-ylmethyl)-1H-pyrazol-4-yl)-1-oxopropan-2-yl)-5-ethynylpyridin-2(1H)-one A target compound was synthesized in a similar manner as step H in example 73 using 1-(2-(5-ethyl-1-(pyridin-2-ylmethyl)-1H-pyrazol-4-yl)-2-oxoethyl)-5-((trimethylsilyl)ethynyl)pyridin-2(1H)-one.

$^1$H NMR (400 MHz, CDCl$_3$): δ 8.58 (d, J=3.95 Hz, 1H), 8.07 (s, 1H), 7.67 (dt, J=1.5, 7.8 Hz, 1H), 7.48 (d, J=2.6 Hz, 1H), 7.42 (dd, J=2.4, 9.4 Hz, 1H), 7.24 (dd, J=5.0, 7.2 Hz, 1H), 7.00 (d, J=7.9 Hz, 1H), 6.57 (d, J=9.6 Hz, 1H), 5.47 (s, 2H), 5.15 (s, 2H), 2.94-3.04 (m, 3H), 1.07 (t, J=7.7 Hz, 3H).

Example 79

1-(1-(5-Methyl-1-(pyridin-2-ylmethyl)-1H-pyrazol-4-yl)-1-oxopropan-2-yl)-5-vinylpyridin-2(1H)-one A) 1-(5-Methyl-1-(pyridin-2-ylmethyl)-1H-pyrazol-4-yl)propan-1-one A target compound was synthesized in a similar manner as step A in example 32 using 2-(hydrazinylmethyl)pyridine and 3-((dimethylamino)methylene)hexane-2,4-dione. A mixture with 1-(5-ethyl-1-(pyridin-2-ylmethyl)-1H-pyrazol-4-yl)ethan-1-one was obtained.

B) 2-Bromo-1-(5-methyl-1-(pyridin-2-ylmethyl)-1H-pyrazol-4-yl)propan-1-one

A target compound was synthesized in a similar manner as step C in example 34 using 1-(5-Methyl-1-(pyridin-2-ylmethyl)-1H-pyrazol-4-yl)propan-1-one. A mixture with 2-bromo-1-(5-ethyl-1-(pyridin-2-ylmethyl)-1H-pyrazol-4-yl)ethan-1-one was obtained.

C) 5-Bromo-1-(1-(5-methyl-1-(pyridin-2-ylmethyl)-1H-pyrazol-4-yl)-1-oxopropan-2-yl)pyridin-2(1H)-one A target compound was synthesized in a similar manner as step D in example 34 using 2-bromo-1-(5-methyl-1-(pyridin-2-ylmethyl)-1H-pyrazol-4-yl)propan-1-one and 5-bromopyridin-2(1H)-one. A mixture with 5-bromo-1-(2-

(5-ethyl-1-(pyridin-2-ylmethyl)-1H-pyrazol-4-yl)-2-oxo-ethyl)pyridin-2(1H)-one was obtained.

D) 1-(1-(5-Methyl-1-(pyridin-2-ylmethyl)-1H-pyrazol-4-yl)-1-oxopropan-2-yl)-5-vinylpyridin-2(1H)-one A target compound was synthesized in a similar manner as example 76 using 5-bromo-1-(1-(5-methyl-1-(pyridin-2-ylmethyl)-1H-pyrazol-4-yl)-1-oxopropan-2-yl)pyridin-2(1H)-one and potassium vinyltrifluoroborate.

$^1$H NMR (400 MHz, CDCl$_3$): δ 8.56 (d, J=4.3 Hz, 1H), 8.13 (s, 1H), 7.67-7.56 (m, 2H), 7.30 (d, J=2.3 Hz, 1H), 7.22 (dd, J=5.0, 7.1 Hz, 1H), 6.97 (d, J=7.8 Hz, 1H), 6.61 (d, J=9.4 Hz, 1H), 6.47-6.32 (m, 2H), 5.48-5.40 (m, 3H), 5.13 (d, J=10.9 Hz, 1H), 2.57 (s, 3H), 1.60 (d, J=7.2 Hz, 3H).

Example 80

1-(2-(5-Ethyl-1-(pyridin-2-ylmethyl)-1H-pyrazol-4-yl)-2-oxoethyl)-5-vinylpyridin-2(1H)-one A target compound was synthesized in a similar manner as example 76 using 5-bromo-1-(2-(5-ethyl-1-(pyridin-2-ylmethyl)-1H-pyrazol-4-yl)-2-oxoethyl)pyridin-2(1H)-one and potassium vinyltrifluoroborate.

$^1$H NMR (400 MHz, CDCl$_3$): δ 8.58 (d, J=4.2 Hz, 1H), 8.09 (s, 1H), 7.69-7.62 (m, 2H), 7.24 (dd, J=5.4, 7.0 Hz, 1H), 7.17 (d, J=2.4 Hz, 1H), 7.00 (d, J=8.2 Hz, 1H), 6.64 (d, J=9.5 Hz, 1H), 6.43 (dd, J=10.9, 17.6 Hz, 1H), 5.52-5.45 (m, 3H), 5.19-5.12 (m, 3H), 3.00 (q, J=7.6 Hz, 2H), 1.08 (t, J=7.5 Hz, 3H).

Example 81

1-(2-(1-Benzyl-5-methyl-1H-pyrazol-4-yl)-2-oxoethyl)-5-(prop-1-en-2-yl)pyridin-2(1H)-one To a solution of 1-(2-(1-benzyl-5-methyl-1H-pyrazol-4-yl)-2-oxoethyl)-5-bromopyridin-2(1H)-one (50 mg) in THF (1 mL) and water (0.2 mL) were added potassium isopropenyltrifluoroborate (95.8 mg), K$_3$PO$_4$ (55 mg, 258.91 umol, 2 eq) and XPhos-Pd-G1 (19.1 mg). The mixture was stirred at 80° C. for 12 hours under nitrogen atmosphere. The reaction mixture was diluted with water and extracted with ethyl acetate. The organic layers were washed with brine, dried over Na$_2$SO$_4$, concentrated, and purified by preparative TLC to give the target compound (30.2 mg) as a solid.

$^1$H NMR (400 MHz, DMSO-d$_6$): δ 8.30-8.25 (m, 1H), 7.81 (dd, J. 2.6, 9.7 Hz, 1H), 7.73 (s, 1H), 7.38-7.26 (m, 3H), 7.15 (d, J=7.0 Hz, 2H), 6.42 (d, J=9.7 Hz, 1H), 5.42 (s, 2H), 5.32 (s, 1H), 5.25 (s, 2H), 4.96 (s, 1H), 2.48 (br s, 3H), 1.97 (s, 3H).

Example 82

1-(2-(1-Benzyl-5-(trifluoromethyl)-1H-pyrazol-4-yl)-2-oxoethyl)-5-vinylpyridin-2(1H)-one A) 1-(1-Benzyl-5-(trifluoromethyl)-1H-pyrazol-4-yl)ethan-1-one A target compound was synthesized in a similar manner as step A in example 32 using benzylhydrazine and 3-(ethoxymethylene)-1,1,1-trifluoropentane-2,4-dione.

$^1$H NMR (400 MHz, CDCl$_3$): δ 7.96 (s, 1H), 7.36-7.31 (m, 3H), 7.22-7.16 (m, 2H), 5.55 (s, 2H), 2.52 (s, 3H).

B) 1-(1-Benzyl-5-(trifluoromethyl)-1H-pyrazol-4-yl)-2-bromoethan-1-one

A target compound was synthesized in a similar manner as step C in example 34 using 1-(1-benzyl-5-(trifluoromethyl)-1H-pyrazol-4-yl)ethan-1-one.

$^1$H NMR (400 MHz, CDCl$_3$): δ 8.02 (s, 1H), 7.36-7.31 (m, 3H), 7.22-7.18 (m, 2H), 5.55 (s, 2H), 4.24 (s, 2H).

C) 1-(2-(1-Benzyl-5-(trifluoromethyl)-1H-pyrazol-4-yl)-2-oxoethyl)-5-bromopyridin-2(1H)-one A target compound was synthesized in a similar manner as step D in example 34 using 1-(1-Benzyl-5-(trifluoromethyl)-1H-pyrazol-4-yl)-2-bromoethan-1-one and 5-bromopyridin-2(1H)-one.

$^1$H NMR (400 MHz, DMSO-d$_6$): δ 8.62 (s, 1H), 7.96 (d, J=2.7 Hz, 1H), 7.67 (d, J=2.7 Hz, 1H), 7.59 (dd, J=2.8, 9.8 Hz, 1H), 7.38-7.27 (m, 3H), 7.09 (s, 1H), 6.34 (d, J=9.5 Hz, 1H), 5.66 (s, 2H), 5.29 (s, 2H).

D) 1-(2-(1-Benzyl-5-(trifluoromethyl)-1H-pyrazol-4-yl)-2-oxoethyl)-5-vinylpyridin-2(1H)-one A target compound was synthesized in a similar manner as example 76 using 1-(2-(1-benzyl-5-(trifluoromethyl)-1H-pyrazol-4-yl)-2-oxoethyl)-5-bromopyridin-2(1H)-one and potassium vinyltrifluoroborate.

$^1$H NMR (400 MHz, Methanol-d$_4$): δ 8.32 (s, 1H), 7.78 (dd, J=2.5, 9.5 Hz, 1H), 7.49 (d, J=2.3 Hz, 1H), 7.28-7.17 (m, 3H), 7.10-7.04 (m, 2H), 6.52-6.37 (m, 2H), 5.57-5.48 (m, 3H), 5.23 (s, 2H), 5.08 (d, J=11.0 Hz, 1H).

Example 83

1-(2-(1-Benzyl-5-methyl-1H-pyrazol-4-yl)-2-oxoethyl)-5-(prop-1-en-2-yl)pyridin-2(1H)-one A) 1-(2-(1-Benzyl-5-methyl-1H-pyrazol-4-yl)-2-oxoethyl)-5-iodopyridin-2(1H)-one A target compound was synthesized in a similar manner as step D in example 361-(1-benzyl-5-methyl-1H-pyrazol-4-yl)-2-bromoethan-1-one and 5-iodopyridin-2(1H)-one.

MS: (M+H$^+$): 419.3

$^1$H NMR (400 MHz, DMSO-d$_6$): δ 8.27 (s, 1H), 7.95 (d, J=2.5 Hz, 1H), 7.61 (dd, J=2.5, 9.5 Hz, 1H), 7.40-7.27 (m, 3H), 7.16 (d, J=7.1 Hz, 2H), 6.29 (d, J=9.5 Hz, 1H), 5.42 (s, 2H), 5.19 (s, 2H), 2.48 (s, 3H).

B) 1-(2-(1-Benzyl-5-methyl-1H-pyrazol-4-yl)-2-oxoethyl)-5-(prop-1-en-2-yl)pyridin-2(1H)-one To a solution of 1-(2-(1-benzyl-5-methyl-1H-pyrazol-4-yl)-2-oxoethyl)-5-iodopyridin-2(1H)-one (170 mg) in 1,3-dimethylimidazolidin-2-one (3 mL) were added (1-fluorovinyl)methyldiphenylsilane (190 mg), CuI (3.74 mg), CsF (179 mg) and Pd(dppf)Cl$_2$ (28.7 mg). The mixture was degassed under vacuum and purged with nitrogen several times and then stirred at 25° C. for 12 hours. Another batch with 100 mg of the starting material was combined, diluted with water, and extracted with ethyl acetate. The organic layers were washed with brine, dried over Na$_2$SO$_4$, concentrated, and purified by HPLC to give the target compound (60.7 mg) as a solid.

$^1$H NMR (400 MHz, DMSO-d$_6$): δ 8.27 (s, 1H), 7.93 (d, J=2.5 Hz, 1H), 7.77 (d, J=9.5 Hz, 1H), 7.39-7.27 (m, 3H), 7.16 (d, J=7.1 Hz, 2H), 6.49 (d, J=9.5 Hz, 1H), 5.41 (s, 2H), 5.28 (s, 2H), 5.19-5.06 (m 1H), 4.81 (dd, J=4.0, 19.8 Hz, 1H), 2.48 (br s, 3H).

Example 84

1-(2-(1-Benzyl-5-methyl-1H-pyrazol-4-yl)-2-oxoethyl)-5-(3,3,3-trifluoroprop-1-en-2-yl)pyridin-2(1H)-one A mixture of 1-(2-(1-benzyl-5-methyl-1H-pyrazol-4-yl)-2-oxoethyl)-5-bromopyridin-2(1H)-one (100 mg), 1-(trifluoromethyl)vinylboronic acid (181 mg), Pd(PPh$_3$)$_2$Cl$_2$ (36.3 mg), K$_2$CO$_3$ (78.6 mg), THF (4.0 mL), and water (0.8 mL) was degassed under vacuum and purged with nitrogen several times. The mixture was stirred at 70° C. for 12 hours. Additional 217 mg of 1-(trifluoromethyl)vinylboronic acid was added and the mixture was stirred at 70° C. for 5 hours. Another batch with 90 mg of the starting material was combined, diluted with water, and ethyl acetate. The organic layer was washed with brine, dried over Na$_2$SO$_4$, concentrated, and purified by HPLC to give the target compound (28 mg) as a solid.

$^1$H NMR (400 MHz, DMSO-d$_6$): δ 8.27 (s, 1H), 7.85 (br s, 1H), 7.66 (dd, J=2.0, 9.5 Hz, 1H), 7.39-7.26 (m, 3H), 7.16 (d, J=7.2 Hz, 2H), 6.51 (d, J=9.7 Hz, 1H), 6.03-5.93 (m, 2H), 5.41 (s, 2H), 5.31 (s, 2H), 2.48 (br s, 3H).

Example 85

1-(2-(1-Benzyl-5-ethyl-1H-pyrazol-4-yl)-2-oxoethyl)-5-vinylpyridin-2(1H)-one

A) Ethyl 1-benzyl-5-ethyl-1H-pyrazole-4-carboxylate

A target compound was synthesized in a similar manner as step A in example 73 using benzylhydrazine and methyl 2-(ethoxymethylene)-3-oxopentanoate.

B) 1-Benzyl-5-ethyl-1H-pyrazole-4-carboxylic acid

A target compound was synthesized in a similar manner as step B in example 73 using ethyl 1-benzyl-5-ethyl-1H-pyrazole-4-carboxylate.

$^1$H NMR (400 MHz, CDCl$_3$): δ 12.23 (s, 1H), 7.78 (s, 1H), 7.35-7.23 (m, 3H), 7.12 (d, J=7.3 Hz, 2H), 5.36 (s, 2H), 2.89 (q, J=7.5 Hz, 2H), 0.93 (t, J=7.4 Hz, 3H).

C) 1-Benzyl-5-ethyl-N-methoxy-N-methyl-1H-pyrazole-4-carboxamide

A target compound was synthesized in a similar manner as step A in example 68 using 1-benzyl-5-ethyl-1H-pyrazole-4-carboxylic acid.
MS: (M+H$^+$): 274.2

C) 1-(1-Benzyl-5-ethyl-1H-pyrazol-4-yl)ethan-1-one

A target compound was synthesized in a similar manner as step B in example 68 using 1-benzyl-5-ethyl-N-methoxy-N-methyl-1H-pyrazole-4-carboxamide and MeMgBr.

$^1$H NMR (400 MHz, CDCl$_3$): δ 7.82 (s, 1H), 7.28-7.20 (m, 3H), 7.07-7.04 (m, 2H), 5.24 (s, 2H), 2.89 (q, J=7.5 Hz, 2H), 2.37 (s, 3H), 0.98 (t, J=7.5 Hz, 3H).

E) 1-(1-Benzyl-5-ethyl-1H-pyrazol-4-yl)-2-bromoethan-1-one

A target compound was synthesized in a similar manner as step E in example 73 using 1-(1-benzyl-5-ethyl-1H-pyrazol-4-yl)ethan-1-one.

F) 1-(2-(1-Benzyl-5-ethyl-1H-pyrazol-4-yl)-2-oxoethyl)-5-bromopyridin-2(1H)-one

A target compound was synthesized in a similar manner as step D in example 34 using 1-(1-benzyl-5-ethyl-1H-pyrazol-4-yl)ethan-1-one and 6 bromopyridazin-3(2H)-one.

$^1$H NMR (400 MHz, DMSO-d$_6$): δ 8.28 (s, 1H), 7.94 (d, J=2.6 Hz, 1H), 7.57 (dd, J=2.9, 9.7 Hz, 1H), 7.36-7.25 (m, 3H), 7.15 (d, J=7.1 Hz, 2H), 6.39 (d, J=9.7 Hz, 1H), 5.42 (s, 2H), 5.20 (s, 2H), 2.89 (q, J=7.3 Hz, 2H), 0.89 (t, J=7.4 Hz, 3H).

G) 1-(2-(1-Benzyl-5-ethyl-1H-pyrazol-4-yl)-2-oxoethyl)-5-vinylpyridin-2(1H)-one

A target compound was synthesized in a similar manner as example 76 using 1-(2-(1-benzyl-5-ethyl-1H-pyrazol-4-yl)-2-oxoethyl)-5-bromopyridin-2(1H)-one and potassium vinyltrifluoroborate.

$^1$H NMR (400 MHz, DMSO-d$_6$): δ 8.31 (s, 1H), 7.80 (dd, J=2.4, 9.5 Hz, 1H), 7.69 (d, J=2.2 Hz, 1H), 7.38-7.27 (m, 3H), 7.17 (d, J=7.3 Hz, 2H), 6.50-6.41 (m, 2H), 5.57 (d, J=17.6 Hz, 1H), 5.44 (s, 2H), 5.23 (s, 2H), 5.10 (d, J=11.0 Hz, 1H), 2.91 (q, J=7.4 Hz, 2H), 0.91 (t, J=7.4 Hz, 3H).

Example 86

1-(2-(1-Benzyl-3,5-dimethyl-1H-pyrazol-4-yl)-2-oxoethyl)-5-vinylpyridin-2(1H)-one A) 1-Benzyl-N-methoxy-N,3,5-trimethyl-1H-pyrazole-4-carboxamide A target compound was synthesized in a similar manner as step A in example 68 using 1-benzyl-3,5-dimethyl-1H-pyrazole-4-carboxylic acid.

$^1$H NMR (400 MHz, CDCl$_3$): δ 7.32-7.22 (m, 3H), 7.06 (d, J=7.1 Hz, 2H), 522 (s, 2H), 3.51 (s, 3H), 3.30 (s, 3H), 2.30 (s, 3H), 221 (s, 3H).

B) 1-(1-Benzyl-3,5-dimethyl-1H-pyrazol-4-yl)ethan-1-one

A target compound was synthesized in a similar manner as step B in example 68 using 1-benzyl-N-methoxy-N,3,5-trimethyl-1H-pyrazole-4-carboxamide and MeMgBr.

$^1$H NMR (400 MHz, CDCl$_3$): δ 7.28-7.17 (m, 3H), 7.04-7.00 (m, 2H), 5.18 (s, 2H), 2.42 (s, 3H), 2.38 (s, 3H), 2.37 (s, 3H).

C) 1-(1-Benzyl-3,5-dimethyl-1H-pyrazol-4-yl)-2-bromoethan-1-one

A target compound was synthesized in a similar manner as step E in example 73 using 1-(1-benzyl-3,5-dimethyl-1H-pyrazol-4-yl)ethan-1-one.

D) 1-(2-(1-Benzyl-3,5-dimethyl-1H-pyrazol-4-yl)-2-oxoethyl)-5-bromopyridin-2(1H)-one A target compound was synthesized in a similar manner as step D in example 34 using 1-(1-benzyl-3,5-dimethyl-1H-pyrazol-4-yl)-2-bromoethan-1-one and 6-bromopyridazin-3(2H)-one.

$^1$H NMR (400 MHz, DMSO-d$_6$): δ 7.92 (d, J=2.7 Hz, 1H), 7.59 (dd, J=2.8, 9.7 Hz, 1H), 7.39-7.27 (m, 3H), 7.17 (d, J=7.2 Hz, 2H), 6.88 (s, 1H), 5.35 (s, 2H), 5.14 (s, 2H), 2.50-2.49 (m, 3H), 2.42 (s, 3H).

E) 1-(2-(1-Benzyl-3,5-dimethyl-1H-pyrazol-4-yl)-2-oxoethyl)-5-vinylpyridin-2(1H)-one A target compound was synthesized in a similar manner as example 76 using 1-(2-(1-Benzyl-3,5-dimethyl-1H-pyrazol-4-yl)-2-oxoethyl)-5-bromopyridin-2(1H)-one and potassium vinyltrifluoroborate.

$^1$H NMR (400 MHz, Methanol-d$_4$): δ 7.87 (dd, J=2.4, 9.4 Hz, 1H), 7.56 (d, J=2.2 Hz, 1H), 7.37-7.26 (m, 3H), 7.15 (d, J=7.1 Hz, 2H), 6.60 (d, J. 9.4 Hz, 1H), 6.53 (dd, J=11.0, 17.6 Hz, 1H), 5.61 (d, J=17.6 Hz, 1H), 5.35 (s, 2H), 5.24 (s, 2H), 5.17 (d, J=11.0 Hz, 1H), 2.54 (s, 3H), 2.52 (s, 3H).

Example 87

1-(2-(1-Benzyl-5-(difluoromethyl)-1H-pyrazol-4-yl)-2-oxoethyl)-5-vinylpyridin-2(1H)-one

A) Ethyl 1-benzyl-5-(difluoromethyl)-1H-pyrazole-4-carboxylate

A target compound was synthesized in a similar manner as step A in example 73 using benzylhydrazine and ethyl 2-(ethoxymethylene)-4,4-difluoro-3-oxobutanoate.
MS: (M+H$^+$): 280.9

B) 1-Benzyl-5-(difluoromethyl)-1H-pyrazole-4-carboxylic Acid

A target compound was synthesized in a similar manner as step B in example 73 using ethyl 1-benzyl-5-(difluoromethyl)-1H-pyrazole-4-carboxylate.

$^1$H NMR (400 MHz, CDCl$_3$): δ 11.52 (br s, 1H), 7.95 (s, 1H), 7.83-7.43 (m, 1H), 7.28-7.20 (m, 5H), 5.46 (s, 2H).

C) 1-Benzyl-5-(difluoromethyl)-N-methoxy-N-methyl-1H-pyrazole-4-carboxamide A target compound was synthesized in a similar manner as step A in example 68 using 1-benzyl-5-(difluoromethyl)-1H-pyrazole-4-carboxylic acid.

$^1$H NMR (400 MHz, CDCl$_3$): δ 7.98 (s, 1H), 7.80-7.52 (m, 1H), 7.37-7.28 (m, 5H), 5.54 (s, 2H), 3.69 (s, 3H), 3.34 (s, 3H).

D) 1-(1-Benzyl-5-(difluoromethyl)-1H-pyrazol-4-yl)ethan-1-one

A target compound was synthesized in a similar manner as step B in example 68 using 1-benzyl-5-(difluoromethyl)-N-methoxy-N-methyl-1H-pyrazole-4-carboxamide and MeMgBr.

$^1$H NMR (400 MHz, CDCl$_3$): δ 7.90 (s, 1H), 7.74-7.46 (m, 1H), 7.37-7.27 (m, 5H), 5.51 (s, 2H), 2.48 (s, 3H).

E) 1-(1-Benzyl-5-(difluoromethyl)-1H-pyrazol-4-yl)-2-bromoethan-1-one

A target compound was synthesized in a similar manner as step E in example 73 using 1-(1-benzyl-5-(difluoromethyl)-1H-pyrazol-4-yl)ethan-1-one.

F) 1-(2-(1-Benzyl-5-(difluoromethyl)-1H-pyrazol-4-yl)-2-oxoethyl)-5-bromopyridin-2(1H)-one A target compound was synthesized in a similar manner as step D in example 34 using 1-(1-benzyl-5-(difluoromethyl)-1H-pyrazol-4-yl)-2-bromoethan-1-one and 6-bromopyridazin-3(2H)-one.

$^1$H NMR (400 MHz, CDCl$_3$): δ 8.06 (s, 1H), 7.64-7.49 (m, 1H), 7.43-7.28 (m, 7H), 6.53 (d, J=9.7 Hz, 1H), 5.54 (s, 2H), 5.09 (s, 2H).

G) 1-(2-(1-Benzyl-5-(difluoromethyl)-1H-pyrazol-4-yl)-2-oxoethyl)-5-vinylpyridin-2(1H)-one A target compound was synthesized in a similar manner as example 76 using 1-(2-(1-benzyl-5-(difluoromethyl)-1H-pyrazol-4-yl)-2-oxoethyl)-5-bromopyridin-2(1H)-one and potassium vinyltrifluoroborate.

$^1$H NMR (400 MHz, DMSO-d$_6$): δ 8.53 (s, 1H), 7.82 (dd, J=2.5, 9.5 Hz, 1H), 7.70 (d, J=2.4 Hz, 1H), 7.67-7.39 (m, 1H), 7.39-7.29 (m, 3H), 7.22-7.19 (m, 2H), 6.50-6.41 (m, 2H), 5.60-5.55 (m, 3H), 5.32 (s, 2H), 5.11 (d, J=11.1 Hz, 1H).

Example 88

1-(2-(1-Benzyl-5-methyl-1H-1,2,3-triazol-4-yl)-2-oxoethyl)-5-ethynylpyridin-2(1H)-one

A) Azidomethylbenzene

To a stirred mixture of bromomethylbenzene (10 g) in a mixed solvent of acetone (100 mL) and water (25 mL) was added NaN$_3$ (5.70 g) in portions at 15° C. Then the mixture was stirred at 15° C. for 12 hours. The reaction mixture was quenched by water and extracted with MTBE. The organic layer was washed with brine, dried over Na$_2$SO$_4$, and filtered. Anhydrous EtOH (150 mL) was added to the mixture and then the whole mixture was concentrated in vacuo to 150 mL. The crude azidomethylbenzene (0.39 M) was used as a solution in next step without further purification.

B) 1-(1-Benzyl-5-methyl-1H-1,2,3-triazol-4-yl)ethan-1-one

To a stirred mixture of 0.39 M of azidomethylbenzene (100 mL) in EtOH (90 mL) were added pentane-2,4-dione (14.02 mL) and K$_2$CO$_3$ (17.3 g) at 15° C. The mixture was degassed and purged with nitrogen for 3 times. Then the solution was stirred at 80° C. for 7 hours. The reaction mixture was diluted with water and extracted with ethyl acetate. The combined organic layers were washed with brine, dried over Na$_2$SO$_4$, concentrated, and purified by silica gel chromatography (petroleum ether:ethyl acetate=6:1) to the target compound (2 g) as an oil.

$^1$H NMR (400 MHz, CDCl$_3$): δ 7.29-7.22 (m, 3H), 7.09 (dd, J=1.7, 7.6 Hz, 2H), 5.43 (s, 2H), 2.60 (s, 3H), 2.38 (s, 3H).

C) 1-(1-Benzyl-5-methyl-1H-1,2,3-triazol-4-yl)-2-bromoethan-1-one

A target compound was synthesized in a similar manner as step E in example 73 using 1-(1-benzyl-5-methyl-1H-1,2,3-triazol-4-yl)ethan-1-one.

D) 1-(2-(1-Benzyl-5-methyl-1H-1,2,3-triazol-4-yl)-2-oxoethyl)-5-bromopyridin-2(1H)-one A target compound was synthesized in a similar manner as step D in example 34 using 1-(1-benzyl-5-methyl-1H-1,2,3-triazol-4-yl)-2-bromoethan-1-one and 6-bromopyridazin-3(2H)-one.
$^1$H NMR (400 MHz, DMSO-$d_6$): δ 8.00 (d, J=2.7 Hz, 1H), 7.60 (dd, J=2.8, 9.8 Hz, 1H), 7.42-7.32 (m, 3H), 7.27-7.23 (m, 2H), 6.42 (d, J=9.7 Hz, 1H), 5.71 (s, 2H), 5.45 (s, 2H), 2.49 (s, 3H).

E) 1-(2-(1-Benzyl-5-methyl-1H-1,2,3-triazol-4-yl)-2-oxoethyl)-5-((trimethylsilyl)ethynyl)pyridin-2(1H)-one A target compound was synthesized in a similar manner as step A in example 36 using 1-(2-(1-benzyl-5-methyl-1H-1,2,3-triazol-4-yl)-2-oxoethyl)-5-bromopyridin-2(1H)-one.
MS: (M+H$^+$): 405.2

F) 1-(2-(1-Benzyl-5-methyl-1H-1,2,3-triazol-4-yl)-2-oxoethyl)-5-ethynylpyridin-2(1H)-one A target compound was synthesized in a similar manner as step H in example 73 using 1-(2-(1-benzyl-5-methyl-1H-1,2,3-triazol-4-yl)-2-oxoethyl)-5-((trimethylsilyl)ethynyl)pyridin-2(1H)-one.
$^1$H NMR (400 MHz, CDCl$_3$): δ 7.46 (d, J=2.3 Hz, 1H), 7.42 (dd, J=2.4, 9.5 Hz, 1H), 7.40-7.34 (m, 3H), 7.21-7.17 (m, 2H), 6.57 (d, J=9.4 Hz, 1H), 5.55 (s, 2H), 5.50 (s, 2H), 3.01 (s, 1H), 2.47 (s, 3H).

Example 89

1-(2-(1-Benzyl-5-methyl-1H-1,2,3-triazol-4-yl)-2-oxoethyl)-5-vinylpyridin-2(1H)-one A target compound was synthesized in a similar manner as example 76 using 1-(2-(1-benzyl-5-methyl-1H-1,2,3-triazol-4-yl)-2-oxoethyl)-5-bromopyridin-2(1H)-one and potassium vinyltrifluoroborate.
$^1$H NMR (400 MHz, DMSO-$d_6$): δ 7.81 (d, J=9.6 Hz, 1H), 7.73 (s, 1H), 7.42-7.31 (m, 3H), 7.24 (d, J=7.0 Hz, 2H), 6.51-6.41 (m, 2H), 5.71 (s, 2H), 5.58 (d, J=17.5 Hz, 1H), 5.45 (s, 2H), 5.10 (d, J=11.0 Hz, 1H), 2.48 (br s, 3H).

Example 90

1-(2-(1-Benzyl-5-methyl-1H-1,2,3-triazol-4-yl)-2-oxoethyl)-5-vinylpyridin-2(1H)-one A target compound was synthesized in a similar manner as example 1 using 1-(1-benzyl-2,5-dimethyl-1H-pyrrol-3-yl)-2-chloroethan-1-one and methyl 6-oxo-1,6-dihydropyridine-3-carboxylate.
$^1$H NMR (500 MHz, CDCl$_3$): δ 8.15 (d, J=2.4 Hz, 1H), 7.92 (dd, J=9.5, 2.4 Hz, 1H), 7.40-7.33 (m, 2H), 7.30 (d, J=7.2 Hz, 1H), 6.92 (d, J=7.2, 1.7 Hz, 2H), 6.60 (d, J=9.5 Hz, 1H), 6.51-6.35 (m, 1H), 5.23 (d, J=1.8 Hz, 2H), 5.09 (s, 2H), 3.87 (d, J=1.8 Hz, 3H), 2.50 (d, J=1.8 Hz, 3H), 2.30-2.12 (m, 3H)

Example 91

1-(2-(2,5-Dimethyl-1-phenethyl-1H-pyrrol-3-yl)-2-oxoethyl)-6-oxo-1,6-dihydropyridine-3-carbonitrile A target compound was synthesized in a similar manner as example 1 using 2-chloro-1-(2,5-dimethyl-1-phenethyl-1H-pyrrol-3-yl)ethan-1-one and 6-oxo-1,6-dihydropyridine-3-carbonitrile.
$^1$H NMR (500 MHz, DMSO-$d_6$): δ 8.51 (d, J=2.5 Hz, 1H), 7.74 (dd, J=9.5, 2.5 Hz, 1H), 7.31 (t, J=7.3 Hz, 2H), 7.25 (t, J=7.2 Hz, 1H), 7.17 (d, J=7.3 Hz, 2H), 6.53 (d, J=9.5 Hz, 1H), 6.40 (s, 1H), 5.15 (s, 2H), 4.07 (t, J=7.4 Hz, 2H), 2.90 (t, J=7.4 Hz, 2H), 2.36 (s, 3H), 2.11 (s, 3H).

Example 92

1-(2-(2,5-Dimethyl-1-(1-phenylethyl)-1H-pyrrol-3-yl)-2-oxoethyl)-6-oxo-1,6-dihydropyridine-3-carbonitrile A target compound was synthesized in a similar manner as example 1 using 2-chloro-1-(2,5-dimethyl-1-(1-phenylethyl)-1H-pyrrol-3-yl)ethan-1-one and 6-oxo-1,6-dihydropyridine-3-carbonitrile.
$^1$H NMR (500 MHz, DMSO-$d_6$): δ 8.50 (d, J=2.5 Hz, 1H), 7.74 (dd, J=9.5, 2.5 Hz, 1H), 7.39 (dd, J=8.3, 7.0 Hz, 2H), 7.32 (t, J=7.3 Hz, 1H), 7.11 (d, J=7.6 Hz, 2H), 6.57-6.47 (m, 2H), 5.71 (d, J=7.2 Hz, 1H), 5.18 (s, 2H), 2.05 (s, 3H), 1.83 (d, J=7.1 Hz, 3H).

Example 93

1-(2-(1-(Benzo[d][1,3]dioxol-5-ylmethyl)-2,5-dimethyl-1H-pyrrol-3-yl)-2-oxoethyl)-6-oxo-1,6-dihydropyridine-3-carbonitrile A target compound was synthesized in a similar manner as example 1 using 1-(1-(benzo[d][1,3]dioxol-5-ylmethyl)-2,5-dimethyl-1H-pyrrol-3-yl)-2-chloroethan-1-one and 6-oxo-1,6-dihydropyridine-3-carbonitrile.
$^1$H NMR (500 MHz, CDCl$_3$): δ 7.77 (t, J=1.9 Hz, 1H), 7.46 (dd, J=9.6, 2.4 Hz, 1H), 6.77 (dd, J=7.8, 1.2 Hz, 1H), 6.64 (dd, J=9.5, 1.3 Hz, 1H), 6.42-6.34 (m, 3H), 5.97 (d, J=1.3 Hz, 2H), 5.19 (d, J=1.3 Hz, 2H), 4.99 (s, 2H), 2.50 (d, J=1.5 Hz, 3H), 2.19 (d, J=1.2 Hz, 3H).

Example 94

1-(2-(2-Benzyloxazol-4-yl)-2-oxoethyl)-5-vinylpyridin-2(1H)-one

A)
2-Benzyl-N-methoxy-N-methyloxazole-4-carboxamide

A target compound was synthesized in a similar manner as step A in example 68 using 2-benzoyloxazole-4-carboxylic acid.
$^1$H NMR (400 MHz, CDCl$_3$): δ 8.09 (s, 1H), 7.39-7.29 (m, 5H), 4.19 (s, 2H), 3.75 (s, 3H), 3.40 (s, 3H).

B) 1-(2-Benzyloxazol-4-yl)ethan-1-one

A target compound was synthesized in a similar manner as step B in example 68 using 2-benzyl-N-methoxy-N-methyloxazole-4-carboxamide and MeMgBr.

¹H NMR (400 MHz, DMSO-d₆): δ 8.83 (s, 1H), 7.37-7.26 (m, 5H), 4.20 (s, 2H), 2.41 (s, 3H).

C) 1-(2-Benzyloxazol-4-yl)-2-bromoethan-1-one

A target compound was synthesized in a similar manner as step E in example 73 using 1-(2-benzyloxazol-4-yl)ethan-1-one.
¹H NMR (400 MHz, CDCl₃): δ 8.24 (s, 1H), 7.39-7.28 (m, 5H), 4.44 (s, 2H), 4.17 (s, 2H).

D) 1-(2-(2-Benzyloxazol-4-yl)-2-oxoethyl)-5-bromopyridin-2(1H)-one

A target compound was synthesized in a similar manner as step D in example 34 using 1-(2-benzyloxazol-4-yl)-2-bromoethan-1-one and 6 bromopyridazin-3 (2H)-one.
MS: (M+H⁺): 374.9

E) 1-(2-(2-Benzyloxazol-4-yl)-2-oxoethyl)-5-vinylpyridin-2(1H)-one

A target compound was synthesized in a similar manner as example 76 using 1-(2-(2-benzyloxazol-4-yl)-2-oxoethyl)-5-bromopyridin-2(1H)-one and potassium vinyltrifluoroborate.
¹H NMR (400 MHz, Methanol-d₄): δ 8.64 (s, 1H), 7.87 (dd, J=2.5, 9.4 Hz, 1H), 7.58 (d, J=2.3 Hz, 1H), 7.30-7.38 (m, 4H), 7.24-7.29 (m, 1H), 6.46-6.61 (m, 2H), 5.61 (d, J=17.6 Hz, 1H), 5.33 (s, 2H), 5.18 (d, J=11.1 Hz, 1H), 4.21 (s, 2H).

Example 95

1-(2-(2-Benzyloxazol-4-yl)-2-oxoethyl)-5-ethynylpyridin-2(1H)-one

A) 1-(2-(2-Benzyloxazol-4-yl)-2-oxoethyl)-5-((trimethylsilyl)ethynyl)pyridin-2(1H)-one A target compound was synthesized in a similar manner as step A in example 36 using 1-(2-(2-benzyloxazol-4-yl)-2-oxoethyl)-5-bromopyridin-2(1H)-one.
MS: (M+H⁺): 391.2

B) 1-(2-(2-Benzyloxazol-4-yl)-2-oxoethyl)-5-ethynylpyridin-2(1H)-one

A target compound was synthesized in a similar manner as step H in example 73 using 1-(2-(2-benzyloxazol-4-yl)-2-oxoethyl)-5-((trimethylsilyl)ethynyl)pyridin-2(1H)-one.
¹H NMR (400 MHz, Methanol-d₄): δ 8.65 (s, 1H), 7.87 (d, J=2.4 Hz, 1H), 7.59 (dd, J=2.4, 9.3 Hz, 1H), 7.37-7.31 (m, 4H), 7.31-7.24 (m, 1H), 6.54 (d, J=9.5 Hz, 1H), 4.89-4.89 (m, 2H), 4.22 (s, 2H), 3.52 (s, 1H).

Example 96

1-(2-(2-Benzylthiazol-4-yl)-2-oxoethyl)-5-vinylpyridin-2(1H)-one

A)
2-Benzyl-N-methoxy-N-methylthiazole-4-carboxamide

A target compound was synthesized in a similar manner as step A in example 68 using 2-benzylthiazole-4-carboxylic acid.
¹H NMR (400 MHz, CDCl₃): δ 7.86 (s, 1H), 7.33-7.22 (m, 5H), 4.33 (s, 2H), 3.71 (s, 3H), 3.39 (s, 3H).

B) 1-(2-Benzylthiazol-4-yl)ethan-1-one

A target compound was synthesized in a similar manner as step B in example 68 using 2-benzyl-N-methoxy-N-methylthiazole-4-carboxamide and MeMgBr.
¹H NMR (400 MHz, CDCl₃): δ 7.93 (s, 1H), 7.31-7.18 (m, 5H), 4.28 (s, 2H), 2.59 (s, 3H).

C) 1-(2-Benzylthiazol-4-yl)-2-bromoethan-1-one

A target compound was synthesized in a similar manner as step E in example 73 using 1-(2-benzylthiazol-4-yl)ethan-1-one.

D) 1-(2-(2-Benzylthiazol-4-yl)-2-oxoethyl)-5-bromopyridin-2(1H)-one

A target compound was synthesized in a similar manner as step D in example 34 using 1-(2-benzylthiazol-4-yl)-2-bromoethan-1-one and 6 bromopyridazin-3 (2H)-one.
¹H NMR (400 MHz, DMSO-d₆): δ 8.55 (s, 1H), 8.00 (d, J=2.6 Hz, 1H), 7.60 (dd, J=2.6, 9.7 Hz, 1H), 7.42-7.35 (m, 4H), 7.32-727 (m, 1H), 6.42 (d, J=9.7 Hz, 1H), 5.41 (s, 2H), 4.45 (s, 2H).

E) 1-(2-(2-Benzylthiazol-4-yl)-2-oxoethyl)-5-vinylpyridin-2(1H)-one

A target compound was synthesized in a similar manner as example 76 using 1-(2-(2-benzylthiazol-4-yl)-2-oxoethyl)-5-bromopyridin-2(1H)-one and potassium vinyltrifluoroborate.
1H NMR (400 MHz, DMSO-d₆): δ 8.54 (s, 1H), 7.82 (dd, J=2.6, 9.5 Hz, 1H), 7.74 (d, J=2.4 Hz, 1H), 7.40-7.35 (m, 4H), 7.33-7.28 (m, 1H), 6.50-6.42 (m, 2H), 5.58 (d, J=17.6 Hz, 1H), 5.42 (s, 2H), 5.11 (d, J=11.5 Hz, 1H), 4.45 (s, 2H).

Example 97

1-(2-(2-Benzylthiazol-4-yl)-2-oxoethyl)-5-ethynylpyridin-2(1H)-one

A) 1-(2-(2-Benzylthiazol-4-yl)-2-oxoethyl)-5-((trimethylsilyl)ethynyl)pyridin-2(1H)-one A target compound was synthesized in a similar manner as step A in example 36 using 1-(2-(2-benzylthiazol-4-yl)-2-oxoethyl)-5-bromopyridin-2(1H)-one.

B) 1-(2-(2-Benzylthiazol-4-yl)-2-oxoethyl)-5-ethynylpyridin-2(1H)-one

A target compound was synthesized in a similar manner as step H in example 73 using 1-(2-(2-benzylthiazol-4-yl)-2-oxoethyl)-5-((trimethylsilyl)ethynyl)pyridin-2(1H)-one.
¹H NMR (400 MHz, DMSO-d₆): δ 8.55 (s, 1H), 8.03 (d, J=2.3 Hz, 1H), 7.51 (dd, J=2.4, 9.4 Hz, 1H), 7.40-7.35 (m, 4H), 7.32-727 (m, 1H), 6.43 (d, J=9.4 Hz, 1H), 5.43 (s, 2H), 4.45 (s, 2H), 4.11 (s, 1H).

Example 98

1-(2-(2-Benzyloxazol-5-yl)-2-oxoethyl)-5-vinylpyridin-2(1H)-one

A) Ethyl (E)-3-(2-phenylacetamido)acrylate

A mixture of 2-phenylacetamide (20 g), ethyl acrylate (48.3 mL), bis(benzonitrile)palladium dichloride (2.84 g), CuCl (1.46 g), and chlorobenzene (100 mL) was stirred at 70° C. for 36 hours under oxygen atmosphere. Another batch with 10 g of the starting material was combined and filtered. The filtrate was concentrated and purified by silica gel chromatography (petroleum ether:ethyl acetate=19:1 to 9:1 to 3:1) to give the target compound (12 g) as an oil.
$^1$H NMR (400 MHz, CDCl$_3$): δ 10.44 (d, J=7.7 Hz, 1H), 7.28-7.52 (m, 6H), 5.10 (d, J=8.9 Hz, 1H), 4.13 (q, J=7.1 Hz, 2H), 3.70 (s, 2H), 1.25 (t, J=7.2 Hz, 3H).

B) Ethyl 2-benzyloxazole-5-carboxylate

PIDA (3.87 g) was carefully added in small portions to a stirred solution of ethyl (E)-3-(2-phenylacetamido)acrylate (2.0 g) and BF$_3$·Et$_2$O (4.50 mL, 47% purity) in 1,2-dichloroethane (10 mL) at 85° C., then the mixture was stirred at 85° C. for 12 hours. The reaction mixture was diluted with water and extracted with ethyl acetate. The organic layer was washed with saturated NaHCO$_3$ solution and brine, dried over Na$_2$SO$_4$, concentrated, and purified by silica gel chromatography (petroleum ether:ethyl acetate=19:1 to 23:2 to 9:1) to give the target compound (1.1 g) as an oil.
$^1$H NMR (400 MHz, CDCl$_3$): δ 7.67 (s, 1H), 7.28-7.37 (m, 5H), 4.37 (q, J=7.13 Hz, 2H), 4.19 (s, 2H), 1.38 (t, J=7.09 Hz, 3H).

C) 2-Benzyloxazole-5-carboxylic Acid

A target compound was synthesized in a similar manner as step B in example 73 using ethyl 2-benzyloxazole-5-carboxylate.
MS: (M+H$^+$): 204.1

D) 2-Benzyl-N-methoxy-N-methyloxazole-5-carboxamide

A target compound was synthesized in a similar manner as step A in example 68 using 2-benzyloxazole-5-carboxylic acid.
$^1$H NMR (400 MHz, CDCl$_3$): δ 7.61 (s, 1H), 7.26-7.36 (m, 5H), 4.20 (s, 2H), 3.74 (s, 3H), 3.34 (s, 3H)

E) 1-(2-Benzyloxazol-5-yl)ethan-1-one

A target compound was synthesized in a similar manner as step B in example 68 using 2-benzyl-N-methoxy-N-methyloxazole-5-carboxamide and MeMgBr.
$^1$H NMR (400 MHz, CDCl$_3$): δ 7.69 (s, 1H), 7.38-7.28 (m, 5H), 4.19 (s, 2H), 2.46 (s, 3H).

F) 1-(2-Benzyloxazol-5-yl)-2-bromoethan-1-one

A target compound was synthesized in a similar manner as step E in example 73 using 1-(2-benzyloxazol-5-yl)ethan-1-one.
MS: (M+H$^+$): 280.0

G) 1-(2-(2-Benzyloxazol-5-yl)-2-oxoethyl)-5-bromopyridin-2(1H)-one

A target compound was synthesized in a similar manner as step D in example 34 using 1-(2-benzyloxazol-5-yl)-2-bromoethan-1-one and 5 bromopyridin-2(1H)-one.

H) 1-(2-(2-Benzyloxazol-5-yl)-2-oxoethyl)-5-vinylpyridin-2(1H)-one

A target compound was synthesized in a similar manner as example 76 using 1-(2-(2-Benzyloxazol-5-yl)-2-oxoethyl)-5-bromopyridin-2(1H)-one and potassium vinyltrifluoroborate.
$^1$H NMR (400 MHz, Methanol-d$_4$): δ 7.88 (s, 1H), 7.64 (dd, J=2.4, 9.4 Hz, 1H), 7.39-7.30 (m, 4H), 7.27 (s, 1H), 7.15 (d, J=2.2 Hz, 1H), 6.62 (d, J=9.6 Hz, 1H), 6.41 (dd, J=11.0, 17.5 Hz, 1H), 5.49 (d, J=17.5 Hz, 1H), 5.17 (d, J=11.0 Hz, 1H), 5.08 (s, 2H), 4.22 (s, 2H).

Example 99

1-(2-(2-Benzyloxazol-5-yl)-2-oxoethyl)-5-ethynylpyridin-2(1H)-one

A) 1-(2-(2-Benzyloxazol-5-yl)-2-oxoethyl)-5-((trimethylsilyl)ethynyl)pyridin-2(1H)-one A target compound was synthesized in a similar manner as step A in example 36 using 1-(2-(2-benzyloxazol-5-yl)-2-oxoethyl)-5-bromopyridin-2(1H)-one.
MS: (M+1-14): 391.1

B) 1-(2-(2-Benzylthiazol-4-yl)-2-oxoethyl)-5-ethynylpyridin-2(1H)-one

A target compound was synthesized in a similar manner as step H in example 73 using 1-(2-(2-benzyloxazol-5-yl)-2-oxoethyl)-5-((trimethylsilyl)ethynyl)pyridin-2(1H)-one.
$^1$H NMR (400 MHz, Methanol-d$_4$): δ 7.88 (s, 1H), 7.46 (d, J=2.2 Hz, 1H), 7.42 (dd, J=2.4, 9.5 Hz, 1H), 7.39-7.28 (m, 5H), 6.56 (d, J=9.4 Hz, 1H), 5.07 (s, 2H), 4.22 (s, 2H), 3.03 (s, 1H).

Example 100

1-(2-(2-Benzylthiazol-5-yl)-2-oxoethyl)-5-vinylpyridin-2(1H)-one

A) 2-Benzyl-N-methoxy-N-methylthiazole-5-carboxamide

A target compound was synthesized in a similar manner as step A in example 68 using 2-benzylthiazole-5-carboxylic acid.
$^1$H NMR (400 MHz, DMSO-d$_6$): δ 8.32 (s, 1H), 7.39-7.32 (m, 4H), 7.30-7.24 (m, 1H), 4.37 (s, 2H), 3.71 (s, 3H), 3.25 (s, 3H).

B) 1-(2-Benzylthiazol-5-yl)ethan-1-one

A target compound was synthesized in a similar manner as step B in example 68 using 2-benzyl-N-methoxy-N-methylthiazole-5-carboxamide and MeMgBr.
$^1$H NMR (400 MHz, CDCl$_3$): δ 8.21 (s, 1H), 7.41-7.27 (m, 5H), 4.34 (s, 2H), 2.54 (s, 3H).

C) 1-(2-Benzylthiazol-5-yl)-2-bromoethan-1-one

A target compound was synthesized in a similar manner as step E in example 73 using 1-(2-benzylthiazol-5-yl)ethan-1-one.

D) 1-(2-(2-Benzylthiazol-5-yl)-2-oxoethyl)-5-bromopyridin-2(1H)-one

A target compound was synthesized in a similar manner as step D in example 34 using 1-(2-benzylthiazol-5-yl)-2-bromoethan-1-one and 5-bromopyridin-2(1H)-one.

E) 1-(2-(2-Benzylthiazol-5-yl)-2-oxoethyl)-5-vinylpyridin-2(1H)-one

A target compound was synthesized in a similar manner as example 76 using 1-(2-(2-benzylthiazol-5-yl)-2-oxoethyl)-5-bromopyridin-2(1H)-one and potassium vinyltrifluoroborate.

$^1$H NMR (400 MHz, Methanol-$d_4$): δ 8.60 (s, 1H), 7.87 (dd, J=2.5, 9.4 Hz, 1H), 7.59 (d, J=2.2 Hz, 1H), 7.40-7.33 (m, 4H), 7.32-7.28 (m, 1H), 6.61-6.47 (m, 2H), 5.61 (d, J=17.6 Hz, 1H), 5.18 (d, J=11.0 Hz, 1H), 4.89-4.88 (m, 2H), 4.41 (s, 2H).

Example 101

1-(2-(2-Benzylthiazol-5-yl)-2-oxoethyl)-5-ethynylpyridin-2(1H)-one

A) 1-(2-(2-Benzylthiazol-5-yl)-2-oxoethyl)-5-((trimethylsilyl)ethynyl)pyridin-2(1H)-one A target compound was synthesized in a similar manner as step A in example 36 using 1-(2-(2-benzylthiazol-5-yl)-2-oxoethyl)-5-bromopyridin-2(1H)-one.

B) 1-(2-(2-Benzylthiazol-5-yl)-2-oxoethyl)-5-ethynylpyridin-2(1H)-one

A target compound was synthesized in a similar manner as step H in example 73 using 1-(2-(2-benzylthiazol-5-yl)-2-oxoethyl)-5-((trimethylsilyl)ethynyl)pyridin-2(1H)-one.

$^1$H NMR (400 MHz, CDCl$_3$): δ 8.43 (s, 1H), 7.47 (d, J=2.1 Hz, 1H), 7.43-7.36 (m, 3H), 7.35-7.30 (m, 3H), 6.56 (d, J=9.4 Hz, 1H), 5.15 (s, 2H), 4.37 (s, 2H), 3.02 (s, 1H).

Example 102

1-(2-(4-Benzyloxazol-2-yl)-2-oxoethyl)-5-vinylpyridin-2(1H)-one

A) 4-Benzyl-2-(prop-1-en-2-yl)oxazole

A mixture of 1-bromo-3-phenylpropan-2-one (8.0 g), methacrylamide (7.00 g) and THF (100 mL) was stirred at 100° C. for 72 hours. The reaction mixture was quenched with saturated NaHCO$_3$ solution and extracted with ether acetate. The combined organic layers were washed with brine, dried over Na$_2$SO$_4$, concentrated, and purified by silica gel chromatography (petroleum ether:ethyl acetate=50:1 to 20:1) to afford the target compound (4.0 g) as an oil.

$^1$H NMR (400 MHz, CDCl$_3$): δ 7.27-7.12 (m, 5H), 7.05 (s, 1H), 5.82 (s, 1H), 5.25 (s, 1H), 3.81 (s, 2H), 2.07 (s, 3H).

B) 4-Benzyl-2-(prop-1-en-2-yl)oxazole

To a mixture of 4-benzyl-2-(prop-1-en-2-yl)oxazole (2.9 g) in dioxane (1 mL) and water (1 mL) was added OsO$_4$ (740 mg) at 0° C. After stirred for 10 min, NaIO$_4$ (6.23 g) was, and the mixture was allowed to warm to 15° C., and stirred for 3 hours. The reaction mixture was quenched by saturated Na$_2$SO$_3$ solution, stirred at room temperature for 0.5 hours, and extracted with ethyl acetate. The combined organic layer was washed with brine, dried over Na$_2$SO$_4$, concentrated, and purified by silica gel chromatography (petroleum ether: ethyl acetate=12:1 to 10:1) to afford the target compound (1.2 g) as an oil.

$^1$H NMR (400 MHz, CDCl$_3$): δ 7.34 (s, 1H), 7.28-7.22 (m, 2H), 7.21-7.16 (m, 3H), 3.87 (s, 2H), 2.57 (s, 3H).

C) 1-(4-Benzyloxazol-2-yl)-2-bromoethan-1-one

A target compound was synthesized in a similar manner as step E in example 73 using 4-benzyl-2-(prop-1-en-2-yl)oxazole.

$^1$H NMR (400 MHz, CDCl$_3$): δ 7.48 (t, J=1.0 Hz, 1H), 7.35-7.30 (m, 3H), 7.26-7.23 (m, 2H), 4.55 (s, 2H), 3.95 (s, 2H).

D) 1-(2-(4-Benzyloxazol-2-yl)-2-oxoethyl)-5-bromopyridin-2(1H)-one

A target compound was synthesized in a similar manner as step D in example 34 using 1-(4-benzyloxazol-2-yl)-2-bromoethan-1-one and 5-bromopyridin-2(1H)-one.

E) 1-(2-(4-Benzyloxazol-2-yl)-2-oxoethyl)-5-vinylpyridin-2(1H)-one

A target compound was synthesized in a similar manner as example 76 using 1-(2-(4-benzyloxazol-2-yl)-2-oxoethyl)-5-bromopyridin-2(1H)-one and potassium vinyltrifluoroborate.

$^1$H NMR (400 MHz, CDCl$_3$): δ 7.64 (dd, J=2.4, 9.7 Hz, 1H), 7.50 (s, 1H), 7.37-7.24 (m, 5H), 7.12 (d, J=2.2 Hz, 1H), 6.62 (d, J=9.7 Hz, 1H), 6.40 (dd, J=11.0, 17.4 Hz, 1H), 5.48 (d, J=17.4 Hz, 1H), 5.35 (s, 2H), 5.16 (d, J=11.0 Hz, 1H), 3.97 (s, 2H).

Example 103

1-(2-(4-Benzyloxazol-2-yl)-2-oxoethyl)-5-ethynylpyridin-2(1H)-one

A) 1-(2-(4-Benzyloxazol-2-yl)-2-oxoethyl)-5-((trimethylsilyl)ethynyl)pyridin-2(1H)-one A target compound was synthesized in a similar manner as step A in example 36 using 1-(2-(4-benzyloxazol-2-yl)-2-oxoethyl)-5-bromopyridin-2(1H)-one.

$^1$H NMR (400 MHz, CDCl$_3$): δ 7.29 (t, J=1.0 Hz, 1H), 7.23-7.17 (m, 2H), 7.15-7.10 (m, 2H), 7.08-7.04 (m, 4H), 5.11 (s, 2H), 3.75 (s, 2H), −0.01-0.01 (m, 9H).

B) 1-(2-(4-Benzyloxazol-2-yl)-2-oxoethyl)-5-ethynylpyridin-2(1H)-one

A target compound was synthesized in a similar manner as step H in example 73 using 1-(2-(4-benzyloxazol-2-yl)-2-oxoethyl)-5-((trimethylsilyl)ethynyl)pyridin-2(1H)-one.

¹H NMR (400 MHz, CDCl₃): δ 7.45 (s, 1H), 7.40-7.33 (m, 2H), 7.31-7.28 (m, 1H), 7.24-7.19 (m, 4H), 6.50 (d, J=9.3 Hz, 1H), 5.28 (s, 2H), 3.91 (s, 2H), 2.98-2.95 (m, 1H).

Example 104

1-(2-(4-Benzyloxazol-2-yl)-2-oxoethyl)-5-ethynylpyridin-2(1H)-one

A) Ethyl 4-benzylthiazole-2-carboxylate

A solution of 1-bromo-3-phenylpropan-2-one (3.0 g), ethyl 2-amino-2-thioxoacetate (2.06 g) in EtOH (30 mL) was stirred at 80° C. for 1.5 hours under nitrogen atmosphere. The reaction mixture was diluted with saturated NaHCO₃ solution and extracted with ethyl acetate. The organic layer was washed with brine, dried over Na₂SO₄, and concentrated to give the target compound (4.0 g) as an oil.
MS: (M+H⁺): 248.1

Example 105

1-(2-(4-Benzylthiazol-2-yl)-2-oxoethyl)-5-ethynylpyridin-2(1H)-one

A) 1-(2-(4-Benzylthiazol-2-yl)-2-oxoethyl)-5-((trimethylsilyl)ethynyl)pyridin-2(1H)-one A target compound was synthesized in a similar manner as step A in example 36 using 1-(2-(4-benzylthiazol-2-yl)-2-oxoethyl)-5-bromopyridin-2(1H)-one.

B) 1-(2-(4-Benzylthiazol-2-yl)-2-oxoethyl)-5-ethynylpyridin-2(1H)-one

A target compound was synthesized in a similar manner as step H in example 73 using 1-(2-(4-Benzylthiazol-2-yl)-2-oxoethyl)-5-((trimethylsilyl)ethynyl)pyridin-2(1H)-one.
¹H NMR (400 MHz, CDCl₃): δ 7.48 (d, J=2.3 Hz, 1H), 7.43 (dd, J=2.4, 9.4 Hz, 1H), 7.38-7.33 (m, 2H), 7.32-7.27 (m, 3H), 7.26 (s, 1H), 6.58 (d, J=9.5 Hz, 1H), 5.49 (s, 2H), 4.22 (s, 2H), 3.03 (s, 1H).

Example 106

1-(2-(1-Benzyl-5-(methyl-d3)-1H-pyrazol-4-yl)-2-oxoethyl)-5-vinylpyridin-2(1H)-one A) 1-Benzyl-1H-pyrazole-4-carbonyl Chloride To a stirred suspension of 1-benzyl-1H-pyrazole-4-carboxylic acid (2.0 g) in dichloromethane (20 mL) were added (COCl)₂ (2.51 g) and DMF (210 μL), and the mixture was stirred for 45 min at 15° C. The result colorless solution was concentrated in vacuum to give the target compound.

B) 1-Benzyl-N-methoxy-N-methyl-1H-pyrazole-4-carboxamide

A solution of 1-benzyl-1H-pyrazole-4-carbonyl chloride (2.38 g) in dichloromethane (10 mL) was added to a solution of N,O-dimethylhydroxylamine hydrochloride (2.89 g) in dichloromethane (10 mL) at 0° C., followed by addition of TEA (5.50 mL). The reaction mixture was stirred for 1 hour at 15° C. The reaction was quenched with a saturated Na₂CO₃ solution. The organic phase was separated, dried over Na₂SO₄, concentrated, and purified by silica gel chromatography (petroleum ether:ethyl acetate=10:1 to 1:1) to give the target compound (2.0 g) as a gum.
¹H NMR (400 MHz, CDCl₃): δ 8.00 (s, 1H), 7.94 (s, 1H), 7.39-7.31 (m, 3H), 7.24 (d, J=6.1 Hz, 2H), 5.31 (s, 2H), 3.69 (s, 3H), 3.31 (s, 3H).

C) 1-Benzyl-N-methoxy-N-methyl-5-(methyl-d3)-1H-pyrazole-4-carboxamide

To a solution of DIPA (1.65 mL) in THF (20 mL) was added 2.5 M solution of nBuLi (4.3 mL) at −70° C. under N₂ atmosphere. The mixture was stirred at 0° C. for 5 min and cooled to −70° C. And the above solution was added dropwise to a suspension of 1-benzyl-N-methoxy-N-methyl-1H-pyrazole-4-carboxamide (1.3 g) in anhydrous THF (20 mL) over 15 min at −70° C. The reaction mixture was stirred at −70° C. for 45 min. Trideuterio(iodo)methane (989.22 uL) was added to the reaction mixture over 1 h and the mixture was allowed to warm to 15° C. for 12.5 hours. The saturated NH₄Cl solution and water were added, and the mixture extracted with ethyl acetate. The combined organic phase was washed with brine, dried with anhydrous Na₂SO₄, and purified by silica gel chromatography (petroleum ether:ethyl acetate=10:1 to 3:1) to the target compound (0.7 g) as an oil.
¹H NMR (400 MHz, CDCl₃): δ 7.95 (s, 1H), 7.36-7.27 (m, 3H), 7.11 (d, J=6.6 Hz, 2H), 5.32 (s, 2H), 3.69 (s, 3H), 3.32 (s, 3H)

D) 1-(1-Benzyl-5-(methyl-d3)-1H-pyrazol-4-yl)ethan-1-one

A target compound was synthesized in a similar manner as step B in example 68 using 1-benzyl-N-methoxy-N-methyl-5-(methyl-d3)-1H-pyrazole-4-carboxamide and MeMgBr.
¹H NMR (400 MHz, CDCl₃): δ 7.97 (s, 1H), 7.36-7.45 (m, 3H), 7.22-7.17 (m, 2H), 5.39 (s, 2H), 2.56-2.49 (m, 3H).

E) 1-(1-Benzyl-5-(methyl-d3)-1H-pyrazol-4-yl)-2-bromoethan-1-one

A target compound was synthesized in a similar manner as step E in example 73 using 1-(1-benzyl-5-(methyl-d3)-1H-pyrazol-4-yl)ethan-1-one.
MS: (M+H⁺): 297.9

F) 1-(2-(1-Benzyl-5-(methyl-d3)-1H-pyrazol-4-yl)-2-oxoethyl)-5-bromopyridin-2(1H)-one A target compound was synthesized in a similar manner as step D in example 34 using 1-(1-benzyl-5-(methyl-d3)-1H-pyrazol-4-yl)-2-bromoethan-1-one and 5-bromopyridin-2(1H)-one.
¹H NMR (400 MHz, DMSO-d₆): δ 8.03 (s, 1H), 7.41 (dd, J=9.7, 2.6 Hz, 1H), 7.37-7.29 (m, 4H), 7.12 (d, J=6.6 Hz, 2H), 6.53 (d, J=9.7 Hz, 1H), 5.35-5.30 (m, 1H), 5.33 (s, 1H), 5.10 (s, 2H), 2.51 (m, 1H).

G) 1-(2-(1-Benzyl-5-(methyl-d3)-1H-pyrazol-4-yl)-2-oxoethyl)-5-vinylpyridin-2(1H)-one A target compound was synthesized in a similar manner as example 76 using 1-(2-(1-benzyl-5-(methyl-d3)-1H-pyrazol-4-yl)-2-oxoethyl)-5-bromopyridin-2(1H)-one and potassium vinyltrifluoroborate.

¹H NMR (400 MHz, DMSO-d₆): δ 8.05 (s, 1H), 7.63 (dd, J=9.4, 2.41 Hz, 1H), 7.38-7.27 (m, 3H), 7.17-7.08 (m, 3H), 6.63 (d, J=9.7 Hz, 1H), 6.40 (dd, J=17.5, 11.0 Hz, 1H), 5.49 (s, 1H), 5.44 (s, 1H), 5.33 (s, 2H), 5.18-5.09 (m, 4H).

Example 107

1-(2-(1-Benzyl-2,5-dimethyl-1H-pyrrol-3-yl)-2-oxoethyl)-5-vinylpyridin-2(1H)-one A) 1-(2-(1-Benzyl-2,5-dimethyl-1H-pyrrol-3-yl)-2-oxoethyl)-5-bromopyridin-2(1H)-one A target compound was synthesized in a similar manner as in example 1 using 1-(1-benzyl-2,5-dimethyl-1H-pyrrol-3-yl)-2-bromoethan-1-one and 5-bromopyridin-2(1H)-one.
MS: (M+H⁺): 401.0

B) 1-(2-(1-Benzyl-2,5-dimethyl-1H-pyrrol-3-yl)-2-oxoethyl)-5-vinylpyridin-2(1H)-one A target compound was synthesized in a similar manner as example 76 using 1-(2-(1-benzyl-2,5-dimethyl-1H-pyrrol-3-yl)-2-oxoethyl)-5-bromopyridin-2(1H)-one and potassium vinyltrifluoroborate.
¹H NMR (400 MHz, CDCl₃): δ 7.62 (dd, J=2.4, 9.5 Hz, 1H), 7.36-7.28 (m, 3H), 7.18 (d, J=2.3 Hz, 1H), 6.90 (d, J=7.2 Hz, 2H), 6.63 (d, J=9.4 Hz, 1H), 6.48-6.37 (m, 2H), 5.46 (d, J=17.5 Hz, 1H), 5.17 (s, 2H), 5.12 (d, J=11.0 Hz, 1H), 5.07 (s, 2H), 2.49 (s, 3H), 2.16 (s, 3H).

Example 108

5-Acetyl-1-(2-(1-benzyl-5-methyl-1H-pyrazol-4-yl)-2-oxoethyl)pyridin-2(1H)-one

To a solution of 1-(2-(1-benzyl-5-methyl-1H-pyrazol-4-yl)-2-oxoethyl)-5-bromopyridin-2(1H)-one (0.2 g) in toluene (5.0 mL) were added Pd(PPh₃)₄ (59.84 mg) and tributyl(1-ethoxyvinyl)stannane (209 μL). The mixture was stirred at 110° C. for 12 hours under nitrogen atmosphere. The mixture was poured into saturated KF solution and extracted with ethyl acetate. The combined organic phase was washed with brine, dried with anhydrous Na₂SO₄, concentrated and purified by HPLC to give the target compound (40 mg) as a solid.
¹H NMR (400 MHz, Methanol-d₄): δ 8.51 (d, J=2.5 Hz, 1H), 8.25 (s, 1H), 8.07 (dd, J=9.5, 2.5 Hz, 1H), 7.41-7.26 (m, 3H), 7.16 (d, J=7.2 Hz, 2H), 6.58 (d, J=9.5 Hz, 1H), 5.43 (s, 2H), 5.38 (s, 2H), 2.52 (s, 3H), 2.47 (s, 3H).

Example 109

1-(2-(1-Benzyl-5-methyl-1H-pyrazol-4-yl)-2-oxoethyl)-2-oxo-5-vinyl-1,2-dihydropyridine-3-carbonitrile A) 1-(2-(1-Benzyl-5-methyl-1H-pyrazol-4-yl)-2-oxoethyl)-5-bromo-2-oxo-1,2-dihydropyridine-3-carbonitrile A mixture of 1-(1-benzyl-5-methyl-1H-pyrazol-4-yl)-2-bromoethan-1-one (0.3 g), 5-bromo-2-oxo-1,2-dihydropyridine-3-carbonitrile (244 mg), K₂CO₃ (353 mg), and DMF (15 mL) was degassed and purged with nitrogen for 3 times, and then the mixture was stirred at 15° C. for 12 hours. The mixture was poured into water and extracted with ethyl acetate. The combined organic phase was washed with brine, dried with anhydrous Na₂SO₄, and purified by silica gel chromatography (petroleum ether:ethyl acetate=4:1 to 0:100) to give the target compound (400 mg) as a solid.
MS: (M+H⁺): 412.9

B) 1-(2-(1-Benzyl-5-methyl-1H-pyrazol-4-yl)-2-oxoethyl)-2-oxo-5-vinyl-1,2-dihydropyridine-3-carbonitrile A target compound was synthesized in a similar manner as example 76 using 1-(2-(1-benzyl-5-methyl-1H-pyrazol-4-yl)-2-oxoethyl)-5-bromo-2-oxo-1,2-dihydropyridine-3-carbonitrile and potassium vinyltrifluoroborate.
¹H NMR (400 MHz, Methanol-d₄): δ 8.42 (d, J=2.6 Hz, 1H), 8.23 (s, 1H), 7.96 (d, J=2.5 Hz, 1H), 7.38-7.28 (m, 3H), 7.17 (d, J=7.0 Hz, 2H), 6.53 (dd, J=17.6, 11.1 Hz, 1H), 5.71 (d, J=17.6 Hz, 1H), 5.42 (s, 2H), 5.37 (s, 2H), 5.27 (d, J=11.1 Hz, 1H), 2.53 (s, 3H).

Example 110

1-(2-(3-Benzyl-4-methylisoxazol-5-yl)-2-oxoethyl)-5-vinylpyridin-2(1H)-one

A) Ethyl 3-benzyl-4-methylisoxazole-5-carboxylate

To a solution of N-hydroxy-2-phenyl-acetimidoyl chloride (1.1 g), chloro(pentamethylcyclopentadienyl)(cyclooctadiene)ruthenium(II) (250 mg) in dichloroethane (15 mL) was added dropwise ethyl but-2-ynoate (680.33 μL) followed by TEA (902.71 μL) in dichloroethane (5 mL) at 15° C., then the mixture was stirred for 16 hours. The reaction mixture was concentrated and purified by silica gel chromatography to give the target compound (1.1 g) as a solid.
¹H NMR (400 MHz, CDCl₃): δ 7.20-7.33 (m, 5H), 4.40 (q, J=7.0 Hz, 2H), 4.05 (s, 2H), 2.08 (s, 3H), 1.40 (t, J=7.0 Hz, 3H).

B) 3-Benzyl-4-methylisoxazole-5-carboxylic acid

A target compound was synthesized in a similar manner as step B in example 73 using ethyl 3-benzyl-4-methylisoxazole-5-carboxylate.
¹H NMR (400 MHz, DMSO-d₆): δ 7.17-7.34 (m, 5H), 3.99-4.07 (m, 2H), 2.03 (s, 3H).

C) 3-Benzyl-N-methoxy-N,4-dimethylisoxazole-5-carboxamide

A target compound was synthesized in a similar manner as step A in example 68 using 3-benzyl-4-methylisoxazole-5-carboxylic acid.
¹H NMR (400 MHz, CDCl₃): δ 7.28-7.33 (m, 2H), 7.19-7.25 (m, 3H), 4.03 (s, 2H), 3.86 (s, 3H), 3.33 (s, 3H), 2.02 (s, 3H).

D) 1-(3-Benzyl-4-methylisoxazol-5-yl)ethan-1-one

A target compound was synthesized in a similar manner as step B in example 68 using 3-benzyl-N-methoxy-N,4-dimethylisoxazole-5-carboxamide and MeMgBr.

¹H NMR (400 MHz, CDCl₃): δ 7.21-7.26 (m, 2H) 7.11-7.18 (m, 3H) 3.98 (s, 2H) 2.48-2.55 (m, 3H) 2.03 (s, 3H).

E) 1-(3-Benzyl-4-methylisoxazol-5-yl)-2-bromoethan-1-one

A target compound was synthesized in a similar manner as step E in example 73 using 1-(3-benzyl-4-methylisoxazol-5-yl)ethan-1-one.
MS: (M+H⁺): 296.1

F) 1-(2-(3-Benzyl-4-methylisoxazol-5-yl)-2-oxoethyl)-5-bromopyridin-2(1H)-one A target compound was synthesized in a similar manner as step D in example 34 using 1-(3-Benzyl-4-methylisoxazol-5-yl)-2-bromoethan-1-one and 5-bromopyridin-2(1H)-one.
¹H NMR (400 MHz, CDCl₃): δ 7.42 (dd, J=9.7, 2.6 Hz, 1H), 7.28-7.35 (m, 3H), 7.21 (d, J=7.5 Hz, 2H), 6.54 (d, J=9.7 Hz, 1H), 5.24 (s, 2H), 4.04-4.10 (m, 2H), 2.10 (s, 3H).

G) 1-(2-(3-Benzyl-4-methylisoxazol-5-yl)-2-oxoethyl)-5-vinylpyridin-2(1H)-one A target compound was synthesized in a similar manner as example 76 using 1-(2-(3-benzyl-4-methylisoxazol-5-yl)-2-oxoethyl)-5-bromopyridin-2(1H)-one and potassium vinyltrifluoroborate.
¹H NMR (400 MHz, DMSO-d₆): δ 7.81 (dd, J=9.6, 2.5 Hz, 1H), 7.69 (d, J=2.4 Hz, 1H), 7.29-7.36 (m, 2H), 7.19-7.27 (m, 3H), 6.40-6.49 (m, 2H), 5.57 (d, J=17.6 Hz, 1H), 5.29 (s, 2H), 5.10 (d, J=11.3 Hz, 1H), 4.12 (s, 2H), 2.07 (s, 3H).

Example 111

1-(2-(3-Benzyl-4-methylisoxazol-5-yl)-2-oxoethyl)-5-ethynylpyridin-2(1H)-one

A) 1-(2-(3-Benzyl-4-methylisoxazol-5-yl)-2-oxoethyl)-5-((trimethylsilyl)ethynyl)pyridin-2(1H)-one A target compound was synthesized in a similar manner as step A in example 36 using 1-(2-(3-benzyl-4-methylisoxazol-5-yl)-2-oxoethyl)-5-bromopyridin-2(1H)-one.
¹H NMR (400 MHz, CDCl₃): δ 7.39-7.44 (m, 2H), 7.21 (d, J=7.0 Hz, 2H), 6.98 (s, 1H), 6.54 (d, J=10.1 Hz, 1H), 5.24 (s, 2H), 4.08 (s, 2H), 2.10 (s, 3H), 0.17-0.24 (m, 9H).

B) 1-(2-(3-Benzyl-4-methyl isoxazol-5-yl)-2-oxoethyl)-5-ethynylpyridin-2(1H)-one A target compound was synthesized in a similar manner as step H in example 73 using 1-(2-(3-benzyl-4-methylisoxazol-5-yl)-2-oxoethyl)-5-((trimethylsilyl)ethynyl)pyridin-2(1H)-one.
¹H NMR (400 MHz, CDCl₃): δ 7.36 (d, J=5.6 Hz, 2H), 7.21-7.28 (m, 3H), 7.14 (d, J=7.8 Hz, 2H), 6.50 (d, J=9.9 Hz, 1H), 5.18 (s, 2H), 4.01 (s, 2H), 2.94 (s, 1H), 2.03 (s, 3H).

Example 112

1-(2-(1-Benzyl-5-methyl-1H-pyrazol-4-yl)-2-oxoethyl)-3-vinylpyridin-2(1H)-one

A) 1-(2-(1-Benzyl-5-methyl-1H-pyrazol-4-yl)-2-oxoethyl)-3-bromopyridin-2(1H-one A target compound was synthesized in a similar manner as step D in example 34 using 1-(1-benzyl-5-methyl-1H-pyrazol-4-yl)-2-bromoethan-1-one and 3-bromopyridin-2(1H)-one.
MS: (M+H⁺): 385.9

B) 1-(2-(1-Benzyl-5-methyl-1H-pyrazol-4-yl)-2-oxoethyl)-3-vinylpyridin-2(1H)-one A target compound was synthesized in a similar manner as example 76 using 1-(2-(1-benzyl-5-methyl-1H-pyrazol-4-yl)-2-oxoethyl)-3-bromopyridin-2(1H)-one and vinyltrifluoroborate.
¹H NMR (400 MHz, Methanol-d₄): δ 8.23 (s, 1H), 7.72 (dd, J=7.2, 1.7 Hz, 1H), 7.52 (dd, J=6.7, 1.8 Hz, 1H), 7.39-7.26 (m, 3H), 7.19-7.13 (m, 2H), 6.80 (dd, J=17.7, 11.4 Hz, 1H), 6.42 (t, J=6.9 Hz, 1H), 5.98 (dd, J=17.7, 1.6 Hz, 1H), 5.41 (s, 2H), 5.34-5.24 (m, 3H), 2.52 (s, 3H).

Example 113

1-(2-(1-Benzyl-5-methyl-1H-pyrazol-4-yl)-2-oxoethyl)-3-fluoro-5-vinylpyridin-2(1H)-one

A) 1-(2-(1-Benzyl-5-methyl-1H-pyrazol-4-yl)-2-oxoethyl)-5-bromo-3-fluoropyridin-2(1H)-one A target compound was synthesized in a similar manner as step D in example 34 using 1-(1-benzyl-5-methyl-1H-pyrazol-4-yl)-2-bromoethan-1-one and 5-bromo-3-fluoropyridin-2(1H)-one.
MS: (M+H⁺): 403.8

B) 1-(2-(1-Benzyl-5-methyl-1H-pyrazol-4-yl)-2-oxoethyl)-3-fluoro-5-vinylpyridin-2(1H)-one A target compound was synthesized in a similar manner as example 76 using 1-(2-(1-benzyl-5-methyl-1H-pyrazol-4-yl)-2-oxoethyl)-5-bromo-3-fluoropyridin-2(1H)-one and vinyltrifluoroborate.
¹H NMR (400 MHz, Methanol-d₄): δ 8.23 (s, 1H), 7.73 (dd, J=10.9, 2.2 Hz, 1H), 7.43 (s, 1H), 7.38-7.27 (m, 3H), 7.17 (d, J=7.4 Hz, 2H), 6.53 (td, J=17.5, 11.0, 1.7 Hz, 1H), 5.62 (d, J=17.5 Hz, 1H), 5.42 (s, 2H), 5.36 (s, 2H), 5.22 (d, J=10.9 Hz, 1H), 2.52 (s, 3H).

Example 114

2-(2-(1-Benzyl-5-methyl-1H-pyrazol-4-yl)ethoxy)-5-vinylpyridine

A target compound was synthesized in a similar manner as example 76 using 2-(2-(1-benzyl-5-methyl-1H-pyrazol-4-yl)ethoxy)-5-bromopyridine and potassium vinyltrifluoroborate.
¹H NMR (400 MHz, Methanol-d₄): δ 8.06 (d, J=2.1 Hz, 1H), 7.82 (dd, J=8.7, 2.3 Hz, 1H), 7.41 (s, 1H), 7.20-7.31 (m, 3H), 7.01 (d, J=7.1 Hz, 2H), 6.62-6.75 (m, 2H), 5.70 (d, J=17.6 Hz, 1H), 5.30 (s, 2H), 5.21 (d, J=11.0 Hz, 1H), 4.38 (t, J=6.8 Hz, 2H), 2.87 (t, J=6.8 Hz, 2H), 2.17 (s, 3H).

Example 115

1-(2-(1-Benzyl-5-methyl-1H-pyrazol-4-yl)-2-oxoethyl)-2-oxo-5-vinyl-1,2-dihydropyridine-3-carbonitrile A mixture of 1-(2-(1-benzyl-5-methyl-1H-pyrazol-4-yl)-2-oxoethyl)-5-bromo-2-oxo-1,2-dihydropyridine-3-carbonitrile (150 mg), 1-(trifluoromethyl)vinylboronic acid (382 mg), Pd(PPh₃)₂Cl₂ (51.2 mg), K₂CO₃ (111 mg), THF (2 mL), and water (0.8 mL) was degassed and purged with nitrogen for 3 times, and then the mixture was stirred at 70° C. for 12 hours. The mixture was poured into water and extracted with ethyl acetate. The combined organic phase was washed with brine, dried with anhydrous $Na_2SO_4$, concentrated, and purified by HPLC to give a target compound (40 mg) as a white solid.

$^1$H NMR (400 MHz, Methanol-$d_4$): δ 8.26 (s, 1H), 823 (s, 1H), 8.10 (d, J=2.6 Hz, 1H), 7.37-7.27 (m, 3H), 7.16 (d, J=6.9 Hz, 2H), 6.07 (s, 1H), 6.00 (s, 1H), 5.42 (s, 4H), 2.53 (s, 3H).

Example 116

1-(2-(1-Benzyl-5-methyl-1H-pyrazol-4-yl)-2-oxoethyl)-2-oxo-5-vinyl-1,2-dihydropyridine-4-carbonitrile A) 1-(2-(1-Benzyl-5-methyl-1H-pyrazol-4-yl)-2-oxoethyl)-5-bromo-2-oxo-1,2-dihydropyridine-4-carbonitrile A target compound was synthesized in a similar manner as step D in example 34 using 1-(1-benzyl-5-methyl-1H-pyrazol-4-yl)-2-bromoethan-1-one and 5-bromo-2-oxo-1,2-dihydropyridine-4-carbonitrile.
MS: (M+H$^+$): 411.1

B) 1-(2-(1-Benzyl-5-methyl-1H-pyrazol-4-yl)-2-oxoethyl)-2-oxo-5-vinyl-1,2-dihydropyridine-4-carbonitrile A target compound was synthesized in a similar manner as example 76 using 1-(2-(1-benzyl-5-methyl-1H-pyrazol-4-yl)-2-oxoethyl)-5-bromo-2-oxo-1,2-dihydropyridine-4-carbonitrile and vinyltrifluoroborate.

$^1$H NMR (400 MHz, Methanol-$d_4$): δ 8.27-8.19 (m, 1H), 8.09-8.01 (m, 1H), 7.39-7.26 (m, 3H), 7.16 (d, J=7.1 Hz, 2H), 7.00 (s, 1H), 6.68 (dd, J. 17.6, 11.2 Hz, 1H), 5.80 (d, J=17.5 Hz, 1H), 5.44-5.28 (m, 5H), 2.52 (s, 3H).

Example 117

1-(1-(1-Benzyl-5-methyl-1H-pyrazol-4-yl)-1-oxopropan-2-yl)-5-vinylpyrazin-2(1H)-one A) 1-(1-(1-Benzyl-5-methyl-1H-pyrazol-4-yl)-1-oxopropan-2-yl)-5-bromopyrazin-2(1H)-one A target compound was synthesized in a similar manner as step D in example 34 using 1-(1-benzyl-5-methyl-1H-pyrazol-4-yl)-2-bromopropan-1-one and 5-bromopyrazin-2(1H)-one.

$^1$H NMR (400 MHz, CDCl$_3$): δ 8.11 (s, 1H), 7.99 (d, J=1.1 Hz, 1H), 7.48 (d, J=1.1 Hz, 1H), 7.38-7.28 (m, 3H), 7.20-7.14 (m, 2H), 6.20 (q, J=7.2 Hz, 1H), 5.32 (s, 2H), 2.53 (s, 3H), 1.64 (d, J=7.3 Hz, 3H).

B) 1-(1-(1-Benzyl-5-methyl-1H-pyrazol-4-yl)-1-oxopropan-2-yl)-5-vinylpyrazin-2(1H)-one A target compound was synthesized in a similar manner as example 76 using 1-(1-(1-benzyl-5-methyl-1H-pyrazol-4-yl)-1-oxopropan-2-yl)-5-bromopyrazin-2(1H)-one and potassium vinyltrifluoroborate.

$^1$H NMR (400 MHz, CDCl$_3$): δ 8.20 (s, 1H), 8.08 (s, 1H), 7.57 (s, 1H), 7.37-7.26 (m, 3H), 7.14 (d, J=7.1 Hz, 2H), 6.65 (dd, J=17.1, 10.9 Hz, 1H), 6.09-5.97 (m, 2H), 5.39 (s, 2H), 5.26 (dd, J=10.9, 1.5 Hz, 1H), 2.50 (s, 3H), 1.69 (d, J=7.2 Hz, 3H).

Example 118

1-(2-(1-Benzyl-5-methyl-1H-pyrazol-4-yl)-2-hydroxyethyl)-5-vinylpyridin-2(1H)-one A) 1-(2-(1-Benzyl-5-methyl-1H-pyrazol-4-yl)-2-hydroxyethyl)-5-bromopyridin-2(1H)-one To a solution of 1-(2-(1-benzyl-5-methyl-1H-pyrazol-4-yl)-2-oxoethyl)-5-bromopyridin-2(1H)-one (4 g) in EtOH (80 mL) was added NaBH$_4$ (1.96 g) at 0° C. The mixture was stirred at 15° C. for 12 hours. The reaction mixture was quenched by addition saturated NH$_4$Cl solution, and then extracted with ethyl acetate. The combined organic layers were dried over Na$_2$SO$_4$, concentrated, and purified by silica gel chromatography (ethyl acetate:MeOH=50:1 to 30:1) to give the target compound (1.2 g) as a solid.

$^1$H NMR (400 MHz, CDCl$_3$): δ 7.80 (d, J=2.7 Hz, 1H), 7.46-7.55 (m, 1H), 7.41 (s, 1H), 7.30-7.36 (m, 2H), 7.22-7.29 (m, 1H), 7.05 (d, J=7.1 Hz, 2H), 6.35 (d, J=9.7 Hz, 1H), 5.37 (d, J=5.3 Hz, 1H), 5.27 (s, 2H), 4.73-4.82 (m, 1H), 4.00-4.12 (m, 1H), 3.91 (dd, J=12.8, 8.6 Hz, 1H), 2.12 (s, 3H).

B) 1-(2-(1-Benzyl-5-methyl-1H-pyrazol-4-yl)-2-hydroxyethyl)-5-vinylpyridin-2(1H)-one A target compound was synthesized in a similar manner as example 76 using 1-(2-(1-benzyl-5-methyl-1H-pyrazol-4-yl)-2-hydroxyethyl)-5-bromopyridin-2(1H)-one and potassium vinyltrifluoroborate.

$^1$H NMR (400 MHz, Methanol-$d_4$): δ 8.05 (s, 1H), 7.87 (dd, J=9.3, 2.4 Hz, 1H), 7.69 (d, J=2.2 Hz, 1H), 7.32-7.43 (m, 3H), 7.15 (d, J=6.8 Hz, 2H), 6.59 (d, J=9.5 Hz, 1H), 6.53 (dd, J=17.5, 10.9 Hz, 1H), 5.62 (d, J=17.6 Hz, 1H), 5.52 (s, 2H), 5.20 (d, J=11.0 Hz, 1H), 5.12 (dd, J=7.9, 4.2 Hz, 1H), 4.36 (dd, J=13.2, 4.2 Hz, 1H), 4.15 (dd, J=13.2, 8.2 Hz, 1H), 2.40 (s, 3H).

Example 119

1-(2-(1-Benzyl-5-methyl-1H-pyrazol-4-yl)-2-methoxyethyl)-5-vinylpyridin-2(1H)-one A) 1-(2-(1-Benzyl-5-methyl-1H-pyrazol-4-yl)-2-methoxyethyl)-5-bromopyridin-2(1H)-one To a solution of 1-(2-(1-benzyl-5-methyl-1H-pyrazol-4-yl)-2-hydroxyethyl)-5-bromopyridin-2(1H)-one (500 mg) in THF (10 mL) was added NaH (77.3 mg, 60% purity). The reaction was stirred for 0.5 hours at 0° C. Then CH$_3$I (160 μL) was added and the mixture was stirred at 15° C. for 11.5 hours. The reaction was with water and extracted with ethyl acetate. The combined organic layers were dried over Na$_2$SO$_4$, concentrated, and purified by silica gel chromatography (petroleum ether:ethyl acetate=1:1 to 1:2) to give the target compound (400 mg) as an oil.

$^1$H NMR (400 MHz, CDCl$_3$): δ 7.49 (s, 1H), 7.45 (d, J=2.7 Hz, 1H), 7.28-7.39 (m, 4H), 7.08 (d, J=7.0 Hz, 2H), 6.47 (d, J=9.7 Hz, 1H), 5.28-5.32 (m, 2H), 4.53 (dd, J=9.0, 3.6 Hz, 1H), 4.27 (dd, J=13.2, 3.7 Hz, 1H), 3.76 (dd, J=13.2, 8.9 Hz, 1H), 3.20 (s, 3H), 2.21 (s, 3H).

B) 1-(2-(1-Benzyl-5-methyl-1H-pyrazol-4-yl)-2-methoxyethyl)-5-vinylpyridin-2(1H)-one A target compound was synthesized in a similar manner as example 76 using 1-(2-(1-benzyl-5-methyl-1H-pyrazol-4-yl)-2-methoxyethyl)-5-bromopyridin-2(1H)-one and potassium vinyltrifluoroborate.

$^1$H NMR (400 MHz, Methanol-d$_4$): δ 7.75-7.91 (m, 2H), 7.62 (d, J=2.3 Hz, 1H), 7.27-7.45 (m, 3H), 7.11 (d, J=6.7 Hz, 2H), 6.45-6.62 (m, 2H), 5.60 (d, J=17.5 Hz, 1H), 5.42-5.49 (m, 2H), 5.19 (d, J=11.0 Hz, 1H), 4.72 (dd, J. 7.5, 4.9 Hz, 1H), 4.18-4.35 (m, 2H), 3.19-3.27 (m, 3H), 2.25-2.38 (m, 3H).

Example 120

1-(2-(1-Benzyl-5-methyl-1H-pyrazol-4-yl)ethyl)-5-vinylpyridin-2(1H)-one

A) 1-Benzyl-4-(2-bromoethyl)-5-methyl-1H-pyrazole

To a solution of 1-(1-benzyl-5-methyl-1H-pyrazol-4-yl)-2-bromoethan-1-one (300 mg) in TFA (10 mL) was added Et$_3$SiH (2 mL). The mixture was stirred at 70° C. for 3 hours. The reaction mixture was concentrated and purified by HPLC to give the target compound (180 mg) as an oil.

$^1$H NMR (400 MHz, CDCl$_3$): δ 7.06-7.22 (m, 3H), 6.89-6.99 (m, 2H), 5.15 (s, 2H), 3.33 (t, J=7.5 Hz, 2H), 2.83 (t, J=7.5 Hz, 2H), 2.01 (s, 3H).

B) 1-(2-(1-Benzyl-5-methyl-1H-pyrazol-4-yl)ethyl)-5-bromopyridin-2(1H)-one

To a solution of 1-benzyl-4-(2-bromoethyl)-5-methyl-1H-pyrazole (150 mg) in DMF (3 mL) were added K$_2$CO$_3$ (185 mg) and 5-bromopyridin-2(1H)-one (112 mg). The mixture was stirred at 20° C. for 12 hours. Another batch with 30 mg of the starting material was combined. The mixture was diluted with water and extracted with ethyl acetate. The combined organic layers were dried over Na$_2$SO$_4$ and concentrated to give the target compound (170 mg) as a mixture of 2-(2-(1-benzyl-5-methyl-1H-pyrazol-4-yl)ethoxy)-5-bromopyridine.

$^1$H NMR (400 MHz, CDCl$_3$): δ 7.56-8.09 (m, 1H), 7.30-7.45 (m, 1H), 7.20-7.29 (m, 3H), 7.15-7.19 (m, 1H), 6.96-7.04 (m, 2H), 6.38-6.55 (m, 1H), 5.19 (d, J=6.9 Hz, 2H), 4.29 (t, J=7.1 Hz, 1H), 3.91 (t, J=6.9 Hz, 1H), 2.75-2.80 (m, 2H), 2.06 (m, 1H), 1.91 (m, 2H).

C) 1-(2-(1-Benzyl-5-methyl-1H-pyrazol-4-yl)ethyl)-5-vinylpyridin-2(1H)-one

A target compound was synthesized in a similar manner as example 76 using 1-(2-(1-benzyl-5-methyl-1H-pyrazol-4-yl)ethyl)-5-bromopyridin-2(1H)-one and potassium vinyltrifluoroborate.

$^1$H NMR (400 MHz, Methanol-d$_4$): δ 7.76 (dd, J=9.4, 2.3 Hz, 1H), 7.18-7.39 (m, 5H), 6.98 (d, J=7.2 Hz, 2H), 6.52 (d, J=9.4 Hz, 1H), 6.38 (dd, J=17.6, 11.0 Hz, 1H), 5.52 (d, J=17.6 Hz, 1H), 5.26 (5, 2H), 5.12 (d, J=11.0 Hz, 1H), 4.11 (t, J=6.7 Hz, 2H), 2.90 (t, J=6.7 Hz, 2H), 1.99 (s, 3H).

Example 121

1-((1-Benzyl-5-methyl-1H-pyrazol-4-yl)methyl)-5-vinylpyridin-2(1H)-one

A) (1-Benzyl-5-methyl-1H-pyrazol-4-yl)methanol

To a solution of ethyl 1-benzyl-5-methyl-1H-pyrazole-4-carboxylate (1.33 g) in THF (20 mL) was added LiAlH$_4$ (413 mg). The mixture was stirred at 0° C. for 1 hour. The reaction was added water (0.5 mL), 15% NaOH solution (0.5 mL), and water (0.5 mL) successively. After stirred for 15 min, the mixture was dried over Na$_2$SO$_4$, concentrated, and purified by silica gel chromatography (petroleum ether:ethyl acetate=20:1 to MeOH:ethyl acetate=19:1) to give the target compound (150 mg) as a solid.

$^1$H NMR (400 MHz, CDCl$_3$): δ 7.51 (s, 1H), 7.28-7.35 (m, 3H), 7.12 (d, J=7.0 Hz, 2H), 5.29 (s, 2H), 4.54 (s, 2H), 2.23 (s, 3H).

B) (1-Benzyl-5-methyl-1H-pyrazol-4-yl)methyl Methanesulfonate

To a solution of (1-benzyl-5-methyl-1H-pyrazol-4-yl)methanol (0.45 g) and TEA (929 uL) in dichloromethane (30 mL) was added MsCl (207 uL) at 0° C. The mixture was stirred at 15° C. for 12 hours. The reaction mixture was diluted with water and extracted with dichloromethane. The combined organic layers were washed with brine, dried over anhydrous Na$_2$SO$_4$, and concentrated to give the target compound (0.5 g) as a yellow oil.

C) 1-((1-Benzyl-5-methyl-1H-pyrazol-4-yl)methyl)-5-bromopyridin-2(1H)-one

A target compound was synthesized in a similar manner as step D in example 34 using (1-benzyl-5-methyl-1H-pyrazol-4-yl)methyl methanesulfonate and 5-bromopyridin-2(1H)-one.

D) 1-((1-Benzyl-5-methyl-1H-pyrazol-4-yl)methyl)-5-vinylpyridin-2(1H)-one

A target compound was synthesized in a similar manner as example 76 using 1-((1-benzyl-5-methyl-1H-pyrazol-4-yl)methyl)-5-bromopyridin-2(1H)-one and vinyltrifluoroborate.

$^1$H NMR (400 MHz, Methanol-d$_4$): δ 7.79 (dd, J=9.4, 2.5 Hz, 1H), 7.68 (d, J=2.5 Hz, 1H), 7.57 (s, 1H), 7.23-7.34 (m, 3H), 7.07 (d, J=6.9 Hz, 2H), 6.47-6.58 (m, 2H), 5.57 (d, J=17.6 Hz, 1H), 5.33 (s, 2H), 5.16 (d, J=11.0 Hz, 1H), 5.03 (s, 2H), 2.29 (s, 3H).

Example 122

1-(2-(1-Benzyl-5-methyl-1H-pyrazol-4-yl)-2-oxoethyl)-4-fluoro-5-vinylpyridin-2(1H)-one A) 1-(2-(1-Benzyl-5-methyl-1H-pyrazol-4-yl)-2-oxoethyl)-5-bromo-4-fluoropyridin-2(1H)-one A target compound was synthesized in a similar manner as step D in example 34 using 1-(1-benzyl-5-methyl-1H-pyrazol-4-yl)-2-bromoethan-1-one and 5-bromo-4-fluoropyridin-2(1H)-one.

¹H NMR (400 MHz, CDCl₃): δ 7.46 (d, J=8.8 Hz, 1H), 7.29-7.39 (m, 4H), 7.13 (d, J=7.5 Hz, 2H), 6.37 (d, J=10.1 Hz, 1H), 5.29-5.40 (m, 2H), 5.13 (s, 2H), 2.52 (s, 3H).

B) 1-(2-(1-Benzyl-5-methyl-1H-pyrazol-4-yl)-2-oxoethyl)-4-fluoro-5-vinylpyridin-2(1H)-one A target compound was synthesized in a similar manner as example 76 using 1-(2-(1-benzyl-5-methyl-1H-pyrazol-4-yl)-2-oxoethyl)-5-bromo-4-fluoropyridin-2(1H)-one and vinyltrifluoroborate.
¹H NMR (400 MHz, Methanol-d₄): δ 8.22 (s, 1H), 7.87 (d, J=9.2 Hz, 1H), 7.24-7.41 (m, 3H), 7.15 (d, J=7.0 Hz, 2H), 6.52 (dd, J=17.8, 11.6 Hz, 1H), 6.26 (d, J=12.7 Hz, 1H), 5.71 (d, J=18.0 Hz, 1H), 5.41 (s, 2H), 5.27-5.33 (m, 3H), 2.52 (s, 3H).

Example 123

1-(1-(1-Benzyl-5-methyl-1H-pyrazol-4-yl)-1-oxopropan-2-yl)-5-vinylpyrimidin-2(1H)-one A) 1-(1-(1-Benzyl-5-methyl-1H-pyrazol-4-yl)-1-oxopropan-2-yl)-5-bromopyrimidin-2(1H)-one A target compound was synthesized in a similar manner as step D in example 34 using 1-(1-benzyl-5-methyl-1H-pyrazol-4-yl)-2-bromopropan-1-one and 5-bromopyrimidin-2(1H)-one.
¹H NMR (400 MHz, CDCl₃): δ 8.57 (d, J=3.3 Hz, 1H), 8.14 (s, 1H), 7.94 (d, J=3.2 Hz, 1H), 7.3-7.28 (m, 3H), 7.16 (d, J=6.9 Hz, 2H), 6.21 (q, J. 7.3 Hz, 1H), 5.33 (s, 2H), 2.52 (s, 3H), 1.66 (d, J=7.5 Hz, 3H).

B) 1-(1-(1-Benzyl-5-methyl-1H-pyrazol-4-yl)-1-oxopropan-2-yl)-5-vinylpyrimidin-2(1H)-one A target compound was synthesized in a similar manner as example 76 using 1-(1-(1-benzyl-5-methyl-1H-pyrazol-4-yl)-1-oxopropan-2-yl)-5-bromopyrimidin-2(1H)-one and potassium vinyltrifluoroborate.
¹H NMR (400 MHz, Methanol-d₄): δ 8.87 (d, J=3.1 Hz, 1H), 8.25-8.21 (m, 2H), 7.38-7.26 (m, 3H), 7.16 (d, J=7.4 Hz, 2H), 6.62 (dd, J=17.8, 11.2 Hz, 1H), 6.02 (q, J=7.3 Hz, 1H), 5.79 (d, J=17.7 Hz, 1H), 5.43-5.36 (m, 2H), 5.29 (d, J=11.3 Hz, 1H), 2.52-2.48 (m, 3H), 1.72 (d, J=7.3 Hz, 3H).

Example 124

1-(1-Benzyl-5-methyl-1H-pyrazol-4-yl)-2-((5-vinylpyrazin-2-yl)oxy)propan-1-one

A) 1-(1-Benzyl-5-methyl-1H-pyrazol-4-yl)-2-((5-bromopyrazin-2-yl)oxy)propan-1-one A target compound was synthesized in a similar manner as step D in example 34 using 1-(1-benzyl-5-methyl-1H-pyrazol-4-yl)-2-bromopropan-1-one and 5-bromopyrazin-2(1H)-one.
¹H NMR (400 MHz, CDCl₃): δ 8.15 (d, J=1.3 Hz, 1H), 8.06 (d, J=1.3 Hz, 1H), 8.01 (s, 1H), 7.39-7.31 (m, 3H), 7.18-7.13 (m, 2H), 5.75 (q, J=7.0 Hz, 1H), 5.31 (s, 2H), 2.52 (s, 3H), 1.68 (d, J=7.1 Hz, 3H).

B) 1-(1-Benzyl-5-methyl-1H-pyrazol-4-yl)-2-((5-vinylpyrazin-2-yl)oxy)propan-1-one A target compound was synthesized in a similar manner as example 76 using 1-(1-benzyl-5-methyl-1H-pyrazol-4-yl)-2-((5-bromopyrazin-2-yl)oxy)propan-1-one and potassium vinyltrifluoroborate.
¹H NMR (400 MHz, Methanol-d₄): δ 8.23 (d, J=17.6 Hz, 2H), 8.01 (s, 1H), 7.40-7.24 (m, 3H), 7.14 (d, J=7.2 Hz, 2H), 6.74 (dd, J=17.4, 10.9 Hz, 1H), 6.12 (d, J=17.4 Hz, 1H), 5.89 (q, J=6.9 Hz, 1H), 5.44-5.33 (m, 3H), 2.49 (s, 3H), 1.64 (d, J=7.0 Hz, 3H).

Example 125

1-(2-(1-Benzyl-5-methyl-1H-pyrazol-4-yl)-2-oxoethyl)-6-fluoro-5-vinylpyridin-2(1H)-one A) 1-(2-(1-Benzyl-5-methyl-1H-pyrazol-4-yl)-2-oxoethyl)-5-bromo-6-fluoropyridin-2(1H)-one A target compound was synthesized in a similar manner as step D in example 34 using 1-(1-benzyl-5-methyl-1H-pyrazol-4-yl)-2-bromoethan-1-one and 5-bromo-6-fluoropyridin-2(1H)-one.
¹H NMR (400 MHz, CDCl₃): δ 7.99 (s, 1H), 7.83 (t, J=8.6 Hz, 1H), 7.30-7.39 (m, 3H), 7.10-7.20 (m, 2H), 6.75 (d, J=8.77 Hz, 1H), 5.32 (s, 4H), 2.52 (s, 3H).

B) 1-(2-(1-Benzyl-5-methyl-1H-pyrazol-4-yl)-2-oxoethyl)-6-fluoro-5-vinylpyridin-2(1H)-one A target compound was synthesized in a similar manner as example 76 using 1-(2-(1-benzyl-5-methyl-1H-pyrazol-4-yl)-2-oxoethyl)-5-bromo-6-fluoropyridin-2(1H)-one and vinyltrifluoroborate.
¹H NMR (400 MHz, Methanol-d₄): δ 8.16 (s, 1H), 7.96-8.04 (m, 1H), 725-7.37 (m, 3H), 7.13 (d, J=7.0 Hz, 2H), 6.81 (d, J=8.8 Hz, 1H), 6.66-6.74 (m, 1H), 5.77 (d, J=17.5 Hz, 1H), 5.37-5.41 (m, 4H), 5.29-5.34 (m, 1H), 2.51 (s, 3H).

Example 126

(E)-1-(2-(1-Benzyl-5-methyl-1H-pyrazol-4-yl)-2-oxoethyl)-5-(3-(dimethylamino)prop-1-en-1-yl)pyridin-2(1H)-one To a solution of 1-(2-(1-benzyl-5-methyl-1H-pyrazol-4-yl)-2-oxoethyl)-5-bromopyridin-2(1H)-one (150 mg) in dioxane (10 mL) were added 2-chloromethylvinylboronic acid pinacol ester (78.6 mg), K₂CO₃ (193 mg), dimethylamine hydrochloride (63.3 mg), H₂O (2 mL), and Pd(PPh₃)₄ (44.9 mg). The sealed tube was heated at 160° C. for 0.5 hours under microwave. The reaction was filtered and the filtrate was purified by HPLC to give the target compound (57.5 mg) as a diastereomeric mixture. The target compound was obtained by SFC (column: DAICEL CHIRALPAK AD (250 mm*50 mm, 10 ☐m).
¹H NMR (400 MHz, CDCl₃): δ 8.06 (s, 1H), 7.30-7.41 (m, 5H), 7.14 (d, J=6.9 Hz, 2H), 6.60 (d, J=9.4 Hz, 1H), 6.26 (d, J=10.2 Hz, 1H), 5.68-5.76 (m, 1H), 5.34 (s, 2H), 5.17 (s, 2H), 3.10 (s, 1H), 2.53 (s, 3H), 2.27 (s, 6H).

Example 127

(Z)-1-(2-(1-Benzyl-5-methyl-1H-pyrazol-4-yl)-2-oxoethyl)-5-(3-(dimethylamino)prop-1-en-1-yl)pyridin-2(1H)-one To a solution of 1-(2-(1-benzyl-5-methyl-1H-pyrazol-4-yl)-2-oxoethyl)-5-bromopyridin-2(1H)-one (150 mg) in dioxane (10 mL) were added 2-chloromethylvinylboronic acid pinacol ester (78.6 mg), $K_2CO_3$ (193 mg), dimethylamine hydrochloride (63.3 mg), $H_2O$ (2 mL), and $Pd(PPh_3)_4$ (44.9 mg). The sealed tube was heated at 160° C. for 0.5 hours under microwave. The reaction was filtered and the filtrate was purified by HPLC to give the target compound (57.5 mg) as a diastereomeric mixture. The target compound was obtained by SFC (column: DAICEL CHIRALPAK AD (250 mm*50 mm, 10 ☐m).

$^1$H NMR (400 MHz, $CDCl_3$): δ 8.05 (s, 1H), 7.60 (dd, J=9.5, 2.57 Hz, 1H), 7.29-7.42 (m, 3H), 7.07-7.16 (m, 3H), 6.62 (d, J=9.5 Hz, 1H), 6.23 (d, J=15.9 Hz, 1H), 5.99 (dt, J=15.8, 6.7 Hz, 1H), 5.33 (s, 2H), 5.13 (s, 2H), 3.05 (d, J=6.6 Hz, 2H), 2.46-2.57 (m, 3H), 2.18-2.33 (m, 6H).

Example 128

(E)-1-(2-(1-Benzyl-5-methyl-1H-pyrazol-4-yl)-2-oxoethyl)-5-(3-morpholinoprop-1-en-1-yl)pyridin-2(1H)-one A target compound was synthesized in a similar manner as example 76 using 1-(2-(1-benzyl-5-methyl-1H-pyrazol-4-yl)-2-oxoethyl)-5-bromopyridin-2(1H)-one and morpholine.

$^1$H NMR (400 MHz, $CDCl_3$): δ 8.06 (s, 1H), 7.31-7.41 (m, 5H), 7.14 (d, J=65 Hz, 2H), 6.60 (d, J=9.8 Hz, 1H), 6.28 (d, J=11.7 Hz, 1H), 5.62-5.78 (m, 1H), 5.34 (s, 2H), 5.17 (s, 2H), 3.69 (d, J=4.0 Hz, 4H), 3.14 (d, J=6.6 Hz, 2H), 2.52 (s, 3H), 2.47 (s, 4H).

Example 129

(Z)-1-(2-(1-Benzyl-5-methyl-1H-pyrazol-4-yl)-2-oxoethyl)-5-(3-morpholinoprop-1-en-1-yl)pyridin-2(1H)-one A target compound was synthesized in a similar manner as example 76 using 1-(2-(1-benzyl-5-methyl-1H-pyrazol-4-yl)-2-oxoethyl)-5-bromopyridin-2(1H)-one and morpholine.

$^1$H NMR (400 MHz, $CDCl_3$): δ 8.05 (s, 1H), 7.59 (dd, J=9.6, 2.51 Hz, 1H), 7.28-7.38 (m, 3H), 7.11-7.16 (m, 3H), 6.62 (d, J=9.5 Hz, 1H), 6.29 (d, J=15.8 Hz, 1H), 5.97 (dt, J=15.8, 6.9 Hz, 1H), 5.28-5.41 (m, 2H), 5.13 (s, 2H), 3.78 (t, J=4.6 Hz, 4H), 3.22 (d, J=6.6 Hz, 2H), 2.61 (s, 3H), 2.47-2.51 (m, 1H), 2.52 (s, 3H).

Example 130

1-((1-Benzyl-1H-pyrazolo[4,3-c]pyridin-4-yl)methyl)-5-bromopyridin-2(1H)-one hydrochloride A) 1-Benzyl-4-chloro-1H-pyrazolo[4,3-c]pyridine To a solution of 4-chloro-1H-pyrazolo[4,3-c]pyridine (3.7 g) in THF (40 mL) was added NaH (1.93 g, 60% purity) at 0° C. After stirring for 1 hour, benzyl bromide (3.15 mL) was added, and the mixture was stirred at 15° C. for 15 hours. The reaction mixture was quenched with water and extracted ethyl acetate. The organic layers were washed with brine, dried over $Na_2SO_4$, concentrated, and purified by silica gel chromatography (petroleum ether:ethyl acetate=50:1 to 20:1) to give the target compound (3.1 g) as a solid.

MS: (M+H$^+$): 244.0

B) Methyl 1-benzyl-1H-pyrazolo[4,3-c]pyridine-4-carboxylate

To a solution of 1-benzyl-4-chloro-1H-pyrazolo[4,3-c]pyridine (0.9 g, 3.69 mmol, 1 eq) in MeOH (20 mL) were added $Et_3N$ (1.03 mL) and $Pd(PPh_3)_2Cl_2$ (259 mg). The suspension was purged with CO several times, and the mixture was stirred at 80° C. for 48 hours under carbon monoxide (50 psi). The reaction mixture was filtered, concentrated, and purified by silica gel chromatography (petroleum ether:ethyl acetate=5:1 to 1:1) to give the target compound (0.3 g) as an oil.

C) (1-Benzyl-1H-pyrazolo[4,3-c]pyridin-4-yl)methanol

To a solution of methyl 1-benzyl-1H-pyrazolo[4,3-c]pyridine-4-carboxylate (0.3 g) in THF (10 mL) was added LAH (42.6 mg) at 0° C., and the mixture was stirred for 1 h at 50° C. under nitrogen atmosphere. The reaction mixture was quenched by addition of water (0.03 mL), 10% NaOH aqueous solution (0.03 mL), and water (0.3 mL) successively. Then the mixture and dried over $Na_2SO_4$, filtered, and concentrated to give the target compound (0.22 g, crude) as a solid.

D) 1-Benzyl-4-(bromomethyl)-1H-pyrazolo[4,3-c]pyridine

To a solution of (1-benzyl-1H-pyrazolo[4,3-c]pyridin-4-yl)methanol (0.38 g) in $CHCl_3$ (15 mL) was added $PBr_3$ (472 mg) at 0° C. The mixture was stirred at 15° C. for 5 hours. The reaction mixture was quenched by water, adjusted to PH=7 to 8 with $NaHCO_3$ solution, extracted with dichloromethane. The combined organic layers were dried over $Na_2SO_4$, concentrated, and purified by silica gel chromatography (petroleum ether:ethyl acetate=3:1 to 1:1) to give the target compound (80 mg) as a yellow solid.

$^1$H NMR (400 MHz, Methanol-$d_4$): δ 8.53 (s, 1H), 8.29 (d, J=6.2 Hz, 1H), 7.65 (d, J=6.0 Hz, 1H), 7.34-7.25 (m, 5H), 5.72-5.69 (m, 2H), 4.96 (s, 2H).

E) 1-((1-Benzyl-1H-pyrazolo[4,3-c]pyridin-4-yl)methyl)-5-bromopyridin-2(1H)-one hydrochloride To a mixture of 1-benzyl-4-(bromomethyl)-1H-pyrazolo[4,3-c]pyridine (20 mg), $K_2CO_3$ (9.15 mg), and DMF (2 mL) was added 5-bromopyridin-2(1H)-one (17.27 mg) in one portion at 20° C., then the mixture was stirred at 20° C. for 12 hours. The mixture was poured into ice-water and extracted with ethyl acetate. The combined organic phase was washed with brine, dried over $Na_2SO_4$, concentrated, and purified by HPLC to give the target compound (11 mg) as a solid.

$^1$H NMR (400 MHz, Methanol-$d_4$): δ 8.57 (s, 1H), 8.41 (d, J=7.0 Hz, 1H), 8.27 (d, J=2.7 Hz, 1H), 8.16 (d, J=7.0 Hz, 1H), 7.75 (dd, J=9.7, 2.7 Hz, 1H), 7.39-7.32 (m, 5H), 6.55 (d, J=9.7 Hz, 1H), 5.84 (s, 2H), 5.80 (s, 2H).

Example 131

1-((1-Benzyl-1H-pyrazolo[4,3-c]pyridin-4-yl) methyl)-5-ethynylpyridin-2(1H)-one hydrochloride A target compound was synthesized in a similar manner as example 76 using 1-benzyl-4-(bromomethyl)-1H-pyrazolo[4,3-c]pyridine and 5 ethynylpyridin-2(1H)-one.

$^1$H NMR (400 MHz, Methanol-$d_4$): δ 8.54 (s, 1H), 8.41 (d, J=6.85 Hz, 1H), 8.30 (d, J=1.96 Hz, 1H), 8.15 (d, J=6.85 Hz, 1H), 7.68 (dd, J=9.54, 2.32 Hz, 1H), 7.36 (s, 5H), 6.57 (d, J=9.41 Hz, 1H), 5.84 (s, 2H), 5.82 (s, 2H), 3.66 (s, 1H).

Example 132

1-((2-Benzyl-1-methyl-1H-imidazo[4,5-c]pyridin-4-yl)methyl)-5-bromopyridin-2(1H)-one

A) N-(3-Aminopyridin-4-yl)-N-methyl-2-phenylacetamide

To a solution of $N^4$-methylpyridine-3,4-diamine (5.3 g) in acetonitrile (40 mL) was added $K_2CO_3$ (11.9 g). Then a solution of 2-phenylacetyl chloride (7.32 g) in acetonitrile (40 mL) was added to the mixture dropwise at 0° C. The resulting mixture was stirred at 15° C. for 12 hours. The reaction mixture was filtered and the filtrate was concentrated to give the target compound (7.7 g) as a solid.

MS: (M+H$^+$): 242.0

B) 2-Benzyl-1-methyl-1H-imidazo[4,5-c]pyridine

To a solution of N-(3-aminopyridin-4-yl)-N-methyl-2-phenylacetamide (7.4 g) in EtOH (70 mL) and $H_2O$ (15 mL) was added NaOH (1.84 g). Then the mixture was stirred at 60° C. for 4 hours under nitrogen atmosphere. The reaction mixture was concentrated, diluted with water, and extracted with dichloromethane. The combined organic layers were washed with brine, dried over $Na_2SO_4$, and concentrated to give the target compound (4.3 g) as a solid.

C) 2-Benzyl-1-methyl-1H-imidazo[4,5-c]pyridine 5-oxide

To a solution of 2-benzyl-1-methyl-1H-imidazo[4,5-c] pyridine (1.0 g) in dichloromethane (10 mL) was added mCPBA (3.1 g) slowly. Then the mixture was stirred at 15° C. for 10 hours then at 40° C., and for 24 hours under nitrogen atmosphere. The reaction mixture was quenched with saturated sodium thiosulfate solution at 15° C., concentrated, and purified by silica gel chromatography (dichloromethane:MeOH=20:1 to 5:1) to give the target compound (0.6 g) as a solid.

MS: (M+H$^+$): 240.0

D) 2-Benzyl-1-methyl-1H-imidazo[4,5-c]pyridine-4-carbonitrile

To a solution of 2-benzyl-1-methyl-1H-imidazo[4,5-c] pyridine 5-oxide (100 mg) in dichloromethane (2 mL) was added dimethylcarbamic chloride (89.9 mg). Then trimethylsilanecarbonitrile (104 uL) was added and the mixture was stirred at 15° C. for 12 hours. The reaction mixture was quenched with water and extracted with ethyl acetate. The combined organic layers were washed with brine, dried over $Na_2SO_4$, and concentrated to give the target compound (90 mg) as a solid.

MS: (M+H$^+$): 249.0

E) Methyl 2-benzyl-1-methyl-1H-imidazo[4,5-c] pyridine-4-carboxylate

A solution of 2-benzyl-1-methyl-1H-imidazo[4,5-c]pyridine-4-carbonitrile (4.3 g) in 4 M HCl in MeOH (3.0 mL) was stirred at 60° C. for 10 hours. The reaction mixture was evaporated and adjusted to pH=7 with saturated $NaHCO_3$ solution. Then the mixture was extracted with ethyl acetate. The combined organic phase was washed with brine, dried with anhydrous $Na_2SO_4$, concentrated, and purified by silica gel chromatography (petroleum ether:ether=2:1 to dichloromethane:MeOH=10:1) to give the target compound (2.4 g) as a solid.

MS: (M+H$^+$): 282.2

F) (2-Benzyl-1-methyl-1H-imidazo[4,5-c]pyridin-4-yl)methanol

To mixture of methyl 2-benzyl-1-methyl-1H-imidazo[4,5-c]pyridine-4-carboxylate (2.4 g) and EtOH (3.0 mL) was added $NaBH_4$ (2.15 g), and the mixture was stirred at 40° C. for 10 hours. The reaction mixture was quenched by $NH_4Cl$ solution and extracted with ethyl acetate. The combined organic phase was washed with brine, dried with anhydrous $Na_2SO_4$, concentrated, and purified by silica gel chromatography (petroleum ether:ethyl acetate=2:1 to 0:100) to give the target compound (1.1 g) as a solid.

MS: (M+H$^+$): 254.2

G) 2-Benzyl-4-(bromomethyl)-1-methyl-1H-imidazo [4,5-c]pyridine

A target compound was synthesized in a similar manner as step D in example 130 using (2-benzyl-1-methyl-1H-imidazo[4,5-c]pyridin-4-yl)methanol.

$^1$H NMR (400 MHz, DMSO-$d_6$): δ 8.67 (d, J=6.1 Hz, 1H), 8.18 (d, J=6.1 Hz, 1H), 7.37-7.28 (m, 5H), 5.13 (s, 2H), 4.52 (s, 2H), 3.90 (s, 3H).

H) 1-((2-Benzyl-1-methyl-1H-imidazo[4,5-c]pyridin-4-yl)methyl)-5-bromopyridin-2(1H)-one A target compound was synthesized in a similar manner as step E in example 130 using 2-benzyl-4-(bromomethyl)-1-methyl-1H-imidazo[4,5-c]pyridine and 5-bromopyridin-2 (1H)-one.

$^1$H NMR (400 MHz, Methanol-$d_4$): δ 8.22 (d, J=5.7 Hz, 1H), 8.05 (d, J=2.4 Hz, 1H), 7.63 (dd, J=9.7, 2.7 Hz, 1H), 7.47 (d, J=5.7 Hz, 1H), 7.38-7.21 (m, 5H), 6.50 (d, J=9.5 Hz, 1H), 5.69 (s, 2H), 4.43 (s, 2H), 3.71 (s, 3H).

Example 133

1-((2-Benzyl-1-methyl-1H-imidazo[4,5-c]pyridin-4-yl)methyl)-5-ethynylpyridin-2(1H)-one A target compound was synthesized in a similar manner as example 76 using 2-benzyl-4-(bromomethyl)-1-methyl-1H-imidazo[4,5-c]pyridine and 5-ethynylpyridin-2(1H)-one.

$^1$H NMR (400 MHz, DMSO-$d_6$): δ 8.19-8.14 (m, 2H), 7.51-7.46 (m, 2H), 7.36-7.25 (m, 5H), 6.37 (d, J=9.5 Hz, 1H), 5.58 (s, 2H), 4.39 (s, 2H), 4.10 (s, 1H), 3.73 (s, 3H).

Example 134

1-(2-(1-Benzyl-5-methyl-1H-pyrazol-4-yl)-2-oxoethyl)-5-ethynyl-3-fluoropyridin-2(1H)-one A) 1-(2-(1-Benzyl-5-methyl-1H-pyrazol-4-yl)-2-oxoethyl)-3-fluoro-5-((trimethylsilyl)ethynyl)pyridin-2(1H)-one A target compound was synthesized in a similar manner as step A in example 36 using 1-(2-(1-benzyl-5-methyl-1H-pyrazol-4-yl)-2-oxoethyl)-5-bromo-3-fluoropyridin-2(1H)-one.
MS: (M+H$^+$): 422.1

B) 1-(2-(1-Benzyl-5-methyl-1H-pyrazol-4-yl)-2-oxoethyl)-5-ethynyl-3-fluoropyridin-2(1H)-one A target compound was synthesized in a similar manner as step H in example 73 using 1-(2-(1-benzyl-5-methyl-1H-pyrazol-4-yl)-2-oxoethyl)-3-fluoro-5-((trimethylsilyl)ethynyl)pyridin-2(1H)-one.
$^1$H NMR (400 MHz, Methanol-d$_4$): δ 8.22 (s, 1H), 7.70 (s, 1H), 7.44 (dd, J=2.0, 10.0 Hz, 1H), 7.37-7.27 (m, 3H), 7.16 (d, J=7.1 Hz, 2H), 5.42 (s, 2H), 5.36 (s, 2H), 3.53 (s, 1H), 2.52 (s, 3H).

Example 135

1-(2-(1-Benzyl-2,5-dimethyl-1H-imidazol-4-yl)-2-oxoethyl)-5-bromopyridin-2(1H)-one A) Ethyl 1-benzyl-2,5-dimethyl-1H-imidazole-4-carboxylate A target compound was synthesized in a similar manner as step A in example 30 using ethyl 2-acetamido-3-oxobutanoate and phenylmethanamine.

B) 1-Benzyl-2,5-dimethyl-1H-imidazole-4-carboxylic Acid

A target compound was synthesized in a similar manner as step B in example 30 using ethyl 1-benzyl-2,5-dimethyl-1H-imidazole-4-carboxylate.
MS: (M+H4): 231.1

C) 1-Benzyl-N-methoxy-N,2,5-trimethyl-1H-imidazole-4-carboxamide

A target compound was synthesized in a similar manner as step A in example 68 using 1-benzyl-2,5-dimethyl-1H-imidazole-4-carboxylic acid.
MS: (M+H$^+$): 274.1

D) 1-(1-Benzyl-2,5-dimethyl-1H-imidazol-4-yl)ethan-1-one

A target compound was synthesized in a similar manner as step B in example 68 using 1-benzyl-N-methoxy-N,2,5-trimethyl-1H-imidazole-4-carboxamide.
$^1$H NMR (400 MHz, CDCl$_3$): δ 7.30-7.22 (m, 3H), 6.87 (d, J=6.7 Hz, 2H), 4.99 (s, 2H), 2.51 (s, 3H), 2.41 (s, 3H), 2.28 (s, 3H).

E) 1-(1-Benzyl-2,5-dimethyl-1H-imidazol-4-yl)-2-bromoethan-1-one

A target compound was synthesized in a similar manner as step C in example 68 using 1-(1-benzyl-2,5-dimethyl-1H-imidazol-4-yl)ethan-1-one.
MS: (M+H$^+$): 306.9

F) 1-(2-(1-Benzyl-2,5-dimethyl-1H-imidazol-4-yl)-2-oxoethyl)-5-bromopyridin-2(1H)-one A target compound was synthesized in a similar manner as step D in example 68 using 1-(1-benzyl-2,5-dimethyl-1H-imidazol-4-yl)-2-bromoethan-1-one and 5-bromopyridin-2(1H)-one.
$^1$H NMR (400 MHz, Methanol-d$_4$): δ 7.86 (d, J=2.3 Hz, 1H), 7.65 (dd, J=9.6, 2.5 Hz, 1H), 7.45-7.28 (m, 3H), 7.04 (d, J=7.3 Hz, 2H), 6.54 (d, J=9.5 Hz, 1H), 5.42 (s, 2H), 5.27 (s, 2H), 2.48 (s, 3H), 2.44-2.34 (m, 3H).

Example 136

5-Ethynyl-1-(2-(1-(4-fluorobenzyl)-2,5-dimethyl-1H-imidazol-4-yl)-2-oxoethyl)pyridin-2(1H)-one A) 1-(2-(1-(4-Fluorobenzyl)-2,5-dimethyl-1H-imidazol-4-yl)-2-oxoethyl)-5-((trimethylsilyl)ethynyl)pyridin-2(1H)-one A target compound was synthesized in a similar manner as step A in example 36 using 5-bromo-1-(2-(1-(4-fluorobenzyl)-2,5-dimethyl-1H-imidazol-4-yl)-2-oxoethyl)pyridin-2(1H)-one.
MS: (M+H$^+$): 436.2

B) 5-Ethynyl-1-(2-(1-(4-fluorobenzyl)-2,5-dimethyl-1H-imidazol-4-yl)-2-oxoethyl)pyridin-2(1H)-one A target compound was synthesized in a similar manner as step H in example 73 using 1-(2-(1-(4-fluorobenzyl)-2,5-dimethyl-1H-imidazol-4-yl)-2-oxoethyl)-5-((trimethylsilyl)ethynyl)pyridin-2(1H)-one.
$^1$H NMR (400 MHz, CDCl$_3$): δ 7.49-7.36 (m, 2H), 7.11-7.01 (m, 2H), 6.97-6.90 (m, 2H), 6.56 (d, J=9.3 Hz, 1H), 5.41 (s, 2H), 5.05 (s, 2H), 3.00 (s, 1H), 2.46 (s, 3H), 2.35 (s, 3H).

Example 137

5-Bromo-1-(2-(1-(4-fluorobenzyl)-5-methyl-1H-pyrazol-4-yl)-2-oxoethyl)pyridin-2(1H)-one A) 1-(1-(4-Fluorobenzyl)-5-methyl-1H-pyrazol-4-yl)ethan-1-one A target compound was synthesized in a similar manner as step A in example 32 using (4-fluorobenzyl)hydrazine and 3-((dimethylamino)methylene)pentane-2,4-dione.
$^1$H NMR (400 MHz, CDCl$_3$): δ 7.87 (s, 1H), 7.06-7.14 (m, 2H), 6.94-7.06 (m, 2H), 5.22-5.29 (m, 2H), 2.50 (s, 3H), 2.42 (s, 3H).

B) 2-Bromo-1-(1-(4-fluorobenzyl)-5-methyl-1H-pyrazol-4-yl)ethan-1-one

A target compound was synthesized in a similar manner as step C in example 68 using 1-(1-(4-Fluorobenzyl)-5-methyl-1H-pyrazol-4-yl)ethan-1-one.

C) 5-Bromo-1-(2-(1-(4-fluorobenzyl)-5-methyl-1H-pyrazol-4-yl)-2-oxoethyl)pyridin-2(1H)-one A target compound was synthesized in a similar manner as step D in example 68 using 2-bromo-1-(1-(4-fluorobenzyl)-5-methyl-1H-pyrazol-4-yl)ethan-1-one and 5-bromopyridin-2(1H)-one.

$^1$H NMR (400 MHz, CDCl$_3$): δ 8.04 (s, 1H), 7.42 (dd, J=2.6, 9.7 Hz, 1H), 7.35 (d, J=2.6 Hz, 1H), 7.09-7.17 (m, 2H), 6.99-7.07 (m, 2H), 6.54 (d, J=10.1 Hz, 1H), 5.30 (s, 2H), 5.10 (s, 2H), 2.53 (s, 3H).

Example 138

3-((4-(2-(5-Bromo-2-oxopyridin-1(2H)-yl)acetyl)-5-methyl-1H-pyrazol-1-yl)methyl)benzonitrile

A) 3-((4-Acetyl-5-methyl-1H-pyrazol-1-yl)methyl)benzonitrile

A target compound was synthesized in a similar manner as step A in example 32 using 3-(hydrazinylmethyl)benzonitrile and 3-((dimethylamino)methylene)pentane-2,4-dione.

$^1$H NMR (400 MHz, DMSO-d$_6$): δ 8.07 (d, J=6.6 Hz, 1H), 7.78 (t, J=6.4 Hz, 1H), 7.65-7.35 (m, 2H), 7.49-7.42 (m, 1H), 5.51-5.33 (m, 2H), 2.49-2.46 (m, 3H), 2.37 (d, J=6.6 Hz, 3H).

B) 3-((4-(2-Bromoacetyl)-5-methyl-1H-pyrazol-1-yl)methyl)benzonitrile

A target compound was synthesized in a similar manner as step C in example 68 using 3-((4-Acetyl-5-methyl-1H-pyrazol-1-yl)methyl)benzonitrile.
MS: (M+H$^+$): 317.9

C) 3-((4-(2-(5-Bromo-2-oxopyridin-1(2H)-yl)acetyl)-5-methyl-1H-pyrazol-1-yl)methyl)benzonitrile A target compound was synthesized in a similar manner as step D in example 68 using 3-((4-(2-bromoacetyl)-5-methyl-1H-pyrazol-1-yl)methyl)benzonitrile and 5-bromopyridin-2(1H)-one.

$^1$H NMR (400 MHz, Methanol-d$_4$): δ 8.24 (s, 1H), 7.83 (d, J=2.7 Hz, 1H), 7.71-7.63 (m, 2H), 7.58-7.53 (m, 2H), 7.50-7.45 (m, 1H), 6.53 (d, J=9.7 Hz, 1H), 5.48 (s, 2H), 5.31-5.25 (m, 2H), 2.55 (s, 3H).

Example 139

3-((4-(2-(5-Ethynyl-2-oxopyridin-1(2H)-yl)acetyl)-5-methyl-1H-pyrazol-1-yl)methyl)benzonitrile

A) 3-((5-Methyl-4-(2-(2-oxo-5-((trimethylsilyl)ethynyl)pyridin-1(2H)-yl)acetyl)-1H-pyrazol-1-yl)methyl)benzonitrile A target compound was synthesized in a similar manner as step A in example 36 using 3-((4-(2-(5-bromo-2-oxopyridin-1(2H)-yl)acetyl)-5-methyl-1H-pyrazol-1-yl)methyl)benzonitrile.

MS: (M+H$^+$): 429.3

B) 3-((4-(2-(5-Ethynyl-2-oxopyridin-1(2H)-yl)acetyl)-5-methyl-1H-pyrazol-1-yl)methyl)benzonitrile A target compound was synthesized in a similar manner as step H in example 73 using 3-((5-methyl-4-(2-(2-oxo-5-((trimethylsilyl)ethynyl)pyridin-1(2H)-yl)acetyl)-1H-pyrazol-1-yl)methyl)benzonitrile.

$^1$H NMR (400 MHz, Methanol-d$_4$): δ 8.24 (s, 1H), 7.85 (d, J=2.4 Hz, 1H), 7.68 (d, J=7.5 Hz, 1H), 7.60-7.56 (m, 1H), 7.54 (d, J=4.6 Hz, 2H), 7.50-7.46 (m, 1H), 6.54 (d, J=9.5 Hz, 1H), 5.48 (s, 2H), 5.30 (s, 2H), 3.50 (s, 1H), 2.55 (s, 3H).

Example 140

5-Ethynyl-1-(2-(1-(4-fluorobenzyl)-5-methyl-1H-pyrazol-4-yl)-2-oxoethyl)pyridin-2(1H)-one

A) 1-(2-(1-(4-Fluorobenzyl)-5-methyl-1H-pyrazol-4-yl)-2-oxoethyl)-5-((trimethylsilyl)ethynyl)pyridin-2(1H)-one A target compound was synthesized in a similar manner as step A in example 36 using 5-bromo-1-(2-(1-(4-fluorobenzyl)-5-methyl-1H-pyrazol-4-yl)-2-oxoethyl)pyridin-2(1H)-one.

B) 5-Ethynyl-1-(2-(1-(4-fluorobenzyl)-5-methyl-1H-pyrazol-4-yl)-2-oxoethyl)pyridin-2(1H)-one A target compound was synthesized in a similar manner as step H in example 73 using 1-(2-(1-(4-fluorobenzyl)-5-methyl-1H-pyrazol-4-yl)-2-oxoethyl)-5-((trimethylsilyl)ethynyl)pyridin-2(1H)-one.

$^1$H NMR (400 MHz, CDCl$_3$): δ 8.04 (s, 1H), 7.39-7.49 (m, 2H), 7.10-7.16 (m, 2H), 7.01-7.07 (m, 2H), 6.57 (d, J=9.4 Hz, 1H), 5.30 (s, 2H), 5.12 (s, 2H), 3.01 (s, 1H), 2.53 (s, 3H).

Example 141

1-(2-(1-Benzyl-5-methyl-1H-pyrazol-4-yl)-2-oxoethyl)-5-bromo-3-fluoropyridin-2(1H)-one A target compound was synthesized in a similar manner as step D in example 34 using 2-bromo-1-(5-methyl-1-(pyridin-3-ylmethyl)-1H-pyrazol-4-yl)ethan-1-one and 5-bromo-3-fluoropyridin-2(1H)-one.

$^1$H NMR (400 MHz, CDCl$_3$): δ 8.29 (s, 1H), 7.86 (s, 1H), 7.79 (dd, J=2.3, 9.7 Hz, 1H), 7.41-7.26 (m, 3H), 7.16 (d, J=7.2 Hz, 2H), 5.42 (s, 2H), 5.30 (s, 2H), 2.48-2.47 (m, 3H).

Example 142

1-(2-(1-Benzyl-5-methyl-1H-pyrazol-4-yl)-2-oxoethyl)-5-bromo-2-oxo-1,2-dihydropyridine-3-carbonitrile A target compound was synthesized in a similar manner as step D in example 34 using 2-bromo-1-(5-methyl-1-(pyridin-3-ylmethyl)-1H-pyrazol-4-yl)ethan-1-one and 5-bromo-2-oxo-1,2-dihydropyridine-3-carbonitrile.

¹H NMR (400 MHz, DMSO-d₆): δ 68.51 (d, J=2.8 Hz, 1H), 8.38 (d, J=2.8 Hz, 1H), 8.30 (s, 1H), 7.35 (d, J=7.5 Hz, 3H), 7.16 (d, J=7.5 Hz, 2H), 5.42 (s, 2H), 5.31 (s, 2H), 2.49-2.47 (m, 3H).

Example 143

1-(2-(1-Benzyl-5-methyl-1H-pyrazol-4-yl)-2-oxoethyl)-4-vinylpyridin-2(1H)-one

A target compound was synthesized in a similar manner as example 76 using 1-(2-(1-benzyl-5-methyl-1H-pyrazol-4-yl)-2-oxoethyl)-4-bromopyridin-2(1H)-one and potassium vinyltrifluoroborate.

¹H NMR (400 MHz, DMSO-d₆): δ 8.27 (s, 1H), 7.55 (d, J=7.1 Hz, 1H), 7.39-7.32 (m, 2H), 7.32-7.26 (m, 1H), 7.15 (d, J=7.3 Hz, 2H), 6.60 (dd, J. 11.0, 17.6 Hz, 1H), 6.50 (dd, J=1.9, 7.2 Hz, 1H), 6.38 (d, J=1.8 Hz, 1H), 6.02 (d, J=17.6 Hz, 1H), 5.52 (d, J=11.0 Hz, 1H), 5.41 (s, 2H), 5.19 (s, 2H), 2.48 (s, 3H).

Example 144

1-(2-(1-(4-Fluorobenzyl)-5-methyl-1H-pyrazol-3-yl)-2-oxoethyl)-5-(prop-1-yn-1-yl)pyridin-2(1H)-one A target compound was synthesized in a similar manner as example 76 using 5-bromo-1-(2-(1-(4-fluorobenzyl)-5-methyl-1H-pyrazol-3-yl)-2-oxoethyl)pyridin-2(1H)-one and potassium trimethyl(prop-1-yn-1-yl)borate.

¹H NMR (400 MHz, CDCl₃): δ 7.37-7.31 (m, 2H), 7.17-7.10 (m, 2H), 7.09-7.01 (m, 2H), 6.63 (s, 1H), 6.53 (d, J=10.1 Hz, 1H), 5.37 (s, 2H), 5.32 (s, 2H), 2.23 (s, 3H), 1.99 (s, 3H).

Example 145

1-(2-(1-Benzyl-5-methyl-1H-pyrazol-3-yl)-2-oxoethyl)-5-ethynylpyridin-2(1H)-one

A) 1-(2-(1-benzyl-5-methyl-1H-pyrazol-3-yl)-2-oxoethyl)-5-((trimethylsilyl)ethynyl)pyridin-2(1H)-one A target compound was synthesized in a similar manner as step A in example 36 using 1-(2-(1-benzyl-5-methyl-1H-pyrazol-3-yl)-2-oxoethyl)-5-bromopyridin-2(1H)-one.

MS: (M+H⁺): 404.1

B) 1-(2-(1-Benzyl-5-methyl-1H-pyrazol-3-yl)-2-oxoethyl)-5-ethynylpyridin-2(1H)-one A target compound was synthesized in a similar manner as step H in example 73 using 1-(2-(1-benzyl-5-methyl-1H-pyrazol-3-yl)-2-oxoethyl)-5-((trimethylsilyl)ethynyl)pyridin-2(1H)-one.

¹H NMR (400 MHz, DMSO-d₆): δ 8.02 (d, J=2.5 Hz, 1H), 7.49 (dd, J=9.4, 2.6 Hz, 1H), 7.40-7.34 (m, 2H), 7.33-7.28 (m, 1H), 7.20-7.15 (m, 2H), 6.64 (d, J=0.61 Hz, 1H), 6.40 (d, J=9.4 Hz, 1H), 5.46 (s, 2H), 5.34 (s, 2H), 4.08 (s, 1H), 2.26 (s, 3H).

Example 146

1-(2-(1-Benzyl-5-methyl-1H-pyrazol-3-1)-2-oxoethyl)-5-bromopyridin-2(1H)-one

A) 1-(4-Fluorobenzyl)-N-methoxy-N,5-dimethyl-1H-pyrazole-3-carboxamide

A target compound was synthesized in a similar manner as step A in example 68 using 1-(4-fluorobenzyl)-5-methyl-1H-pyrazole-3-carboxylic acid.

MS: (M+H⁺): 260.2

B) 1-(1-(4-Fluorobenzyl)-5-methyl-1H-pyrazol-3-yl)ethan-1-one

A target compound was synthesized in a similar manner as step B in example 68 using 1-(4-fluorobenzyl)-N-methoxy-N,5-dimethyl-1H-pyrazole-3-carboxamide

MS: (M+H⁺): 215.1

C) 2-Bromo-1-(1-(4-fluorobenzyl)-5-methyl-1H-pyrazol-3-yl)ethan-1-one

A target compound was synthesized in a similar manner as step C in example 68 using 1-(1-(4-Fluorobenzyl)-5-methyl-1H-pyrazol-3-yl)ethan-1-one ¹H NMR (400 MHz, CDCl₃): δ 7.37-7.27 (m, 3H), 7.11 (d, J=6.8 Hz, 2H), 6.65 (s, 1H), 5.34 (s, 2H), 4.60 (s, 2H), 2.22 (s, 3H).

D) 1-(2-(1-Benzyl-5-methyl-1H-pyrazol-3-yl)-2-oxoethyl)-5-bromopyridin-2(1H)-one A target compound was synthesized in a similar manner as step D in example 34 using 2-bromo-1-(1-(4-fluorobenzyl)-5-methyl-1H-pyrazol-3-yl)ethan-1-one and 5-bromopyridin-2(1H)-one.

¹H NMR (400 MHz, DMSO-d₆): δ 7.99 (d, J=2.9 Hz, 1H), 7.57 (dd, J=9.7, 2.9 Hz, 1H), 7.40-7.33 (m, 2H), 7.33-7.27 (m, 1H), 7.16 (d, J=7.3 Hz, 2H), 6.63 (s, 1H), 6.39 (d, J=9.7 Hz, 1H), 5.45 (s, 2H), 5.31 (s, 2H), 2.26 (s, 3H).

Example 147—Liver Fibrosis Model

To test whether the compounds described herein act as S1PR₂ antagonists in vivo, their effect was tested in BDL, a clinically relevant liver cholestasis model. The common bile duct was ligated and resected as described herein to cause biliary epithelial damage. One day post-surgery, mice were treated daily with 30 mg/kg of compound 29 or JTE-013:

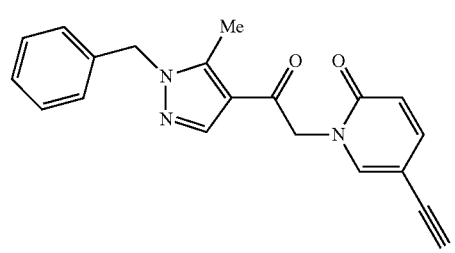

29

-continued

JTE-013

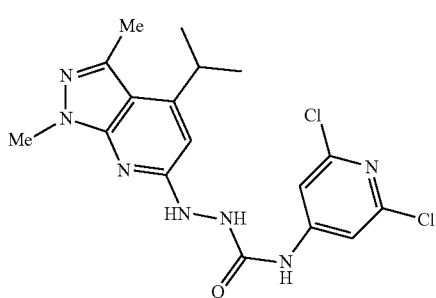

Figure 1B:
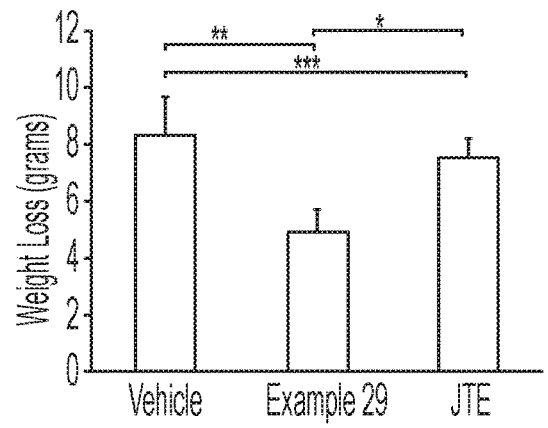
FIG. 1B is a plot of weight loss for mice treated with compound 29 (30 mg/kg), JTE-013 (30 mg/kg) or vehicle in bile duct ligated mice.
Figure 2A:
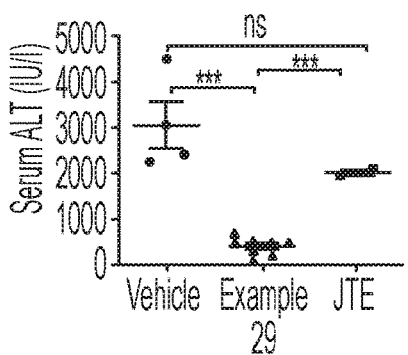
FIG. 2A is a plot of serum ALT levels for mice treated with compound 29 (30 mg/kg), JTE-013 (30 mg/kg) or vehicle in bile duct ligated mice.
Figure 2B:
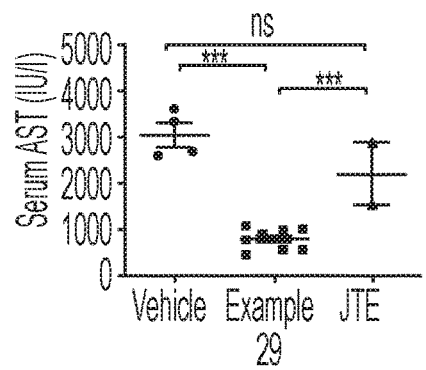
FIG. 2B is a plot of serum AST levels for mice treated with compound 29 (30 mg/kg), JTE-013 (30 mg/kg) or vehicle in bile duct ligated mice.
Figure 2C:
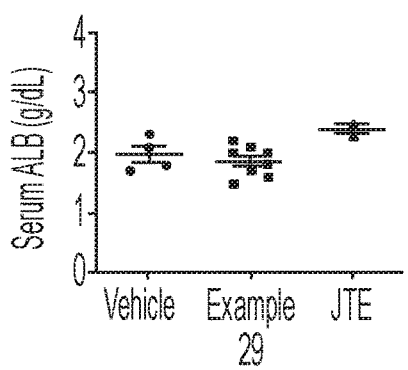
FIG. 2C is a plot of serum ALB levels for mice treated with compound 29 (30 mg/kg), JTE-013 (30 mg/kg) or vehicle in bile duct ligated mice.
Figure 2D:
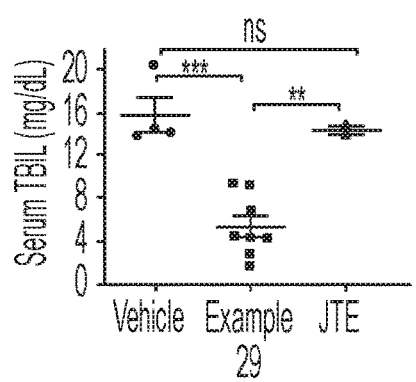
FIG. 2D is a plot of serum total bilirubin (TBIL) levels for mice treated with compound 29 (30 mg/kg), JTE-013 (30 mg/kg) or vehicle in bile duct ligated mice.

In this double-blind mouse BDL study, the compounds were administered orally by gavage. As shown in FIG. 1A, mortality in this study was elevated, with survival of mice treated with JTE-013 lower than that observed for the vehicle arm. In contrast, mortality was substantially reduced for mice treated with compound 29. In addition, mice treated with compound 29 lost significantly less body weight relative to vehicle and JTE-013 treatment arms. See FIG. 1B.

Compound 29 was statistically differentiated from vehicle and JTE-013 in its impact on serum ALT, AST, and total bilirubin (TBIL). See FIGS. 2A-2D. Serum ALB levels remained constant in all treatment arms, indicating no preexisting chronic liver disease in these mice.

Figure 3:
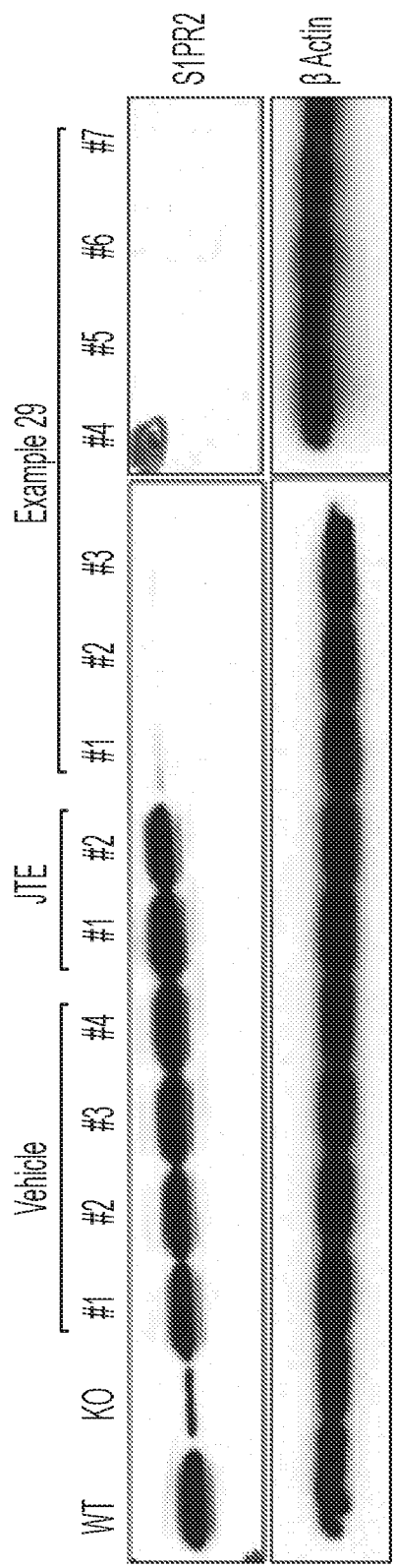
FIG. 3 is an immunoblot analysis of liver samples of S1PR₂ levels in liver tissue from a mouse BDL study. Each vehicle or drug treatment lane represents results obtained from a single animal (and its treatment dosage) that survived to the end of an eight-day study. Liver tissues were collected at necropsy, flash frozen, and pulverized. The powder was resuspended in RIPA lysis buffer with PI, NAF, and sodium deoxy cholate. Blots were probed for S1PR₂ and a housekeeping gene (beta-acting) to ensure comparable protein loading.

S1PR$_2$ levels were obtained from this mouse BDL study via immunoblot analysis of liver samples (FIG. 3). Liver samples collected in an identical manner from S1PR$_2$ global KO and WT mice served as positive controls. S1PR$_2$ is visible in the WT-, vehicle-, and JTE-013-treated controls. However, in animals treated with compound 29 only nominal levels of S1PR$_2$ are present. In the KO lane, a potentially nonspecific band was noted whose identity is unknown; while it may indeed be residual S1PR$_2$, it was not observed in prior studies.

In summary, in a murine BDL model, a compound 29 dose of 10 mg/kg orally once daily for 10 days resulted in increased survival, reduced ALT and AST levels, coupled to a reduction in fibrosis (collagen deposition) as exhibited by Sirius Red and Mason Trichrome staining (experiments not shown). Furthermore, the livers of animals treated with compound 29 (10 mg/kg) exhibited reduced S1PR$_2$ levels, indicating compound 29 functioned to inhibit S1PR$_2$ through degrading the receptor in vivo.

In a separate experiment, one day post-surgery, mice were treated daily with 10 mg/kg of compound 34, 30 mg/kg of compound 34 or vehicle:

34

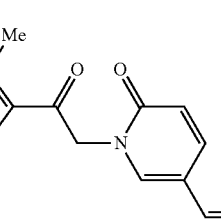

Figure 4:
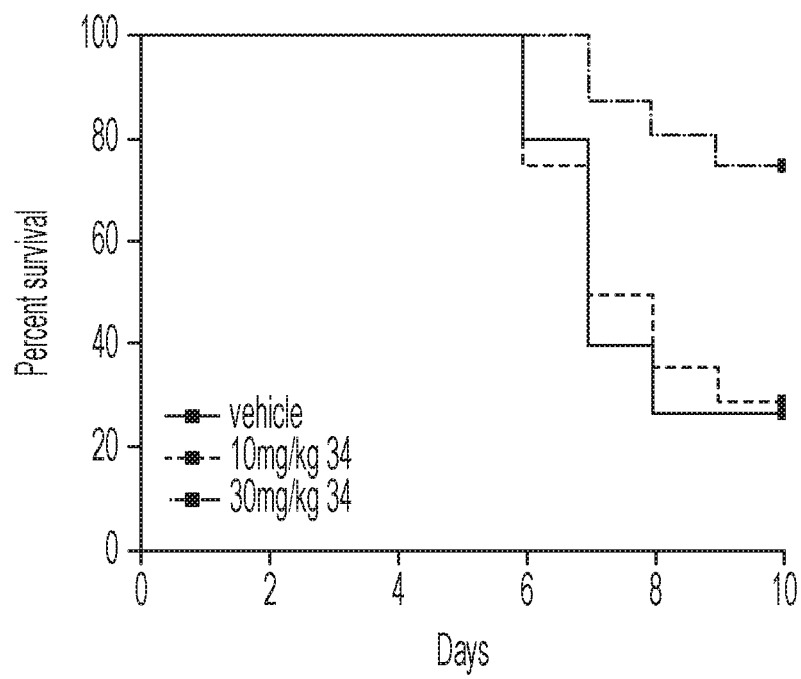
FIG. 4 is a plot of percent survival as a function of days post bile duct ligation (BDL) showing the survival of mice treated with compound 34 (10 mg/kg and 30 mg/kg) or vehicle in bile duct ligated mice.
Figure 5:
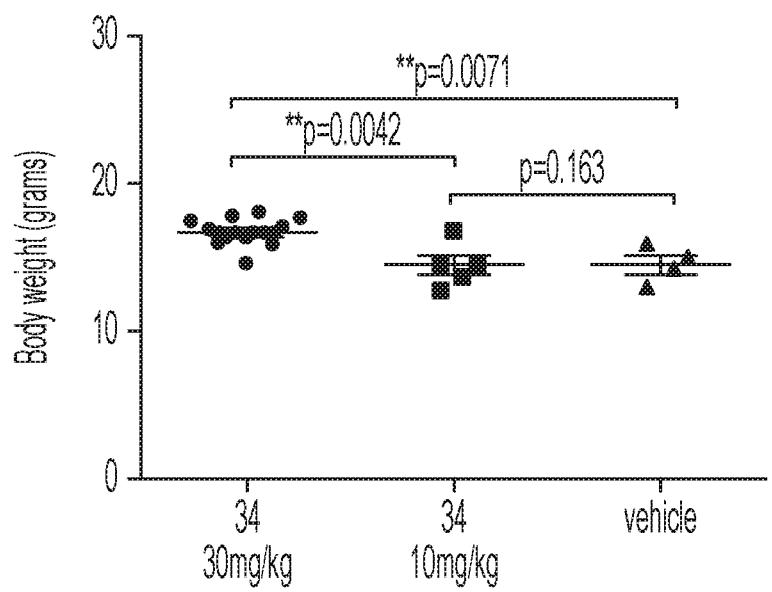
FIG. 5 is a plot of weight loss for mice treated with compound 34 (10 mg/kg and 30 mg/kg) or vehicle in bile duct ligated mice.

In this double-blind mouse BDL study, the compounds were administered orally by gavage. As shown in FIG. 4, mortality was substantially reduced for mice treated with 30 mg/kg compound 34 relative to vehicle. In addition, mice treated with compound 34 lost significantly less body weight relative to the vehicle treatment arm. See FIG. 5.

Figure 6A:
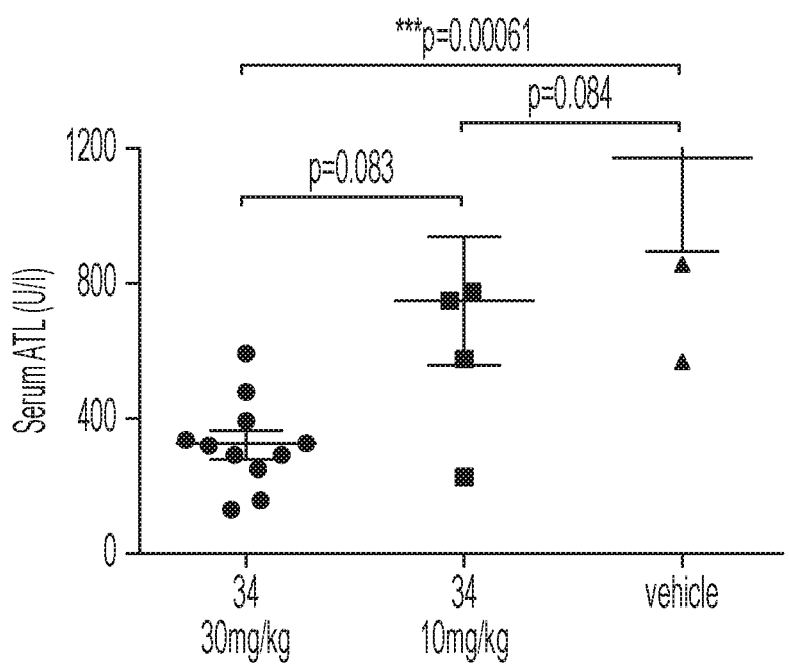
FIG. 6A is a plot of serum ALT levels for mice treated with compound 34 (10 mg/kg and 30 mg/kg) or vehicle in bile duct ligated mice.
Figure 6B:
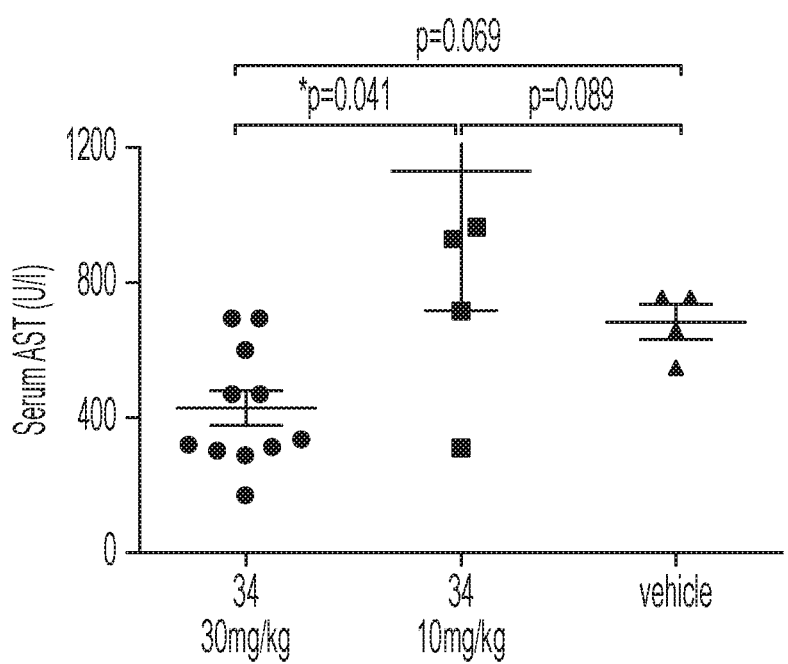
FIG. 6B is a plot of serum AST levels for mice treated with compound 34 (10 mg/kg and 30 mg/kg) or vehicle in bile duct ligated mice.

Compound 34 was statistically differentiated from vehicle in its impact on serum ALT and AST. See FIGS. 6A-6B.

Figure 7:
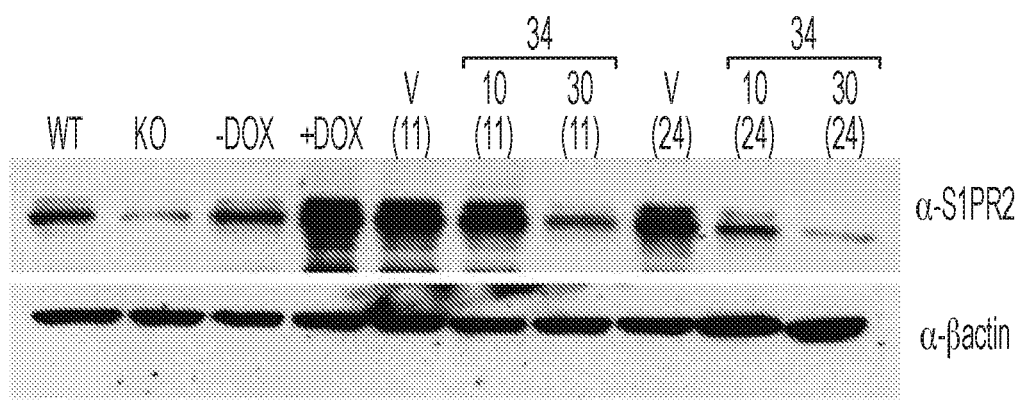
FIG. 7 is an immunoblot analysis of liver samples of S1PR₂ levels in liver tissue from a mouse BDL study. Each vehicle or drug treatment lane represents results obtained from a single animal (and its treatment dosage) that survived to the end of a ten-day study. Liver tissues were collected at necropsy, flash frozen, and pulverized. The powder was resuspended in RIPA lysis buffer with PI, NAF, and sodium deoxy cholate. Blots were probed for S1PR₂ and a housekeeping gene (beta-acting) to ensure comparable protein loading.

S1PR$_2$ levels were obtained from this mouse BDL study via immunoblot analysis of liver samples (FIG. 7). Liver samples collected in an identical manner from S1PR$_2$ global KO and WT mice served as positive controls. S1PR$_2$ is visible in the WT- and vehicle-treated controls. However, in animals treated with 30 mg/kg compound 34 only nominal levels of S1PR$_2$ are present. In the KO lane, a potentially nonspecific band was noted whose identity is unknown; while it may indeed be residual S1PR$_2$, it was not observed in prior studies.

In summary, in a murine BDL model, a compound 34 dose of 30 mg/kg orally once daily for 10 days resulted in increased survival, reduced ALT and AST levels, coupled to a reduction in fibrosis (collagen deposition) as exhibited by Sirius Red and Mason Trichrome staining (experiments not shown). Furthermore, the livers of animals treated with compound 34 (30 mg/kg) exhibited reduced S1PR$_2$ levels, indicating compound 34 functioned to inhibit S1PR$_2$ through degrading the receptor in vivo.

Example 148

Selected compounds described herein were evaluated using the GLISA RhoA activation—Antagonist Assay ("GLISA antagonist assay) and the FLIPR calcium activation—Antagonist Assay ("FLIPR antagonist assay") described herein. The results from the evaluation of the compounds are shown in Table 2.

TABLE 2

| Compound ID | GLISA antagonist assay | | FLIPR antagonist assay IC$_{50}$ (nM) |
|---|---|---|---|
| | IC$_{50}$ (nM) | % inhibition at 1 µM | |
| 1 | 52 | 87 | 58 |
| 2 | 1470 | 57 | NT |
| 3 | 134 | 69 | 89 |
| 4 | 26 | 86 | NT |
| 5 | | 48 | NT |
| 6 | | 29 | NT |
| 7 | | 58 | NT |
| 8 | | 20 | NT |
| 9 | | 32 | NT |
| 10 | | 39 | NT |
| 11 | | 30 | NT |
| 12 | | 41 | NT |
| 13 | | 29 | NT |
| 14 | | 35 | NT |
| 15 | | 70 | NT |
| 16 | | 39 | NT |
| 17 | | 63 | NT |
| 18 | | 76 | NT |
| 19 | | 44 | NT |
| 20 | | 46 | NT |
| 21 | | 42 | NT |
| 22 | 793 | 73 | NT |
| 23 | 297 | 69 | NT |
| 24 | | 73 | NT |
| 25 | | 39 | NT |
| 26 | 194 | 55 | NT |
| 27 | 4.9 | 92 | 11 |
| 28 | | 58 | NT |
| 29 | 69 | 79 | 23 |
| 30 | 595 | 64 | NT |
| 31 | 253 | 69 | NT |
| 32 | | <10 | 8700 |
| 33 | | 14 | 5600 |
| 34 | 82 | 79 | 150 |
| 35 | | 69 | 386 |
| 36 | | <10 | 9800 |

TABLE 2-continued

| | GLISA antagonist assay | | FLIPR antagonist assay |
|---|---|---|---|
| Compound ID | $IC_{50}$ (nM) | % inhibition at 1 μM | $IC_{50}$ (nM) |
| 37 | | 15 | 4400 |
| 38 | | 17 | 3600 |
| 39 | | 69 | 364 |
| 40 | | 67 | 395 |
| 41 | | 63 | 694 |
| 42 | | 64 | 567 |
| 43 | 200 | 70 | 297 |
| 44 | >10000 | | NT |
| 45 | >10000 | | NT |
| 46 | >10000 | | NT |
| 47 | >10000 | | NT |
| 48 | >10000 | | NT |
| 49 | >10000 | | NT |
| 50 | >10000 | | NT |
| 51 | >10000 | | NT |
| 52 | >10000 | | NT |
| 53 | >10000 | | NT |
| 54 | >10000 | | NT |
| 55 | 110 | | NT |
| 56 | 200 | | NT |
| 57 | | 10 | NT |
| 58 | | <10 | NT |
| 59 | | <10 | NT |
| 60 | | <10 | NT |
| 61 | | 18 | NT |
| 62 | | 11 | NT |
| 63 | | 17 | NT |
| 64 | | <10 | NT |
| 65 | | 11 | NT |
| 66 | | <10 | NT |
| 67 | | 42 | NT |
| 68 | | 18 | NT |
| 69 | 50 | | NT |
| 70 | 181 | | NT |
| 71 | 22 | | NT |
| 72 | 91 | | NT |
| 73 | 59 | | NT |
| 74 | 46 | | NT |
| 75 | 58 | | NT |
| 76 | 130 | | NT |
| 77 | 100 | | NT |
| 78 | 43 | | NT |
| 79 | 50 | | NT |
| 80 | 97 | | NT |
| 81 | 181 | | NT |
| 82 | 74 | | NT |
| 83 | 82 | | NT |
| 84 | 43 | | NT |
| 85 | 108 | | NT |
| 86 | 92 | | NT |
| 87 | 107 | | NT |
| 88 | 72 | | NT |
| 89 | 65 | | NT |
| 90 | | <10 | NT |
| 91 | | 12 | NT |
| 92 | | 31 | NT |
| 93 | | 10 | NT |
| 130 | 140 | | NT |
| 131 | 58 | | NT |

Additional compounds contemplated herein include those in Table 3:

TABLE 3

| Chemical name | Structure |
|---|---|
| 1-(2-(2-benzyloxazol-4-yl)-2-oxoethyl)-5-vinylpyridin-2(1H)-one | 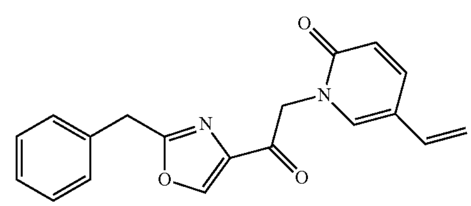 [SMILES: C=Cc1ccc(=O)n(CC(=O)c2coc(Cc3ccccc3)n2)c1] |
| 1-(2-(2-benzyloxazol-4-yl)-2-oxoethyl)-5-ethynylpyridin-2(1H)-one | 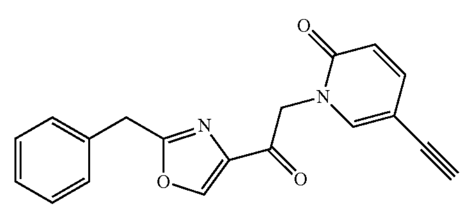 [SMILES: C#Cc1ccc(=O)n(CC(=O)c2coc(Cc3ccccc3)n2)c1] |
| 1-(2-(2-benzylthiazol-4-yl)-2-oxoethyl)-5-vinylpyridin-2(1H)-one | 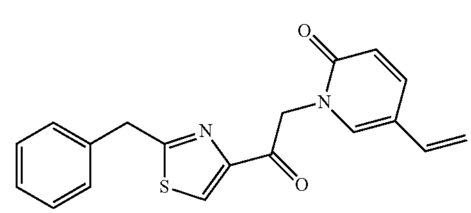 [SMILES: C=Cc1ccc(=O)n(CC(=O)c2csc(Cc3ccccc3)n2)c1] |

TABLE 3-continued

| Chemical name | Structure |
|---|---|
| 1-(2-(2-benzylthiazol-4-yl)-2-oxoethyl)-5-ethynylpyridin-2(1H)-one | 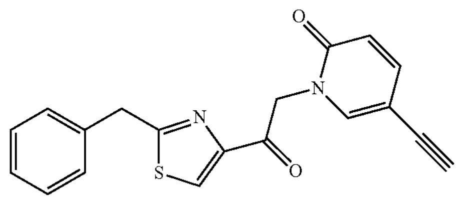 |
| 1-(2-(2-benzyloxazol-5-yl)-2-oxoethyl)-5-vinylpyridin-2(1H)-one | |
| 1-(2-(2-benzyloxazol-5-yl)-2-oxoethyl)-5-ethynylpyridin-2(1H)-one | 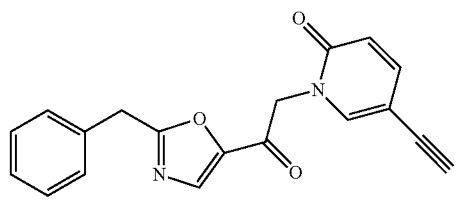 [SMILES: C#Cc1ccc(=O)n(CC(=O)c2cnc(Cc3ccccc3)o2)c1] |
| 1-(2-(2-benzylthiazol-5-yl)-2-oxoethyl)-5-vinylpyridin-2(1H)-one | 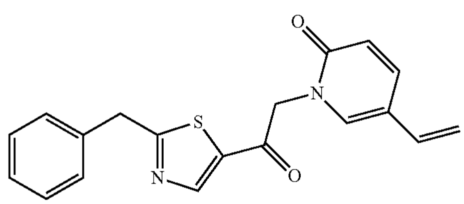 [SMILES: C=Cc1ccc(=O)n(CC(=O)c2cnc(Cc3ccccc3)s2)c1] |
| 1-(2-(2-benzylthiazol-5-yl)-2-oxoethyl)-5-ethynylpyridin-2(1H)-one | 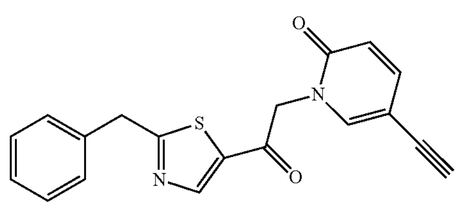 |
| 1-(2-(4-benzyloxazol-2-yl)-2-oxoethyl)-5-vinylpyridin-2(1H)-one | 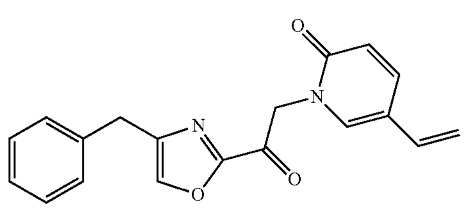 [SMILES: C=Cc1ccc(=O)n(CC(=O)c2nc(Cc3ccccc3)co2)c1] |
| 1-(2-(4-benzyloxazol-2-yl)-2-oxoethyl)-5-ethynylpyridin-2(1H)-one | 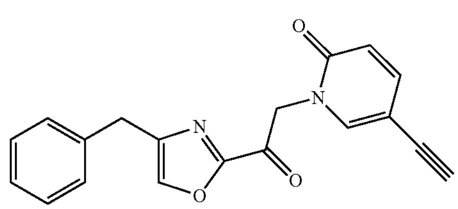 [SMILES: C#Cc1ccc(=O)n(CC(=O)c2nc(Cc3ccccc3)cs2)c1] |

TABLE 3-continued

| Chemical name | Structure |
|---|---|
| 1-(2-(4-benzylthiazol-2-yl)-2-oxoethyl)-5-vinylpyridin-2(1H)-one | 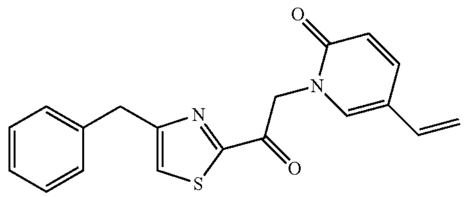 |
| 1-(2-(4-benzylthiazol-2-yl)-2-oxoethyl)-5-ethynylpyridin-2(1H)-one | |
| 1-(2-(1-benzyl-5-(methyl-d3)-1H-pyrazol-4-yl)-2-oxoethyl)-5-vinylpyridin-2(1H)-one | |
| 5-acetyl-1-(2-(1-benzyl-5-methyl-1H-pyrazol-4-yl)-2-oxoethyl)pyridin-2(1H)-one | 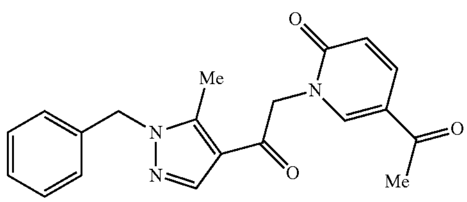 [SMILES: CC(=O)c1ccc(=O)n(CC(=O)c2cnn(Cc3ccccc3)c2C)c1] |
| 1-(2-(1-benzyl-5-methyl-1H-pyrazol-4-yl)-2-oxoethyl)-2-oxo-5-vinyl-1,2-dihydropyridine-3-carbonitrile | 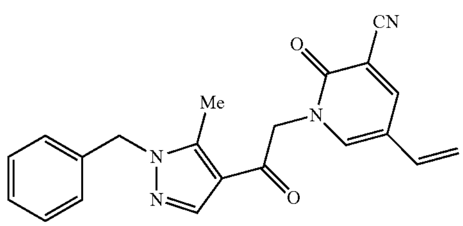 |
| 1-(2-(3-benzyl-4-methylisoxazol-5-yl)-2-oxoethyl)-5-vinylpyridin-2(1H)-one | 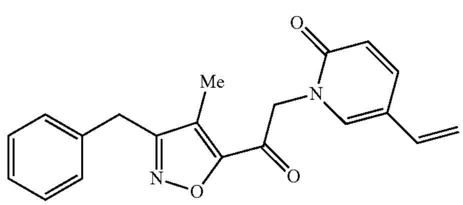 [SMILES: C=Cc1ccc(=O)n(CC(=O)c2onc(Cc3ccccc3)c2C)c1] |
| 1-(2-(3-benzyl-4-methylisoxazol-5-yl)-2-oxoethyl)-5-ethynylpyridin-2(1H)-one | 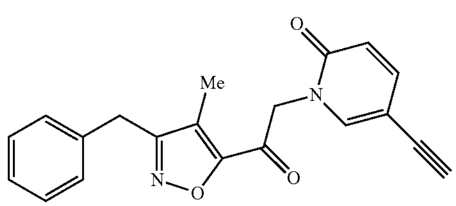 [SMILES: C#Cc1ccc(=O)n(CC(=O)c2onc(Cc3ccccc3)c2C)c1] |
| 1-(2-(1-benzyl-5-methyl-1H-pyrazol-4-yl)-2-oxoethyl)-3-vinylpyridin-2(1H)-one | 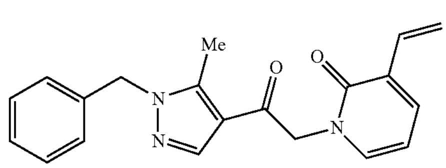 [SMILES: C=Cc1cccn(CC(=O)c2cnn(Cc3ccccc3)c2C)c1=O] |

TABLE 3-continued

| Chemical name | Structure |
|---|---|
| 1-(2-(1-benzyl-5-methyl-1H-pyrazol-4-yl)-2-oxoethyl)-3-fluoro-5-vinylpyridin-2(1H)-one | 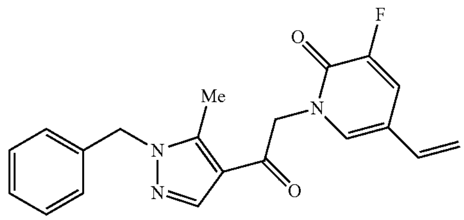 [SMILES: C=Cc1cc(F)c(=O)n(CC(=O)c2cnn(Cc3ccccc3)c2C)c1] |
| 2-(2-(1-benzyl-5-methyl-1H-pyrazol-4-yl)ethoxy)-5-vinylpyridine | 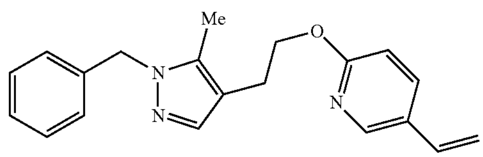 [SMILES: C=Cc1ccc(OCCc2cnn(Cc3ccccc3)c2C)nc1] |
| 1-(2-(1-benzyl-5-methyl-1H-pyrazol-4-yl)-2-oxoethyl)-2-oxo-5-(3,3,3-trifluoroprop-1-en-2-yl)-1,2-dihydropyridine-3-carbonitrile | 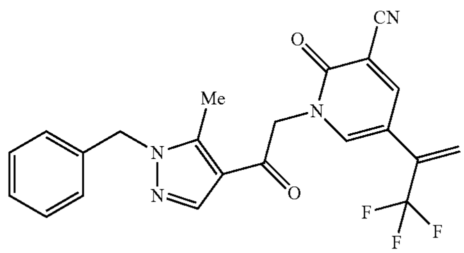 [SMILES: C=C(c1cc(C#N)c(=O)n(CC(=O)c2cnn(Cc3ccccc3)c2C)c1)C(F)(F)F] |
| 1-(2-(1-benzyl-5-methyl-1H-pyrazol-4-yl)-2-oxoethyl)-2-oxo-5-vinyl-1,2-dihydropyridine-4-carbonitrile | 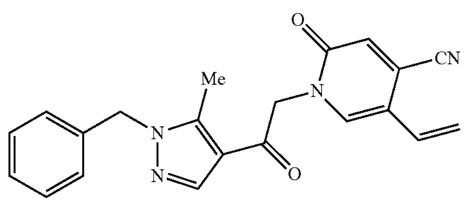 [SMILES: C=Cc1cn(CC(=O)c2cnn(Cc3ccccc3)c2C)c(=O)cc1C#N] |
| 1-(1-(1-benzyl-5-methyl-1H-pyrazol-4-yl)-1-oxopropan-2-yl)-5-vinylpyrazin-2(1H)-one | 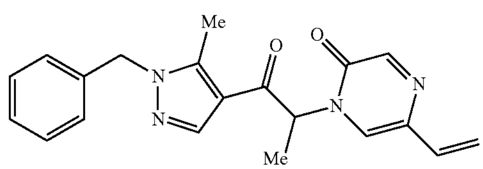 [SMILES: C=Cc1cn(C(C)C(=O)c2cnn(Cc3ccccc3)c2C)c(=O)cn1] |
| 1-(2-(1-benzyl-5-methyl-1H-pyrazol-4-yl)-2-hydroxyethyl)-5-vinylpyridin-2(1H)-one | 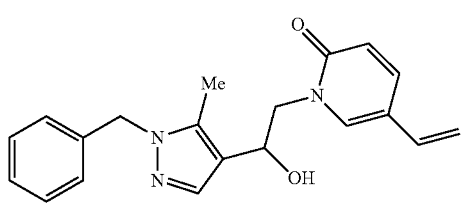 [SMILES: C=Cc1ccc(=O)n(CC(O)c2cnn(Cc3ccccc3)c2C)c1] |
| 1-(2-(1-benzyl-5-methyl-1H-pyrazol-4-yl)-2-methoxyethyl)-5-vinylpyridin-2(1H)-one | 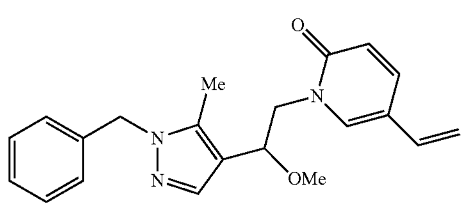 |

TABLE 3-continued

| Chemical name | Structure |
|---|---|
| 1-(2-(1-benzyl-5-methyl-1H-pyrazol-4-yl)ethyl)-5-vinylpyridin-2(1H)-one | 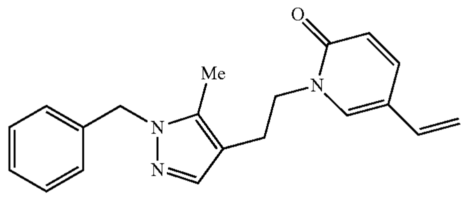 [SMILES: C=Cc1ccc(=O)n(CCc2cnn(Cc3ccccc3)c2C)c1] |
| 1-((1-benzyl-5-methyl-1H-pyrazol-4-yl)methyl)-5-vinylpyridin-2(1H)-one | |
| 1-(2-(1-benzyl-5-methyl-1H-pyrazol-4-yl)-2-oxoethyl)-4-fluoro-5-vinylpyridin-2(1H)-one | 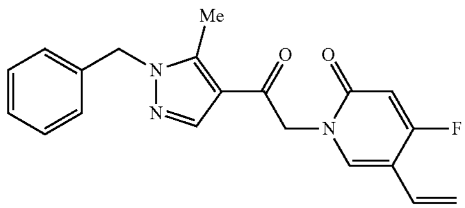 [SMILES: C=Cc1cn(CC(=O)c2cnn(Cc3ccccc3)c2C)c(=O)cc1F] |
| 1-(1-(1-benzyl-5-methyl-1H-pyrazol-4-yl)-1-oxopropan-2-yl)-5-vinylpyrimidin-2(1H)-one | 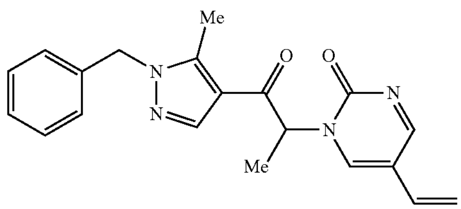 [SMILES: C=Cc1cnc(=O)n(C(C)C(=O)c2cnn(Cc3ccccc3)c2C)c1] |
| 1-(1-benzyl-5-methyl-1H-pyrazol-4-yl)-2-((5-vinylpyrazin-2-yl)oxy)propan-1-one | 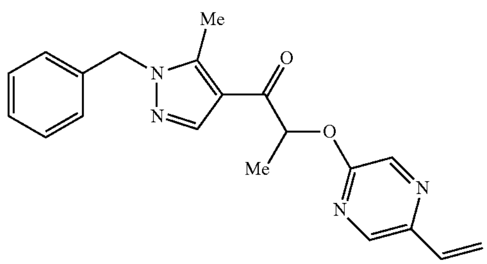 [SMILES: C=Cc1cnc(OC(C)C(=O)c2cnn(Cc3ccccc3)c2C)cn1] |
| 1-(2-(1-benzyl-5-methyl-1H-pyrazol-4-yl)-2-oxoethyl)-6-fluoro-5-vinylpyridin-2(1H)-one | 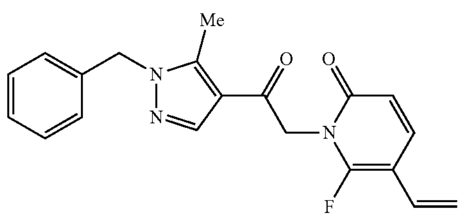 [SMILES: C=Cc1ccc(=O)n(CC(=O)c2cnn(Cc3ccccc3)c2C)c1F] |
| (E)-1-(2-(1-benzyl-5-methyl-1H-pyrazol-4-yl)-2-oxoethyl)-5-(3-(dimethylamino)prop-1-en-1-yl)pyridin-2(1H)-one | 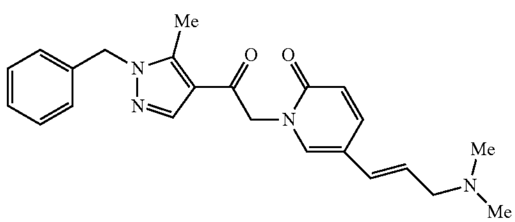 [SMILES: Cc1c(C(=O)Cn2cc(/C=C/CN(C)C)ccc2=O)cnn1Cc1ccccc1] |

TABLE 3-continued

| Chemical name | Structure |
| --- | --- |
| (Z)-1-(2-(1-benzyl-5-methyl-1H-1-pyrazol-4-yl)-2-oxoethyl)-5-(3-(dimethylamino)prop-1-en-1-yl)pyridin-2(1H)-one | 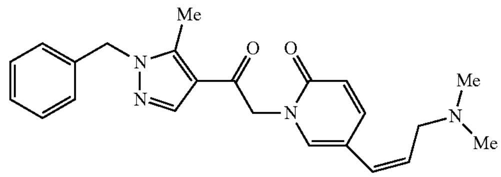 [SMILES: Cc1c(C(=O)Cn2cc(/C=C\CN(C)C)ccc2=O)cnn1Cc1ccccc1] |
| (E)-1-(2-(1-benzyl-5-methyl-1H-pyrazol-4-yl)-2-oxoethyl)-5-(3-morpholinoprop-1-en-1-yl)pyridin-2(1H)-one | 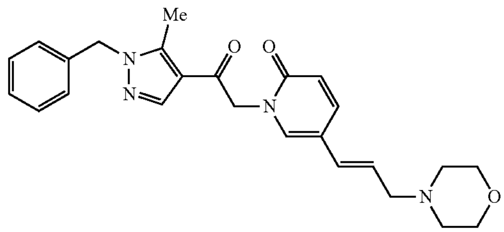 [SMILES: Cc1c(C(=O)Cn2cc(/C=C/CN3CCOCC3)ccc2=O)cnn1Cc1ccccc1] |
| (Z)-1-(2-(1-benzyl-5-methyl-1H-pyrazol-4-yl)-2-morpholinoprop-1-en-1-yl)pyridin-2(1H)-one | 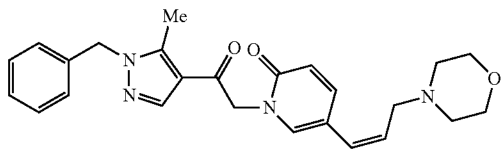 [SMILES: Cc1c(C(=O)Cn2cc(/C=C\CN3CCOCC3)ccc2=O)cnn1Cc1ccccc1] |
| 1-((2-benzyl-1-methyl-1H-imidazo[4,5-c]pyridin-4-yl)methyl)-5-bromopyridin-2(1H)-one | 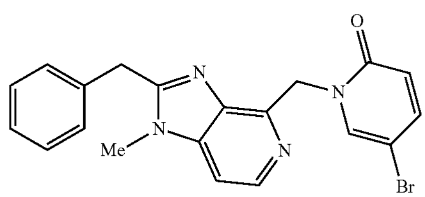 [SMILES: Cn1c(Cc2ccccc2)nc2c(Cn3cc(Br)ccc3=O)nccc21] |
| 1-((2-benzyl-1-methyl-1H-imidazo[4,5-c]pyridin-4-yl)methyl)-5-ethynylpyridin-2(1H)-one | 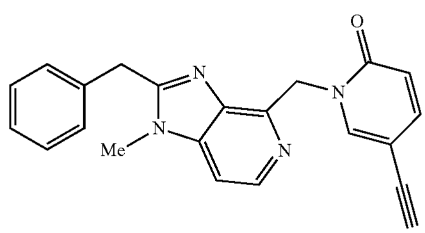 [SMILES: C#Cc1ccc(=O)n(Cc2nccc3c2nc(Cc2ccccc2)n3C)c1] |
| 1-(2-(5-benzyloxazol-2-yl)-2-oxoethyl)-5-vinylpyridin-2(1H)-one | |
| 1-(2-(1-benzyl-5-methyl-1H-pyrazol-4-yl)-2-oxoethyl)-5-ethynyl-3-fluoropyridin-2(1H)-one | 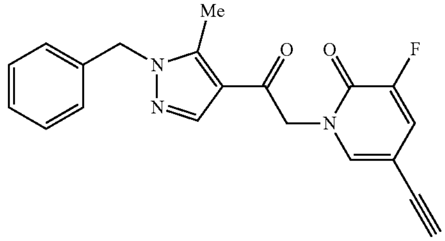 [SMILES: C#Cc1cc(F)c(=O)n(CC(=O)c2cnn(Cc3ccccc3)c2C)c1] |

TABLE 3-continued

| Chemical name | Structure |
|---|---|
| 1-(2-(1-benzyl-2,5-dimethyl-1H-imidazol-4-yl)-2-oxoethyl)-5-bromopyridin-2(1H)-one | 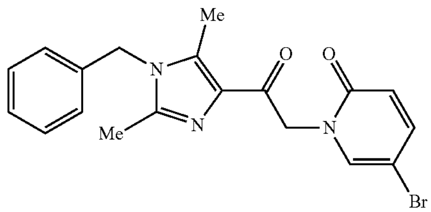 [SMILES: Cc1nc(C(=O)Cn2cc(Br)ccc2=O)c(C)n1Cc1ccccc1] |
| 5-ethynyl-1-(2-(1-(4-fluorobenzyl)-2,5-dimethyl-1H-imidazol-4-yl)-2-oxoethyl)pyridin-2(1H)-one | |
| 5-bromo-1-(2-(1-(4-fluorobenzyl)-5-methyl-1H-pyrazol-4-yl)-2-oxoethyl)pyridin-2(1H)-one | |
| 3-((4-(2-(5-bromo-2-oxopyridin-1(2H)-yl)acetyl)-5-methyl-1H-pyrazol-1-yl)methyl)benzonitrile | 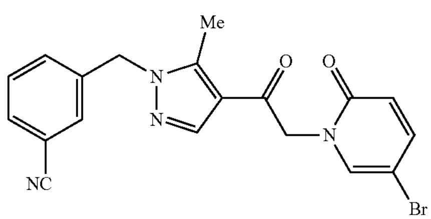 [SMILES: Cc1c(C(=O)Cn2cc(Br)ccc2=O)cnn1Cc1cccc(C#N)c1] |
| 3-((4-(2-(5-ethynyl-2-oxopyridin-1(2H)-yl)acetyl)-5-methyl-1H-pyrazol-1-yl)methyl)benzonitrile | 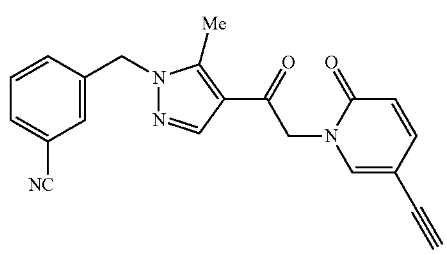 [SMILES: C#Cc1ccc(=O)n(CC(=O)c2cnn(Cc3cccc(C#N)c3)c2C)c1] |
| 5-ethynyl-1-(2-(1-(4-fluorobenzyl)-5-methyl-1H-pyrazol-4-yl)-2-oxoethyl)pyridin-2(1H)-one | |

What is claimed is:

1. A compound of the formula:

wherein:

A is:

G is N;
Y is N or C(CH₃);
X is CH or C(CH₃);
Z is CH, C(CH₃) or N;
R² is H or CH₃;
Q is N or CH;
L is N or CH;
T is N, CH or C—CN; and
R³ is bromo, —CHCH₂, —C≡CH, —CFCH₂, —C(CF₃)CH₂, —C(CH₃)CH₂ or —C≡C(CH₃);

wherein:

R³ is not bromo when A is phenyl, X is C(CH₃), Y is C(CH₃), Z is CH, R² is H, and Q, T, and L are CH.

2. The compound of claim 1, wherein the group of the formula:

is a group of the formula:

3. The compound of claim 1, wherein R³ is —CHCH₂, —C≡CH, or —C(CF₃)CH₂.

4. A pharmaceutical composition comprising one or more compounds of claim 1 and a pharmaceutically acceptable carrier.

5. A compound selected from:

271
-continued
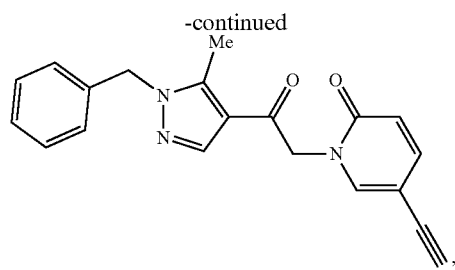
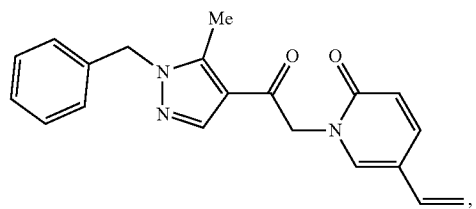
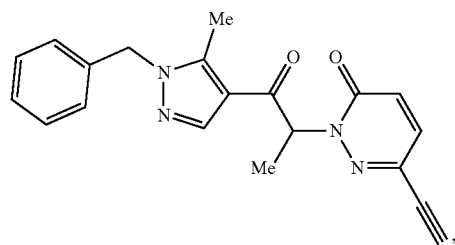
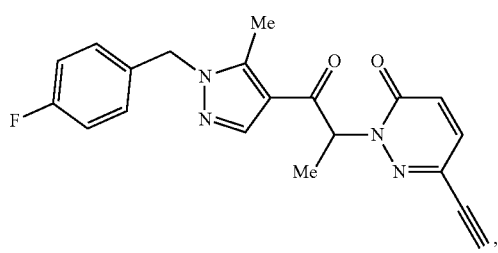
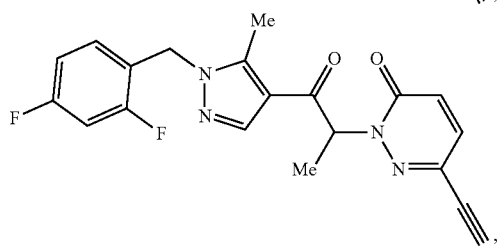
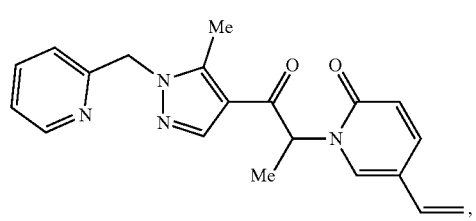
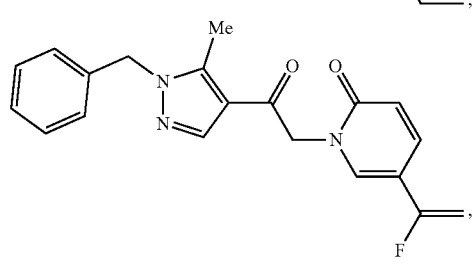
272
-continued
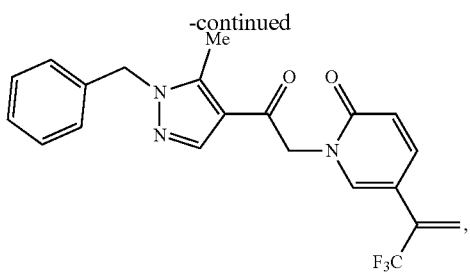
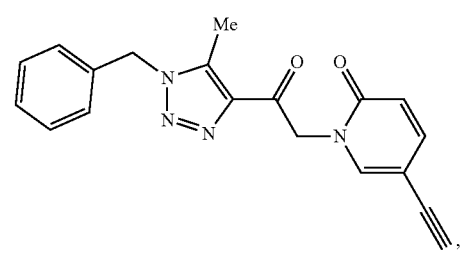
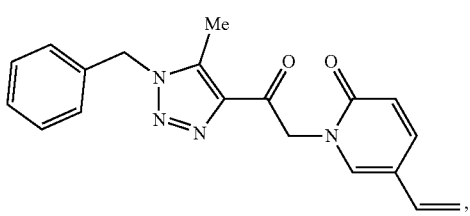
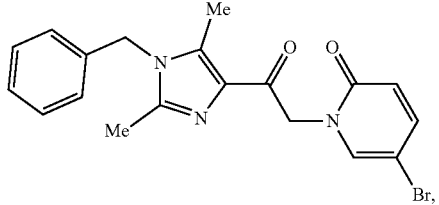
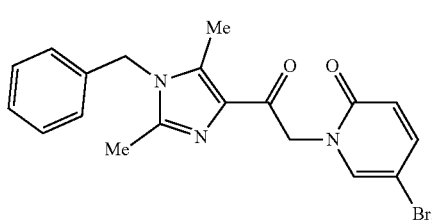
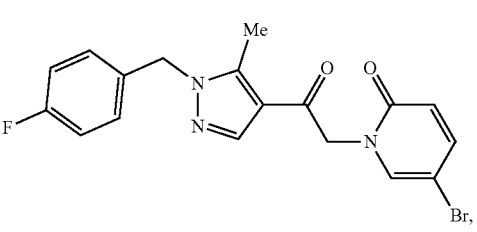

-continued or a pharmaceutically acceptable salt thereof.

* * * * *